US008748624B2

(12) United States Patent
Chakravarty et al.

(10) Patent No.: US 8,748,624 B2
(45) Date of Patent: *Jun. 10, 2014

(54) PICOLINAMIDO-PROPANOIC ACID DERIVATIVES USEFUL AS GLUCAGON RECEPTOR ANTAGONISTS

(75) Inventors: Devraj Chakravarty, Hillsborough, NJ (US); Kevin Kreutter, Plainsboro, NJ (US); Mark Powell, Newtown, PA (US); Brian Shook, Gilbertsville, PA (US); Fengbin Song, Princeton, NJ (US); Guozhang Xu, Bensalem, PA (US); Shyh-Ming Yang, Doylestown, PA (US); Rui Zhang, Belle Mead, NJ (US); Bao-Ping Zhao, West Windsor, NJ (US)

(73) Assignee: Janssen Pharmaceutica NV, Beerse (BE)

(*) Notice: Subject to any disclaimer, the term of this patent is extended or adjusted under 35 U.S.C. 154(b) by 0 days.

This patent is subject to a terminal disclaimer.

(21) Appl. No.: 13/478,534

(22) Filed: May 23, 2012

(65) Prior Publication Data
US 2012/0302610 A1 Nov. 29, 2012

Related U.S. Application Data

(60) Provisional application No. 61/488,842, filed on May 23, 2011.

(51) Int. Cl.
*A61K 31/44* (2006.01)
*C07D 211/70* (2006.01)

(52) U.S. Cl.
USPC .......................................... 546/328; 514/354

(58) Field of Classification Search
None
See application file for complete search history.

(56) References Cited

U.S. PATENT DOCUMENTS 5,739,083 A    4/1998  Endo et al.

FOREIGN PATENT DOCUMENTS

| WO | WO 2007/024922 A1 | 3/1997 |
| WO | WO 97/13756 A1 | 4/1997 |
| WO | WO 00/69810 A1 | 11/2000 |
| WO | WO 03/048109 A1 | 6/2003 |
| WO | WO 2004/056763 A2 | 7/2004 |
| WO | WO 2007/111864 A2 | 10/2007 |

OTHER PUBLICATIONS

Silverman, R. "The Organic Chemistry of Drug Design and Drug Action," 2004, Elsevier, pp. 29-32.*
International Search Report relating to corresponding International Patent Application No. PCT/US2012/039171. Date of Mailing of International Search Report: Jul. 9, 2012.
Written Opinion of the International Searching Authority relating to corresponding International Patent Application No. PCT/US2012/039171. Date of Mailing of Written Opinion: Jul. 9, 2012.
Barger, P.M., "p38 Mitogen-Activated Protein Kinase Activates Peroxisome Proliferator-activated Receptor α", *J. Biol. Chem.* 2001, pp. 44495-444501, vol. 276.
Barger, P.M., et al., "Deactivation of Peroxisome Proliferator-Activated Receptor-α During Cardiac Hypertrophic Growth", *The J. of Clinical Investigation,* 2000, pp. 1723-1730, vol. 105.
Bottger, I., et al., "The Effect of Exercise on Glucagon Secretion", *J. Clin. Endocrinology and Metabolism,* 1972, pp. 117-125, vol. 35.
Conarello, S.L., et al., "Glucagon Receptor Knockout Mice are Resistant to Diet-Induced Obesity and Streptozotocin-Mediated Beta Cell Loss and Hyperglycemia", *Diabetologia* 2007, pp. 142-150, vol. 20.
Consoli, A., et al., "Predominant Role of Gluconeogenesis in Increased Hepatic Glucose Production in NIDDM", *Diabetes,* 1989, pp. 550-557, vol. 38.
Defronzo, R.A., et al., "Fasting Hyperglycemia in Non-Insulin-Dependent Diabetes Mellitus: Contributions of Excessive Hepatic Glucose Production and Impaired Tissue Glucose Uptake", *Metabolism,* 1989, pp. 387-395, vol. 38.
Gelling, R., et al., "Lower Blood Glucose, Hyperglucagonemia and Pancreatic Alpha Cell Hyperplasia in Glucagon Receptor Knockout Mice", *PNAS* 2003, pp. 1438-1443, vol. 100.
Gu, W., et al., "Glucagon Receptor Antagonist-Mediated Improvements in Glycemic Control are Dependent on Functional Pancreatic GLP-1 Receptor", *Am. J. Physiol. Endocrinol. Metab.*, 2010, E624-E632, vol. 299.
Guette, C., et al., "Effect of Chronic Glucagon Administration on Lipoprotein Composition in Normally Fed, Fasted and Cholesterol-Fed Rats", *Lipids,* 1991, pp. 451-458, vol. 26.
Hansen L.H., et al., "Glucagon Receptor mRNA Expression in Rat Tissues", *Peptides,* 1995, pp. 1163-1166, vol. 16.
Hansen, L.H., et al., "The Gly40Ser Mutation in the Human Glucagon Receptor Gene Associated with NIDDM Results in a Receptor with Reduced Sensitivity to Glucagon", *Diabetes* 1996, pp. 725-730, vol. 45.
Hippen,A.R., "Glucagon as a Potential Therapy for Ketosis and Fatty Liver" *Vet. Clin. North Am. Food Anim. Pract.*, 2000, pp. 267-282, vol. 16.
Hippen, A.R., et al., "Alleviation of Fatty Liver in Dairy Cows with 14-Day Intravenous Infusions of Glucagon", *J. Dairy Sci.*, 1999, pp. 1139-1152, vol. 82.
Jiang, G., et al., "Glucagon and Regulation of Glucose Metabolism", *Am. J. Physiol. Endocrinol. Metab.*, 2003, pp. 671-678, vol. 284.
Koo, S-H, et al., "The CREB Coactivator TORC2 is a Key Regulator of Fasting Glucose Metabolism", *Nature,* 2005, pp. 1109-1114, vol. 437.
Liang, Y., et al., "Reduction in Glucagon Receptor Expression by an Antisense Oligonucleotide Ameliorates Diabetic Syndrome in db/db Mice", *Diabetes,* 2004, pp. 410-417, vol. 53.

(Continued)

*Primary Examiner* — Heidi Reese
(74) *Attorney, Agent, or Firm* — Jeremy K. McKown

(57) ABSTRACT

The present invention is directed to picolanmido-propanoic acid derivatives, pharmaceutical compositions containing them and their use in the treatment and/or prevention of disorders and conditions ameliorated by antagonizing one or more glucagon receptors, including for example metabolic diseases such as Type II diabetes mellitus and obesity.

22 Claims, No Drawings

(56) References Cited

OTHER PUBLICATIONS

Longuet, C., et al., "The Glucagon Receptor is Required for the Adaptive Metabolic Response to Fasting", *Cell Metabolism*, 2008, pp. 359-371, vol. 8.

MacDonald, P.E., et al., "A KATP Channel-Dependent Pathway within α-Cells Regulates Glucagon Release from Both Rodent and Human Islets of Langerhans", *PLOS Biology*, 2007, pp. 1236-1247, vol. 5.

Mayo K.E., et al., "International Union of Pharmacology. XXXV. The Glucagon Receptor Family.", *Pharmacological Reviews*, 2003, pp. 167-194, vol. 55.

Parnaud, G., et al., "Proliferation of Sorted Human and Rat Beta Cells", *Diabetologia*, 2008, pp. 91-100, vol. 51.

Quesada, I., et al., "Physiology of the Pancreatic alpha-cell and Glucagon Secretion: Role in Glucose Homeostasis and Diabetes", *Endocrinology*, 2008; pp. 5-19, vol. 199.

Reaven, G., et al., "Documentation of Hyperglucagonemia Throughout the Day in Nonobese and Obese Patients with Noninsulin-Dependent Diabetes Mellitus" *J Clin Endocrinol Metab*, 1987; pp. 106-110, vol. 64.

Rodbell M., et al., "The Glucagon-Sensitive Adenyl Cylcase System in Plasma Membranes of Rat Liver. 3. Binging of Glucagon: Method of Assay and Specificity.", *J. Biol. Chem.*, 1971, pp. 1861-1871, vol. 246.

Rouille, Y., et al., "Role of the Prohormone Convertase PC2 in the processing of Proglucagon to Glucagon", *FEBS Letters*, 1997, pp. 119-123, vol. 413.

Shah, P. et al., "Lack of Suppression of Glucagon Contributes to Postprandial Hyperglycemia in Subjects with Type 2 Diabetes Mellitus" *J Clin Endocrinol Metab*, 2000, pp. 4053-4059, vol. 85.

Sloop, K.W., et al., "Hepatic and Glucagon-Like Peptide-1-Mediated Reversal of Diabetes by Glucagon Receptor Antisense Oligonucleotide Inhibitors", *J Clin Invest*, 2004, pp. 1571-1581, vol. 113.

Trabelsi, F., et al., "Arginine-Induced Pancreatic Hormone Secretion During Exercise in Rats" *J. Appl. Physiol.*, 1996, pp. 2528-2533, vol. 81.

World Health Organization (accessed 2007, Dec. 2005) www.who.int/mediacentre/factsheets/fs312/en/.

Xiong, Y., et al., "p38 Mitogen-activated Protein Kinase Plays an Inhibitory Role in Hepatic Lipogenesis", *J. Biol. Chem.*, 2007, pp. 4975-4982, vol. 282.

Yu, R. et al., "Nesidioblastosis and Hyperplasia of a Cells, Microglucagonoma, and Nonfunctioning Islet Cell Tumor of the Pancreas", *Pancreas*, 2008, pp. 428-431, vol. 36.

Zhuo, C., et al., "Homozygous P86S Mutation of the Human Glucagon Receptor Is Associated with Hyperglucagonemia, a Cell Hyperplasia, and Islet Cell Tumor", *Pancreas*, 2009, pp. 941-946, vol. 38.

Jurukulasuriya et al., "Biaryl amide glucagon receptor antagonists." *Biorganic & Medicinal Chemistry Letters*, Jan. 1, 2004, pp. 2047-2050, vol. 14(9), Pergamon, Elsevier Science, GB.

\* cited by examiner

PICOLINAMIDO-PROPANOIC ACID DERIVATIVES USEFUL AS GLUCAGON RECEPTOR ANTAGONISTS

CROSS REFERENCE TO RELATED APPLICATIONS

This application claims the benefit of U.S. Provisional Application 61/488,842 filed on May 23, 2011, which is incorporated by reference herein in its entirety.

FIELD OF THE INVENTION

The present invention is directed to picolamido-propanoic acid derivatives, pharmaceutical compositions containing them and their use in the treatment and/or prevention of disorders and conditions ameliorated by antagonizing one or more glucagon receptors, including for example metabolic diseases such as Type II diabetes mellitus and obesity.

BACKGROUND OF THE INVENTION

The World Health Organization (WHO) reports a worldwide prevalence of 177 million patients with diabetes, a number that is likely to more than double by the year 2030. TYPE II diabetes accounts for approximately 90% of all diabetes cases (World Health Organization, www.who.int/mediacentre/factsheets/fs312/en/ (accessed 2007, December 2005) Long-term complications of TYPE II diabetes include atherosclerosis, heart disease, stroke, end-stage renal disease, retinopathy leading to blindness, nerve damage, sexual dysfunction, frequent infections and recalcitrant foot ulcers that can result in lower limb amputation. Diabetics are twice as likely to develop cardiovascular disease or have a stroke, 2 to 6 times more likely to have transient ischemic attacks, and 15 to 40 times more likely to require lower-limb amputation compared with the general population. In 2007, the total economic cost of diabetes was estimated to be US $174 billion accounting for 1 of every 8 health care dollars spent in the United States.

Hyperglycemia in patients with TYPE II diabetes mellitus (previously designated non-insulin-dependent diabetes mellitus, or NIDDM) results from a combination of peripheral insulin resistance and inadequate pancreatic insulin secretion. These abnormalities lead to decreased glucose disposal and increased endogenous glucose production. Reversal of these abnormalities, either individually or in combination, can provide an improvement in blood glucose control.

One site that is critically involved in the maintenance of euglycemia is the liver. Glucose production is maintained by the opposing actions of insulin and glucagon on hepatic glucose output. In TYPE II diabetes, the normal glucagon-insulin ratio is disrupted. Studies investigating the relationship between hepatic glucose production and plasma glucagon concentrations have suggested that in patients with TYPE II diabetes, increased glucagon action is largely responsible for the hepatic insulin resistance and increased rates of glucose production (REAVEN, G., et al., "Documentation of Hyperglucagonemia Throughout the Day in Nonobese and Obese Patients with Noninsulin-Dependent Diabetes Mellitus", *J Clin Endocrinol Metab*, 1987; pp 106-110, Vol. 64; and SHAH, P. et al., "Lack of Suppression of Glucagon Contributes to Postprandial Hyperglycemia in Subjects with TYPE II Diabetes Mellitus", *J Clin Endocrinol Metab*, 2000, pp 4053-4059, Vol. 85). Both elevated fasting glucagon levels and impaired suppression of glucagon secretion after meals result in hyperglycemia during the postabsorptive and postprandial states. A positive correlation of plasma glucagon levels and hepatic glucose output and fasting glucose levels has been documented in humans (DEFRONZO, R. A., et al., "Fasting Hyperglycemia in Non-Insulin-Dependent Diabetes Mellitus Contributions of Excessive Hepatic Glucose Production and Impaired Tissue Glucose Uptake" *Metabolism*, 1989, pp 387-395, Vol. 38; and CONSOLI, A., et al., "Predominant Role of Gluconeogenesis in Increased Hepatic Glucose Production in NIDDM", *Diabetes*, 1989, pp 550-557, Vol. 38). Therefore, glucagon receptor antagonist provide a promising approach in reducing hepatic glucose output as a mechanism in improving glycemia in TYPE II diabetics.

Glucagon is a 29 amino-acid peptide hormone, that is encoded within the proglucagon gene, and is cleaved specifically in pancreatic α-cells by prohormone convertase 2 (PC2) (ROUILLE, Y., et al., "Role of the Prohormone Convertase PC2 in the processing of Proglucagon to Glucagon", *FEBS Letters*, 1997, pp 119-123, Vol. 413). Within the proglucagon gene also sequences for the glucagon-like peptide 1 (GLP1), glucagon like peptide 2 (GLP2), oxyntomodulin and glicentin are encoded. Glucagon's secretion from α-cells is tightly regulated by a number of factors with the most important being glucose and insulin (QUESADA, I., et al., "Physiology of the Pancreatic alpha-cell and Glucagon Secretion: Role in Glucose Homeostasis and Diabetes", *Endocrinology*, 2008; pp 5-19, Vol. 199). In the face of low glucose levels specific ATP-sensitive $K^+$ channels are activated generating action potentials and stimulating glucagon secretion (MACDONALD, P. E., et al., "A KATP Channel-Dependent Pathway within α-Cells Regulates Glucagon Release from Both Rodent and Human Islets of Langerhans", *PLOS Biology*, 2007, pp 1236-1247, Vol. 5). Additional stimuli such as amino acids (TRABELSI, F., et al., "Arginine-Induced Pancreatic Hormone Secretion During Exercise in Rats", *J. Appl. Physiol.*, pp 2528-2533, Vol. 81) and exercise (BOTTGER, I., et al., "The Effect of Exercise on Glucagon Secretion", *J. Clin. Endocrinology and Metabolism*, 1972, pp 117-125, Vol. 35) are known to stimulate glucagon secretion but the underlying mechanisms are not well understood.

The major physiological role of glucagon is to counteract the action of insulin on hepatic glucose output. Glucagon mediates its effects by binding to and activating the glucagon receptor that was first described by Rodbell and colleagues (RODBELL M., et al., "The Glucagon-Sensitive Adenyl Cylcase System in Plasma Membranes of Rat Liver. 3. Binging of Glucagon: Method of Assay and Specificity.", *J. Biol. Chem.*, 1971, pp 1861-1871, Vol. 246). By sequence homology analysis, glucagon receptor (GCGR) is a member of the Class B family of heptahelical guanosine triphosphate (GTP)-binding protein (G protein) coupled receptors, which includes those for the related peptides, glucagon-like peptide-1 (GLP-1) and glucose-dependent insulinotropic polypeptide (MAYO K. E., et al., "International Union of Pharmacology. XXXV. The Glucagon Receptor Family.", *Pharmacological Reviews*, 2003, pp 167-194, Vol. 55). The receptor is mainly expressed in liver and in kidney with lesser amounts found in heart, adipose tissue, adrenal glands, pancreas, cerebral cortex and gastrointestinal tract (HANSEN L H, et al., "Glucagon Receptor mRNA Expression in Rat Tissues." *Peptides*, 1995, pp 1163-1166, Vol. 16).

The immediate action of glucagon is rapid and transient. Specifically on the liver one of the main actions of glucagon is to regulate glycogenolysis. The molecular basis for the action of the hormone is mediated through activation of its cognate receptor, signal transduction to Gsa subunits and activation of adenylate cyclase resulting in a rise of intracellular cAMP levels, and subsequent activation of protein kinase A (PKA). Activation of PKA results in activation of glycogen phopshorylase and inactivation of glycogen synthase resulting in a net increase in gluconeogenesis via glycogenolysis (JIANG, G., et al., "Glucagon and Regulation of Glucose Metabolism", *Am. J. Physiol. Endocrinol. Metab.*, 2003, pp 671-678, Vol. 284). In addition to glycogenolysis glucagon potentiates gluconeogenesis from precursors such as lactate, alanine, pyruvate and glycerol. The level of regulation appears to be genomic dependent on and in part through cAMP-dependent PKA activation of CREB and transcriptional activation of gluconeogenic genes including PGC1α and PEPCK (KOO, S-H, et al., "The CREB Coactivator TORC2 is a Key Regulator of Fasting Glucose Metabolism", *Nature*, 2005, pp 1109-1114, Vol. 437).

The role of GCGR in glucose homeostasis has been studied in mice lacking the receptor. GCGR null mice show slightly reduced plasma glucose and insulin levels; these mice also have improved glucose tolerance compared to wild type mice (GELLING, R., et al., "Lower Blood Glucose, Hyperglucagonemia and Pancreatic Alpha Cell Hyperplasia in Glucagon Receptor Knockout Mice", *PNAS*, 2003, pp 1438-1443, Vol. 100). The heterozygote mice have no obvious phenotype. When challenged with streptozotocin, the GCGR null mice were resistant to hyperglycemia and pancreatic β-cell destruction suggesting that inhibition of glucagon signaling promotes β-cell survival and function (CONARELLO, S. L., et al., "Glucagon Receptor Knockout Mice are Resistant to Diet-Induced Obesity and Streptozotocin-Mediated Beta Cell Loss and Hyperglycemia", *Diabetologia*, 2007, pp 142-150, Vol. 20). The GCGR null mice did not exhibit hypoglycemia for fasting periods less than 24 hours, and also recovered normally after an insulin challenge (GELLING, R., et al., "Lower Blood Glucose, Hyperglucagonemia and Pancreatic Alpha Cell Hyperplasia in Glucagon Receptor Knockout Mice", *PNAS*, 2003, pp 1438-1443, Vol. 100). This suggests presence of alternate signaling pathways from counter regulatory hormones that offset hypoglycemia in the absence of the glucagon receptor. Liver membranes from GCGR null mice were found to have an increased response to epinephrine-induced cAMP production. Additionally, null animals had a 2-fold increase of fasting corticosterone levels under prolonged fasting (12-14 hours). When fasting was extended post 24 hours, these mice developed severe hypoglycemia.

GCGR null mice exhibit α-cell hyperplasia and increased expression levels of the proglucagon gene (GELLING, R., et al., "Lower Blood Glucose, Hyperglucagonemia and Pancreatic Alpha Cell Hyperplasia in Glucagon Receptor Knockout Mice", *PNAS*, 2003, pp 1438-1443, Vol. 100). The long term safety of chronic blockade of this pathway in humans is not known but it is worth mentioning that rodents have a higher capacity of islet cell replication than humans (PARNAUD, G., et al., "Proliferation of Sorted Human and Rat Beta Cells", *Diabetoloqia*, 2008, pp 91-100, Vol. 51). Specifically rat β-cells can proliferate when plated on extracellular matrix and this proliferation is further enhanced in the presence of exogenous factors such as liraglutide. In contrast, human β-cells fail to proliferate in vitro. The consequence of α-cell hyperplasia in the null mouse is an increased processing of proglucagon and generation of GLP-1 derived from the pancreas. It is well established that intestinally processed forms of GLP-1 act to inhibit glucagon secretion, increase insulin secretion as well as to improve β-cell glucose sensitivity and βcell mass. GLP-1 also inhibits food intake via the central nervous system (CNS). Therefore, the elevated pancreatic-derived GLP-1 levels in GCGR null mice may account for the enhancement of glucose-stimulated insulin secretion and glucose tolerance (SLOOP, K. W., et al., "Hepatic and Glucagon-Like Peptide-1-Mediated Reversal of Diabetes by Glucagon Receptor Antisense Oligonucleotide Inhibitors", *J Clin Invest*, 2004, pp 1571-1581, Vol. 113). This has been recently validated in an investigation by Gu et al., in which the authors evaluated a mouse GCGR neutralizing antibody in GLP-1 KO mice and found that the antibody provided no improvement in glucose tolerance during an ipGTT. Based on these results, pancreatic GLP-1 would be a significant contributor to the efficacy of glucagon receptor antagonists in rodents (GU, W., et al., "Glucagon Receptor Antagonist-Mediated Improvements in Glycemic Control are Dependent on Functional Pancreatic GLP-1 Receptor", *Am. J. Physiol. Endocrinol. Metab.*, 2010, ppE624-E632, Vol. 299).

More recent studies have focused on the function of glucagon receptor on hepatic fatty acid oxidation, lipogenesis and hepatocyte survival. Administration of glucagon promotes a hypolipidemic effect in rats (GUETTE, C., et al., "Effect of Chronic Glucagon Administration on Lipoprotein Composition in Normally Fed, Fasted and Cholesterol-Fed Rats", *Lipids*, 1991, pp 451-458, Vol. 26) and resolves steatosis in lactating dairy cows (HIPPEN, A. R., et al., "Alleviation of Fatty Liver in Dairy Cows with 14-Day Intravenous Infusions of Glucagon", *J. Dairy Sci.*, 1999, pp 1139-1152, Vol. 82). In fact, glucagon has been proposed as a treatment of hepatic steatosis (HIPPEN, A. R., "Glucagon as a Potential Therapy for Ketosis and Fatty Liver", *Vet. Clin. North Am. Food Anim. Pract.*, 2000, pp 267-282, Vol. 16). Fasting GCGR null mice for 16 hours produces a phenotype with defects in triglyceride clearance and lipid synthesis. Hepatocytes isolated from these animals have reduced capacity for fatty acid beta-oxidation (LONGUET, C., et al., "The Glucagon Receptor is Required for the Adaptive Metabolic Response to Fasting", *Cell Metabolism*, 2008, pp 359-371, Vol. 8). In some instances but not all (CONARELLO, S. L., et al., "Glucagon Receptor Knockout Mice are Resistant to Diet-Induced Obesity and Streptozotocin-Mediated Beta Cell Loss and Hyperglycemia", *Dioabetolopia*, 2007, pp 142-150, Vol. 20), steatosis has been observed in the GCGR knockout animals (LONGUET, C., et al., "The Glucagon Receptor is Required for the Adaptive Metabolic Response to Fasting", *Cell Metabolism*, 2008, pp 359-371, Vol. 8) and in pre-clinical models that have been pharmacologically treated with ASO's (LIANG, Y., et al., "Reduction in Glucagon Receptor Expression by an Antisense Oligonucleotide Ameliorates Diabetic Syndrome in db/db Mice", *Diabetes*, 2004, pp 410-417, Vol. 53). The mechanism is PKA independent suggesting alternate glucagon signaling pathways in the liver. The exact mechanism by which glucagon signaling in the liver increases fatty acid oxidation is unclear but part of it appears to be mediated by activation of PPARα via the mitogen activated protein kinase pathway. Glucagon can activate both p38 and ERK1/2 in hepatocytes with the former increasing (BARGER, P. M., et al., "Deactivation of Peroxisome Proliferator-Activated Receptor-α During Cardiac Hypertrophic Growth", *The J. of Clinical Investigation*, 2000, pp 1723-1730, Vol. 105) and the latter decreasing PPARα activity (BARGER, P. M., "p38 Mitogen-Activated Protein Kinase Activates Peroxisome Proliferator-activated Receptor α", *J. Biol. Chem.*, 2001, pp 44495-444501, Vol. 276). The p38 pathway also modulates hepatic lipogenesis with glucagon being inhibitory and insulin stimulatory (XIONG, Y., et al., "p38 Mitogen-activated Protein Kinase Plays an Inhibitory Role in Hepatic Lipogenesis", *J. Biol. Chem.*, 2007, pp 4975-4982, Vol. 282). These observations are suggestive that glucagon signaling is required for the regulation of fatty acid oxidation and synthesis in the liver. The fact that this mechanism is dissociated from the classical glucagon G-protein PKA signal transduction indicates a potential in developing biased antagonists that can favorably affect one signaling arm vs. others thereby alleviating potential concerns of sustained inactivation of all glucagon signaling pathways.

A heterozygous missense mutation Gly40Ser that results in a loss of function has been associated with TYPE II diabetes in a French population (HANSEN, L. H., et al., "The Gly40Ser Mutation in the Human Glucagon Receptor Gene Associated with NIDDM Results in a Receptor with Reduced Sensitivity to Glucagon", *Diabetes*, 1996, pp 725-730, Vol. 45). It is not apparent why this mutation has deleterious effects on glucose control since deletion of GCGR in rodents improves glucose tolerance. Recently a patient with a homozygous mutation, Pro86Ser, was described in the literature. This patient was presented with a benign pancreatic tumor and further examination revealed elevated glucagon levels (~60,000 µg/mL) in the presence of normal fasting glucose and insulin levels (YU, R. et al., "Nesidioblastosis and Hyperplasia of a Cells, Microglucagonoma, and Non-functioning Islet Cell Tumor of the Pancreas", *Pancreas*, 2008, pp 428-431, Vol. 36). The tumor was resected and histological examination revealed α-cell hyperplasia. Hyperglucagonemia persisted postoperatively which was suppressed with somatostatin treatment. The glucagon receptor gene was sequenced in this patient where she was identified to be homozygous for the Pro86Ser mutation and further characterization of this mutation revealed a 10-fold loss of functional response (ZHUO, C., et al., "Homozygous P86S Mutation of the Human Glucagon Receptor Is Associated with Hyperglucagonemia, a Cell Hyperplasia, and Islet Cell Tumor", *Pancreas*, 2009, pp 941-946, Vol. 38). The presence of elevated glucagon levels was most likely sufficient to maintain glucagon receptor signaling and euglycemia. Since the homozygous mutation was inherited from both parents it suggests the heterozygous mutation is benign. Since this is a single case report, the association of this mutation to α-cell hyperplasia remains to be determined.

Glucagon antagonism may provide therapeutic agents to control Type II diabetes mellitus, along with traditional diabetes drugs focused on increasing insulin secretion or improving insulin sensitivity. Preclinical data indicate that the anti-diabetic effects of the GCGR antagonist may be related to dual mechanisms including, 1) a reduction of hepatic glucose output that is due to attenuation of glucagon action in the liver, and 2) a secondary increase in active GLP-1, which occurs as a result of increased processing of pre-proglucagon in the pancreas.

Thus there remains a need for novel glucagon antagonists for the treatment of metabolic disorders such as Type II diabetes mellitus and obesity.

SUMMARY OF THE INVENTION

The present invention is directed to compounds of formula (I)

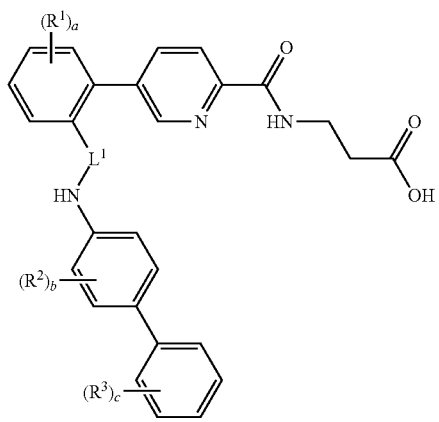

(I)

wherein $L^1$ is selected from the group consisting of —CH$_2$—, —CH(CH$_3$)— and —C(O)—;

a is an integer from 0 to 3;

each $R^1$ is independently selected from the group consisting of halogen, hydroxy, cyano, $C_{1-4}$alkyl, fluorinated $C_{1-4}$alkyl, $C_{2-4}$alkenyl, $C_{1-4}$alkoxy, fluorinated $C_{1-4}$alkoxy, —SO$_2$—(C$_{1-2}$alkyl), —C(O)—C$_{1-2}$alkyl, phenyl, $C_{3-6}$cycloalkyl and $C_{5-6}$cyaloalkenyl;

b is an integer from 0 to 3;

each $R^2$ is independently selected from the group consisting of halogen, cyano, $C_{1-4}$alkyl, fluorinated $C_{1-4}$alkyl, $C_{1-4}$alkoxy and fluorinated $C_{1-4}$alkoxy;

c is an integer from 0 to 4;

each $R^3$ is independently selected from the group consisting of halogen, cyano, nitro, $C_{1-4}$alkyl, fluorinated $C_{1-4}$alkyl, $C_{1-4}$alkoxy, fluorinated $C_{1-4}$alkoxy and —C(O)—C$_{1-2}$alkyl;

and pharmaceutically acceptable salts thereof.

The present invention is further directed to processes for the preparation of the compounds of formula (I). The present invention is further directed to a product prepared according to the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder ameliorated by antagonizing a glucagon receptor (selected from the group consisting of Type I diabetes, Type II diabetes mellitus, obesity and renal disease (including, but not limited to, renal failure as a complication of diabetes) comprising administering to a subject in need thereof a therapeutically effective amount of any of the compounds or pharmaceutical compositions described above.

In an embodiment, the present invention is directed to a compound of formula (I) for use as a medicament. In another embodiment, the present invention is directed to a compound of formula (I) for use in the treatment of a disorder ameliorated by antagonizing a glucagon receptor (selected from the group consisting of Type I diabetes, Type II diabetes mellitus, obesity and renal disease (including but not limited to, renal failure as a complication of diabetes). In another embodiment, the present invention is directed to a composition comprising a compound of formula (I) for the treatment of a disorder ameliorated by a antagonizing glucagon receptor (selected from the group consisting of Type I diabetes, Type II diabetes mellitus, obesity and renal disease (including but not limited to, renal failure as a complication of diabetes).

Another example of the invention is the use of any of the compounds described herein in the preparation of a medicament for treating: (a) Type I diabetes, (b) Type II diabetes mellitus (c) obesity, (d) renal disease, in a subject in need thereof. In another example, the present invention is directed to a compound as described herein for use in a methods for treating a disorder selected from the group consisting of Type I diabetes, Type II diabetes mellitus, obesity, renal disease (for example renal failure as a complication of diabetes), in a subject in need thereof.

DETAILED DESCRIPTION OF THE INVENTION

The present invention is directed to compounds of formula (I)

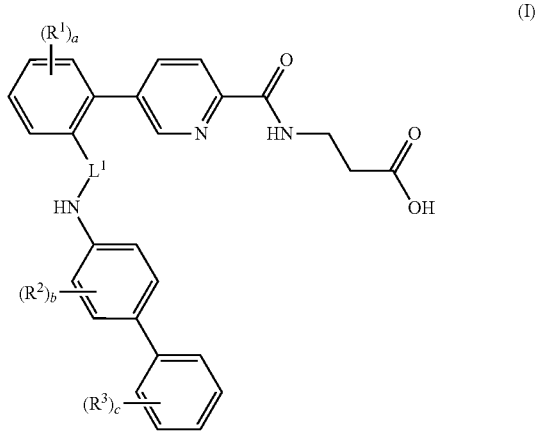

wherein $L^1$, a, $R^1$, b, $R^2$, c and $R^3$ are as herein defined. The compounds of the present invention are useful in the treatment of conditions and disorders which are meliorated by antagonizing glucagon receptors, including but not limited to Type I diabetes, Type II diabetes mellitus, obesity and renal disease.

For compounds of formula (I) of the present invention, when defining the binding position of the $R^1$, $R^2$, $R^3$ and $R^4$ substituent groups, the following numbering convention is applied:

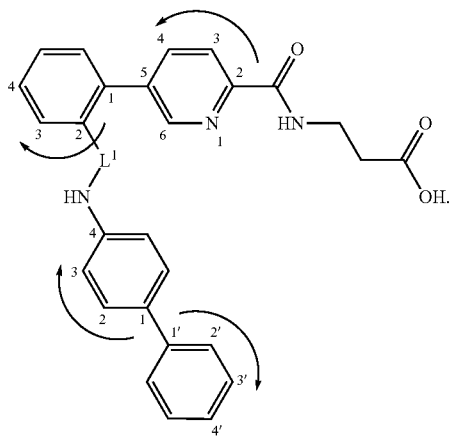

In an embodiment, the present invention is directed to compounds of formula (I) wherein $L^1$ is selected from the group consisting of —$CH_2$— and —C(O)—. In another embodiment, the present invention is directed to compounds of formula (I) wherein $L^1$ is —$CH(CH_3)$—. In another embodiment, the present invention is directed to compounds of formula (I) wherein $L^1$ is —$CH_2$—. In another embodiment, the present invention is directed to compounds of formula (I) wherein $L^1$ is —C(O)—.

In an embodiment, the present invention is directed to compounds of formula (I) wherein a is an integer from 0 to 2. In another embodiment, the present invention is directed to compounds of formula (I) wherein a is an integer selected from 1 or 2. In another embodiment, the present invention is directed to compounds of formula (I) wherein a is 0. In another embodiment, the present invention is directed to compounds of formula (I) wherein a is 1. In another embodiment, the present invention is directed to compounds of formula (I) wherein a is 2.

In an embodiment, the present invention is directed to compounds of formula (I) wherein each $R^1$ is independently selected from the group consisting of halogen, hydroxy, cyano, $C_{1-4}$alkyl, fluorinated $C_{1-4}$alkyl, $C_{1-4}$alkoxy, fluorinated $C_{1-2}$alkoxy, —$SO_2$—$C_{1-2}$alkyl, phenyl, $C_{3-6}$cycloalkyl and $C_{5-6}$cycloalkenyl. In another embodiment, the present invention is directed to compounds of formula (I) wherein each $R^1$ is independently selected from the group consisting of halogen, hydroxy, cyano, $C_{1-4}$alkyl, fluorinated $C_{1-2}$alkyl, $C_{1-2}$alkoxy, —$SO_2$—$C_{1-2}$alkyl, phenyl, $C_{3-6}$cycloalkyl and cyclohexenyl.

In an embodiment, the present invention is directed to compounds of formula (I) wherein the $R^1$ substituent group(s) are bound at the 2-, 3-, 4-, 5- and/or 6-position(s). In another embodiment, the present invention is directed to compounds of formula (I) wherein the $R^1$ substituent group(s) are bound at the 3-, 4- and/or 5-position(s). In another embodiment, the present invention is directed to compounds of formula (I) wherein the $R^1$ substituent group(s) are bound at the 3- and/or 5-position(s). In another embodiment, the present invention is directed to compounds of formula (I) wherein the $R^1$ substituent group(s) are bound at the 4- and/or 5-position(s). In another embodiment, the present invention is directed to compounds of formula (I) wherein the $R^1$ is bound at the 5-position.

In another embodiment, the present invention is directed to compounds of formula (I) wherein each $R^1$ is independently selected from the group consisting of chloro, fluoro, hydroxy, cyano, methyl, isopropyl, isopropen-1-yl, trifluoromethyl, methoxy, methylsulfonyl-, phenyl, cyclopropyl, cyclohexyl and cyclohexen-1-yl. In another embodiment, the present invention is directed to compounds of formula (I) wherein each $R^1$ is independently selected from the group consisting of 3-chloro, 4-chloro, 5-chloro, 4-fluoro, 5-fluoro, 3-hydroxy, 6-cyano, 3-methyl, 5-methyl, 6-methyl, 3-isopropyl, 5-isopropyl, 5-(isopropen-1-yl), 3-trifluoromethyl, 4-trifluoromethyl, 5-trifluoromethyl, 6-trifluoromethyl, 3-methoxy, 4-methoxy, 5-methoxy, 3-hydroxy, 5-(methylsulfonyl-), 3-phenyl, 5-phenyl, 3-cyclopropyl, 5-cyclohexyl and 5-(cyclohexen-1-yl).

In another embodiment, the present invention is directed to compounds of formula (I) wherein each $R^1$ is independently selected from the group consisting of 3-chloro, 4-chloro, 5-chloro, 4-fluoro, 5-fluoro, 5-methyl, 5-isopropyl, 5-isopropenyl, 3-trifluoromethyl, 5-trifluoromethyl, 5-phenyl, 5-cyclohexyl and 5-cyclohexenyl. In another embodiment, the present invention is directed to compounds of formula (I) wherein each $R^1$ is independently selected from the group consisting of 3-chloro, 4-chloro, 5-chloro, 4-fluoro, 5-fluoro, 5-isopropyl, 5-trifluoromethyl, 5-cyclohexyl and 5-cyclohexenyl.

In another embodiment, the present invention is directed to compounds of formula (I) wherein each $R^1$ is independently selected from the group consisting of 3-chloro, 4-chloro, 5-chloro, 4-fluoro, 5-fluoro, 3-hydroxy, 3-methyl, 5-methyl, 3-isopropyl, 3-trifluoromethyl, 5-trifluoromethyl, 3-methoxy, 3-hydroxy, 3-phenyl, 5-phenyl, 3-cyclopropyl and 5-cyclohexyl. In another embodiment, the present invention is directed to compounds of formula (I) wherein each $R^1$ is independently selected from the group consisting of 3-chloro, 4-chloro, 5-chloro, 3-methyl, 3-isopropyl, 3-trifluoromethyl, 5-trifluoromethyl, 3-methoxy, 3-phenyl, 3-cyclopropyl and 5-cyclohexyl. In another embodiment, the present invention is directed to compounds of formula (I) wherein each $R^1$ is independently selected from the group consisting of 3-chloro, 3-methyl, 3-isopropyl, 3-trifluoromethyl 5-trifluoromethyl, 3-phenyl and 3-cyclopropyl.

In an embodiment, the present invention is directed to compounds of formula (I) wherein $(R^1)_a$ is selected from the group consisting of 5-chloro, 5-trifluoromethyl, 3-chloro-5-trifluoromethyl 3-methyl-5-trifluoromethyl and 3-cyclopropyl-5-trifluoromethyl. In another embodiment, the present invention is directed to compounds of formula (I) wherein $(R^1)_a$ is 3-chloro-5-trifluoromethyl. In another embodiment, the present invention is directed to compounds of formula (I) wherein $(R^1)_a$ is 5-trifluoromethyl;

In an embodiment, the present invention is directed to compounds of formula (I) wherein b is an integer from 0 to 2. In another embodiment, the present invention is directed to compounds of formula (I) wherein b is an integer selected from 1 or 2. In another embodiment, the present invention is directed to compounds of formula (I) wherein b is 0. In another embodiment, the present invention is directed to compounds of formula (I) wherein b is 1. In another embodiment, the present invention is directed to compounds of formula (I) wherein b is 2.

In an embodiment, the present invention is directed to compounds of formula (I) wherein each $R^2$ is independently selected from the group consisting of halogen, cyano, $C_{1-4}$alkyl, fluorinated $C_{1-2}$alkyl, $C_{1-2}$alkoxy and fluorinated $C_{1-2}$alkoxy. In another embodiment, the present invention is directed to compounds of formula (I) wherein each $R^2$ is independently selected from the group consisting of halogen, cyano, $C_{1-2}$alkyl, fluorinated $C_{1-2}$alkyl and $C_{1-2}$alkoxy.

In an embodiment, the present invention is directed to compounds of formula (I) wherein the $R^2$ substituent group(s) are bound at the 2-, 3-, 5- and/or 6-position(s). In another embodiment, the present invention is directed to compounds of formula (I) wherein the $R^2$ substituent group(s) are bound at the 2-position.

In another embodiment, the present invention is directed to compounds of formula (I) wherein each $R^2$ is independently selected from the group consisting of chloro, fluoro, cyano, methyl, trifluoromethyl and methoxy. In another embodiment, the present invention is directed to compounds of formula (I) wherein each $R^2$ is independently selected from the group consisting of 2-chloro, 6-chloro, 2-fluoro, 3-fluoro, 2-cyano, 2-methyl, 2-trifluoromethyl and 5-methoxy.

In another embodiment, the present invention is directed to compounds of formula (I) wherein $R^2$ is selected from the group consisting of 2-chloro, 2-fluoro, 3-fluoro, 2-cyano, 2-methyl and 5-methoxy. In another embodiment, the present invention is directed to compounds of formula (I) wherein $R^2$ is selected from the group consisting of 2-chloro, 2-fluoro and 2-methyl.

In another embodiment, the present invention is directed to compounds of formula (I) wherein $R^2$ is selected from the group consisting of 2-chloro, 2-cyano, 2-methyl and 2-trifluoromethyl. In another embodiment, the present invention is directed to compounds of formula (I) wherein $R^2$ is selected from the group consisting of 2-chloro, 2-methyl and 2-trifluoromethyl. In another embodiment, the present invention is directed to compounds of formula (I) wherein $R^2$ is selected from the group consisting of 2-chloro and 2-methyl.

In another embodiment, the present invention is directed to compounds of formula (I) wherein $(R^2)_b$ is absent or selected from the group consisting of 2-chloro and 2-methyl. In another embodiment, the present invention is directed to compounds of formula (I) wherein $(R^2)_b$ is 2-chloro.

In an embodiment, the present invention is directed to compounds of formula (I) wherein c is an integer from 0 to 2. In another embodiment, the present invention is directed to compounds of formula (I) wherein c is an integer selected from 1 or 2. In another embodiment, the present invention is directed to compounds of formula (I) wherein c is 0. In another embodiment, the present invention is directed to compounds of formula (I) wherein c is 1. In another embodiment, the present invention is directed to compounds of formula (I) wherein c is 2.

In an embodiment, the present invention is directed to compounds of formula (I) wherein each $R^3$ is independently selected from the group consisting of halogen, $C_{1-4}$alkyl, fluorinated $C_{1-2}$alkyl, $C_{1-4}$alkoxy, fluorinated $C_{1-2}$alkoxy and —C(O)—$C_{1-2}$alkyl. In another embodiment, the present invention is directed to compounds of formula (I) wherein each $R^3$ is independently selected from the group consisting of halogen, $C_{1-2}$alkyl, fluorinated $C_{1-2}$alkyl, $C_{1-2}$alkoxy, fluorinated $C_{1-2}$alkoxy and —C(O)—$C_{1-2}$alkyl.

In an embodiment, the present invention is directed to compounds of formula (I) wherein the $R^3$ substituent group(s) are bound at the 2-, 3-, 4-, 5- and/or 6-position(s). In another embodiment, the present invention is directed to compounds of formula (I) wherein the $R^3$ substituent group(s) are bound at the 2-, 3-, 4- and/or 6-position(s). In another embodiment, the present invention is directed to compounds of formula (I) wherein the $R^3$ substituent group(s) are bound at the 2-, 3- and/or 4-position(s). In another embodiment, the present invention is directed to compounds of formula (I) wherein the $R^3$ substituent group(s) are bound at the 2- and/or 4-position(s). In another embodiment, the present invention is directed to compounds of formula (I) wherein the $R^3$ substituent group(s) are bound at the 3- and/or 4-position(s). In another embodiment, the present invention is directed to compounds of formula (I) wherein the $R^3$ is bound at the 4-position.

In another embodiment, the present invention is directed to compounds of formula (I) wherein each $R^3$ is independently selected from the group consisting of chloro, fluoro, methyl, t-butyl, trifluoromethyl, methoxy, trifluoromethoxy and methylcarbonyl-. In another embodiment, the present invention is directed to compounds of formula (I) wherein each $R^3$ is independently selected from the group consisting of 2'-chloro, 3'-chloro, 4'-chloro, 6'-chloro, 2'-fluoro, 3'-fluoro, 4'-fluoro, 5'-fluoro, 6'-fluoro, 2'-methyl, 3'-methyl, 4'-methyl, 4'-t-butyl, 2'-trifluoromethyl, 3'-trifluoromethyl, 4'-trifluoromethyl, 4'-methoxy, 2'-trifluoromethoxy, 3'-trifluoromethoxy, 4'-trifluoromethoxy and 4'-(methylcarbonyl-).

In another embodiment, the present invention is directed to compounds of formula (I) wherein each $R^3$ is independently selected from the group consisting of 2'-chloro, 3'-chloro, 4'-chloro, 2'-fluoro, 3'-fluoro, 4'-fluoro, 6'-fluoro, 2'-methyl, 3'-methyl, 4'-methyl, 4'-t-butyl, 2'-trifluoromethyl, 3'-trifluoromethyl, 4'-trifluoromethyl, 4'-methoxy, 4'-trifluoromethoxy and 4'-(methylcarbonyl-). In another embodiment, the present invention is directed to compounds of formula (I) wherein each $R^3$ is independently selected from the group consisting of 2'-chloro, 3'-chloro, 4'-chloro, 2'-fluoro, 4'-fluoro, 2'-methyl, 3'-trifluoromethyl, 4'-trifluoromethyl and 4'-trifluoromethoxy.

In another embodiment, the present invention is directed to compounds of formula (I) wherein each $R^3$ is independently selected from the group consisting of 2'-chloro, 3'-chloro, 4'-chloro, 6'-chloro, 2'-fluoro, 3'-fluoro, 4'-fluoro, 2'-methyl, 4'-methyl, 3'-trifluoromethyl, 4'-trifluoromethyl and 4'-trifluoromethoxy. In another embodiment, the present invention is directed to compounds of formula (I) wherein each R³ is independently selected from the group consisting of 2'-chloro, 3'-chloro, 4'-chloro, 2'-fluoro, 4'-fluoro, 2'-methyl, 3'-trifluoromethyl and 4'-trifluoromethyl. In another embodiment, the present invention is directed to compounds of formula (I) wherein each R³ is independently selected from the group consisting of 2'-chloro, 3'-chloro, 4'-chloro, 4'-fluoro, 2'-methyl, 3'-trifluoromethyl and 4'-trifluoromethyl.

In another embodiment, the present invention is directed to compounds of formula (I) wherein (R³)$_c$ is selected from the group consisting of 4'-chloro, 2'-methyl-4'-chloro and 2'methyl-4'-trifluoromethyl. In another embodiment, the present invention is directed to compounds of formula (I) wherein (R³)$_c$ is selected from the group consisting of 4'-chloro, 3'-chloro-4'-fluoro and 3'-trifluoromethyl-4'-fluoro. In another embodiment, the present invention is directed to compounds of formula (I) wherein (R³)$_c$ is selected from the group consisting of 2'-methyl-4'chloro, 2'-methyl-4'-trifluoromethyl and 4'-chloro.

In an embodiment the present invention is directed to compounds of formula (I) selected from the group consisting of 3-(5-(2-(((2-chloro-2'-methyl-4'-(trifluoromethyl))-[1,1'-biphenyl]-4-yl)amino)methyl)-5-(trifluoromethyl)phenyl)picolinamido)propanoic acid; and pharmaceutically acceptable salts thereof.

Additional embodiments of the present invention, include those wherein the substituents selected for one or more of the variables defined herein (i.e. L¹, a, R¹, b, R², c and R³) are independently selected to be any individual substituent or any subset of substituents selected from the complete list as defined herein.

In another embodiment of the present invention is any single compound or subset of compounds selected from the representative compounds listed in Table 1, below. Representative compounds of the present invention are as listed in Table 1, below.

TABLE 1

Representative Compounds of Formula (I)

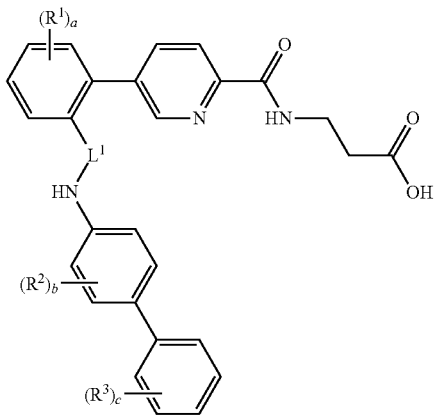

| ID No | L¹- | (R¹)$_a$ | (R²)$_b$ | (R³)$_c$ |
|---|---|---|---|---|
| 1 | —CH₂— | a = 0 | b = 0 | c = 0 |
| 2 | —CH₂— | a = 0 | b = 0 | 4'-chloro |
| 3 | —CH₂— | a = 0 | b = 0 | 4'-t-butyl |
| 4 | —CH₂— | 4-chloro | b = 0 | 4'-chloro |
| 5 | —CH₂— | 4-chloro | b = 0 | 2',4'-dichloro |
| 6 | —CH₂— | 5-chloro | b = 0 | 4'-chloro |
| 7 | —CH₂— | 5-chloro | b = 0 | 2',4'-dichloro |
| 8 | —CH₂— | a = 0 | b = 0 | 3',4'-dichloro |
| 9 | —CH₂— | a = 0 | b = 0 | 4-trifluoro-methyl |
| 10 | —CH₂— | 5-chloro | 2-chloro | 4'-chloro |
| 11 | —CH₂— | 5-chloro | 3-fluoro | 2',4'-dichloro |
| 12 | —CH₂— | 5-chloro | 3-fluoro | 4'-chloro |
| 13 | —CH₂— | 5-chloro | 3-fluoro | 3'-fluoro-4'-chloro |
| 14 | —CH₂— | 5-chloro | b = 0 | 3'-chloro |
| 15 | —CH₂— | 5-chloro | b = 0 | 4'-fluoro |
| 16 | —C(O)— | 5-chloro | b = 0 | 4'-chloro |
| 17 | —CH(CH₃)— | 5-chloro | b = 0 | 4'-chloro |
| 18 | —CH₂— | 5-chloro | b = 0 | 2',4'-difluoro |
| 19 | —C(O)— | 5-chloro | b = 0 | 2',4'-dichloro |
| 20 | —C(O)— | 5-chloro | b = 0 | 4'-fluoro |
| 21 | —CH₂— | 5-trifluoro-methyl | b = 0 | 2',4'-dichloro |
| 22 | —CH₂— | 5-trifluoro-methyl | b = 0 | 2'-methyl-4'-chloro |
| 23 | —CH₂— | 5-trifluoro-methyl | b = 0 | 2'-chloro-4'-fluoro |
| 24 | —CH₂— | 5-trifluoro-methyl | b = 0 | 2'-chloro-4'-trifluoro-methyl |
| 25 | —CH₂— | 5-trifluoro-methyl | b = 0 | 2'-trifluoro-methyl-4'-chloro |
| 26 | —CH₂— | 5-trifluoro-methyl | b = 0 | 3'-trifluoro-methyl-4'-fluoro |
| 27 | —CH₂— | 5-trifluoro-methyl | 2-chloro | 2',4'-dichloro |
| 28 | —CH₂— | 5-trifluoro-methyl | 2-chloro | 4'-chloro |
| 29 | —CH₂— | 5-trifluoro-methyl | b = 0 | 4'-trifluoro-methyl |
| 30 | —CH₂— | 5-trifluoro-methyl | b = 0 | 2'-methyl-4'-trifluoro-methyl |
| 31 | —CH₂— | 5-trifluoro-methyl | 2-chloro | 3'-trifluoro-methyl-4'-fluoro |
| 32 | —CH₂— | 5-trifluoro-methyl | 2-chloro | 3'-trifluoro-methyl-4'-chloro |
| 33 | —CH₂— | 5-trifluoro-methyl | 2-chloro | 2'-chloro-4'-fluoro |
| 34 | —CH₂— | 5-trifluoro-methyl | 2-chloro | 2'-methyl-4'-chloro |
| 35 | —CH₂— | 5-trifluoro-methyl | 2-chloro | 3'-chloro-4'-fluoro |
| 36 | —C(O)— | 5-chloro | b = 0 | 2',4'-difluoro |
| 37 | —CH₂— | 5-trifluoro-methyl | 2-chloro | 2'-fluoro-4'-chloro |
| 38 | —CH₂— | 5-trifluoro-methyl | 2-chloro | 2'-chloro-3'-trifluoro-methyl |
| 39 | —CH₂— | 5-trifluoro-methyl | 2-chloro | 3'-fluoro-4'-trifluoro-methyl |
| 40 | —CH₂— | 5-trifluoro-methyl | b = 0 | 2'-fluoro-4'-chloro |

TABLE 1-continued

Representative Compounds of Formula (I)

| ID No | L¹- | (R¹)ₐ | (R²)ᵦ | (R³)ᶜ |
|---|---|---|---|---|
| 41 | —CH₂— | 5-trifluoro-methyl | b = 0 | 2'-chloro-3'-trifluoro-methyl |
| 42 | —CH₂— | 5-trifluoro-methyl | 2-chloro | 2'-chloro-4'-trifluoro-methyl |
| 43 | —CH₂— | 5-trifluoro-methyl | 2-chloro | 2'-methyl-4'-trifluoro-methyl |
| 44 | —CH₂— | 5-trifluoro-methyl | b = 0 | 4'-chloro |
| 45 | —CH₂— | 5-methoxy | b = 0 | 4'-chloro |
| 46 | —CH₂— | 5-methoxy | b = 0 | 2',4'-dichloro |
| 47 | —CH₂— | 5-methoxy | b = 0 | 4'-trifluoro-methyl |
| 48 | —CH₂— | 5-methoxy | b = 0 | 4'-trifluoro-methoxy |
| 49 | —CH₂— | 5-methoxy | b = 0 | 4'-t-butyl |
| 50 | —CH₂— | 5-methoxy | b = 0 | 3'-trifluoro-methoxy |
| 51 | —CH₂— | 5-chloro | 2-chloro | 2',4'-dichloro |
| 52 | —CH₂— | 5-chloro | 2-chloro | 4'-fluoro |
| 53 | —CH₂— | 5-fluoro | 2-fluoro | 3',4'-dichloro |
| 54 | —CH₂— | 5-chloro | 5-methoxy | 4'-trifluoro-methyl |
| 55 | —CH₂— | 5-chloro | 2-trifluoro-methyl | 3',4'-dichloro |
| 56 | —CH₂— | 5-fluoro | 2-fluoro | 4'-trifluoro-methyl |
| 57 | —CH₂— | 5-fluoro | 2-fluoro | 2',4'-dichloro |
| 58 | —CH₂— | 5-chloro | b = 0 | 3',4'-dichloro |
| 59 | —CH₂— | 5-chloro | b = 0 | 4'-t-butyl |
| 60 | —CH₂— | 4-methoxy | b = 0 | 2',4'-dichloro |
| 61 | —CH₂— | 4-methoxy | b = 0 | 3',4'-dichloro |
| 62 | —CH₂— | 5-trifluoro-methyl | b = 0 | 3'-fluoro |
| 63 | —CH₂— | 5-chloro | 2-chloro | 2',4'-difluoro |
| 64 | —CH₂— | 6-trifluoro-methyl | b = 0 | 4'-chloro |
| 65 | —CH₂— | 3-methyl | b = 0 | 4'-chloro |
| 66 | —CH₂— | 6-cyano | b = 0 | 4'-chloro |
| 67 | —CH₂— | 3-chloro-5-trifluoro-methyl | b = 0 | 4'-chloro |
| 68 | —CH₂— | 5-methyl | b = 0 | 4'-chloro |
| 69 | —CH₂— | 6-methyl | b = 0 | 4'-chloro |
| 70 | —CH₂— | 5-methyl-sulfonyl | b = 0 | 4'-chloro |
| 71 | —CH₂— | 3,-5-di(trifluoro-methyl) | b = 0 | 4'-chloro |
| 72 | —CH₂— | 3-chloro-5-trifluoro-methyl | b = 0 | 2',4'-dichloro |
| 73 | —CH₂— | 3-chloro-5-trifluoro-methyl | b = 0 | 2'-methyl-4'-chloro |
| 74 | —CH₂— | 3-chloro-5-trifluoro-methyl | 2-chloro | 4'-chloro |
| 75 | —CH₂— | 3-chloro-5-trifluoro-methyl | 2-methyl | 4'-chloro |
| 76 | —CH₂— | 3,5-di(trifluoro-methyl) | 2-chloro | 4'-chloro |
| 77 | —CH₂— | 4-chloro-5-trifluoro-methyl | b = 0 | 2'-methyl-4'-chloro |
| 78 | —CH₂— | 4-chloro-5-trifluoro-methyl | 2-chloro | 4'-chloro |
| 79 | —CH₂— | 4-chloro-5-trifluoro-methyl | 2-methyl | 4'-chloro |
| 80 | —CH₂— | 4-chloro-5-trifluoro-methyl | b = 0 | 4'-chloro |
| 81 | —CH₂— | 3,5-di(trifluoro-methyl) | b = 0 | 2'-methyl-4'-chloro |
| 82 | —CH₂— | 4-chloro-5-trifluoro-methyl | b = 0 | 2',4'-dichloro |
| 83 | —CH₂— | 3,5-di(trifluoro-methyl) | b = 0 | 2'-methyl-4'-trifluoro-methyl |
| 84 | —CH₂— | 3,5-di(trifluoro-methyl) | b = 0 | 2',3'-dichloro |
| 85 | —CH₂— | 3,5-di(trifluoro-methyl) | b = 0 | 2',6'-dichloro |
| 86 | —CH₂— | 3,5-di(trifluoro-methyl) | 2-methyl | 4'-chloro |
| 87 | —CH₂— | 3,5-di(trifluoro-methyl) | b = 0 | 2',4'-dichloro |
| 88 | —CH₂— | 5-chloro | 2-fluoro | 4'-fluoro |
| 89 | —CH₂— | 5-chloro | 2-fluoro | 2',4'-difluoro |
| 90 | —CH₂— | 5-chloro | 2-fluoro | 4'-trifluoro-methyl |
| 91 | —CH₂— | 5-chloro | 2-fluoro | 4'-chloro |
| 92 | —CH₂— | 5-chloro | 2-fluoro | 2',4'-dichloro |
| 93 | —CH₂— | 5-chloro | 2-fluoro | 3'-fluoro-4'-chloro |
| 94 | —C(O)— | 4,5-difluoro | b = 0 | 2',4'-dichloro |
| 95 | —C(O)— | 4,5-difluoro | b = 0 | 4'-fluoro |
| 96 | —C(O)— | 4,5-difluoro | b = 0 | 4'-trifluoro-methyl |
| 97 | —C(O)— | 4,5-difluoro | b = 0 | 4'-chloro |
| 98 | —CH₂— | 4-chloro | 2-cyano | 3'-trifluoro-methyl-4'-chloro |
| 99 | —CH₂— | 5-chloro | 2-cyano | 2',4'-dichloro |
| 100 | —CH₂— | 5-chloro | 2-cyano | 3'-trifluoro-methyl-4'-fluoro |
| 101 | —CH₂— | 5-chloro | 2-cyano | 2'-chloro-3'-trifluoro-methyl |
| 102 | —CH₂— | 4,5-difluoro | 2-chloro | 3'-trifluoro-methyl-4'-fluoro |
| 103 | —CH₂— | 4,5-difluoro | 2-chloro | 4'-chloro |
| 104 | —CH₂— | 4,5-difluoro | 2-chloro | 2'-fluoro-4'-chloro |
| 105 | —CH₂— | 4,5-difluoro | 2-chloro | 2'-fluoro-4'-methyl |
| 106 | —CH₂— | 4,5-difluoro | 2-chloro | 3'-trifluoro-methyl-4'-chloro |

TABLE 1-continued

Representative Compounds of Formula (I)

| ID No | L¹- | (R¹)ₐ | (R²)ᵦ | (R³)꜀ |
|---|---|---|---|---|
| 107 | —CH₂— | 4,5-difluoro | 2-chloro | 2'-chloro-3'-trifluoro-methyl |
| 108 | —CH₂— | 4,5-difluoro | 2-chloro | 2',4'-dichloro |
| 109 | —CH₂— | 4,5-difluoro | 2-cyano | 3'-trifluoro-methyl-4'-fluoro |
| 110 | —CH₂— | 4,5-difluoro | 2-cyano | 4'-chloro |
| 111 | —CH₂— | 4,5-difluoro | 2-cyano | 2'-fluoro-4'-chloro |
| 112 | —CH₂— | 4,5-difluoro | 2-cyano | 2'-fluoro-4'-methyl |
| 113 | —CH₂— | 4,5-difluoro | 2-cyano | 3'-trifluoro-methyl-4'-chloro |
| 114 | —CH₂— | 4,5-difluoro | 2-cyano | 2',4'-dichloro |
| 115 | —CH₂— | 4,5-difluoro | 2-cyano | 3'-methyl-4'-fluoro |
| 116 | —CH₂— | 4,5-difluoro | 2-cyano | 3'-trifluoro-methyl-5-fluoro |
| 117 | —CH₂— | 4,5-difluoro | b = 0 | 4'-chloro |
| 118 | —CH₂— | 4,5-difluoro | b = 0 | 2',4'-dichloro |
| 119 | —CH₂— | 5-trifluoro-methyl | 2-trifluoro-methyl | 2'-methyl-4'-chloro |
| 120 | —CH₂— | 5-trifluoro-methyl | 2-trifluoro-methyl | 2'-methyl-4'-trifluoro-methyl |
| 121 | —CH₂— | 5-trifluoro-methyl | 2-trifluoro-methyl | 3'-trifluoro-methyl-4'-fluoro |
| 122 | —CH₂— | 5-trifluoro-methyl | 2-trifluoro-methyl | 2',4'-dichloro |
| 123 | —CH₂— | 5-trifluoro-methyl | 2-trifluoro-methyl | 4'-chloro |
| 124 | —CH₂— | 5-trifluoro-methyl | 2-trifluoro-methyl | 4'-t-butyl |
| 125 | —CH₂— | 5-trifluoro-methyl | 2-trifluoro-methyl | 2',4'-fluoro |
| 126 | —CH₂— | 5-trifluoro-methyl | 2-trifluoro-methyl | 2'-fluoro-4'-chloro |
| 127 | —CH₂— | 5-trifluoro-methyl | 2-trifluoro-methyl | 4'-trifluoro-methyl |
| 128 | —CH₂— | 5-trifluoro-methyl | 2-trifluoro-methyl | 2'-chloro-4'-trifluoro-methyl |
| 129 | —CH₂— | 5-chloro | b = 0 | 3'-trifluoro-methoxy |
| 130 | —CH₂— | 5-choro | b = 0 | 3'-trifluoro-methyl |
| 131 | —CH₂— | 5-chloro | b = 0 | 2'-trifluoro-methyl |
| 132 | —CH₂— | 5-chloro | b = 0 | 2'-trifluoro-methoxy |
| 133 | —CH₂— | 5-chloro | b = 0 | 2'-fluoro |
| 134 | —CH₂— | 5-chloro | b = 0 | 3'-fluoro |
| 135 | —CH₂— | 5-chloro | b = 0 | 2'-chloro |
| 136 | —CH₂— | 5-chloro | b = 0 | 3',4'-difluoro |
| 137 | —CH₂— | 5-chloro | b = 0 | 3',5'-difluoro |
| 138 | —CH₂— | 5-chloro | 2-chloro | 2'chloro-4'-fluoro |
| 139 | —CH₂— | 5-chloro | 2-chloro | 3'-methyl-4'-fluoro |
| 140 | —CH₂— | 5-chloro | 2-chloro | 4'-trifluoro-methoxy |
| 141 | —CH₂— | 5-chloro | b = 0 | 2'-chloro-6'-fluoro |
| 142 | —CH₂— | 5-chloro | 2-chloro | 2'-trifluoro-methyl-4'-fluoro |
| 143 | —CH₂— | 5-chloro | b = 0 | 2'-chloro-4'-methoxy |
| 144 | —CH₂— | 5-chloro | 2-chloro | 3'-trifluoro-methyl-4'-fluoro |
| 145 | —C(O)— | 5-methyl | b = 0 | 4'-chloro |
| 146 | —CH₂— | 5-chloro | b = 0 | 3'-methyl-4'-fluoro |
| 147 | —CH₂— | 5-chloro | b = 0 | 2'-chloro-4-trifluoro-methyl |
| 148 | —CH₂— | 5-chloro | b = 0 | 2'-methyl-4'-chloro |
| 149 | —CH₂— | 5-chloro | b = 0 | 2'-trifluoro-methyl-4'-fluoro |
| 150 | —CH₂— | 5-chloro | b = 0 | 3'-chloro-4'-fluoro |
| 151 | —CH₂— | 5-chloro | b = 0 | 2'-methyl-4'-fluoro |
| 152 | —CH₂— | 5-chloro | b = 0 | 2'-chloro-4'-fluoro |
| 153 | —C(O)— | 5-chloro | b = 0 | 2'-methyl-4'-chloro |
| 154 | —C(O)— | 5-trifluoro-methyl | b = 0 | 2'-methyl-4'-chloro |
| 155 | —CH(CH₃)— | 5-chloro | b = 0 | 4'-fluoro |
| 156 | —CH₂— | 5-chloro | b = 0 | 4'-methyl-carbonyl |
| 157 | —CH₂— | 5-(C(=CH₂)—CH₃) | b = 0 | 4'-fluoro |
| 158 | —CH₂— | 5-isopropyl | b = 0 | 4'-fluoro |
| 159 | —CH₂— | 3-methoxy-5-trifluoro-methyl | 2-chloro | 4'-trifluoro-methyl |
| 160 | —CH₂— | 3-methoxy-5-trifluoro-methyl | 2,6-dichloro | 4'-chloro |
| 161 | —CH₂— | 3-methoxy-5-trifluoro-methyl | b = 0 | 2'-chloro-4'-trifluoro-methyl |
| 162 | —CH₂— | 3-methoxy-5-trifluoro-methyl | 2-chloro | 4'-chloro |
| 163 | —CH₂— | 3-methyl-5-trifluoro-methyl | 2-chloro | 4'-trifluoro-methyl |
| 164 | —CH₂— | 3-hydroxy-5-trifluoro-methyl | 2-chloro | 4'-chloro |
| 165 | —CH₂— | 3-methyl-5-trifluoro-methyl | 2-chloro | 2'-methyl-4'-chloro |
| 166 | —CH₂— | 3-methyl-5-trifluoro-methyl | 2-chloro | 2'-methyl-4'-trifluoro-methyl |
| 167 | —CH₂— | 3-isopropyl-5-trifluoro-methyl | 2-chloro | 2'-methyl-4'-trifluoro-methyl |

TABLE 1-continued

Representative Compounds of Formula (I)

| ID No | L¹- | (R¹)ₐ | (R²)ᵦ | (R³)𝒸 |
|---|---|---|---|---|
| 168 | —CH₂— | 5-chloro | 2-chloro | 4'-t-butyl |
| 169 | —CH₂— | 5-chloro | 2-chloro | 3'-trifluoro-methyl-4'-chloro |
| 170 | —CH₂— | 5-chloro | 2-chloro | 3'-trifluoro-methyl |
| 171 | —CH₂— | 5-chloro | 2-chloro | 3'-chloro-4'-fluoro |
| 172 | —CH₂— | 5-chloro | 2-chloro | 4'-methyl |
| 173 | —CH₂— | 5-phenyl | b = 0 | 2',4'-dichloro |
| 174 | —CH₂— | 5-(cyclo-hexen-1-yl) | b = 0 | 4'-fluoro |
| 175 | —CH₂— | 5-cyclohexyl | b = 0 | 4'-fluoro |
| 176 | —CH₂— | 5-(cyclo-hexen-1-yl) | b = 0 | 2',4'-dichloro |
| 177 | —CH₂— | 3-cyclopropyl-5-trifluoro-methyl | 2-chloro | 2'-methyl-4'-trifluoro-methyl |
| 178 | —CH₂— | 3-cyclopropyl-5-trifluoro-methyl | 2-chloro | 2'-methyl-4'-chloro |
| 179 | —CH₂— | 3-phenyl-5-trifluoro-methyl | 2-chloro | 2'-methyl-4'-trifluoro-methyl |
| 180 | —CH₂— | 3-cyclopropyl-5-trifluoro-methyl | 2-methoxy | 2'-methyl-4'-chloro |
| 181 | —CH₂— | 3-cyclopropyl-5-trifluoro-methyl | 2-methoxy | 2'-methyl-4'-trifluoro-methyl |
| 182 | —CH₂— | 3-cyclopropyl-5-trifluoro-methyl | 2-chloro | 2'-chloro-4'-methoxy |

As used herein, "halogen" shall mean chlorine, bromine, fluorine and iodine. Preferably, the halogen is selected from the group consisting of chlorine, bromine and fluorine.

As used herein, the term "$C_{X-Y}$alkyl" wherein X and Y are integers, whether used alone or as part of a substituent group, include straight and branched chains containing between X and Y carbon atoms. For example, $C_{1-4}$alkyl radicals include straight and branched chains of between 1 and 4 carbon atoms, including methyl, ethyl, propyl, isopropyl, butyl, isobutyl, sec-butyl and t-butyl.

As used herein, unless otherwise noted, the term "fluorinated $C_{1-4}$alkyl" shall mean any $C_{1-4}$alkyl group as defined above substituted with at least one fluorine atom, Suitable examples include but are not limited to —CF₃, —CH₂—CF₃, —CF₂—CF₂—CF₂—CF₃, and the like.

As used herein, unless otherwise noted, the term "$C_{2-4}$alkynyl" shall mean any straight or branched, partially unsaturated carbon chain containing 2 to 4 carbon atoms and at least one double bond; preferably one double bond. Suitable example include —CH═CH₂, —CH₂—CH═CH₃, —CH═CH—CH₃, —C(═CH₂)—CH₃, and the like.

As used herein, unless otherwise noted, "$C_{1-4}$alkoxy" denote an oxygen ether radical of the above described straight or branched chain alkyl groups containing one to four carbon atoms. For example, methoxy, ethoxy, n-propoxy, isopropoxy, sec-butoxy, t-butoxy, and the like.

As used herein, unless otherwise noted, the term "fluorinated $C_{1-4}$alkoxy" shall mean any $C_{1-4}$alkoxy group as defined above substituted with at least one fluoro atom. Suitable examples include but are not limited to —OCF₃, —OCH₂—CF₃, —OCF₂—CF₂—CF₂—CF₃, and the like.

As used herein, unless otherwise noted, the term "$C_{3-6}$cycloalkyl" shall mean any stable 3- to 6-membered monocyclic, saturated ring system, for example cyclopropyl, cyclobutyl, cyclopentyl and cyclohexyl.

As used herein, unless otherwise noted, the term "$C_{6-6}$cycloalkenyl" shall denote any stable 5- to 6-membered monocyclic, partially unsaturated ring system. Preferably, the $C_{5-6}$cycloalkenyl contains one unsaturated double bond. Suitable examples include, but are not limited to, cyclopentenyl, cyclohexenyl, and the like.

When a particular group is "substituted" (e.g., nsuf, cycloalkyl, aryl, heteroaryl, heterocycloalkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Abbreviations used in the specification, particularly the Schemes and Examples, are as follows:

| | |
|---|---|
| AcOH or HOAc = | Acetic acid |
| AIBN = | Azobisisobutyronitrile |
| BSA = | Bovine Serum Albumin |
| t-BuOK = | Potassium tert-butoxide |
| n-BuLi = | n-Butyl lithium |

| | |
|---|---|
| t-BuLi = | tert-Butyl lithium |
| CDI = | Carbonyldiimidazole |
| DCE = | 1,1-Dichloroethane |
| DCM = | Dichloromethane |
| DIPEA or i-$Pr_2$NEt = | Diisopropylethylamine |
| DME = | Dimethoxyethane |
| DMEM = | Dulbecco's modified Eagle's medium |
| DMF = | N,N-Dimethylformamide |
| DMSO = | Dimethylsulfoxide |
| EDC or EDCI = | 1-Ethyl-3-(3-dimethylaminopropyl) carbodiimide |
| $Et_3N$ = | Triethylamine |
| $Et_2O$ = | Diethyl ether |
| EtOAc = | Ethyl acetate |
| EtOH = | Ethanol |
| FBS = | Fetal bovine serum |
| HATU = | O-(7-Azabenzotriazol-1-yl)-N,N,N'',N''-Tetramethyl Uronium Hexafluorophosphate |
| HBSS = | Hank's Buffered Saline solution |
| HEPES (buffer) = | 4-(2-Hydroxyethyl)-1-piperizine ethane sulfonic acid |
| HOBt = | 1-Hydroxybenzotriazole |
| HPLC = | High Pressure Liquid Chromatography |
| KOAc = | Potassium acetate |
| LDA = | Lithium Diisopropylamide |
| MeCN = | Acetonitrile |
| MeOH = | Methanol |
| Mesyl = | Methylsulfonyl |
| $NaBH(OAc)_3$ = | Sodium triacetoxyborohydride |
| NBS = | N-Bromosuccinimide |
| NMP = | N-methylpyrrolidone |
| Pd—C = | Palladium on Carbon Catalyst |
| $Pd(OAc)_2$ = | Palladium(II)acetate |
| $Pd(dba)_2$ = | Tris(dibenzylideneacetone)dipalladium(0) |
| $Pd(dppf)Cl_2$ = | 1,1'-Bis(diphenylphosphino) ferrocenepalladium dichloride |
| PhMe = | Toluene |
| $PPh_3$ = | Tri-phenyl Phosphine |
| S-PHOS = | 2-Dicyclohexylphosphino-2',6'-dimethoxybiphenyl |
| t-BOC or Boc = | Tert-Butoxycarbonyl |
| TEA = | Triethylamine |
| TFA = | Trifluoroacetic Acid |
| THF = | Tetrahydrofuran |
| TLC = | Thin Layer Chromatography |
| TMEDA = | N,N,N',N'-Tetramethylethylenediamine |
| Tosyl = | p-Toluenesulfonyl |

As used herein, unless otherwise noted, the term "isolated form" shall mean that the compound is present in a form which is separate from any solid mixture with another compound(s), solvent system or biological environment. In an embodiment of the present invention, the compound of formula (I) is present in an isolated form. In an embodiment of the present invention, the compound of formula (I) is present in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is present as a substantially pure form.

As used herein, unless otherwise noted, the term "substantially free of a corresponding salt form(s)" when used to described the compound of formula (I) shall mean that mole percent of the corresponding salt form(s) in the isolated compound of formula (I) is less than about 5 mole percent, preferably less than about 2 mole percent, more preferably, less than about 0.5 mole percent, most preferably less than about 0.1 mole percent. In an embodiment of the present invention, the compound of formula (I) is present in a form which is substantially free of corresponding salt form(s).

As used herein, unless otherwise noted the term "condition, disease or disorder ameliorated by antagonizing a glucagon receptor" shall mean and condition, disease or disorders wherein at least one symptom of said condition, disease or disorder is alleviated or eliminated when one or more glucagon receptors are antagonized. Suitable examples include, but are not limited to Type I diabetes, Type II diabetes mellitus, obesity and renal disease, for example renal failure as a complication of diabetes. Preferably, the condition, disease or disorder ameliorated by antagonizing a glucagon receptor is selected from the group consisting of Type II diabetes mellitus and obesity.

As used herein, unless otherwise noted, the term "renal disease" shall include renal disease relating to renal hypertrophy, glomerular injury and microalbuminuria in glucose intolerant individuals characterized by persistent hyperglucagonemia.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e. the product of the first of the two consecutive reaction or process steps), then the first and second reaction or process steps may be run in the same solvent or solvent system; or alternatively may be run in different solvents or solvent systems following solvent exchange, which may be completed according to known methods.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, triflate, and the like; preferably Br, Cl or I; more preferably Br.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to a oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles - Smoles)/(Rmoles + Smoles)] \times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee = ([\alpha\text{-obs}]/[\alpha\text{-max}]) \times 100.$$

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, nsufflations acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

General Synthesis Methods

Compounds of formula (I) wherein $L^1$ is selected from the group consisting of —CH$_2$— and —CH(CH$_3$)— may be prepared according to the process outlined in Scheme 1.

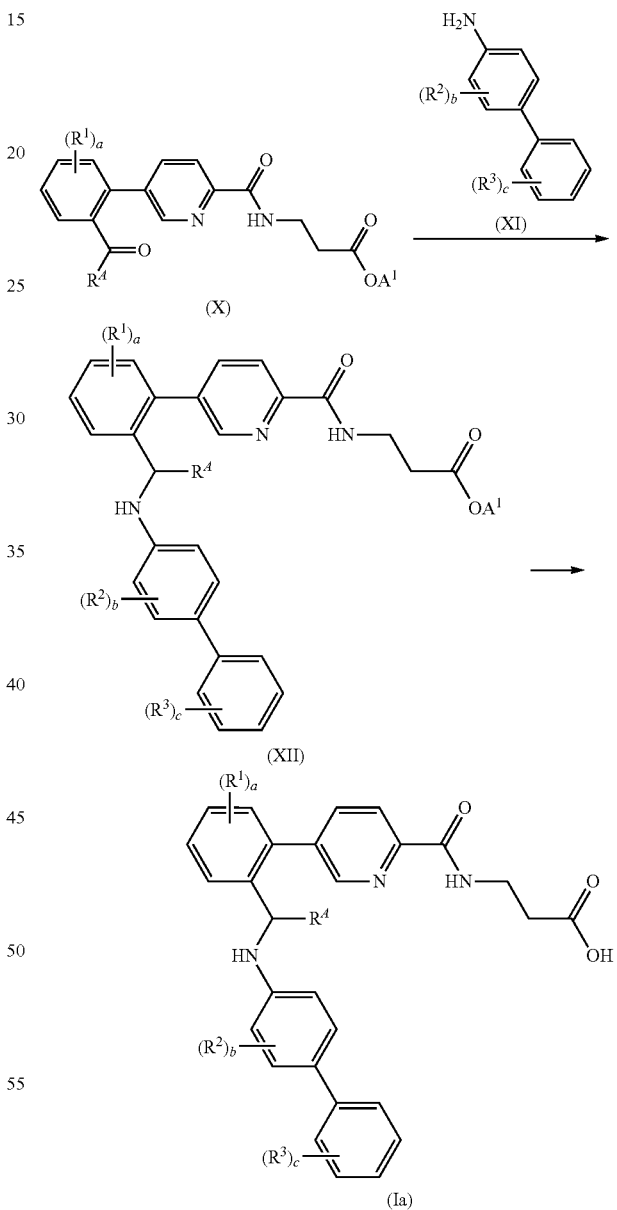

Accordingly, a suitably substituted compound of formula (X), wherein $R^A$ is hydrogen or methyl, and wherein $A^1$ is a suitably selected $C_{1-4}$alkyl, preferably ethyl or t-butyl, is reacted with a suitably substituted compound of formula (XI), a known compound or compound prepared by known methods, for example as described in Scheme 3 below, in the presence of a suitably selected coupling agent such as sodium triacetoxyborohydride (NaBH(Oac)$_3$), sodium cyanoborohydride, sodium borohydride, and the like; in the presence of a suitably selected acid or Lewis acid such as acetic acid, titanium tetrachloride, and the like; in an suitably selected organic solvent such as DCE, DCM, THF, and the like; to yield the corresponding compound of formula (XII).

The compound of formula (XII) is hydrolyzed by reacting with a suitably selected acid or base such as NaOH, TFA, and the like; in a suitably selected solvent or mixture of solvents such as THF/methanol, DCE, DCM, and the like; to yield the corresponding compound of formula (Ia).

Compounds of formula (X) may be prepared according to the process outlined in Scheme 2.

in the presence of a suitably selected palladium catalyst such as Pd(dppf)Cl$_2$, Pd(dba)$_2$, Pd(Oac)$_2$, and the like; in the presence of a suitably selected inorganic base such as K$_2$CO$_3$, Na$_2$CO$_3$, and the like; in a suitably selected solvent or mixture of solvents, such as THF/water, 1,4-dioxane/water, ethanol/toluene, DME/water, and the like; to yield the corresponding compound of formula (X).

Alternatively, wherein the compound of formula (VII) LG$^1$ is bromo, the compound of formula (VII) may be reacted with pincoldiboron, a known compound, in the presence of a suitably selected palladium catalyst such as Pd(dppf)Cl$_2$, and the like; in the presence of a suitably selected inorganic base such as potassium acetate, and the like; in a suitably selected organic solvent such as 1,4-dioxane, and the like; to yield the

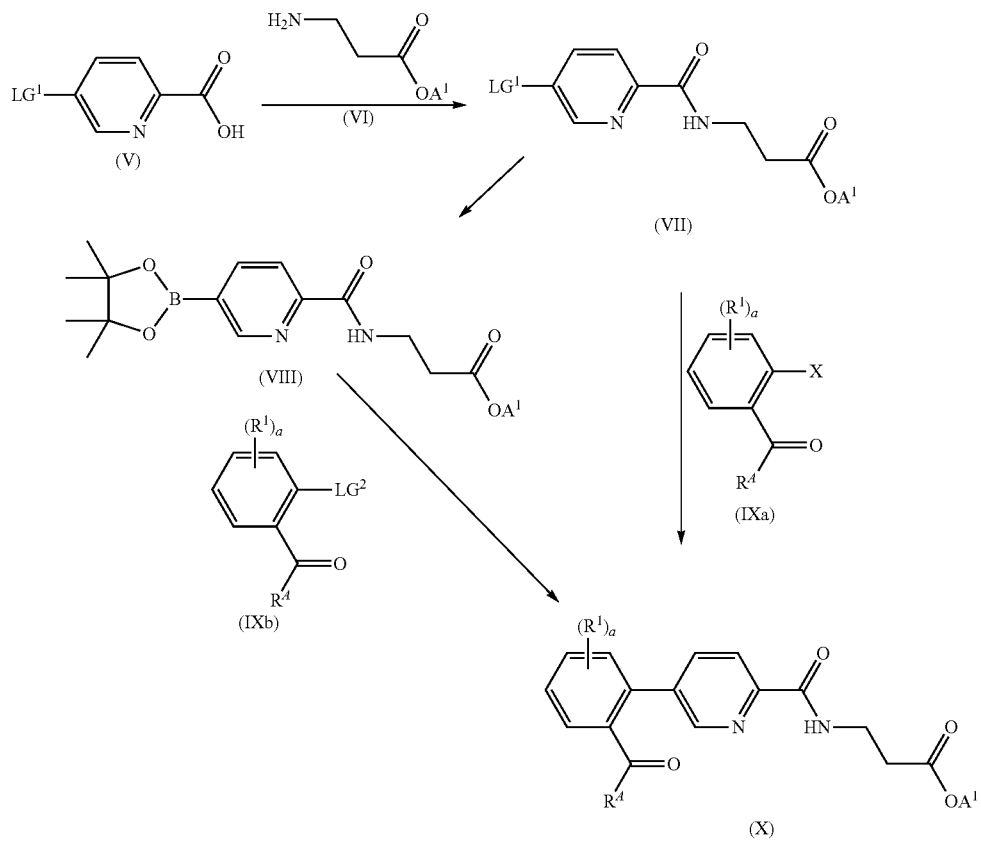

Scheme 2

Accordingly, a suitably substituted compound of formula (V), wherein LG$^1$ is a suitably selected leaving group such as Br, Cl, I, and the like, preferably bromo, a known compound or compound prepared by known methods, is reacted with a suitably substituted compound of formula (VI), wherein A$^1$ is a suitably selected C$_{1-4}$alkyl such as ethyl, t-butyl, and the like; in the presence of a suitably selected organic base such as DIPEA, TEA, pyridine, and the like, preferably DIPEA; in the presence of a suitably selected coupling agent such as HATU, HOBt in combination with EDCI, and the like; to yield the corresponding compound of formula (VII).

The compound of formula (VII) is reacted with a suitably substituted compound of formula (Ixa), wherein R$^A$ is hydrogen or methyl, and wherein X is a suitably selected boronic acid (i.e. —B(OH)$_2$) or a suitably selected boronic ester, a known compound or compound prepared by known methods, corresponding compound of formula (VIII) wherein bromo (LG$^1$) is converted to the corresponding pincol boronic ester.

The compound of formula (VIII) is then reacted with suitably substituted compound of formula (Ixb), wherein R$^A$ is hydrogen or methyl, and wherein LG$^2$ is a suitably selected leaving group such as Br, Cl, I, and the like, a known compound or compound prepared by known methods, in the presence of a suitably selected palladium catalyst such as Pd(dppf)Cl$_2$, Pd(dba)$_2$, Pd(Oac)$_2$, and the like; in the presence of a suitably selected inorganic base such as K$_2$CO$_3$, Na$_2$CO$_3$, and the like; in a suitably selected organic solvent such as THF/water, 1,4-dioxane/water, ethanol/toluene, DME/water, and the like; to yield the corresponding compound of formula (X).

Compounds of formula (XI) may be prepared according to the process outlined in Scheme 3, below.

Scheme 3

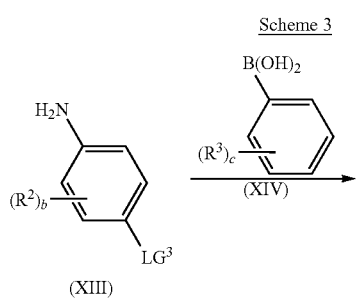

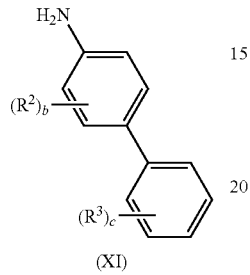

Accordingly, a suitably substituted compound of formula (XIII), wherein LG³ is a suitably selected leaving group such as Br, Cl, I, and the like; is reacted with a suitably substituted compound of formula (XIV); in the presence of a suitably selected palladium catalyst such as Pd(dppf)Cl₂, Pd(dba)₂, Pd(Oac)₂, and the like; in the presence of a suitably selected inorganic base such as K₂CO₃, Na₂CO₃, and the like; in a suitably selected organic solvent such as THF/water, 1,4-dioxane/water, ethanol/toluene, DME/water, and the like; to yield the corresponding compound of formula (XI).

Compounds of formula (I) wherein L¹ is selected from the group consisting of —CH₂— and —CH(CH₃)— may alternatively be prepared according to the process outlined in Scheme 4.

Scheme 4

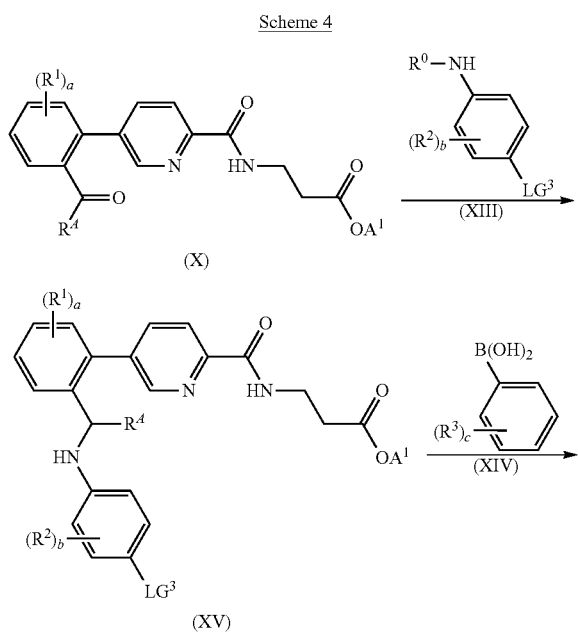

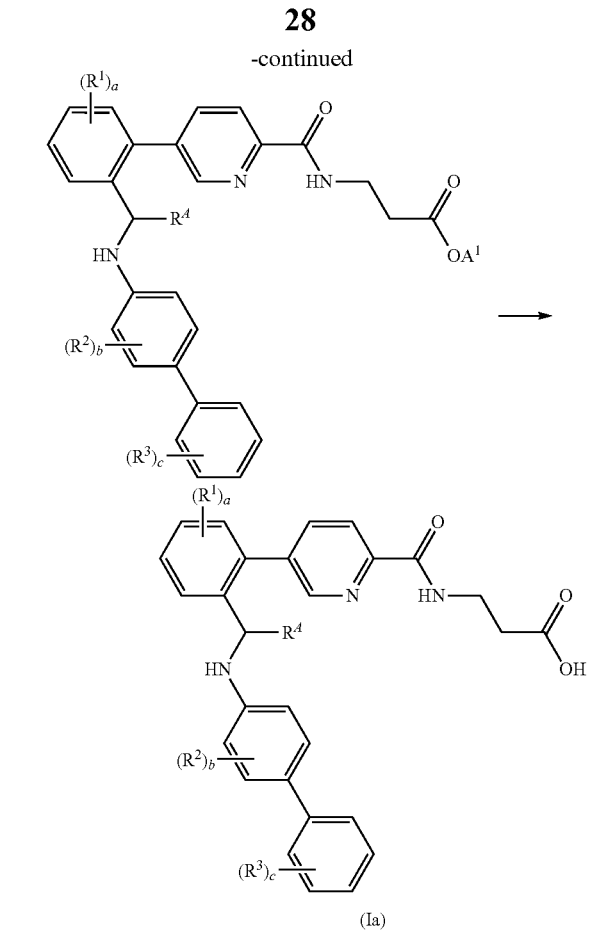

Accordingly, a suitably substituted compound of formula (X), wherein $R^A$ is hydrogen or methyl, and wherein A¹ is a suitably selected C$_{1-4}$alkyl, preferably ethyl or t-butyl, a compound prepared for example as described in Scheme 1 above, is reacted with a suitably substituted compound of formula (XIII), wherein LG³ is a suitably selected leaving group such as Br, Cl, I, and the like; in the presence of a suitably selected coupling agent such as sodium triacetoxyborohydride (NaBH(Oac)₃), sodium cyanoborohydride, sodium borohydride, and the like; in the presence of a suitably selected acid or Lewis acid such as acetic acid, titanium tetrachloride, and the like; in an suitably selected organic solvent such as DCE, DCM, THF, and the like; to yield the corresponding compound of formula (XV).

The compound of formula (XV) is reacted with a suitably substituted boronic acid of formula (XIV), a known compound or compound prepared by known methods, in the presence of a suitably selected palladium catalyst such as Pd(dppf)Cl₂, Pd(dba)₂, Pd(Oac)₂, and the like; in the presence of a suitably selected inorganic base such as K₂CO₃, Na₂CO₃, and the like; in a suitably selected organic solvent such as THF/water, 1,4-dioxane/water, ethanol/toluene, DME/water, and the like; to yield the corresponding compound of formula (XII).

The compound of formula (XII) is hydrolyzed by reacting with a suitably selected acid or base such as NaOH, TFA, and the like; in a suitably selected solvent or mixture of solvents such as THF/methanol, DCE, DCM, and the like; to yield the corresponding compound of formula (Ia).

Compounds of formula (I) wherein L¹ is selected the group consisting of —CH₂— and —CH(CH₃)— may alternatively be prepared according to the process outlined in Scheme 5.

Scheme 5

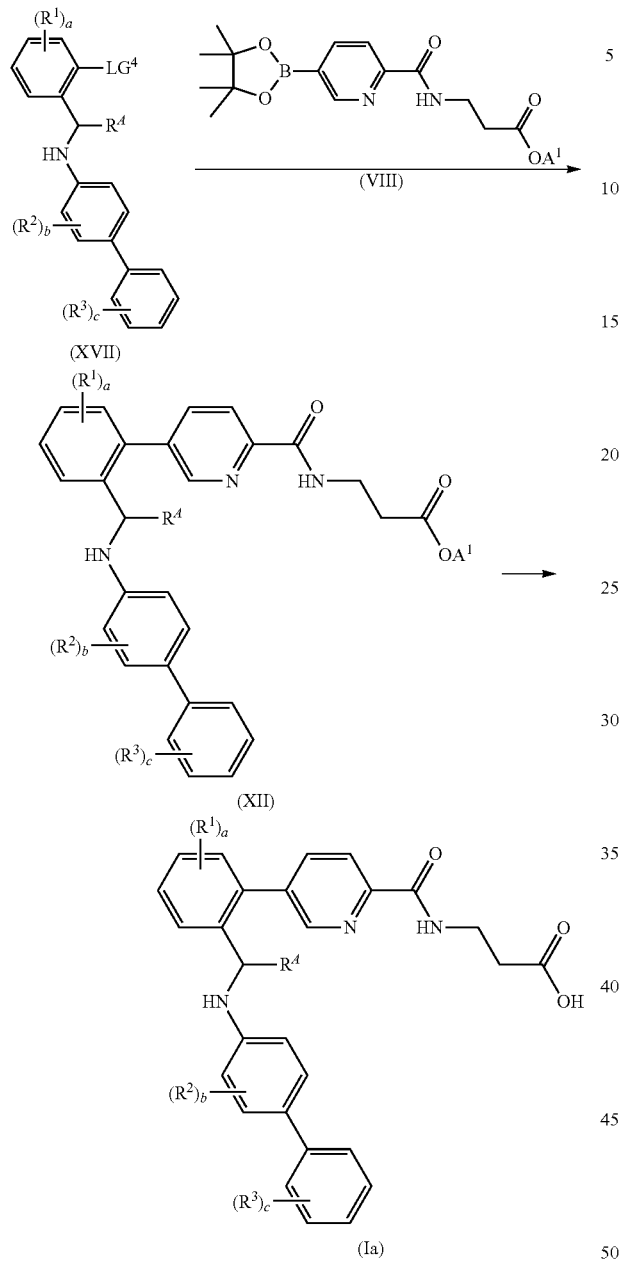

Scheme 6

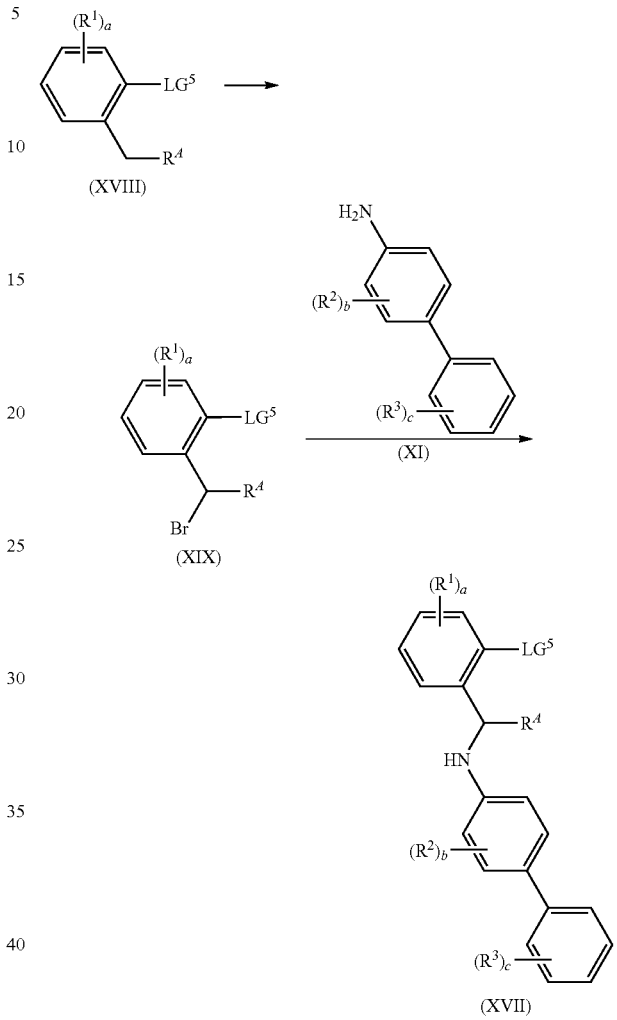

Compounds of formula (XVII) may be prepared according to the process outlined in Scheme 6, below.

Accordingly, a suitably substituted compound of formula (XVII), wherein $R^A$ is hydrogen or methyl, and wherein $LG^4$ is a suitably selected leaving group such as Br, Cl, I, and the like, is reacted with a suitably substituted compound of formula (VIII), wherein $A^1$ is a suitably selected $C_{1-4}$alkyl, preferably ethyl or t-butyl, prepared for example, as described in Scheme 2 above; in the presence of a suitably selected palladium catalyst such as Pd(dppf)Cl$_2$, Pd(dba)$_2$, Pd(OAc)$_2$, and the like; in the presence of a suitably selected inorganic base such as K$_2$CO$_3$, Na$_2$CO$_3$, and the like; in a suitably selected organic solvent such as THF/water, 1,4-dioxane/water, ethanol/toluene/water, DME/water, and the like; to yield the corresponding compound of formula (XII).

The compound of formula (XII) is hydrolyzed by reacting with a suitably selected acid or base such as NaOH, LiOH, TFA, and the like; in a suitably selected solvent or mixture of solvents such as THF/methanol/water, DCE, DCM, and the like; to yield the corresponding compound of formula (Ia).

Accordingly, a suitably substituted compound of formula (XVIII), wherein $R^A$ is hydrogen or methyl, and wherein $LG^5$ is a suitably selected leaving group such as Br, Cl, I, and the like, a known compound or compound prepared by known methods, is reacted with a suitably selected source of bromine such as NBS, dibromodimethylhydantoin, and the like; in the presence of a suitably selected radical initiator such as benzoyl peroxide, AIBN, and the like; in a suitably selected solvent such as benzene, dichloroethane, dichlorobenzene, and the like; preferably at a temperature in the range of from about 65° C. to about 80° C.; to yield the corresponding compound of formula (XIX).

The compound of formula (XIX) is reacted with a suitably substituted compound of formula (XI), prepared for example as described in Scheme 3 above, in the presence of a suitably selected organic or inorganic base such as TEA, DIPEA, K$_2$CO$_3$, sodium carbonate, cesium carbonate, and the like; in a suitably selected organic solvent such as DMF, NMP, and the like; to yield the corresponding compound of formula (XVII).

Compounds of formula (I) wherein $L^1$ is selected from group consisting of —CH$_2$— and —CH(CH$_3$)— may alternatively be prepared according to the process outlined in Scheme 7, below.

Scheme 7

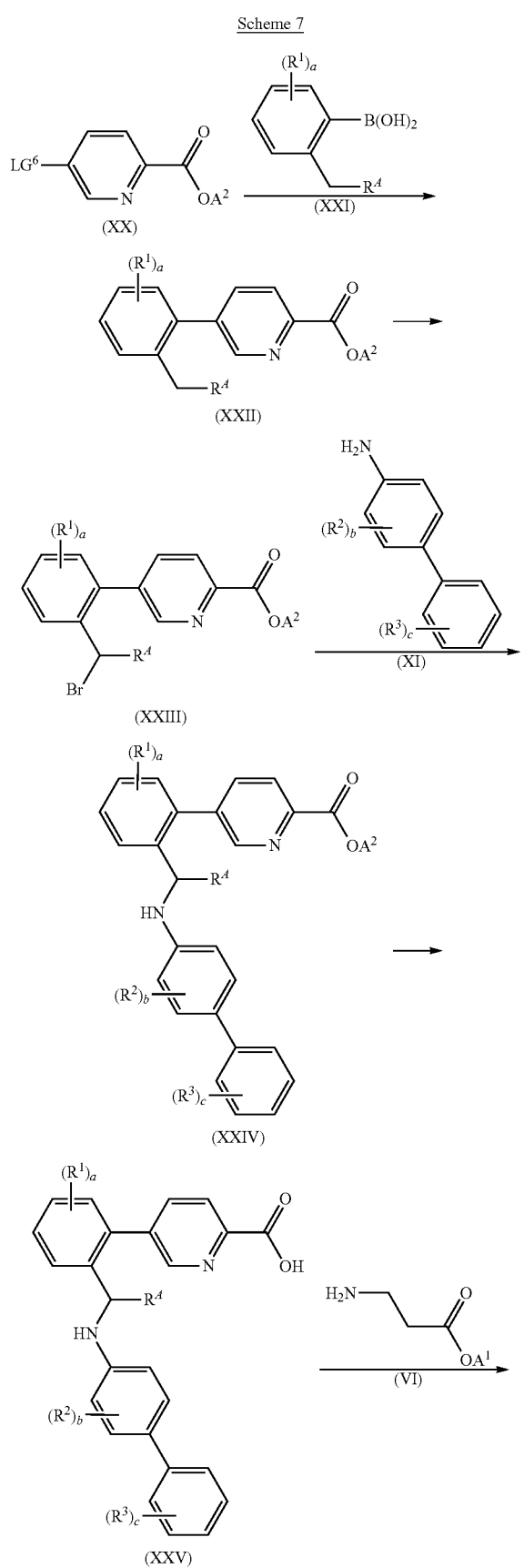

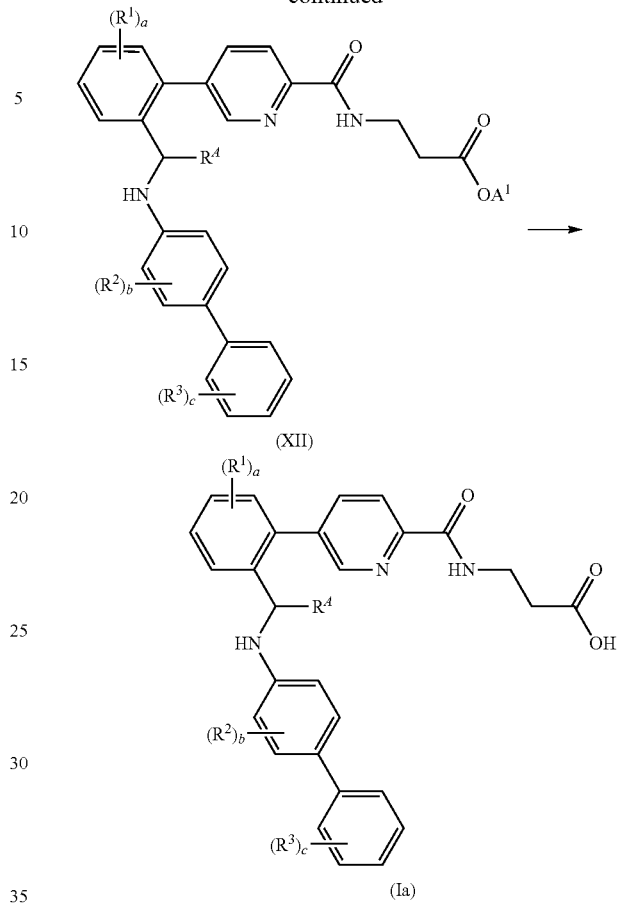

Accordingly, a suitably substituted compound of formula (XX), wherein LG⁶ is a suitably selected leaving group such as Br, Cl, I, and the like, a known compound or compound prepared by known methods, is reacted with a suitably substituted boronic acid compound of formula (XXI), wherein $R^A$ is hydrogen or methyl, a known compound or compound prepared by known methods; in the presence of a suitably selected palladium catalyst such as Pd(dppf)Cl₂, Pd(dba)₂, Pd(Oac)₂, and the like; in the presence of a suitably selected inorganic base such as K₂CO₃, Na₂CO₃, and the like; in a suitably selected organic solvent such as THF/water, 1,4-dioxane/water, ethanol/toluene, DME/water, and the like; to yield the corresponding compound of formula (XXII).

The compound of formula (XXII) is reacted with a suitably selected source of bromine such as NBS, dibromodimethylhydantoin, and the like; in the presence of a suitably selected radical initiator such as benzoyl peroxide, AIBN, and the like; in a suitably selected solvent such as benzene, dichloroethane, dichlorobenzene, and the like; preferably at a temperature of about 80° C.; to yield the corresponding compound of formula (XXIII).

The compound of formula (XXIII) is reacted with a suitably substituted compound of formula (XI), prepared for example as described in Scheme 3 above; in the presence of a suitably selected organic or inorganic base such as TEA, DIPEA, K₂CO₃, sodium carbonate, cesium carbonate, and the like; in a suitably selected organic solvent such as DMF, NMP, and the like; to yield the corresponding compound of formula (XXIV).

The compound of formula (XXIV) is reacted with a suitably selected base such as NaOH, KOH, LiOH, and the like;

in a suitably selected solvent or mixture of solvents, such as THF/methanol, and the like; to yield the corresponding compound of formula (XXV).

The compound of formula (XXV) is reacted with a suitably substituted compound of formula (VI), wherein $A^1$ is a suitably selected $C_{1-4}$alkyl, preferably ethyl or t-butyl, a known compound or compound prepared by known methods; in the presence of a suitably selected organic base such as DIPEA, TEA, pyridine, and the like, preferably DIPEA; in the presence of a suitably selected coupling agent such as HATU, HOBt in combination with EDCI, and the like; in a suitably selected solvent such as THF, DMF, and the like; to yield the corresponding compound of formula (XII).

The compound of formula (XII) is hydrolyzed by reacting with a suitably selected acid or base such as NaOH, TFA, and the like; in a suitably selected solvent or mixture of solvents such as THF/methanol, DCE, DCM, and the like; to yield the corresponding compound of formula (Ia).

Compounds of formula (I) wherein $L^1$ is selected from group consisting of —$CH_2$— and —$CH(CH_3)$— may alternatively be prepared according to the process outlined in Scheme 8, below.

Scheme 8

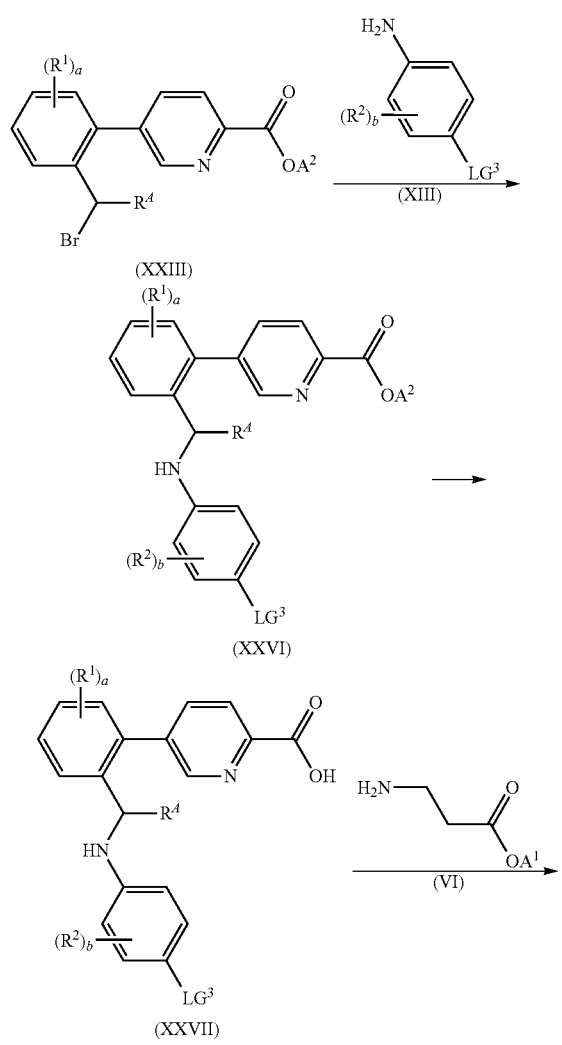

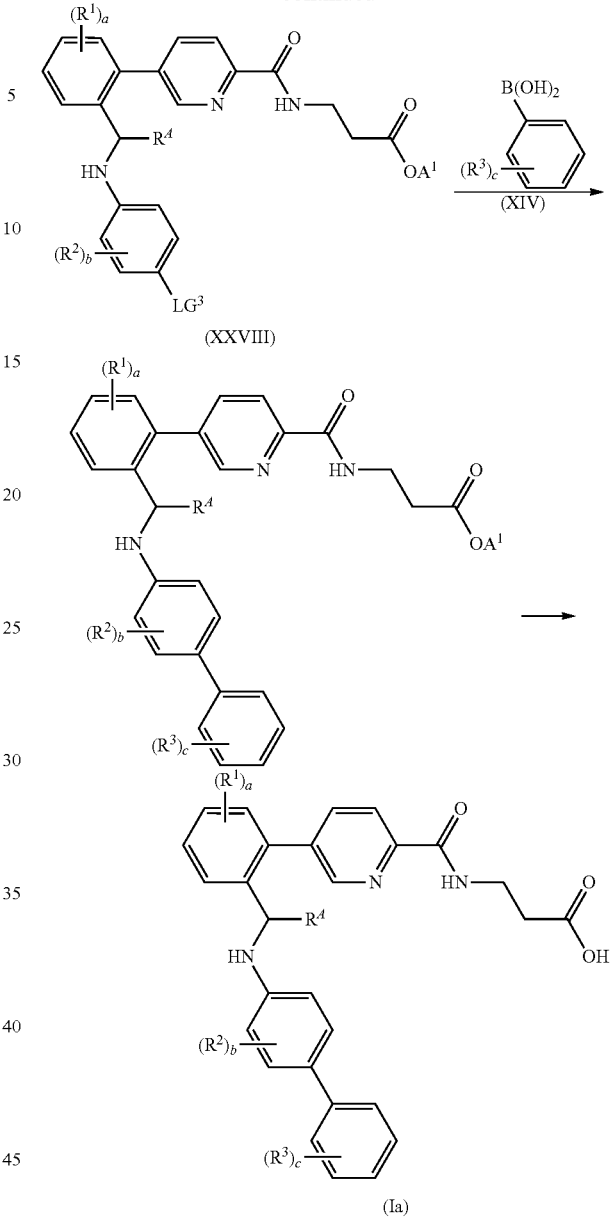

Accordingly, a suitably substituted compound of formula (XXIII), wherein $R^A$ is hydrogen or methyl, and wherein $A^2$ is a suitably selected $C_{1-4}$alkyl, preferably ethyl or t-butyl, prepared for example as described in Scheme 7 above, is reacted with a suitably substituted compound of formula (XIII), wherein $LG^2$ is a suitably selected leaving group such as Br, Cl, I, and the like; in the presence of a suitably selected organic or inorganic base such as TEA, DIPEA, $K_2CO_3$, sodium carbonate, cesium carbonate, and the like; in a suitably selected organic solvent such as DMF, NMP, and the like; to yield the corresponding compound of formula (XXVI).

The compound of formula (XXVI) is reacted with a suitably selected base such as NaOH, KOH, LiOH, and the like; in a suitably selected solvent or mixture of solvents, such as THF/methanol, and the like; to yield the corresponding compound of formula (XXVII).

The compound of formula (XXVII) is reacted with a suitably substituted compound of formula (VI), wherein $A^1$ is a suitably selected $C_{1-4}$alkyl, preferably ethyl or t-butyl, a known compound or compound prepared by known methods; in the presence of a suitably selected organic base such as DIPEA, TEA, pyridine, and the like, preferably DIPEA; in the presence of a suitably selected coupling agent such as HATU, HOBt in combination with EDCI, and the like; in a suitably selected solvent such as THF, DMF, and the like; to yield the corresponding compound of formula (XXVIII).

The compound of formula (XXVIII) is reacted with a suitably substituted boronic acid of formula (XIV), a known compound or compound prepared by known methods; in the presence of a suitably selected palladium catalyst such as Pd(dppf)Cl$_2$, Pd(dba)$_2$, Pd(Oac)$_2$, and the like; in the presence of a suitably selected inorganic base such as K$_2$CO$_3$, Na$_2$CO$_3$, and the like; in a suitably selected organic solvent such as THF/water, 1,4-dioxane/water, ethanol/toluene, DME/water, and the like; to yield the corresponding compound of formula (XII).

The compound of formula (XII) is hydrolyzed by reacting with a suitably selected acid or base such as NaOH, TFA, and the like; in a suitably selected solvent or mixture of solvents such as THF/methanol, DCE, DCM, and the like; to yield the corresponding compound of formula (Ia).

Compounds of formula (I) wherein L1 is selected from the group consisting of —CH$_2$— and —CH(CH$_3$)— may alternatively be prepared according to the process outlined in Scheme 9, below.

Scheme 9

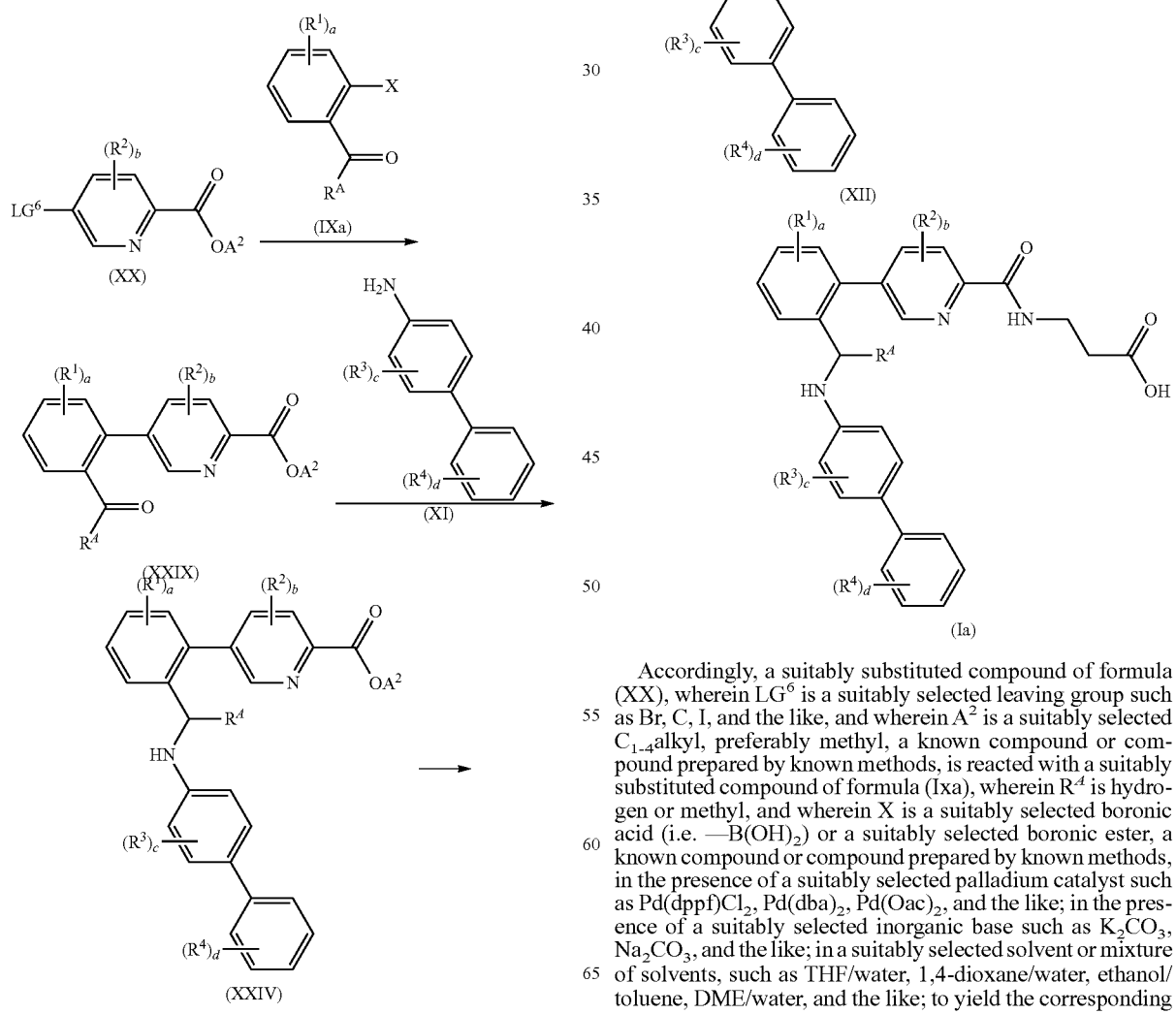

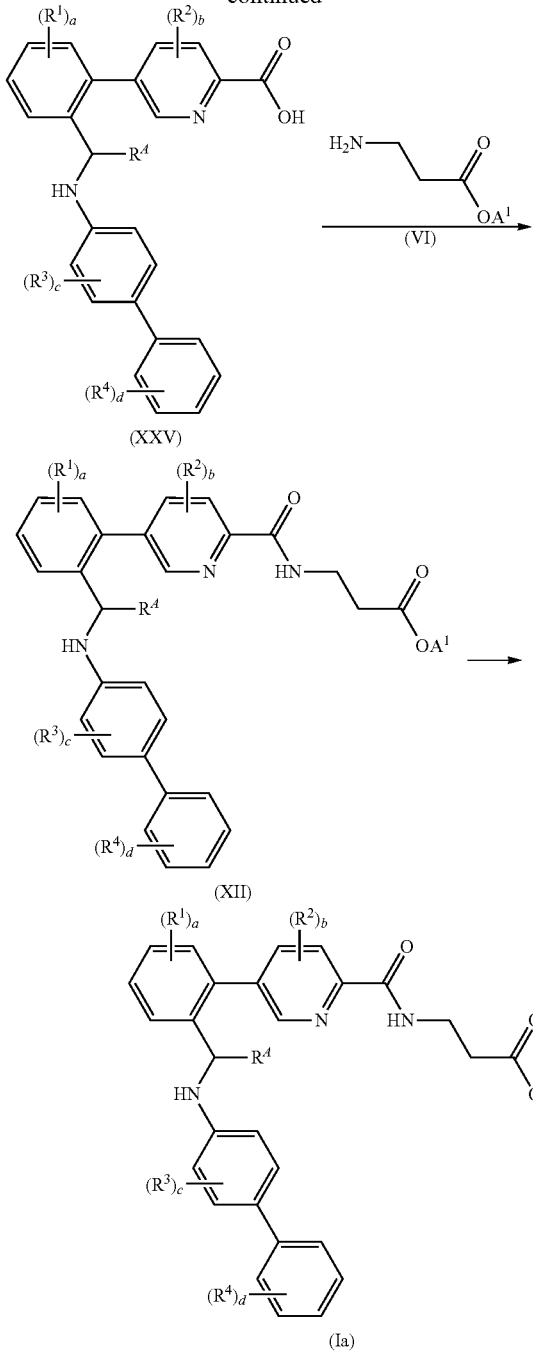

Accordingly, a suitably substituted compound of formula (XX), wherein LG$^6$ is a suitably selected leaving group such as Br, C, I, and the like, and wherein A$^2$ is a suitably selected C$_{1-4}$alkyl, preferably methyl, a known compound or compound prepared by known methods, is reacted with a suitably substituted compound of formula (Ixa), wherein R$^A$ is hydrogen or methyl, and wherein X is a suitably selected boronic acid (i.e. —B(OH)$_2$) or a suitably selected boronic ester, a known compound or compound prepared by known methods, in the presence of a suitably selected palladium catalyst such as Pd(dppf)Cl$_2$, Pd(dba)$_2$, Pd(Oac)$_2$, and the like; in the presence of a suitably selected inorganic base such as K$_2$CO$_3$, Na$_2$CO$_3$, and the like; in a suitably selected solvent or mixture of solvents, such as THF/water, 1,4-dioxane/water, ethanol/toluene, DME/water, and the like; to yield the corresponding compound of formula (XXIX).

The compound of formula (XXIX) is reacted with a suitably substituted compound of formula (XI), a known compound or compound prepared by known methods, for example as described in Scheme 3 below, in the presence of a suitably selected coupling agent such as sodium triacetoxyborohydride (NaBH(Oac)$_3$), sodium cyanoborohydride, sodium borohydride, and the like; in the presence of a suitably selected acid or Lewis acid such as acetic acid, titanium tetrachloride, and the like; in an suitably selected organic solvent such as DCE, DCM, THF, and the like; to yield the corresponding compound of formula (XXIV).

The compound of formula (XXIV) is reacted with a suitably selected base such as NaOH, KOH, LiOH, and the like; in a suitably selected solvent or mixture of solvents, such as THF/methanol, and the like; to yield the corresponding compound of formula (XXV).

The compound of formula (XXV) is reacted with a suitably substituted compound of formula (VI), wherein A$^1$ is a suitably selected C$_{1-4}$alkyl, preferably ethyl or t-butyl, a known compound or compound prepared by known methods; in the presence of a suitably selected organic base such as DIPEA, TEA, pyridine, and the like, preferably DIPEA; in the presence of a suitably selected coupling agent such as HATU, HOBt in combination with EDCI, and the like; in a suitably selected solvent such as THF, DMF, and the like; to yield the corresponding compound of formula (XII)

The compound of formula (XII) is hydrolyzed by reacting with a suitably selected acid or base such as NaOH, TFA, and the like; in a suitably selected solvent or mixture of solvents such as THF/methanol, DCE, DCM, and the like; to yield the corresponding compound of formula (Ia).

Compounds of formula (I) wherein L$^1$ is —C(O)— may be prepared according to the process outlined in Scheme 10, below.

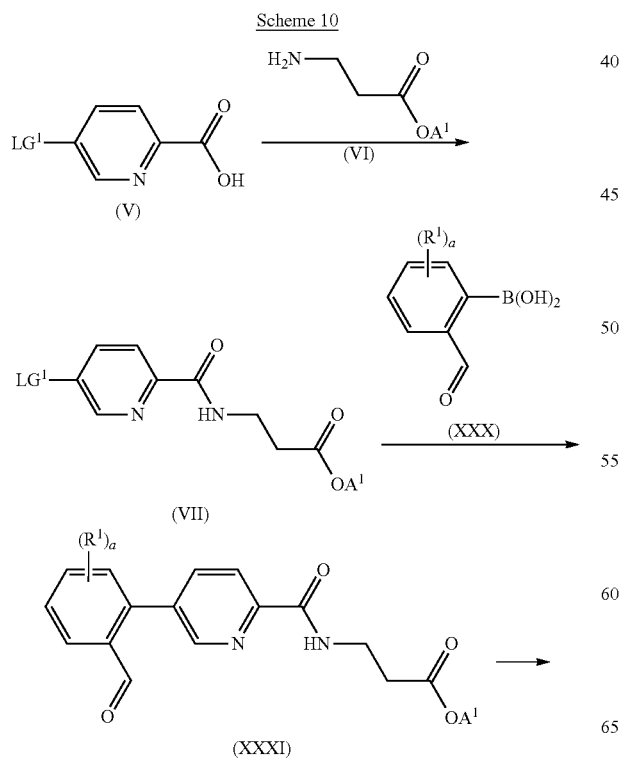

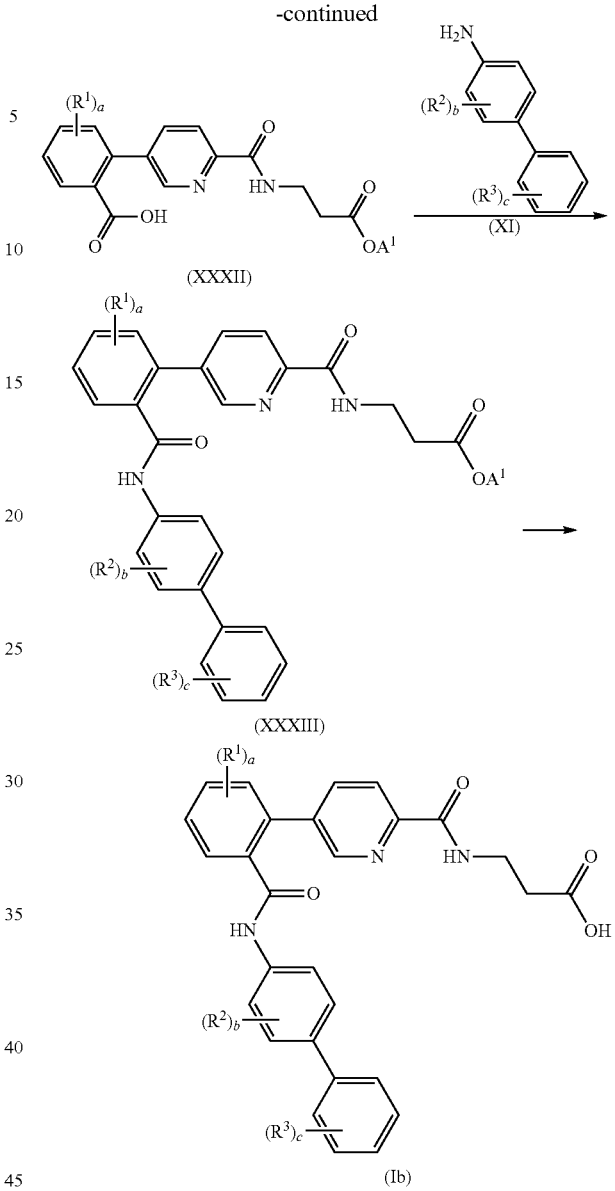

Accordingly, a suitably substituted compound of formula (IV) wherein LG1 is a suitably selected leaving group such as Br, Cl, I, and the like, a known compound or compound prepared by known methods, is reacted with a suitably substituted compound of formula (VI), wherein A$^1$ is a suitably selected C$_{1-4}$alkyl, preferably ethyl or t-butyl, a known compound or compound prepared by known methods; in the presence of a suitably selected organic base such as DIPEA, TEA, pyridine, and the like, preferably DIPEA; in the presence of a suitably selected coupling agent such as HATU, HOBt in combination with EDCI, and the like; in a suitably selected solvent such as THF, DMF, and the like; to yield the corresponding compound of formula (VII).

The compound of formula (VII) is reacted with a suitably substituted compound of formula (XXX), a known compound or compound prepared by known methods; in the presence of a suitably selected palladium catalyst such as Pd(dppf)Cl$_2$, Pd(dba)$_2$, Pd(Oac)$_2$, and the like; in the presence of a suitably selected inorganic base such as K$_2$CO$_3$, Na$_2$CO$_3$, and the like; in a suitably selected organic solvent such as THF/water, 1,4-dioxane/water, ethanol/toluene, DME/water, and the like; to yield the corresponding compound of formula (XXXI).

The compound of formula (XXXI) is reacted with a suitably selected oxidizing agent such as $KmnO_4$, and the like; in a suitably selected solvent or mixture of solvents, such as acetone/water mixture, and the like; to yield the corresponding compound of formula (XXXII).

The compound of formula (XXXII) is reacted with a suitably substituted compound of formula (XI), prepared for example as described in Scheme 3 above; in the presence of a suitably selected organic base such as DIPEA, TEA, pyridine, and the like, preferably DIPEA; in the presence of a suitably selected coupling agent such as HATU, HOBt in combination with EDCI, and the like; in a suitably selected solvent such as THF, DMF, and the like; to yield the corresponding compound of formula (XXXIII).

The compound of formula (XXXIII) is hydrolyzed by reacting with a suitably selected acid or base such as NaOH, TFA, and the like; in a suitably selected solvent or mixture of solvents such as THF/methanol, DCE, DCM, and the like; to yield the corresponding compound of formula (Ib).

Pharmaceutical Compositions

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.1 mg/kg/day to about 50 mg/kg/day, or any amount or range therein, preferably from about 0.05 mg/kg/day to about 15 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflations. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating conditions, diseases or disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of conditions, disorders or diseases, which are ameliorated by antagonizing a glucagon receptor is required.

The daily dosage of the products may be varied over a wide range from about 0.01 mg to about 10,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any amount or range therein. Preferably, the range is from about 0.1 to about 1000.0 mg/kg of body weight per day, or any amount or range therein. More preferably, from about 0.1 to about 50.0 mg/kg of body weight per day, or any amount or range therein. More preferably, from about 0.5 to about 25.0 mg/kg of body weight per day, or any amount or range therein. More preferably, from about 0.5 to about 15 mg/kg of body weight per day, or any amount or range therein. More preferably, from about 0.75 to about 7.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

SYNTHESIS EXAMPLES

The following Examples are set forth to aid in the understanding of the invention, and are not intended and should not be construed to limit in any way the invention set forth in the claims which follow thereafter. In the examples which follow herein, the Example number corresponds to the Compound (ID) number, as listed in Table 1, above.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

3-(5-(2-(([1,1'-biphenyl]-4-ylamino)methyl)phenyl)picolinamido)propanoic acid

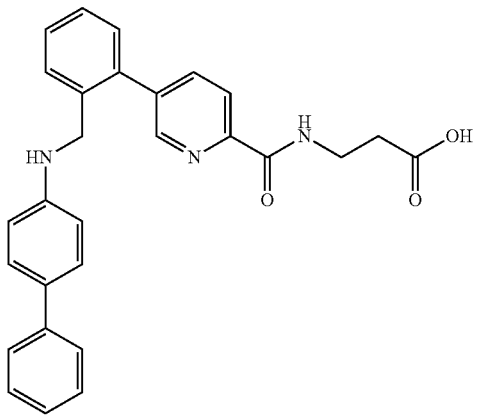 [SMILES: O=C(O)CCNC(=O)c1ccc(-c2ccccc2CNc2ccc(-c3ccccc3)cc2)cn1]

STEP A: Ethyl 3-(5-bromopicolinamido)propanoate

Solid HATU (3.8 g, 9.9 mmol) was added to a THF solution (100 mL) of 5-bromopicolinic acid (2.0 g, 9.9 mmol), i-Pr$_2$NEt (5.2 mL, 29.7 mmol), and (3-alanine ethyl ester hydrochloride (1.7 g, 10.9) and the resulting mixture was warmed to 45° C. After 16 h the resulting mixture was diluted with EtOAc, washed with water and brine, dried (Na$_2$SO$_4$), concentrated and purified via column chromatography to yield the title compound.

STEP B: Ethyl 3-(5-(2-formylphenyl)picolinamido)propanoate

Ethyl 3-(5-bromopicolinamido)propanoate (800 mg, 2.7 mmol), 2-formylphenylboronic acid (518 mg, 3.5 mmol), Pd(dppf)Cl$_2$ (217 mg, 0.27 mmol), and K$_2$CO$_3$ (734 mg, 5.3 mmol) were dissolved in 1,4-dioxane (16 mL) and water (4 mL) and heated to 80° C. After 3 h the resulting mixture was cooled to room temperature, diluted with EtOAc washed with water and brine, dried (Na$_2$SO$_4$), dry-packed onto silica gel and purified via column chromatography to yield the title compound.

STEP C: Ethyl 3-(5-(2-(([1,1'-biphenyl]-4-ylamino)methyl)phenyl)picolinamido)propanoate Solid NaBH(OAc)$_3$ (214 mg, 1.0 mmol) was added to a THF solution of ethyl 3-(5-(2-formylphenyl)picolinamido)propanoate (220 mg, 0.7 mmol), [1,1'-biphenyl]-4-amine (171 mg, 1.0 mmol), and AcOH (0.04 mL, 0.7 mmol) and the resulting mixture was warmed to 40° C. After 18 h the resulting mixture diluted with EtOAc washed with water and brine, dried (Na$_2$SO$_4$), dry-packed onto silica gel and purified via column chromatography to yield the title compound.

STEP D: 3-(5-(2-(([1,1'-biphenyl]-4-ylamino)methyl)phenyl)picolinamido)propanoic acid A 3M aqueous solution of NaOH (0.1 mL, 0.30 mmol) was added to a THF (1 mL) and MeOH (0.5 mL) solution of ethyl 3-(5-(2-(([1,1'-biphenyl]-4-ylamino)methyl)phenyl)picolinamido)propanoate (73 mg, 0.15 mmol) and the homogeneous mixture was stirred at room temperature. After 3 h the resulting mixture was concentrated in vacuo, suspended in water, and acidified with 2M HCl. The resulting precipitate was filtered off and dried in vacuo to yield the title compound.

$^1$H NMR (400 MHz, DMSO-d$_6$) δ 8.86 (t, J=5.99 Hz, 1H), 8.72 (s, 1H), 8.05-8.12 (m, 2H), 7.61 (d, J=7.09 Hz, 1H), 7.52 (d, J=7.09 Hz, 2H), 7.40-7.50 (m, 2H), 7.32-7.40 (m, 5H), 7.18-7.25 (m, 1H), 6.61 (d, J=8.56 Hz, 2H), 4.20 (s, 2H), 3.53 (q, J=6.77 Hz, 2H), 2.52-2.59 (m, 2H). MS m/z 452 (M+H)

Example 2

3-(5-(2-(((4'-chloro-[1,1'-biphenyl]-4-yl)amino)methyl)phenyl)picolinamido)propanoic acid

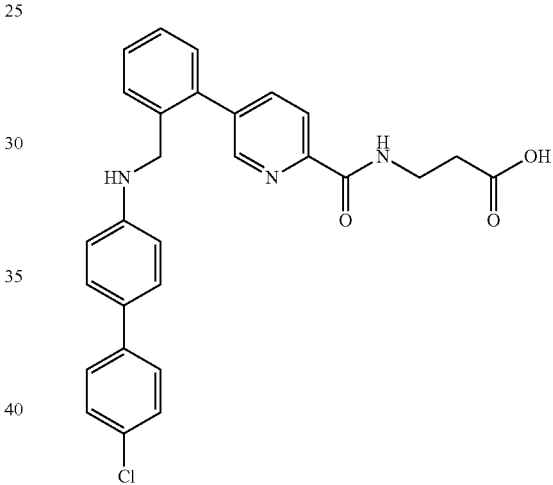

STEP A: tert-butyl 3-(5-bromopicolinamido)propanoate

Solid HATU (4.0 g, 10.6 mmol) was added to a THF solution (100 mL) of 5-bromopicolinic acid (2.1 g, 10.6 mmol), i-Pr$_2$NEt (7.4 mL, 42.4 mmol), and (3-alanine t-butyl ester hydrochloride (2.1 g, 11.7) and the resulting mixture was warmed to 45° C. After 16 h the resulting mixture was diluted with EtOAc, washed with water and brine, dried (Na$_2$SO$_4$), concentrated and purified via column chromatography to yield the title compound.

STEP B: tert-butyl 3-(5-(2-formylphenyl)picolinamido)propanoate tert-Butyl 3-(5-bromopicolinamido)propanoate (1.0 g, 3.0 mmol), 2-formylphenylboronic acid (547 mg, 3.6 mmol), Pd(dppf)Cl$_2$ (249 mg, 0.3 mmol), and K$_2$CO$_3$ (840 mg, 6.1 mmol) were dissolved in 1,4-dioxane (20 mL) and water (5 mL) and heated to 80° C. After 3 h the resulting mixture was cooled to room temperature, diluted with EtOAc washed with water and brine, dried (Na$_2$SO$_4$), dry-packed onto silica gel and purified via column chromatography to yield the title compound.

STEP C: tert-butyl 3-(5-(2-(((4'-chloro-[1,1'-biphenyl]-4-yl)amino)methyl)phenyl)picolinamido)propanoate Solid NaBH(OAc)$_3$ (90 mg, 0.42 mmol) was added to a THF solution (1.5 mL) of tert-butyl 3-(5-(2-formylphenyl)picolinamido)propanoate (100 mg, 0.28 mmol), 4'-chloro-[1,1'-biphenyl]-4-amine (86 mg, 0.42 mmol), and AcOH (16 µL, 0.28 mmol) and the resulting mixture was stirred at room temperature. After 16 h the resulting mixture diluted with EtOAc washed with water and brine, dried (Na$_2$SO$_4$), dry-packed onto silica gel and purified via column chromatography to yield the title compound.

STEP D: 3-(5-(2-(((4'-chloro-[1,1'-biphenyl]-4-yl)amino)methyl)phenyl)picolinamido)propanoic acid Neat TFA (0.04 mL, 0.55 mmol) was added to a DCM solution (1 mL) of tert-butyl 3-(5-(2-(((4'-chloro-[1,1'-biphenyl]-4-yl)amino)methyl)phenyl)picolinamido)propanoate (34 mg, 0.06 mmol). After 16 h the resulting mixture was concentrated in vacuo, dissolved in DCM and 1N HCl in ether was added. The resulting solution was concentrated in vacuo and the DCM/HCl process was repeated 2×. The resulting solid was characterized as the corresponding HCl salt of the title compound.
$^1$H NMR (400 MHz, DMSO-d$_6$) δ 8.86 (t, J=5.87 Hz, 1H), 8.72 (s, 1H), 8.06-8.11 (m, 2H), 7.51-7.62 (m, 3H), 7.32-7.50 (m, 7H), 6.58 (d, J=8.31 Hz, 2H), 4.19 (s, 2H), 3.46-3.58 (m, 2H), 2.54-2.60 (m, 2H); MS m/z 554 (M+H).

Example 3

3-(5-(2-(((4'-(tert-butyl)-[1,1'-biphenyl]-4-yl)amino)methyl)phenyl)picolinamido)propanoic acid

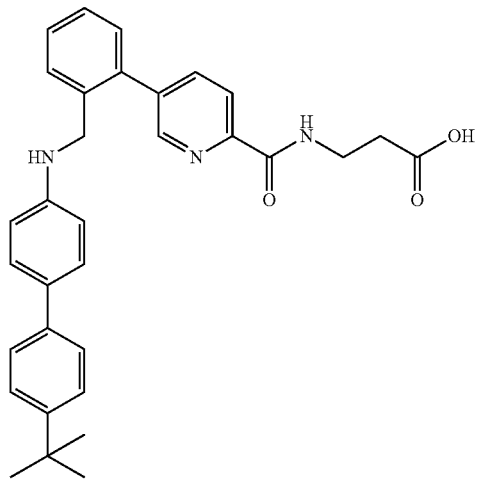 [SMILES: CC(C)(C)c1ccc(-c2ccc(NCc3ccccc3-c3ccc(C(=O)NCCC(=O)O)nc3)cc2)cc1]

STEP A: 4'-(tert-butyl)-[1,1'-biphenyl]-4-amine

4-Bromoaniline (4.0 g, 23.3 mmol), (4-(tert-butyl)phenyl)boronic acid (4.6 g, 25.6 mmol), Pd(dppf)Cl$_2$ (1.9 g, 2.3 mmol), and K$_2$CO$_3$ (6.4 g, 46.5 mmol) were dissolved in 1,4-dioxane (100 mL) and water (25 mL) and the resulting mixture was heated to 80° C. After 3 h the resulting mixture was cooled to room temperature, diluted with EtOAc, washed with water and brine, dried (Na$_2$SO$_4$), and dry packed onto silica gel. Column chromatography yielded the title compound.

STEP B: 3-(5-(2-(((4'-(tert-butyl)-[1,1'-biphenyl]-4-yl)amino)methyl)phenyl)picolinamido)propanoic acid The title compound was prepared according to the procedure as described in Example 2 substituting 4'-(tert-butyl)[1,1'-biphenyl]-4-amine for 4'-chloro-[1,1'-biphenyl]-4-amine.
$^1$H NMR (400 MHz, DMSO-d$_6$) δ 8.86 (t, J=5.75 Hz, 1H), 8.72 (s, 1H), 8.04-8.13 (m, 2H), 7.61 (d, J=7.82 Hz, 1H), 7.40-7.50 (m, 4H), 7.34 (d, J=8.56 Hz, 2H), 7.38 (d, J=8.56 Hz, 3H), 6.59 (d, J=8.56 Hz, 2H), 4.19 (s, 2H), 3.47-3.57 (m, 2H), 2.52-2.58 (m, 2H), 1.29 (s, 9H); MS m/z 508 (M+H).

Example 4

3-(5-(4-chloro-2-(((4'-chloro-[1,1'-biphenyl]-4-yl)amino)methyl)phenyl)picolinamido)propanoic acid

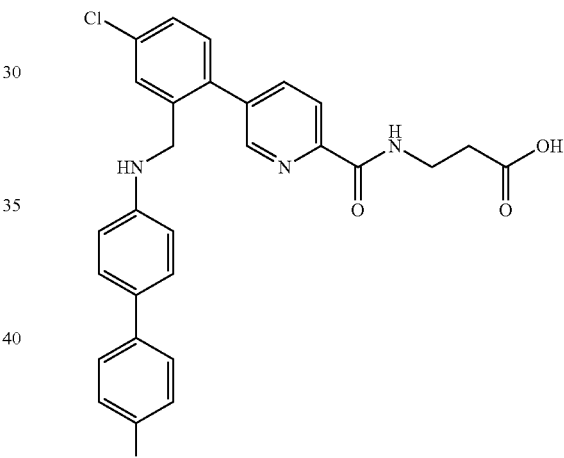

STEP A: ethyl 3-(5-(4-chloro-2-formylphenyl)picolinamido)propanoate

Ethyl 3-(5-bromopicolinamido)propanoate, prepared as in Example 1, (1.5 g, 5.0 mmol), (4-chloro-2-formylphenyl)boronic acid (1.0 g, 5.5 mmol), Pd(dppf)Cl$_2$ (408 mg, 0.5 mmol), and K$_2$CO$_3$ (1.4 g, 10.0 mmol) were dissolved in 1,4-dioxane (20 mL) and water (5 mL) and heated to 80° C. After 3 h the resulting mixture was cooled to room temperature, diluted with EtOAc washed with water and brine, dried (Na$_2$SO$_4$), dry-packed onto silica gel and purified via column chromatography to yield the title compound.

STEP B: ethyl 3-(5-(4-chloro-2-(((4'-chloro-[1,1'-biphenyl]-4-yl)amino)methyl)phenyl)picolinamido)propanoate Solid NaBH(OAc)$_3$ (110 mg, 0.52 mmol) was added to a THF solution (1.7 mL) of ethyl 3-(5-(4-chloro-2-formylphenyl)picolinamido)propanoate (125 mg, 0.35 mmol), 4'-chloro-[1,1'-biphenyl]-4-amine (106 mg, 0.52 mmol), and AcOH (0.02 mL, 0.35 mmol) and the resulting mixture was stirred at room temperature. After 16 h the resulting mixture diluted with EtOAc washed with water and brine, dried ($Na_2SO_4$), dry-packed onto silica gel and purified via column chromatography to yield the title compound.

STEP C: 3-(5-(4-chloro-2-(((4'-chloro-[1,1'-biphenyl]-4-yl)amino)methyl)phenyl)picolinamido)propanoic acid A 3M aqueous solution of NaOH (0.08 mL, 0.25 mmol) was added to a THF (1 mL) and MeOH (0.5 mL) solution of ethyl 3-(5-(4-chloro-2-(((4'-chloro-[1,1'-biphenyl]-4-yl)amino)methyl)phenyl)picolinamido)propanoate (45 mg, 0.08 mmol) and the homogeneous mixture was stirred at room temperature. After 3 h the resulting mixture was concentrated in vacuo, suspended in water, and acidified with 2 M HCl. The resulting precipitate was filtered off and dried in vacuo to yield the title compound.

$^1$H NMR (400 MHz, DMSO-$d_6$) δ 12.30 (br. s., 1H), 8.88 (s, 1H), 8.73 (s, 1H), 8.11 (s, 2H), 7.44-7.62 (m, 5H), 7.30-7.44 (m, 5H), 6.53 (d, J=8.56 Hz, 2H), 4.19 (s, 2H), 3.38-3.60 (m, 2H), 2.50-2.59 (m, 2H); MS m/z 520 (M+H).

Example 5

3-(5-(4-chloro-2-(((2',4'-dichloro-[1,1'-biphenyl]-4-yl)amino)methyl)phenyl)picolinamido)propanoic acid

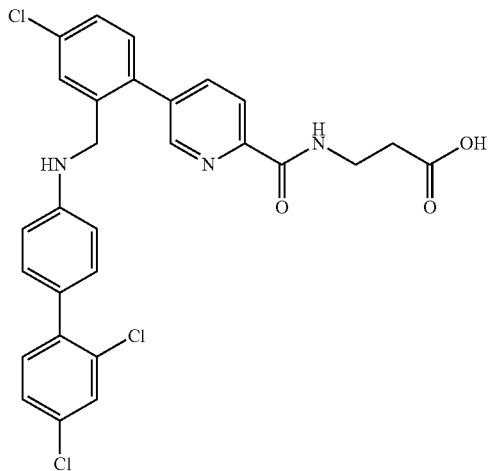 [SMILES: O=C(O)CCNC(=O)c1ccc(-c2ccc(Cl)cc2CNc2ccc(-c3ccc(Cl)cc3Cl)cc2)cn1]

STEP A: 2',4'-dichloro-[1,1'-biphenyl]-4-amine

4-Iodoaniline (10.0 g, 45.7 mmol), (2,4-dichlorophenyl) boronic acid (10.5 g, 54.8 mmol), Pd(dppf)Cl$_2$ (3.7 g, 4.6 mmol), and K$_2$CO$_3$ (12.6 g, 91.3 mmol) were dissolved in 1,4-dioxane (200 mL) and water (50 mL) and the resulting mixture was heated to 80° C. After 16 h the resulting mixture was cooled to room temperature, diluted with EtOAc, washed with water and brine, dried (Na$_2$SO$_4$), and dry packed onto silica gel. Column chromatography yielded the title compound.

STEP B: 3-(5-(4-chloro-2-(((2',4'-dichloro-[1,1'-biphenyl]-4-yl)amino)methyl)phenyl)picolinamido) propanoic acid The title compound was prepared as described in Example 4 substituting 2',4'-dichloro-[1,1'-biphenyl]-4-amine for 4'-chloro-[1,1'-biphenyl]-4-amine.

$^1$H NMR (400 MHz, DMSO-$d_6$) δ 12.30 (br. s., 1H), 8.88 (s, 1H), 8.73 (s, 1H), 8.11 (s, 2H), 7.60 (d, J=2.20 Hz, 1H), 7.64 (d, J=2.20 Hz, 1H), 7.46-7.54 (m, 1H), 7.39-7.46 (m, 2H), 7.30-7.38 (m, 1H), 7.14 (d, J=8.56 Hz, 2H), 6.52 (d, J=8.80 Hz, 3H), 4.18 (br. s., 2H), 3.53 (q, J=6.11 Hz, 2H), 2.47-2.59 (m, 2H); MS m/z 554 (M+H).

Example 6

3-(5-(5-chloro-2-(((4'-chloro-[1,1'-biphenyl]-4-yl)amino)methyl)phenyl)picolinamido)propanoic acid

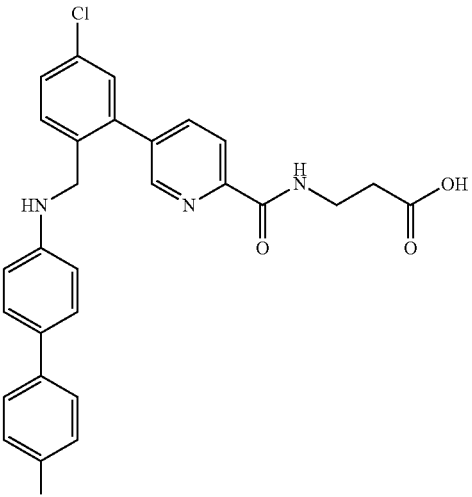

STEP A: ethyl 3-(5-(5-chloro-2-formylphenyl)picolinamido)propanoate

Ethyl 3-(5-bromopicolinamido)propanoate, prepared as in Example 1, (1.5 g, 5.0 mmol), (5-chloro-2-formylphenyl) boronic acid (1.0 g, 5.5 mmol), Pd(dppf)Cl$_2$ (408 mg, 0.5 mmol), and K$_2$CO$_3$ (1.4 g, 10.0 mmol) were dissolved in 1,4-dioxane (20 mL) and water (5 mL) and heated to 80° C. After 3 h the resulting mixture was cooled to room temperature, diluted with EtOAc washed with water and brine, dried (Na$_2$SO$_4$), dry-packed onto silica gel and purified via column chromatography to yield the title compound.

STEP B: ethyl 3-(5-(5-chloro-2-(((4'-chloro-[1,1'-biphenyl]-4-yl)amino)methyl)phenyl)picolinamido) propanoate Solid NaBH(OAc)$_3$ (388 mg, 1.83 mmol) was added to a DCE solution (2 mL) of ethyl 3-(5-(5-chloro-2-formylphenyl)picolinamido)propanoate (330 mg, 0.92 mmol), 4'-chloro-[1,1'-biphenyl]-4-amine (186 mg, 0.92 mmol), and AcOH (0.21 mL, 3.66 mmol) and the resulting mixture was stirred at room temperature. After 16 h the resulting mixture diluted with EtOAc washed with water and brine, dried STEP C: 3-(5-(5-chloro-2-(((4% chloro-[1,1'-biphenyl]-4-yl)amino)methyl)phenyl)picolinamido)propanoic acid A 3M aqueous solution of NaOH (0.17 mL, 0.52 mmol) was added to a THF (1 mL) and MeOH (0.5 mL) solution of ethyl 3-(5-(5-chloro-2-(((4'-chloro-[1,1'-biphenyl]-4-yl)amino)methyl)phenyl)picolinamido)propanoate (95 mg, 0.17 mmol) and the resulting homogeneous mixture was stirred at room temperature. After 16 h the resulting mixture was concentrated in vacuo, suspended in water, and acidified with 2 M HCl. The resulting precipitate was filtered off and dried in vacuo to yield the title compound.

Example 7

3-(5-(5-chloro-2-(((2',4'-dichloro-[1,1'-biphenyl]-4-yl)amino)methyl)phenyl)picolinamido)propanoic acid

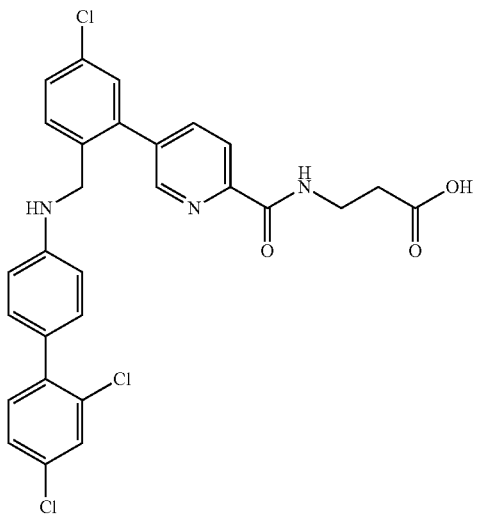 [SMILES: O=C(O)CCNC(=O)c1ccc(-c2cc(Cl)ccc2CNc2ccc(-c3ccc(Cl)cc3Cl)cc2)cn1]

STEP A: ethyl 3-(5-(5-chloro-2-(((2',4'-dichloro-[1,1'-biphenyl]-4-yl)amino)methyl)phenyl)picolinamido)propanoate Solid NaBH(OAc)$_3$ (4.9 g, 22.9 mmol) was added to a DCE solution (37 mL) of ethyl 3-(5-(5-chloro-2-formylphenyl)picolinamido)propanoate, prepared as in Example 6, (4.1 g, 11.5 mmol), 2',4'-dichloro-[1,1'-biphenyl]-4-amine, prepared as in example x (3.0 g, 12.6 mmol), and AcOH (2.6 mL, 45.8 mmol) and the resulting mixture was stirred at room temperature. After 16 h the resulting mixture diluted with EtOAc washed with water and brine, dried (Na$_2$SO$_4$), dry-packed onto silica gel and purified via column chromatography to yield the title compound.

STEP B: 3-(5-(5-chloro-2-(((2',4'-dichloro-[1,1'-biphenyl]-4-yl)amino)methyl)phenyl)picolinamido)propanoic acid A 3M aqueous solution of NaOH (7.5 mL, 22.6 mmol) was added to a THF (40 mL) and MeOH (20 mL) solution of ethyl 3-(5-(5-chloro-2-(((2',4'-dichloro-[1,1'-biphenyl]-4-yl)amino)methyl)phenyl)picolinamido)propanoate (6.6 g, 11.3 mmol) and the resulting homogeneous mixture was stirred at room temperature. After 16 h the resulting mixture was concentrated in vacuo, suspended in water, and acidified with 2 M HCl. The resulting precipitate was filtered off and dried in vacuo to yield the title compound.

$^1$H NMR (400 MHz, DMSO-d$_6$) δ 12.35 (br. s., 1H), 8.88 (br. s., 1H), 8.74 (s, 1H), 8.11 (s, 2H), 7.50-7.66 (m, 5H), 7.32-7.49 (m, 5H), 6.54 (d, J=8.31 Hz, 2H), 4.17 (s, 2H), 3.53 (d, J=6.36 Hz, 2H), 2.50-2.61 (m, 2H). $^1$H NMR (400 MHz, DMSO-d$_6$) δ 12.30 (br. s., 1H), 8.86-8.92 (m, 1H), 8.76 (s, 1H), 8.08-8.16 (m, 2H), 7.63 (d, J=2.20 Hz, 1H), 7.39-7.60 (m, 5H), 7.30-7.36 (m, 1H), 7.12 (d, J=8.56 Hz, 2H), 6.51 (d, J=8.56 Hz, 2H), 4.15 (br. s., 2H), 3.48-3.63 (m, 2H), 2.5-2.61 (m, 2H); MS m/z 554 (M+H).

Example 8

3-(5-(2-(((3',4'-dichloro-[1,1'-biphenyl]-4-yl)amino)methyl)phenyl)picolinamido)propanoic acid

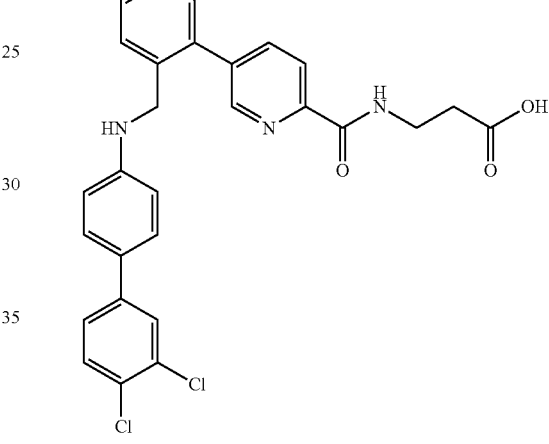

STEP A: tert-butyl 3-(5-(2-(((4-bromophenyl)amino)methyl)phenyl)picolinamido)propanoate Solid NaBH(OAc)$_3$ (210 mg, 1.0 mmol) was added to a THF solution (4 mL) of tert-butyl 3-(5-(2-formylphenyl)picolinamido)propanoate (270 mg, 0.8 mmol), 4'-chloro-[1,1'-biphenyl]-4-amine (197 mg, 1.1 mmol), and AcOH (43 µL, 0.8 mmol) and the resulting mixture was stirred at room temperature. After 16 h the resulting mixture diluted with EtOAc washed with water and brine, dried (Na$_2$SO$_4$), dry-packed onto silica gel and purified via column chromatography to yield the title compound.

STEP B: tert-butyl 3-(5-(2-(((3',4'-dichloro-[1,1'-biphenyl]-4-yl)amino)methyl)phenyl)picolinamido)propanoate tert-butyl 3-(5-(2-(((4-bromophenyl)amino)methyl)phenyl)picolinamido)propanoate (80 mg, 0.16 mmol), (3,4-dichlorophenyl)boronic acid (34 mg, 0.18 mmol), Pd(dppf)Cl$_2$ (13 mg, 0.02 mmol), and K$_2$CO$_3$ (43 mg, 0.31 mmol) were dissolved in 1,4-dioxane (1.2 mL) and water (0.3 mL) and heated to 80° C. After 3 h the resulting mixture was cooled to room temperature, diluted with EtOAc washed with water and brine, dried (Na$_2$SO$_4$), dry-packed onto silica gel and purified via column chromatography to yield the title compound.

STEP C: 3-(5-(2-(((3',4'-dichloro-[1,1'-biphenyl]-4-yl)amino)methyl)phenyl)picolinamido)propanoic acid Neat TFA (0.09 mL, 1.15 mmol) was added to a DCM solution (1 mL) of tert-butyl 3-(5-(2-(((3',4'-dichloro-[1,1'-biphenyl]-4-yl)amino)methyl)phenyl)picolinamido)propanoate (44 mg, 0.08 mmol). After 16 h the resulting mixture was concentrated in vacuo, dissolved in DCM and 1 N HCl in diethyl ether was added. The resulting solution was concentrated in vacuo and the DCM/HCl process was repeated 2×. The resulting solid was characterized as the corresponding HCl salt of the title compound.

Example 9

3-(5-(2-(((4'-trifluoromethyl)-[1,1'-biphenyl]-4-yl)amino)methyl)phenyl)picolinamido)propanoic acid

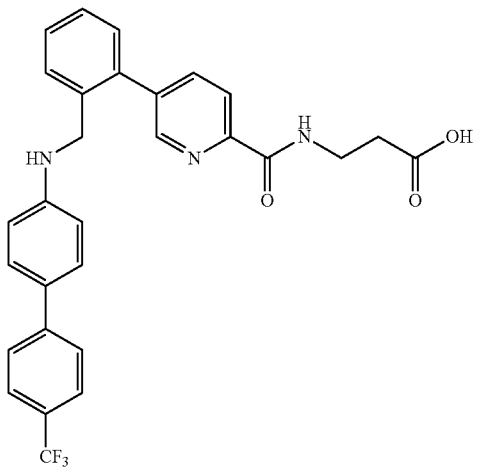 [SMILES: O=C(O)CCNC(=O)c1ccc(-c2ccccc2CNc2ccc(-c3ccc(C(F)(F)F)cc3)cc2)cn1]

The title compound was prepared as described in Example 8 substituting (4-(trifluoromethylphenyl)boronic acid for (3,4-dichlorophenyl)boronic acid.

Example 10

3-(5-(5-chloro-2-(((2,4'-dichloro-[1,1'-biphenyl]-4-yl)amino)methyl)phenyl)picolinamido)propanoic acid

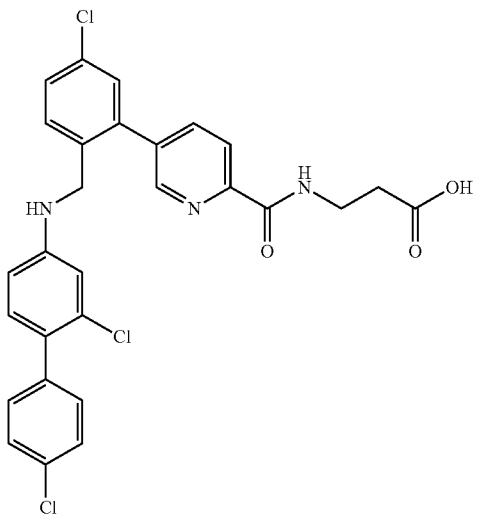 [SMILES: O=C(O)CCNC(=O)c1ccc(-c2cc(Cl)ccc2CNc2ccc(-c3ccc(Cl)cc3)c(Cl)c2)cn1]

STEP A: 2,4'-Dichloro-[1,1'-biphenyl]-4-amine 4-bromo-3-chloroaniline (3.0 g, 14.5 mmol), (4-chlorophenyl)boronic acid (2.7 g, 17.4 mmol), Pd(dppf)Cl$_2$ (1.2 g, 1.5 mmol), and K$_2$CO$_3$ (4.0 g, 29.1 mmol) were dissolved in 1,4-dioxane (60 mL) and water (15 mL) and the resulting mixture was heated to 80° C. After 16 h the resulting mixture was cooled to room temperature, diluted with EtOAc, washed with water and brine, dried (Na$_2$SO$_4$), and dry packed onto silica gel. Column chromatography yielded the title compound.

STEP B: Ethyl 3-(5-(5-chloro-2-(((2,4'-dichloro-[1,1'-biphenyl]-4-yl)amino)methyl)phenyl)picolinamido)propanoate Solid NaBH(OAc)$_3$ (2.7 g, 12.7 mmol) was added to a DCE solution (22 mL) of ethyl 3-(5-(5-chloro-2-formylphenyl)picolinamido)propanoate, prepared as in Example 6, (2.3 g, 6.3 mmol), 2,4'-dichloro-[1,1'-biphenyl]-4-amine (1.7 g, 7.0 mmol), and AcOH (1.5 mL, 25.4 mmol) and the resulting mixture was stirred at room temperature. After 16 h the resulting mixture diluted with EtOAc washed with water and brine, dried (Na$_2$SO$_4$), dry-packed onto silica gel and purified via column chromatography to yield the title compound.

STEP C: 3-(5-(5-Chloro-2-(((2,4'-dichloro-[1,1'-biphenyl]-4-yl)amino)methyl)phenyl)picolinamido)propanoic acid A 3M aqueous solution of NaOH (6.5 mL, 22.6 mmol) was added to a THF (10 mL) and MeOH (5 mL) solution of ethyl 3-(5-(5-chloro-2-(((2,4'-dichloro-[1,1'-biphenyl]-4-yl)amino)methyl)phenyl)picolinamido)propanoate (3.8 g, 6.5 mmol) and the resulting homogeneous mixture was stirred at room temperature. After 16 h the resulting mixture was concentrated in vacuo, suspended in water, and acidified with 2 M HCl. The resulting precipitate was filtered off, dried in vacuo and purified via HPLC to yield the title compound.

$^1$H NMR (400 MHz, DMSO-d$_6$) δ 8.84-8.94 (m, 1H), 8.73 (s, 1H), 8.11 (s, 2H), 7.56 (s, 2H), 7.40-7.51 (m, 4H), 7.35 (d, J=8.31 Hz, 2H), 7.05 (d, J=8.56 Hz, 1H), 6.56 (d, J=1.96 Hz, 1H), 6.48 (dd, J=2.08, 8.44 Hz, 1H), 4.16 (s, 2H), 3.53 (q, J=6.77 Hz, 2H), 2.50-2.60 (m, 2H); MS m/z 554 (M+H).

Example 11

3-(5-(5-chloro-2-(((2',4'-dichloro-3-fluoro-[1,1'-biphenyl]-4-yl)amino)methyl)phenyl)picolinamido)propanoic acid

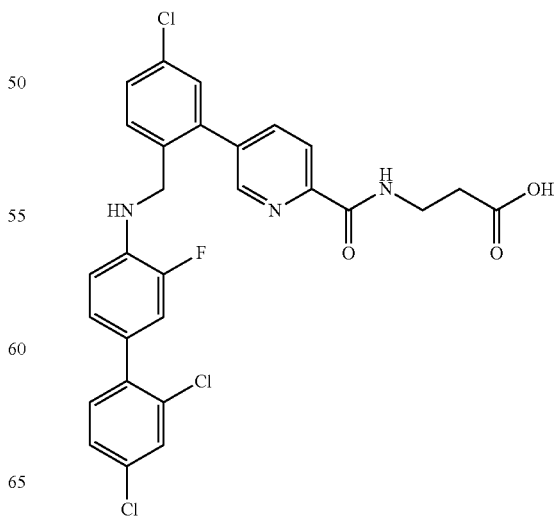

STEP A: Ethyl 3-(5-(2-(((4-bromo-2-fluorophenyl)amino)methyl)-5-chlorophenyl)picolinamido)propanoate Solid NaBH(OAc)₃ (623 mg, 2.9 mmol) was added to a DCE solution (3 mL) of ethyl 3-(5-(5-chloro-2-formylphenyl)picolinamido)propanoate, prepared as describe in Example 6, (530 mg, 1.5 mmol), 4-bromo-2-fluoroaniline (293 g, 1.5 mmol), and AcOH (0.34 mL, 5.9 mmol) and the resulting mixture was stirred at room temperature. After 16 h the resulting mixture diluted with EtOAc washed with water and brine, dried (Na₂SO₄), dry-packed onto silica gel and purified via column chromatography to yield the title compound.

STEP B: ethyl 3-(5-(5-chloro-2-(((2',4'-dichloro-3-fluoro-[1,1'-biphenyl]-4-yl)amino)methyl)phenyl)picolinamido)propanoate Ethyl 3-(5-(2-(((4-bromo-2-fluorophenyl)amino)methyl)-5-chlorophenyl)picolinamido)propanoate (138 mg, 0.26 mmol), (2,4-dichlorophenyl)boronic acid (57 mg, 0.30 mmol), Pd(dppf)Cl₂ (21 mg, 0.03 mmol), and K₂CO₃ (71 mg, 0.52 mmol) were dissolved in 1,4-dioxane (1.0 mL) and water (0.25 mL) and the resulting mixture was heated to 80° C. After 3 h the resulting mixture was cooled to room temperature, diluted with EtOAc, washed with water and brine, dried (Na₂SO₄), and dry packed onto silica gel. Column chromatography yielded the title compound.

STEP C: 3-(5-(5-chloro-2-(((2',4'-dichloro-3-fluoro-[1,1'-biphenyl]-4-yl)amino)methyl)phenyl)picolinamido)propanoic acid A 3M aqueous solution of NaOH (0.13 mL, 0.37 mmol) was added to a THF (4 mL) and MeOH (2 mL) solution of ethyl 3-(5-(5-chloro-2-(((2,4'-dichloro-[1,1'-biphenyl]-4-yl)amino)methyl)phenyl)picolinamido)propanoate (75 mg, 0.13 mmol) and the resulting homogeneous mixture was stirred at room temperature. After 16 h the resulting mixture was concentrated in vacuo, suspended in water, and acidified with 2 M HCl. The resulting precipitate was filtered off and dried in vacuo to yield the title compound.

¹H NMR (400 MHz, DMSO-d₆) δ 8.84-8.98 (m, 1H), 8.68-8.83 (m, 1H), 8.14 (d, J=1.47 Hz, 2H), 7.63-7.69 (m, 1H), 7.50-7.58 (m, 2H), 7.33-7.50 (m, 4H), 7.11-7.19 (m, 1H), 6.94 (d, J=8.07 Hz, 1H), 6.29-6.45 (m, 1H), 4.25 (s, 2H), 3.54 (q, J=6.60 Hz, 2H), 2.52-2.63 (m, 2H); MS m/z 572 (M+H).

Example 12

3-(5-(5-chloro-2-(((4'-chloro-3-fluoro-[1,1'-biphenyl]-4-yl)amino)methyl)phenyl)picolinamido)propanoic acid

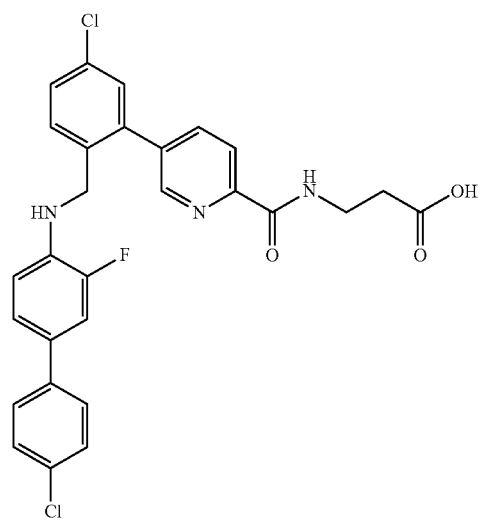 [SMILES: O=C(O)CCNC(=O)c1ccc(-c2cc(Cl)ccc2CNc2ccc(-c3ccc(Cl)cc3)cc2F)cn1]

The title compound was prepared as described in Example 11 substituting (4-chlorophenyl)boronic acid for (2,4-dichlorophenyl)boronic acid.

¹H NMR (400 MHz, DMSO-d₆) δ 8.90 (t, J=5.87 Hz, 1H), 8.75 (s, 1H), 8.09-8.18 (m, 2H), 7.55-7.61 (m, 2H), 7.48-7.55 (m, 2H), 7.36-7.47 (m, 4H), 7.19 (dd, J=1.96, 8.31 Hz, 1H), 6.36 (t, J=8.93 Hz, 1H), 4.26 (s, 2H), 3.46-3.60 (m, 2H), 2.54-2.60 (m, 2H); MS m/z 538 (M+H).

Example 13

3-(5-(5-chloro-2-(((4'-chloro-3,3'-difluoro-[1,1'-biphenyl]-4-yl)amino)methyl)phenyl)picolinamido)propanoic acid

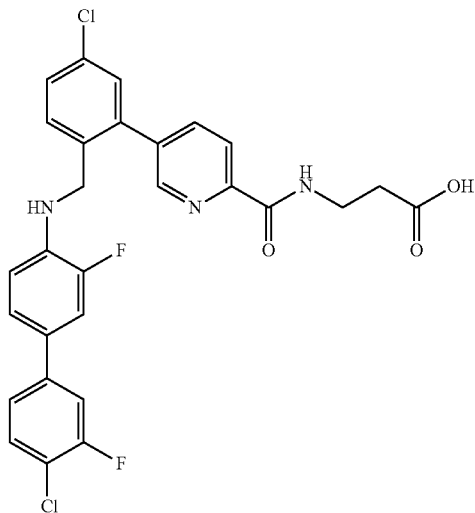 [SMILES: O=C(O)CCNC(=O)c1ccc(-c2cc(Cl)ccc2CNc2ccc(-c3ccc(Cl)c(F)c3)cc2F)cn1]

The title compound was prepared as described in Example 11 substituting (4-chloro-3-fluorophenyl)boronic acid for (2,4-dichlorophenyl)boronic acid.

¹H NMR (400 MHz, DMSO-d₆) δ 8.85-8.96 (m, 1H), 8.75 (s, 1H), 8.10-8.19 (m, 2H), 7.61-7.74 (m, 3H), 7.41-7.54 (m, 5H), 7.26 (dd, J=1.83, 8.44 Hz, 1H), 6.35 (t, J=8.93 Hz, 1H), 4.27 (s, 2H), 3.54 (q, J=6.68 Hz, 2H), 2.54-2.61 (m, 2H); MS m/z 556 (M+H).

Example 14

3-(5-(5-chloro-2-(((3'-chloro-[1,1'-biphenyl]-4-yl)amino)methyl)phenyl)picolinamido)propanoic acid

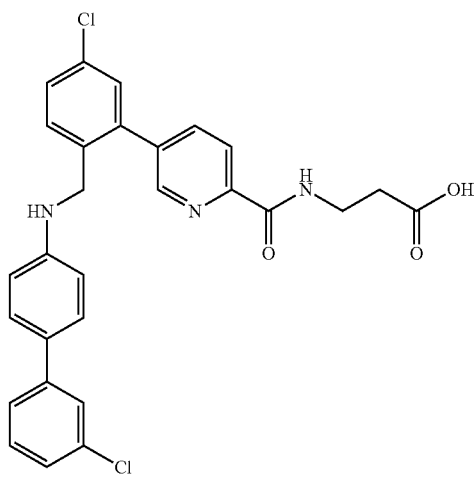 [SMILES: O=C(O)CCNC(=O)c1ccc(-c2cc(Cl)ccc2CNc2ccc(-c3cccc(Cl)c3)cc2)cn1]

The title compound was prepared as described in Example 7 substituting 3'-chloro-[1,1'-biphenyl]-4-amine for 2',4'-dichloro-[1,1'-biphenyl]-4-amine.

$^1$H NMR (400 MHz, DMSO-d$_6$) δ 8.83-8.93 (m, 1H), 8.71-8.78 (m, 1H), 8.08-8.16 (m, 2H), 7.51-7.56 (m, 3H), 7.44-7.50 (m, 3H), 7.35-7.41 (m, 3H), 7.25 (d, J=8.07 Hz, 1H), 6.52 (d, J=8.56 Hz, 2H), 4.16 (s, 2H), 3.49-3.56 (m, 2H), 2.52-2.57 (m, 2H); MS m/z 520 (M+H).

Example 15

3-(5-(5-chloro-2-(((4'-fluoro-[1,1'-biphenyl]-4-yl)amino)methyl)phenyl)picolinamido)propanoic acid

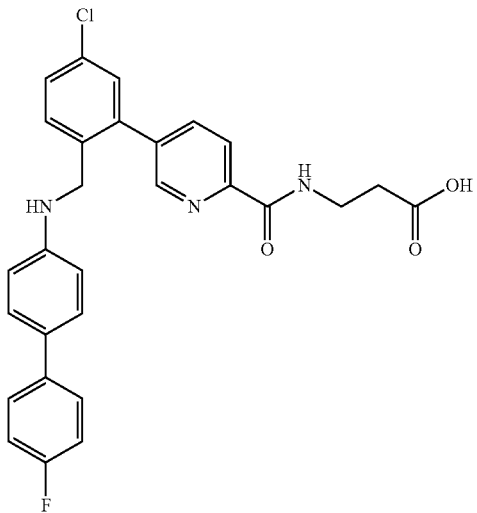 [SMILES: O=C(O)CCNC(=O)c1ccc(-c2cc(Cl)ccc2CNc2ccc(-c3ccc(F)cc3)cc2)cn1]

The title compound was prepared as described in Example 7 substituting 4'-fluoro-[1,1'-biphenyl]-4-amine for 2',4'-dichloro-[1,1'-biphenyl]-4-amine.

$^1$H NMR (400 MHz, DMSO-d$_6$) δ 8.84-8.95 (m, 1H), 8.71-8.80 (m, 1H), 8.07-8.20 (m, 2H), 7.49-7.64 (m, 5H), 7.46 (d, J=1.96 Hz, 1H), 7.33 (d, J=8.56 Hz, 2H), 7.12-7.25 (m, 2H), 6.52 (d, J=8.56 Hz, 2H), 4.15 (s, 2H), 3.53 (q, J=6.77 Hz, 2H), 2.54-2.63 (m, 2H); MS m/z 504 (M+H).

Example 16

3-(5-(5-chloro-2-((4% chloro-[1,1'-biphenyl]-4-yl)carbamoyl)phenyl)picolinamido)propanoic acid

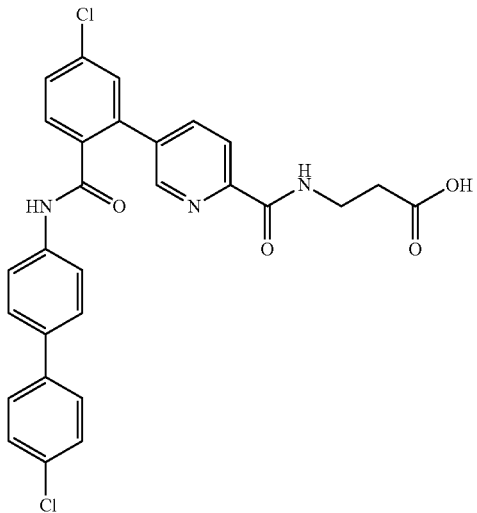 [SMILES: O=C(O)CCNC(=O)c1ccc(-c2cc(Cl)ccc2C(=O)Nc2ccc(-c3ccc(Cl)cc3)cc2)cn1]

STEP A: 2-(6-((2-carboxyethyl)carbamoyl)pyridin-3-yl)-4-chlorobenzoic acid

Solid KMnO$_4$ (460 mg, 2.9 mmol) was added to an acetone (14 mL) and water (5 mL) solution of ethyl 3-(5-(5-chloro-2-formylphenyl)picolinamido)propanoate, prepared as described in Example 6, (700 mg, 1.9 mmol) and the resulting mixture was heated to 50° C. After 20 h the resulting mixture was cooled, filtered through CELITE and washed with EtOAc. The aqueous phase was extracted with EtOAc and the combined extracts were washed with water and brine, dried (Na$_2$SO$_4$), and concentrated to yield the title compound, which was used in the next step without further purification.

STEP B: ethyl 3-(5-(5-chloro-2-((4'-chloro-[1,1'-biphenyl]-4-yl)carbamoyl)phenyl)picolinamido)propanoate Solid HATU (101 mg, 0.27 mmol) was added to a DMF solution (2 mL) of 2-(6-((2-carboxyethyl)carbamoyl)pyridin-3-yl)-4-chlorobenzoic acid (100 mg, 0.27 mmol), i-Pr$_2$NEt (0.2 mL, 1.1 mmol), and 4'-chloro-[1,1'-biphenyl]-4-amine (57 mg, 0.28 mmol) and the resulting mixture was warmed to 45° C. After 16 h the resulting mixture was diluted with EtOAc, washed with water and brine, dried (Na$_2$SO$_4$), concentrated and purified via column chromatography to yield the title compound.

STEP C: 3-(5-(5-chloro-2-((4'-chloro-[1,1'-biphenyl]-4-yl)carbamoyl)phenyl)picolinamido)propanoic acid A 3M aqueous solution of NaOH (0.21 mL, 0.64 mmol) was added to a THF (1 mL) and MeOH (0.5 mL) solution of ethyl 3-(5-(5-chloro-2-((4'-chloro-[1,1'-biphenyl]-4-yl)carbamoyl)phenyl)picolinamido)propanoate (119 mg, 0.21 mmol) and the homogeneous mixture was stirred at room temperature. After 16 h the resulting mixture was concentrated in vacuo, suspended in water, and acidified with 2 M HCl. The resulting precipitate was filtered off and dried in vacuo to yield the title compound.

$^1$H NMR (400 MHz, DMSO-d$_6$) δ 10.61 (s, 1H), 8.83 (br. s., 1H), 8.68 (s, 1H), 8.00-8.09 (m, 2H), 7.57-7.79 (m, 9H), 7.49 (d, J=8.56 Hz, 2H), 3.45-3.59 (m, 2H), 2.53-2.63 (m, 2H); MS m/z 534 (M+H).

Example 17

3-(5-(5-chloro-2-(((4'-chloro-[1,1'-biphenyl]-4-yl)(methyl)amino)methyl)phenyl)picolinamido)propanoic acid

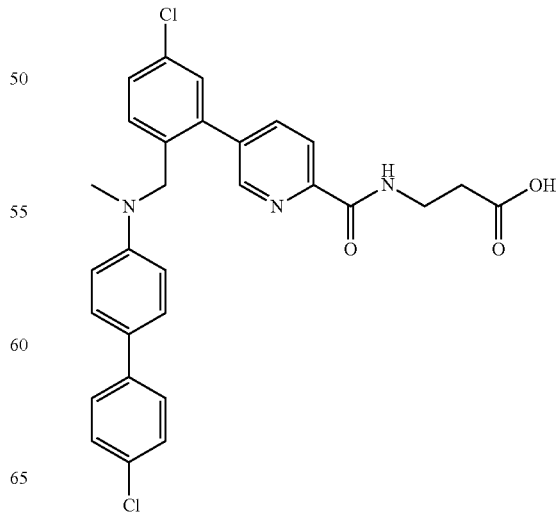

STEP A: 4'-chloro-N-methyl-[1,1'-biphenyl]-4-amine

4-Bromo-N-methylaniline (0.7 mL, 5.4 mmol), (4-chlorophenyl)boronic acid (967 mg, 6.2 mmol), Pd(dppf)Cl$_2$ (440 mg, 0.5 mmol), and K$_2$CO$_3$ (1.5 g, 10.8 mmol) were dissolved in 1,4-dioxane (40 mL) and water (10 mL) and the resulting mixture was heated to 80° C. After 16 h the resulting mixture was cooled to room temperature, diluted with EtOAc, washed with water and brine, dried (Na$_2$SO$_4$), and dry packed onto silica gel. Column chromatography yielded the title compound.

STEP B: methyl 5-(5-chloro-2-methylphenyl)picolinate

Methyl 5-bromopicolinate (5.0 g, 23.1 mmol), (5-chloro-2-methylphenyl)boronic acid (4.5 g, 26.6 mmol), Pd(dppf)Cl$_2$ (1.9 g, 2.3 mmol), and K$_2$CO$_3$ (6.4 g, 46.3 mmol) were dissolved in 1,4-dioxane (100 mL) and water (25 mL) and the resulting mixture was heated to 80° C. After 16 h the resulting mixture was cooled to room temperature, diluted with EtOAc, washed with water and brine, dried (Na$_2$SO$_4$), and dry packed onto silica gel. Column chromatography yielded the title compound.

STEP C: methyl 5-(2-(bromomethyl)-5-chlorophenyl)picolinate

Solid benzoyl peroxide (496 mg, 2.0 mmol) was added to a benzene solution (50 mL) of methyl 5-(5-chloro-2-methylphenyl)picolinate (3.6 g, 13.6 mmol) and NBS (2.7 g, 15.0 mmol) and the resulting mixture was refluxed. After 16 h the resulting mixture was cooled, diluted with EtOAc, washed with water and brine, dried (Na$_2$SO$_4$), and dry packed onto silica gel. Column chromatography yielded the title compound.

STEP D: methyl 5-(5-chloro-2-(((4'-chloro-[1,1'-biphenyl]-4-yl)(methyl)amino)methyl)phenyl)picolinate Methyl 5-(2-(bromomethyl)-5-chlorophenyl)picolinate (200 mg, 0.59 mmol), 4'-chloro-N-methyl-[1,1'-biphenyl]-4-amine (141 mg, 0.65 mmol), and K$_2$CO$_3$ (122 mg, 0.88 mmol) were diluted with acetone (3 mL) and heated to 50° C. After 18 h the resulting mixture was diluted with EtOAc, washed with water and brine, dried (Na$_2$SO$_4$), and dry packed onto silica gel. Column chromatography yielded the title compound.

STEP E: 5-(5-chloro-2-(((4'-chloro-[1,1'-biphenyl]-4-yl)(methyl)amino)methyl)phenyl)picolinic acid A 3M aqueous solution of NaOH (0.47 mL, 1.42 mmol) was added to a THF (2 mL) and MeOH (1 mL) solution of methyl 5-(5-chloro-2-(((4'-chloro-[1,1'-biphenyl]-4-yl)(methyl)amino)methyl)phenyl)picolinate (226 mg, 0.47 mmol) and the resulting homogeneous mixture was stirred at room temperature. After 16 h the resulting mixture was concentrated in vacuo, suspended in water, and acidified with 2 M HCl. The resulting precipitate was filtered off and dried in vacuo to yield the title compound.

STEP F: ethyl 3-(5-(5-chloro-2-(((4'-chloro-[1,1'-biphenyl]-4-yl)(methyl)amino)methyl)phenyl)picolinamido)propanoate Solid HATU (127 mg, 0.34 mmol) was added to a THF solution (3 mL) of 5-(5-chloro-2-(((4'-chloro-[1,1'-biphenyl]-4-yl)(methyl)amino)methyl)phenyl)picolinic acid (155 mg, 0.34 mmol), i-Pr$_2$NEt (0.29 mL, 1.67 mmol), and β-alanine ethyl ester hydrochloride (54 mg, 0.35) and the resulting mixture was warmed to 45° C. After 16 h the resulting mixture was diluted with EtOAc, washed with water and brine, dried (Na$_2$SO$_4$), concentrated and purified via column chromatography to yield the title compound.

STEP G: 3-(5-(5-chloro-2-(((4'-chloro-[1,1'-biphenyl]-4-yl)(methyl)amino)methyl)phenyl)picolinamido)propanoic acid A 3M aqueous solution of NaOH (0.29 mL, 0.88 mmol) was added to a THF (2 mL) and MeOH (1 mL) solution of ethyl 3-(5-(5-chloro-2-(((4'-chloro-[1,1'-biphenyl]-4-yl)(methyl)amino)methyl)phenyl)picolinamido)propanoate (165 mg, 0.29 mmol) and the resulting homogeneous mixture was stirred at room temperature. After 16 h the mixture was concentrated in vacuo, suspended in water, and acidified with 2 M HCl. The resulting precipitate was filtered off and dried in vacuo to yield the title compound.

$^1$H NMR (400 MHz, DMSO-d$_6$) δ 8.82-8.87 (m, 1H), 8.73 (d, J=1.22 Hz, 1H), 8.10-8.16 (m, 2H), 7.62-7.68 (m, 2H), 7.54-7.58 (m, 2H), 7.37-7.51 (m, 4H), 7.22 (d, J=8.07 Hz, 1H), 6.65 (d, J=8.80 Hz, 2H), 4.52 (s, 2H), 3.49-3.59 (m, 2H), 2.94 (s, 3H), 2.51-2.57 (m, 2H); MS m/z 534 (M+H).

Example 18

3-(5-(5-chloro-2-(((2',4'-difluoro-[1,1'-biphenyl]-4-yl)amino)methyl)phenyl)picolinamido)propanoic acid

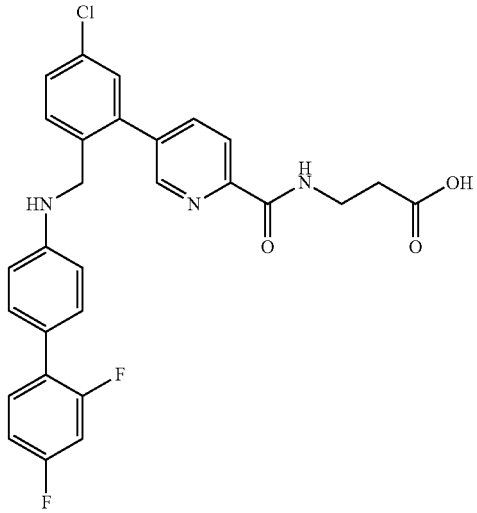 [SMILES: O=C(O)CCNC(=O)c1ccc(-c2cc(Cl)ccc2CNc2ccc(-c3ccc(F)cc3F)cc2)cn1]

STEP A: 2',4'-difluoro-[1,1'-biphenyl]-4-amine

4-Bromoaniline (2.0 g, 11.6 mmol), (2,4-difluorophenyl)boronic acid (2.1 g, 13.4 mmol), Pd(dppf)Cl$_2$ (952 mg, 1.2 mmol), and K$_2$CO$_3$ (3.2 g, 23.3 mmol) were dissolved in 1,4-dioxane (80 mL) and water (20 mL) and the resulting mixture was heated to 80° C. After 16 h the resulting mixture was cooled to room temperature, diluted with EtOAc, washed with water and brine, dried (Na$_2$SO$_4$), and dry packed onto silica gel. Column chromatography yielded the title compound.

STEP B: 3-(5-(5-chloro-2-(((2',4'-difluoro-[1,1'-biphenyl]-4-yl)amino)methyl)phenyl)picolinamido) propanoic acid The title compound was prepared as described in Example 7 substituting 2',4'-difluoro-[1,1'-biphenyl]-4-amine for 2',4'-dichloro-[1,1'-biphenyl]-4-amine.

¹H NMR (400 MHz, DMSO-d₆) δ 8.88 (t, J=5.99 Hz, 1H), 8.74 (d, J=1.22 Hz, 1H), 8.07-8.16 (m, 2H), 7.50-7.61 (m, 2H), 7.40-7.49 (m, 2H), 7.17-7.29 (m, 3H), 7.06-7.14 (m, 1H), 6.54 (d, J=8.80 Hz, 2H), 4.16 (s, 2H), 3.53 (q, J=6.85 Hz, 2H), 2.52-2.58 (m, 2H); MS m/z 522 (M+H).

Example 19

3-(5-(5-chloro-2-((2',4'-dichloro-[1,1'-biphenyl]-4-yl)carbamoyl)phenyl)picolinamido)propanoic acid

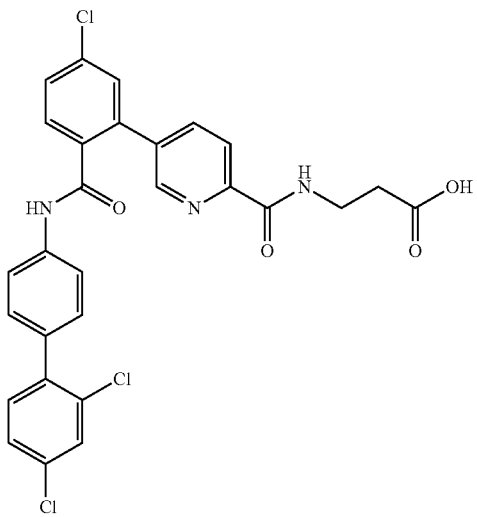 [SMILES: O=C(O)CCNC(=O)c1ccc(-c2cc(Cl)ccc2C(=O)Nc2ccc(-c3ccc(Cl)cc3Cl)cc2)cn1]

The title compound was prepared as described in Example 16 substituting 2',4'-dichloro-[1,1'-biphenyl]-4-amine for 4'-chloro-[1,1'-biphenyl]-4-amine.
¹H NMR (400 MHz, DMSO-d₆) δ 10.67 (s, 1H), 8.86 (s, 1H), 8.65-8.72 (m, 1H), 8.02-8.12 (m, 2H), 7.68-7.79 (m, 5H), 7.64 (d, J=8.56 Hz, 2H), 7.48-7.52 (m, 1H), 7.35-7.45 (m, 3H), 3.44-3.55 (m, 2H), 2.52-2.63 (m, 2H); MS m/z 568 (M+H).

Example 20

3-(5-(5-chloro-2-((4'-fluoro-[1,1'-biphenyl]-4-yl)carbamoyl)phenyl)picolinamido)propanoic acid

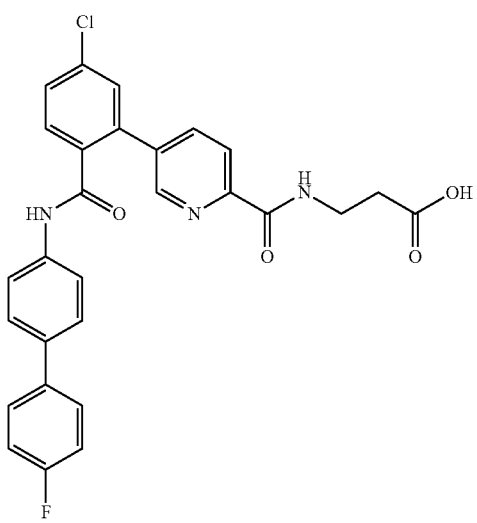 [SMILES: O=C(O)CCNC(=O)c1ccc(-c2cc(Cl)ccc2C(=O)Nc2ccc(-c3ccc(F)cc3)cc2)cn1]

The title compound was prepared as described in Example 16 substituting 4'-fluoro-[1,1'-biphenyl]-4-amine for 4'-chloro-[1,1'-biphenyl]-4-amine.

¹H NMR (400 MHz, DMSO-d₆) δ 10.60 (s, 1H), 8.80-8.92 (m, 1H), 8.68 (s, 1H), 8.06 (s, 2H), 7.54-7.84 (m, 9H), 7.20-7.35 (m, 2H), 3.49 (q, J=6.77 Hz, 2H), 2.50-2.60 (m, 2H); MS m/z 518 (M+H).

Example 21

3-(5-(2-(((2',4'-dichloro-[1,1'-biphenyl]-4-yl)amino)methyl)-5-(trifluoromethyl)phenyl)picolinamido)propanoic acid

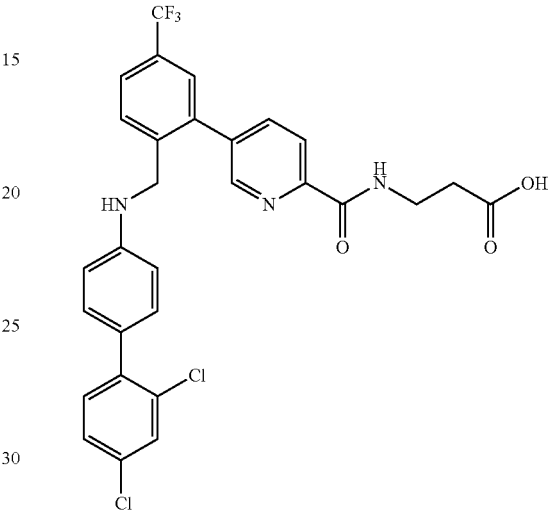

STEP A: ethyl 3-(5-(4,4,5,5-tetramethyl-1,3,2-dioxaborolan-2-yl)picolinamido)propanoate Ethyl 3-(5-bromopicolinamido)propanoate, prepared as in Example 1 (100 g, 0.32 mol), Bis(pinacolato)diboron (93.8 g, 0.36 mol), Pd(dppf)Cl₂ (13.8 g, 0.02 mol), and KOAc (97.8 g, 0.99 mol) were dissolved in 1,4-dioxane (1 L) and the resulting mixture was heated to 85° C. After 1 h the resulting mixture was cooled to room temperature, diluted with EtOAc and water, filtered through CELITE and the layers were separated. The organic phase was washed with brine, dried (MgSO₄), and concentrated. The resulting oil was diluted with DCM and heptane and purified via silica gel column chromatography to yield the title compound.

STEP B: N-(2-bromo-4-(trifluoromethyl)benzyl)-2',4'-dichloro-[1,1'-biphenyl]-4-amine Solid NaBH(OAc)₃ (39 mg, 1.9 mmol) was added to a DCE solution (3 mL) of 2-bromo-4-(trifluoromethyl)benzaldehyde (235 mg, 0.9 mmol), 2',4'-dichloro-[1,1'-biphenyl]-4-amine (233 g, 1.0 mmol), and AcOH (0.21 mL, 3.7 mmol) and the resulting mixture was stirred at room temperature. After 16 h the resulting mixture diluted with EtOAc washed with water and brine, dried (Na₂SO₄), dry-packed onto silica gel and purified via column chromatography to yield the title compound.

STEP C: ethyl 3-(5-(2-(((2',4'-dichloro-[1,1'-biphenyl]-4-yl)amino)methyl)-5-(trifluoromethyl)phenyl)picolinamido)propanoate N-(2-bromo-4-(trifluoromethyl)benzyl)-2',4'-dichloro-[1,1'-biphenyl]-4-amine (386 mg, 0.8 mmol), ethyl 3-(5-(4,4,5, 5-tetramethyl-1,3,2-dioxaborolan-2-yl)picolinamido)propanoate, prepared as in step a, (424 mg, 1.2 mmol), Pd(dppf)Cl$_2$ (67 mg, 0.1 mmol), and K$_2$CO$_3$ (225 mg, 1.6 mmol) were dissolved in 1,4-dioxane (8 mL) and water (2 mL) and the resulting mixture was heated to 80° C. After 16 h the resulting mixture was cooled to room temperature, diluted with EtOAc, washed with water and brine, dried (Na$_2$SO$_4$), and dry packed onto silica gel. Column chromatography yielded the title compound.

STEP D: 3-(5-(2-(((2',4'-dichloro-[1,1'-biphenyl]-4-yl)amino)methyl)-5-(trifluoromethyl)phenyl)picolinamido)propanoic acid A 3M aqueous solution of NaOH (0.63 mL, 1.9 mmol) was added to a THF (4 mL) and MeOH (2 mL) solution of ethyl 3-(5-(2-(((2',4'-dichloro-[1,1'-biphenyl]-4-yl)amino)methyl)-5-(trifluoromethyl)phenyl)picolinamido)propanoate (388 mg, 0.6 mmol) and the homogeneous mixture was stirred at room temperature. After 16 h the resulting mixture was concentrated in vacuo, suspended in water, and acidified with 2 M HCl. The resulting precipitate was filtered off and dried in vacuo to yield the title compound.

$^1$H NMR (400 MHz, DMSO-d$_6$) δ 8.89 (br. s., 1H), 8.80 (s, 1H), 8.10-8.23 (m, 2H), 7.84 (br. s., 1H), 7.75-7.81 (m, 1H), 7.71 (s, 1H), 7.63 (d, J=2.20 Hz, 1H), 7.37-7.46 (m, 1H), 7.30-7.37 (m, 1H), 7.13 (d, J=8.56 Hz, 2H), 6.52 (d, J=8.56 Hz, 2H), 4.26 (br. s., 2H), 3.54 (d, J=6.11 Hz, 2H), 2.50-2.59 (m, 2H); MS m/z 588 (M+H).

Example 22

3-(5-(2-(((4'-chloro-2'-methyl-[1,1'-biphenyl]-4-yl)amino)methyl)-5-(trifluoromethyl)phenyl)picolinamido)propanoic acid

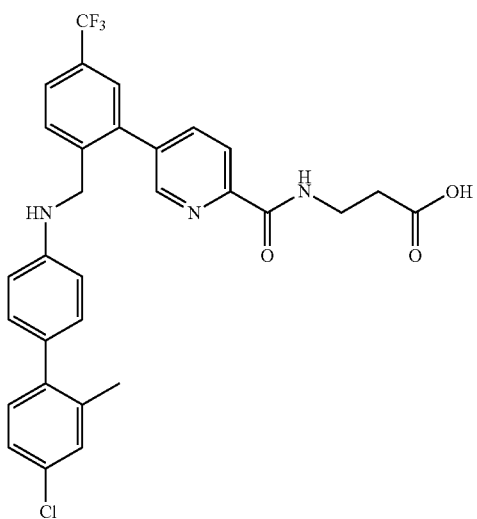 [SMILES: Cc1cc(Cl)ccc1-c1ccc(NCc2ccc(C(F)(F)F)cc2-c2ccc(C(=O)NCCC(=O)O)nc2)cc1]

STEP A: ethyl 3-(5-(2-formyl-5-(trifluoromethyl)phenyl)picolinamido)propanoate 2-bromo-4-(trifluoromethyl)benzaldehyde (1.3 g, 5.1 mmol), ethyl 3-(5-(4,4,5,5-tetramethyl-1,3,2-dioxaborolan-2-yl)picolinamido)propanoate, prepared as in example 19, (2.7 g, 7.7 mmol), Pd(dppf)Cl$_2$ (421 mg, 0.5 mmol), and K$_2$CO$_3$ (1.4 g, 10.3 mmol) were dissolved in 1,4-dioxane (40 mL) and water (10 mL) and the resulting mixture was heated to 80° C. After 16 h the resulting mixture was cooled to room temperature, diluted with EtOAc, washed with water and brine, dried (Na$_2$SO$_4$), and dry packed onto silica gel. Column chromatography yielded the title compound.

STEP B: ethyl 3-(5-(2-(((4-iodophenyl)amino)methyl)-5-(trifluoromethyl)phenyl)picolinamido)propanoate Solid NaBH(OAc)$_3$ (2.2 g, 10.1 mmol) was added to a DCE solution (22 mL) of ethyl 3-(5-(2-formyl-5-(trifluoromethyl)phenyl)picolinamido)propanoate (2.0 g, 5.1 mmol), 4-iodoaniline (1.2 g, 5.6 mmol), and AcOH (1.2 mL, 20.3 mmol) and the resulting mixture was stirred at room temperature. After 16 h the resulting mixture diluted with EtOAc washed with water and brine, dried (Na$_2$SO$_4$), dry-packed onto silica gel and purified via column chromatography to yield the title compound.

STEP C: ethyl 3-(5-(2-(((4'-chloro-2'-methyl-[1,1'-biphenyl]-4-yl)amino)methyl)-5-(trifluoromethyl)phenyl)picolinamido)propanoate Ethyl 3-(5-(2-(((4-iodophenyl)amino)methyl)-5-(trifluoromethyl)phenyl)picolinamido)propanoate (150 mg, 0.25 mmol), (4-chloro-2-methylphenyl)boronic acid (51 mg, 0.30 mmol), Pd(dppf)Cl$_2$ (21 mg, 0.03 mmol), and K$_2$CO$_3$ (69 mg, 0.50 mmol) were dissolved in 1,4-dioxane (1.6 mL) and water (0.4 mL) and the resulting mixture was heated to 80° C. After 16 h the resulting mixture was cooled to room temperature, diluted with EtOAc, washed with water and brine, dried (Na$_2$SO$_4$), and dry packed onto silica gel. Column chromatography yielded the title compound.

STEP D: 3-(5-(2-(((4'-chloro-2'-methyl-[1,1'-biphenyl]-4-yl)amino)methyl)-5-(trifluoromethyl)phenyl)picolinamido)propanoic acid A 3M aqueous solution of NaOH (0.10 mL, 0.30 mmol) was added to a THF (4 mL) and MeOH (2 mL) solution of ethyl 3-(5-(2-(((4'-chloro-2'-methyl-[1,1'-biphenyl]-4-yl)amino)methyl)-5-(trifluoromethyl)phenyl)picolinamido)propanoate (60 mg, 0.10 mmol) and the resulting homogeneous mixture was stirred at room temperature. After 16 h the resulting mixture was concentrated in vacuo, suspended in water, and acidified with 2 M HCl. The resulting precipitate was filtered off, dried in vacuo, and purified via HPLC to yield the title compound.

$^1$H NMR (400 MHz, DMSO-d$_6$) δ 8.90 (t, J=5.99 Hz, 1H), 8.79 (d, J=1.22 Hz, 1H), 8.09-8.20 (m, 2H), 7.78-7.89 (m, 2H), 7.71 (s, 1H), 7.31 (d, J=2.20 Hz, 1H), 7.23 (dd, J=2.20, 8.31 Hz, 1H), 7.12 (d, J=8.07 Hz, 1H), 7.02 (d, J=8.56 Hz, 2H), 6.53 (d, J=8.56 Hz, 2H), 4.26 (s, 2H), 3.48-3.58 (m, 2H), 2.54-2.58 (m, 2H), 2.20 (s, 3H); MS m/z 568 (M+H).

Example 23

3-(5-(2-(((2'-chloro-4'-fluoro-[1,1'-biphenyl]-4-yl)amino)methyl)-5-(trifluoromethyl)phenyl)picolinamido)propanoic acid

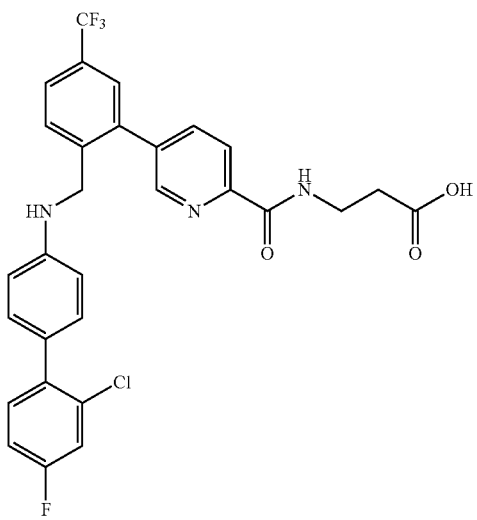 [SMILES: O=C(O)CCNC(=O)c1ccc(-c2cc(C(F)(F)F)ccc2CNc2ccc(-c3ccc(F)cc3Cl)cc2)cn1]

The title compound was prepared as described in Example 22 substituting (2-chloro-4-fluorophenyl)boronic acid for (4-chloro-2-methylphenyl)boronic acid.

$^1$H NMR (400 MHz, DMSO-d$_6$) δ 8.91 (t, J=5.99 Hz, 1H), 8.79 (s, 1H), 8.07-8.21 (m, 2H), 7.77-7.89 (m, 2H), 7.71 (s, 1H), 7.47 (dd, J=2.69, 8.80 Hz, 1H), 7.36 (dd, J=6.36, 8.56 Hz, 1H), 7.23 (td, J=2.69, 8.44 Hz, 1H), 7.11 (d, J=8.56 Hz, 2H), 6.55 (d, J=8.56 Hz, 2H), 4.27 (s, 2H), 3.54 (q, J=6.85 Hz, 2H), 2.54-2.59 (m, 2H); MS m/z 572 (M+H).

Example 24

3-(5-(2-(((2'-chloro-4'-(trifluoromethyl)-[1,1'-biphenyl]-4-yl)amino)methyl)-5-(trifluoromethyl)phenyl)picolinamido)propanoic acid

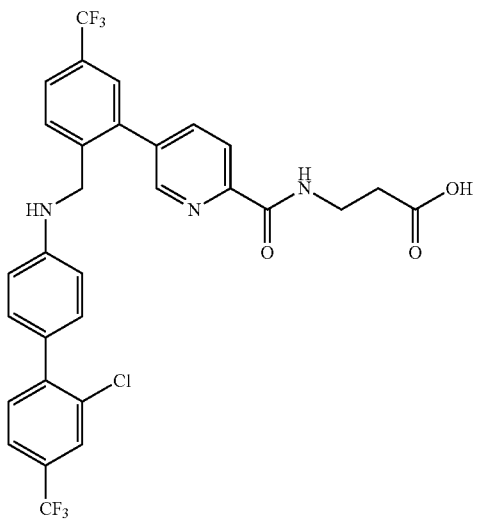

The title compound was prepared as described in Example 22 substituting (2-chloro-4-(trifluoromethyl)phenyl)boronic acid for (4-chloro-2-methylphenyl)boronic acid.

$^1$H NMR (400 MHz, DMSO-d$_6$) δ 8.91 (t, J=5.87 Hz, 1H), 8.80 (d, J=1.47 Hz, 1H), 8.10-8.22 (m, 2H), 7.83-7.91 (m, 2H), 7.76-7.81 (m, 1H), 7.66-7.75 (m, 2H), 7.55 (d, J=8.07 Hz, 1H), 7.16-7.24 (m, J=8.56 Hz, 2H), 6.49-6.60 (m, J=8.80 Hz, 2H), 4.28 (s, 2H), 3.54 (q, J=6.68 Hz, 2H), 2.54-2.59 (m, 2H); MS m/z 622 (M+H).

Example 25

3-(5-(2-(((4'-chloro-2-(trifluoromethyl)-[1,1'-biphenyl]-4-yl)amino)methyl)-5-(trifluoromethyl)phenyl)picolinamido)propanoic acid

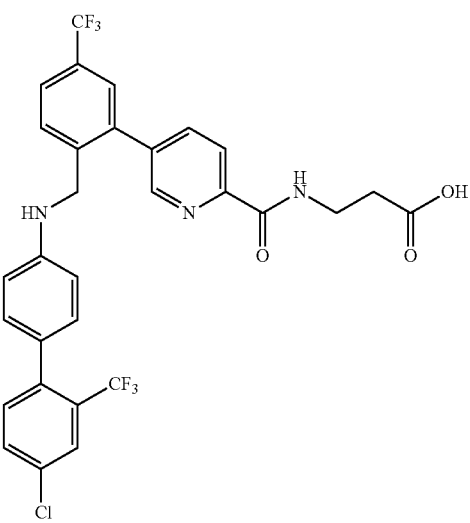

The title compound was prepared as described in Example 22 substituting (4-chloro-2-(trifluoromethyl)phenyl)boronic acid for (4-chloro-2-methylphenyl)boronic acid.

$^1$H NMR (400 MHz, DMSO-d$_6$) δ 8.90 (br. s., 1H), 8.79 (br. s., 1H), 8.08-8.25 (m, 2H), 7.78-7.91 (m, 3H), 7.65-7.78 (m, 2H), 7.25-7.43 (m, 1H), 7.00 (d, J=8.31 Hz, 2H), 6.53 (d, J=8.31 Hz, 2H), 4.26 (br. s., 2H), 3.61 (br. s., 1H), 3.50-3.60 (m, 2H), 2.54-2.61 (m, 2H); MS m/z 622 (M+H).

Example 26

3-(5-(2-(((4'-fluoro-3'-(trifluoromethyl)-[1,1'-biphenyl]-4-yl)amino)methyl)-5-(trifluoromethyl)phenyl)picolinamido)propanoic acid

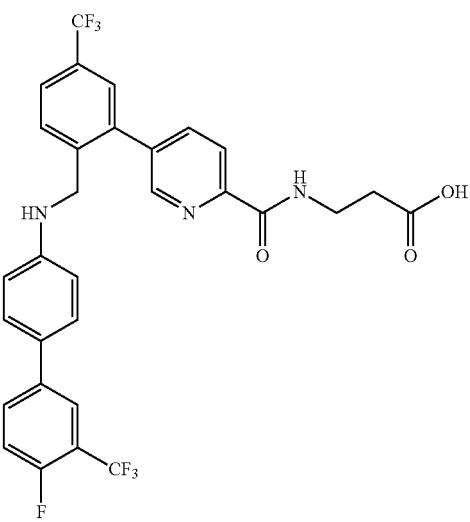 [SMILES: O=C(O)CCNC(=O)c1ccc(-c2cc(C(F)(F)F)ccc2CNc2ccc(-c3ccc(F)c(C(F)(F)F)c3)cc2)cn1]

The title compound was prepared as described in Example 22 substituting (4-fluoro-3-(trifluoromethyl)phenyl)boronic acid for (4-chloro-2-methylphenyl)boronic acid.

$^1$H NMR (400 MHz, DMSO-$d_6$) δ 8.90 (t, J=5.99 Hz, 1H), 8.79 (d, J=1.22 Hz, 1H), 8.09-8.22 (m, 2H), 7.75-7.90 (m, 4H), 7.70-7.73 (m, 1H), 7.46-7.53 (m, 1H), 7.39-7.45 (m, J=8.80 Hz, 2H), 6.50-6.60 (m, J=8.80 Hz, 2H), 4.29 (s, 2H), 3.54 (q, J=6.85 Hz, 2H), 2.54-2.60 (m, 2H); MS m/z 606 (M+H).

Example 27

3-(5-(2-(((2,2',4'-trichloro-[1,1'-biphenyl]-4-yl)amino)methyl)-5-(trifluoromethyl)phenyl)picolinamido)propanoic acid

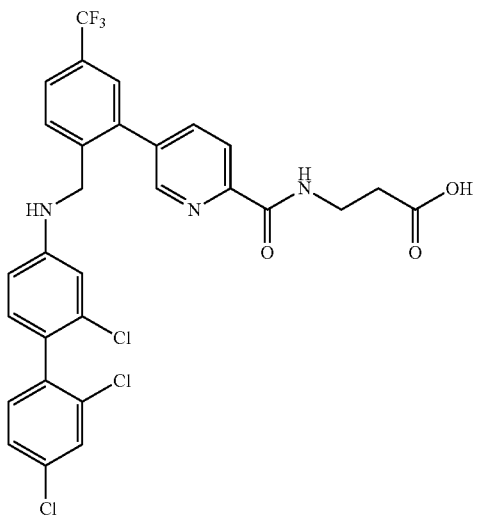

STEP A: 2,2',4'-trichloro-[1,1'-biphenyl]-4-amine

4-Bromo-3-chloroaniline (3.0 g, 14.5 mmol), (2,4-dichlorophenyl)boronic acid (3.6 g, 18.9 mmol), Pd(dppf)Cl$_2$ (1.2 g, 1.5 mmol), and K$_2$CO$_3$ (4.0 g, 29.1 mmol) were dissolved in 1,4-dioxane (60 mL) and water (15 mL) and the resulting mixture was heated to 80° C. After 16 h the resulting mixture was cooled to room temperature, diluted with EtOAc, washed with water and brine, dried (Na$_2$SO$_4$), and dry packed onto silica gel. Column chromatography yielded the title compound.

STEP B: 3-(5-(2-(((2,2',4'-trichloro-[1,1'-biphenyl]-4-yl)amino)methyl)-5-(trifluoromethyl)phenyl)picolinamido)propanoic acid The title compound was prepared as described in Example 21 substituting 2,2',4'-trichloro-[1,1'-biphenyl]-4-amine for 2',4'-dichloro-[1,1'-biphenyl]-4-amine.

$^1$H NMR (400 MHz, DMSO-$d_6$) δ 8.91 (t, J=5.99 Hz, 1H), 8.79 (s, 1H), 8.09-8.21 (m, 2H), 7.87 (d, J=8.31 Hz, 1H), 7.80 (d, J=8.07 Hz, 1H), 7.72 (s, 1H), 7.67 (d, J=1.96 Hz, 1H), 7.44 (dd, J=1.96, 8.31 Hz, 1H), 7.29 (d, J=8.31 Hz, 1H), 6.96 (d, J=8.31 Hz, 1H), 6.60 (d, J=1.96 Hz, 1H), 6.48 (dd, J=2.20, 8.31 Hz, 1H), 4.27 (s, 2H), 3.54 (q, J=6.77 Hz, 2H), 2.56 (t, J=6.97 Hz, 2H); MS m/z 622 (M+H).

Example 28

3-(5-(2-(((2,4'-dichloro-[1,1'-biphenyl]-4-yl)amino)methyl)-5-(trifluoromethyl)phenyl)picolinamido)propanoic acid

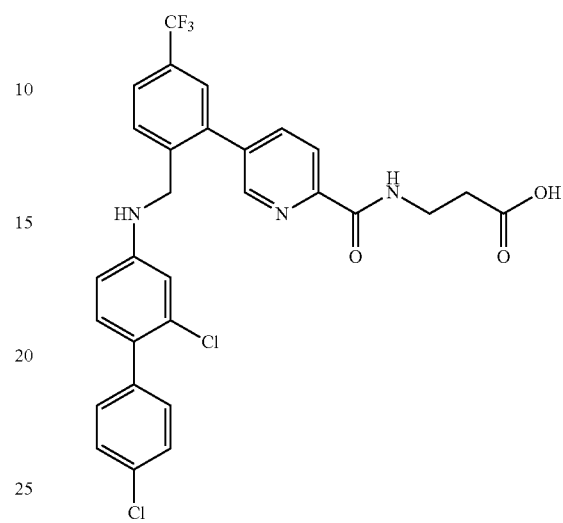

The title compound was prepared as described in Example 21 substituting 2,4'-dichloro-[1,1'-biphenyl]-4-amine, prepared as in Example 8, for 2',4'-dichloro-[1,1'-biphenyl]-4-amine.

$^1$H NMR (400 MHz, DMSO-$d_6$) δ 8.85-8.96 (m, 1H), 8.78 (s, 1H), 8.09-8.24 (m, 2H), 7.86 (d, J=8.07 Hz, 1H), 7.67-7.82 (m, 2H), 7.43 (d, J=8.56 Hz, 2H), 7.31-7.40 (m, 2H), 7.06 (d, J=8.31 Hz, 1H), 6.59 (d, J=2.20 Hz, 1H), 6.45-6.55 (m, 1H), 4.27 (s, 2H), 3.48-3.61 (m, 2H), 2.53-2.62 (m, 2H); MS m/z 588 (M+H).

Example 29

3-(5-(5-(trifluoromethyl)-2-(((4'-(trifluoromethyl)-[1,1'-biphenyl]-4-yl)amino)methyl)phenyl)picolinamido)propanoic acid

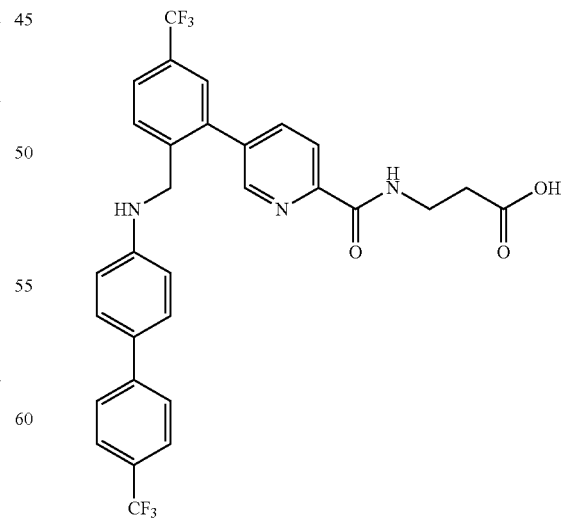

The title compound was prepared as described in Example 22 substituting (4-(trifluoromethyl)phenyl)boronic acid for (4-chloro-2-methylphenyl)boronic acid.

¹H NMR (400 MHz, DMSO-d₆) δ 8.90 (t, J=5.87 Hz, 1H), 8.76-8.81 (m, 1H), 8.11-8.21 (m, 2H), 7.81-7.87 (m, 1H), 7.66-7.79 (m, 6H), 7.43-7.49 (m, J=8.56 Hz, 2H), 6.52-6.61 (m, J=8.56 Hz, 2H), 4.29 (s, 2H), 3.50-3.58 (m, 2H), 2.52-2.58 (m, 1H); MS m/z 588 (M+H).

Example 30

3-(5-(2-(((2'-methyl-4'-(trifluoromethyl)-[1,1'-biphenyl]-4-yl)amino)methyl)-5-(trifluoromethyl)phenyl)picolinamido)propanoic acid

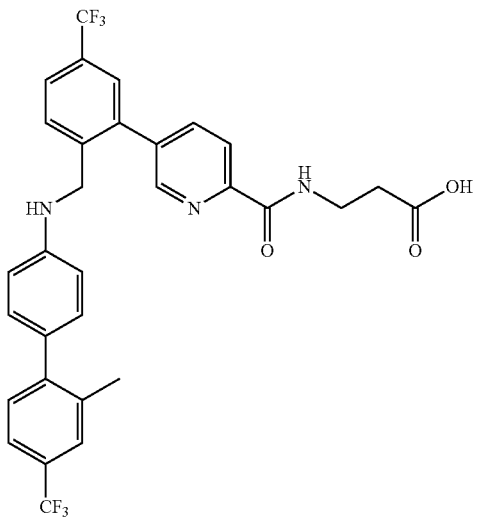 [SMILES: Cc1cc(C(F)(F)F)ccc1-c1ccc(NCc2ccc(C(F)(F)F)cc2-c2ccc(C(=O)NCCC(=O)O)nc2)cc1]

The title compound was prepared as described in Example 22 substituting (2-methyl-4-(trifluoromethyl)phenyl)boronic acid for (4-chloro-2-methylphenyl)boronic acid.

¹H NMR (400 MHz, DMSO-d₆) δ 8.86-8.95 (m, 1H), 8.79 (br. s., 1H), 8.10-8.23 (m, 2H), 7.85 (q, J=8.07 Hz, 2H), 7.72 (s, 1H), 7.60 (s, 1H), 7.52 (d, J=7.83 Hz, 1H), 7.33 (d, J=7.83 Hz, 1H), 7.10 (d, J=8.56 Hz, 2H), 6.58 (d, J=8.31 Hz, 2H), 4.28 (s, 2H), 3.54 (q, J=6.68 Hz, 2H), 2.54-2.59 (m, 2H), 2.30 (s, 3H); MS m/z 602 (M+H).

Example 31

3-(5-(2-(((2-chloro-4'-fluoro-3'-(trifluoromethyl)-[1,1'-biphenyl]-4-yl)amino)methyl)-5-(trifluoromethyl)phenyl)picolinamido)propanoic acid

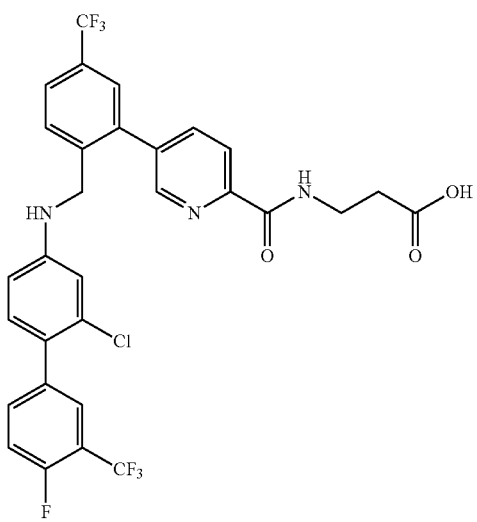 [SMILES: O=C(O)CCNC(=O)c1ccc(-c2cc(C(F)(F)F)ccc2CNc2ccc(-c3ccc(F)c(C(F)(F)F)c3)c(Cl)c2)cn1]

STEP A: ethyl 3-(5-(2-(((3-chloro-4-iodophenyl)amino)methyl)-5-(trifluoromethyl)phenyl)picolinamido)propanoate Solid NaBH(OAc)₃ (4.2 g, 19.8 mmol) was added to a DCE solution (45 mL) of ethyl 3-(5-(2-formyl-5-(trifluoromethyl)phenyl)picolinamido)propanoate, prepared as described in Example 22, (3.9 g, 9.9 mmol), 3-chloro-4-iodoaniline (3.0 g, 11.9 mmol), and AcOH (2.8 mL, 49.4 mmol) and the resulting mixture was stirred at room temperature. After 16 h the resulting mixture diluted with EtOAc washed with water and brine, dried (Na₂SO₄), dry-packed onto silica gel and purified via column chromatography to yield the title compound.

STEP B: ethyl 3-(5-(2-(((2-chloro-4'-fluoro-3'-(trifluoromethyl))-[1,1'-biphenyl]-4-yl)amino)methyl)-5-(trifluoromethyl)phenyl)picolinamido)propanoate Ethyl 3-(5-(2-(((3-chloro-4-iodophenyl)amino)methyl)-5-(trifluoromethyl)phenyl)picolinamido)propanoate (300 mg, 0.48 mmol), (4-fluoro-3-(trifluoromethyl)phenyl)boronic acid (138 mg, 0.67 mmol), Pd(dppf)Cl₂ (39 mg, 0.05 mmol), and K₂CO₃ (131 mg, 0.95 mmol) were dissolved in 1,4-dioxane (1.6 mL) and water (0.4 mL) and the resulting mixture was heated to 80° C. After 16 h the resulting mixture was cooled to room temperature, diluted with EtOAc, washed with water and brine, dried (Na₂SO₄), and dry packed onto silica gel. Column chromatography yielded the title compound.

STEP C: 3-(5-(2-(((2-chloro-4'-fluoro-3'-(trifluoromethyl)-[1,1'-biphenyl]-4-yl)amino)methyl)-5-(trifluoromethyl)phenyl)picolinamido)propanoic acid A 3M aqueous solution of NaOH (0.38 mL, 1.13 mmol) was added to a THF (4 mL) and MeOH (2 mL) solution of ethyl ethyl 3-(5-(2-(((2-chloro-4'-fluoro-3'-(trifluoromethyl)-[1,1'-biphenyl]-4-yl)amino)methyl)-5-(trifluoromethyl)phenyl)picolinamido)propanoate (251 mg, 0.38 mmol) and the resulting homogeneous mixture was stirred at room temperature. After 16 h the resulting mixture was concentrated in vacuo, suspended in water, and acidified with 2 M HCl. The resulting precipitate was filtered off, dried in vacuo, and purified via HPLC to yield the title compound.

¹H NMR (400 MHz, DMSO-d₆) δ 8.88 (t, J=5.99 Hz, 1H), 8.77 (d, J=1.22 Hz, 1H), 8.09-8.20 (m, 2H), 7.83-7.90 (m, 1H), 7.76 (d, J=8.07 Hz, 1H), 7.63-7.73 (m, 3H), 7.49-7.58 (m, 1H), 7.13 (d, J=8.56 Hz, 1H), 6.60 (d, J=2.20 Hz, 1H), 6.49 (dd, J=2.32, 8.44 Hz, 1H), 4.29 (s, 2H), 3.54 (q, J=6.85 Hz, 2H), 2.52-2.58 (m, 1H); MS m/z 640 (M+H).

Example 32

3-(5-(2-(((2,4'-dichloro-3'-(trifluoromethyl)-[1,1'-biphenyl]-4-yl)amino)methyl)-5-(trifluoromethyl)phenyl)picolinamido)propanoic acid

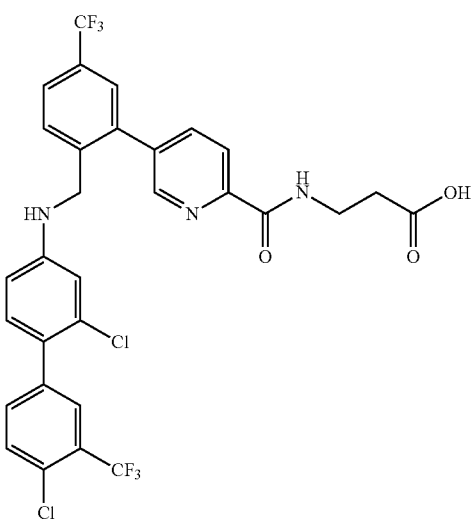 [SMILES: O=C(O)CCNC(=O)c1ccc(-c2cc(C(F)(F)F)ccc2CNc2ccc(-c3ccc(Cl)c(C(F)(F)F)c3)c(Cl)c2)cn1]

The title compound was prepared as described in Example 31 substituting (4-chloro-3-(trifluoromethyl)phenyl)boronic acid for (4-fluoro-3-(trifluoromethyl)phenyl)boronic acid.

$^1$H NMR (400 MHz, DMSO-$d_6$) δ 8.90 (t, J=5.99 Hz, 1H), 8.73-8.81 (m, 1H), 8.09-8.20 (m, 2H), 7.86 (d, J=8.07 Hz, 1H), 7.70-7.78 (m, 4H), 7.63-7.70 (m, 1H), 7.15 (d, J=8.31 Hz, 1H), 6.61 (d, J=2.20 Hz, 1H), 6.50 (dd, J=2.20, 8.56 Hz, 1H), 4.29 (s, 2H), 3.54 (q, J=6.85 Hz, 2H), 2.54-2.61 (m, 1H); MS m/z 656 (M+H).

Example 33

3-(5-(2-(((2,2'-dichloro-4'-fluoro-[1,1'-biphenyl]-4-yl)amino)methyl)-5-(trifluoromethyl)phenyl)picolinamido)propanoic acid

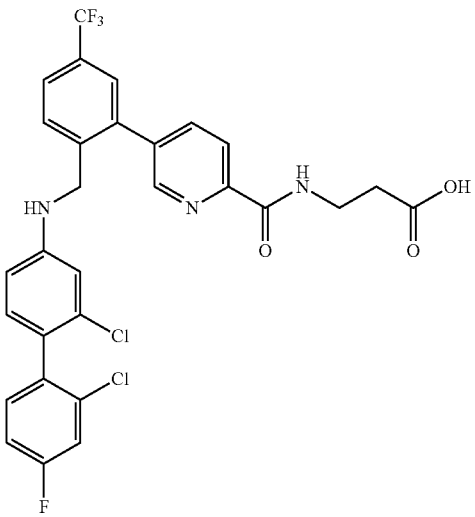

The title compound was prepared as described in Example 22 substituting (2-chloro-4-fluorophenyl)boronic acid for (4-fluoro-3-(trifluoromethyl)phenyl)boronic acid.

$^1$H NMR (400 MHz, DMSO-$d_6$) δ 8.91 (t, J=5.99 Hz, 1H), 8.78 (d, J=1.22 Hz, 1H), 8.09-8.20 (m, 2H), 7.87 (d, J=8.31 Hz, 1H), 7.78 (d, J=8.31 Hz, 1H), 7.73 (s, 1H), 7.50 (dd, J=2.57, 8.93 Hz, 1H), 7.20-7.34 (m, 2H), 6.95 (d, J=8.31 Hz, 1H), 6.58 (d, J=2.20 Hz, 1H), 6.47 (dd, J=2.20, 8.31 Hz, 1H), 4.27 (s, 2H), 3.54 (q, J=6.85 Hz, 2H), 2.54-2.59 (m, 2H); MS m/z 606 (M+H).

Example 34

3-(5-(2-(((2,4'-dichloro-2'-methyl-[1,1'-biphenyl]-4-yl)amino)methyl)-5-(trifluoromethyl)phenyl)picolinamido)propanoic acid

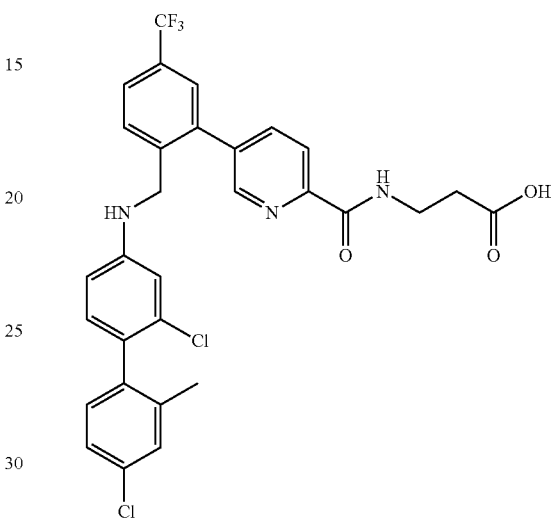

STEP A: 2,4'-dichloro-2'-methyl-[1,1'-biphenyl]-4-amine

3-Chloro-4-iodoaniline (3.0 g, 11.8 mmol), (4-chloro-2-methylphenyl)boronic acid (2.4 g, 14.2 mmol), Pd(dppf)Cl$_2$ (1.0 g, 1.2 mmol), and K$_2$CO$_3$ (3.3 g, 23.7 mmol) were dissolved in 1,4-dioxane (40 mL) and water (10 mL) and the resulting mixture was heated to 80° C. After 16 h the resulting mixture was cooled to room temperature, diluted with EtOAc, washed with water and brine, dried (Na$_2$SO$_4$), and dry packed onto silica gel. Column chromatography yielded the title compound.

STEP B: 2-bromo-1-(bromomethyl)-4-(trifluoromethyl)benzene

Solid benzoyl peroxide (1.5 g, 6.3 mmol) was added to a benzene solution (200 mL) of 2-bromo-1-methyl-4-(trifluoromethyl)benzene (10.0 g, 41.8 mmol) and NBS (8.2 g, 46.0 mmol) and the resulting mixture was refluxed. After 16 h the resulting mixture was cooled, diluted with EtOAc, washed with water and brine, dried (Na$_2$SO$_4$), and dry packed onto silica gel. Column chromatography yielded the title compound.

STEP C: N-(2-bromo-4-(trifluoromethyl)benzyl)-2,4'-dichloro-2'-methyl-[1,1'-biphenyl]-4-amine 2-Bromo-1-(bromomethyl)-4-(trifluoromethyl)benzene (2.0 g, 6.3 mmol), 2,4'-dichloro-2'-methyl-[1,1'-biphenyl]-4-amine (1.7 g, 6.9 mmol), and K$_2$CO$_3$ (1.3 g, 9.4 mmol) were diluted with DMF (20 mL) and heated to 80° C. After 3 h the resulting mixture was diluted with EtOAc, washed with water and brine, dried (Na2SO4), and dry packed onto silica gel. Column chromatography yielded the title compound.

STEP D: ethyl 3-(5-(2-(((2,4'-dichloro-2'-methyl-[1,1'-biphenyl]-4-yl)amino)methyl)-5-(trifluoromethyl)phenyl)picolinamido)propanoate N-(2-bromo-4-(trifluoromethyl)benzyl)-2,4'-dichloro-2'-methyl-[1,1'-biphenyl]-4-amine (2.7 g, 5.5 mmol), ethyl 3-(5-(4,4,5,5-tetramethyl-1,3,2-dioxaborolan-2-yl)picolinamido)propanoate, prepared as in Step A above, (2.3 g, 6.6 mmol), Pd(dppf)Cl$_2$ (452 mg, 0.6 mmol), and K$_2$CO$_3$ (1.5 g, 11.0 mmol) were dissolved in 1,4-dioxane (50 mL) and water (13 mL) and the resulting mixture was heated to 80° C. After 16 h the resulting mixture was cooled to room temperature, diluted with EtOAc, washed with water and brine, dried (Na$_2$SO$_4$), and dry packed onto silica gel. Column chromatography yielded the title compound.

STEP E: 3-(5-(2-(((2,4'-dichloro-2'-methyl-[1,1'-biphenyl]-4-yl)amino)methyl)-5-(trifluoromethyl)phenyl)picolinamido)propanoic acid A 3M aqueous solution of NaOH (5.6 mL, 16.7 mmol) was added to a THF (20 mL) and MeOH (10 mL) solution of ethyl 3-(5-(2-(((2,4'-dichloro-2'-methyl-[1,1'-biphenyl]-4-yl)amino)methyl)-5-(trifluoromethyl)phenyl)picolinamido)propanoate (3.5 g, 5.6 mmol) and the resulting homogeneous mixture was stirred at room temperature. After 16 h the resulting mixture was concentrated in vacuo, suspended in water, and acidified with 2 M HCl. The resulting precipitate was filtered off, dried in vacuo, and purified via HPLC to yield the title compound.

$^1$H NMR (400 MHz, DMSO-d$_6$) δ 8.83-8.93 (m, 1H), 8.77 (s, 1H), 8.08-8.18 (m, 2H), 7.83-7.91 (m, 1H), 7.76-7.81 (m, 1H), 7.72 (s, 1H), 7.34 (d, J=1.71 Hz, 1H), 7.20-7.28 (m, 1H), 7.05 (d, J=8.31 Hz, 1H), 6.90 (d, J=8.31 Hz, 1H), 6.58 (d, J=2.20 Hz, 1H), 6.46 (dd, J=2.32, 8.19 Hz, 1H), 4.26 (s, 2H), 3.54 (q, J=6.36 Hz, 2H), 2.54-2.58 (m, 2H), 2.02 (s, 3H) MS m/z 554 (M+H); MS m/z 602 (M+H).

Example 35

3-(5-(2-(((2,3'-dichloro-4'-fluoro-[1,1'-biphenyl]-4-yl)amino)methyl)-5-(trifluoromethyl)phenyl)picolinamido)propanoic acid

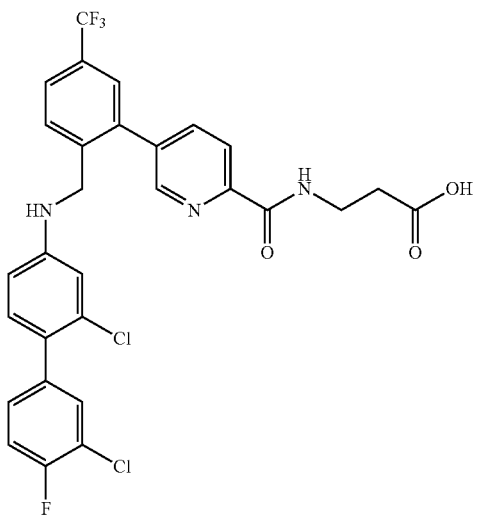 [SMILES: O=C(O)CCNC(=O)c1ccc(-c2cc(C(F)(F)F)ccc2CNc2ccc(-c3ccc(F)c(Cl)c3)c(Cl)c2)cn1]

The title compound was prepared as described in Example 31 substituting (3-chloro-4-fluorophenyl)boronic acid for (4-fluoro-3-(trifluoromethyl)phenyl)boronic acid.

$^1$H NMR (400 MHz, DMSO-d$_6$) δ 8.88 (t, J=5.99 Hz, 1H), 8.77 (d, J=0.98 Hz, 1H), 8.09-8.18 (m, 2H), 7.86 (d, J=8.31 Hz, 1H), 7.75 (d, J=8.31 Hz, 1H), 7.70-7.73 (m, 1H), 7.51 (dd, J=2.20, 7.34 Hz, 1H), 7.42 (t, J=8.93 Hz, 1H), 7.33 (ddd, J=2.20, 4.65, 8.56 Hz, 1H), 7.08 (d, J=8.31 Hz, 1H), 6.58 (d, J=2.20 Hz, 1H), 6.47 (dd, J=2.20, 8.56 Hz, 1H), 4.28 (s, 2H), 3.54 (q, J=6.85 Hz, 2H), 2.52-2.59 (m, 2H); MS m/z 606 (M+H).

Example 36

3-(5-(5-chloro-2-((2',4'-difluoro-[1,1'-biphenyl]-4-yl)carbamoyl)phenyl)picolinamido)propanoic acid

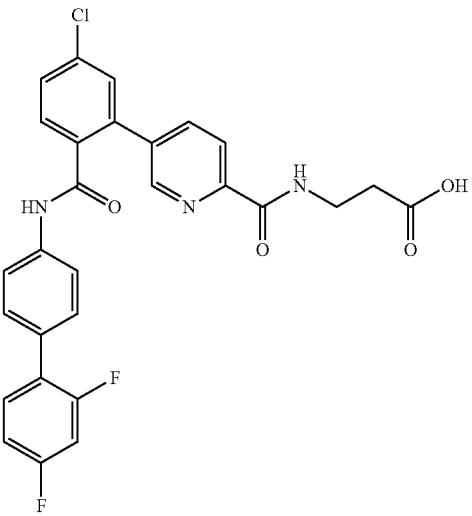 [SMILES: O=C(O)CCNC(=O)c1ccc(-c2cc(Cl)ccc2C(=O)Nc2ccc(-c3ccc(F)cc3F)cc2)cn1]

The title compound was prepared as described in Example 16 substituting 2',4'-difluoro-[1,1'-biphenyl]-4-amine for 4'-chloro-[1,1'-biphenyl]-4-amine.

$^1$H NMR (400 MHz, DMSO-d$_6$) δ 12.28 (br. s., 1H), 10.63 (s, 1H), 8.86 (t, J=5.75 Hz, 1H), 8.65-8.70 (m, 1H), 8.06 (s, 2H), 7.68-7.78 (m, 3H), 7.61-7.67 (m, J=8.56 Hz, 2H), 7.51-7.59 (m, 1H), 7.44-7.49 (m, J=8.31 Hz, 2H), 7.32-7.39 (m, 1H), 7.14-7.22 (m, 1H), 3.45-3.55 (m, 2H), 2.52-2.58 (m, 2H); MS m/z 536 (M+H).

Example 37

3-(5-(2-(((2,4'-dichloro-2'-fluoro-[1,1'-biphenyl]-4-yl)amino)methyl)-5-(trifluoromethyl)phenyl)picolinamido)propanoic acid

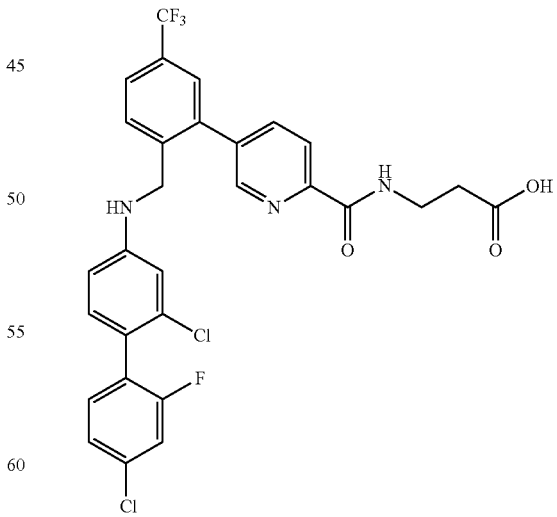

The title compound was prepared as described in Example 31 substituting (4-chloro-2-fluorophenyl)boronic acid for (4-fluoro-3-(trifluoromethyl)phenyl)boronic acid.

$^1$H NMR (400 MHz, DMSO-d$_6$) δ 8.90 (t, J=5.99 Hz, 1H), 8.78 (s, 1H), 8.09-8.22 (m, 2H), 7.87 (d, J=7.83 Hz, 1H), 7.69-7.81 (m, 2H), 7.44-7.51 (m, 1H), 7.25-7.35 (m, 2H), 7.03 (d, J=8.56 Hz, 1H), 6.61 (d, J=1.96 Hz, 1H), 6.42-6.54 (m, 1H), 4.28 (s, 2H), 3.54 (q, J=6.85 Hz, 2H), 2.54-2.59 (m, 2H); MS m/z 606 (M+H).

Example 38

3-(5-(2-(((2,2'-dichloro-3'-(trifluoromethyl)-[1,1'-biphenyl]-4-yl)amino)methyl)-5-(trifluoromethyl)phenyl)picolinamido)propanoic acid

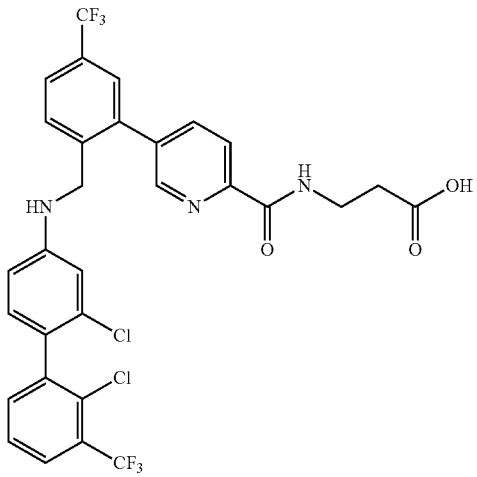 [SMILES: O=C(O)CCNC(=O)c1ccc(-c2cc(C(F)(F)F)ccc2CNc2ccc(-c3cccc(C(F)(F)F)c3Cl)c(Cl)c2)cn1]

The title compound was prepared as described in Example 31 substituting (2-chloro-3-(trifluoromethyl)phenyl)boronic acid for (4-fluoro-3-(trifluoromethyl)phenyl)boronic acid.

$^1$H NMR (400 MHz, DMSO-d$_6$) δ 8.91 (t, J=5.99 Hz, 1H), 8.74-8.82 (m, 1H), 8.10-8.21 (m, 2H), 7.84-7.91 (m, 2H), 7.76-7.82 (m, 1H), 7.73 (s, 1H), 7.53-7.61 (m, 2H), 6.99 (d, J=8.31 Hz, 1H), 6.61 (d, J=2.20 Hz, 1H), 6.50 (dd, J=2.32, 8.44 Hz, 1H), 4.28 (s, 2H), 3.54 (q, J=6.68 Hz, 2H), 2.54-2.59 (m, 2H); MS m/z 656 (M+H).

Example 39

3-(5-(2-(((2-chloro-3'-fluoro-4'-(trifluoromethyl)-[1,1'-biphenyl]-4-yl)amino)methyl)-5-(trifluoromethyl)phenyl)picolinamido)propanoic acid

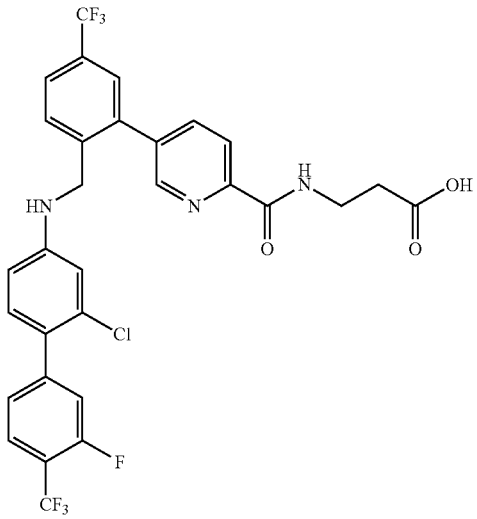 [SMILES: O=C(O)CCNC(=O)c1ccc(-c2cc(C(F)(F)F)ccc2CNc2ccc(-c3ccc(C(F)(F)F)c(F)c3)c(Cl)c2)cn1]

The title compound was prepared as described in Example 31 substituting (3-fluoro-4-(trifluoromethyl)phenyl)boronic acid for (4-fluoro-3-(trifluoromethyl)phenyl)boronic acid.

$^1$H NMR (400 MHz, DMSO-d$_6$) δ 8.90 (t, J=5.99 Hz, 1H), 8.78 (s, 1H), 8.10-8.21 (m, 2H), 7.86 (d, J=8.07 Hz, 1H), 7.71-7.81 (m, 4H), 7.61-7.69 (m, 1H), 7.15 (d, J=8.31 Hz, 1H), 6.62 (d, J=1.96 Hz, 1H), 6.50 (dd, J=1.83, 8.44 Hz, 1H), 4.30 (s, 2H), 3.54 (q, J=6.68 Hz, 2H), 2.54-2.60 (m, 2H); MS m/z 640 (M+H).

Example 40

3-(5-(2-(((4'-chloro-2'-fluoro-[1,1'-biphenyl]-4-yl)amino)methyl)-5-(trifluoromethyl)phenyl)picolinamido)propanoic acid

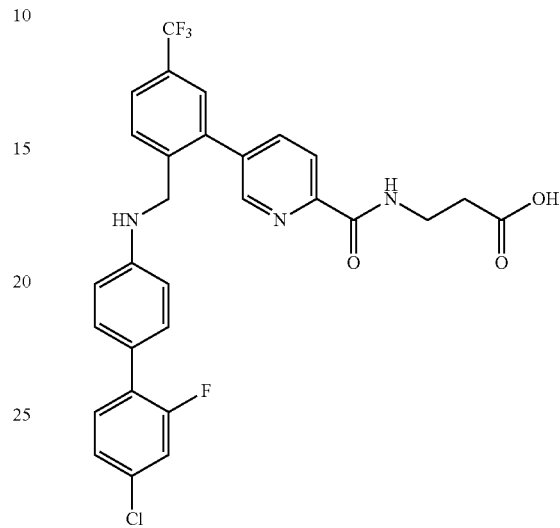

The title compound was prepared as described in Example 22 substituting (4-chloro-2-fluorophenyl)boronic acid for (4-chloro-2-methylphenyl)boronic acid.

$^1$H NMR (400 MHz, DMSO-d$_6$) δ 8.90 (t, J=5.99 Hz, 1H), 8.76-8.81 (m, 1H), 8.09-8.21 (m, 2H), 7.84 (d, J=8.07 Hz, 1H), 7.76 (d, J=8.07 Hz, 1H), 7.71 (s, 1H), 7.40-7.49 (m, 2H), 7.27-7.32 (m, 1H), 7.24 (d, J=7.34 Hz, 2H), 6.55 (d, J=8.56 Hz, 2H), 4.27 (s, 2H), 3.54 (q, J=6.85 Hz, 2H), 2.54-2.59 (m, 2H); MS m/z 572 (M+H).

Example 41

3-(5-(2-(((2'-chloro-3'-(trifluoromethyl)-[1,1'-biphenyl]-4-yl)amino)methyl)-5-(trifluoromethyl)phenyl)picolinamido)propanoic acid

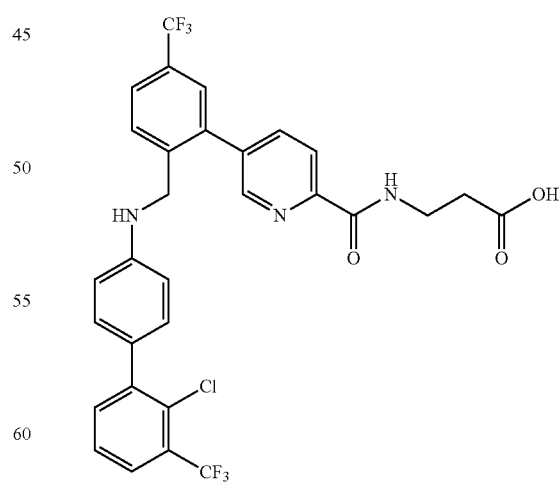

The title compound was prepared as described in Example 22 substituting (2-chloro-3-(trifluoromethyl)phenyl)boronic acid for (4-chloro-2-methylphenyl)boronic acid.

$^1$H NMR (400 MHz, DMSO-d$_6$) δ 8.90 (t, J=6.11 Hz, 1H), 8.76-8.82 (m, 1H), 8.10-8.21 (m, 2H), 7.85 (s, 1H), 7.75-7.81

(m, 2H), 7.72 (s, 1H), 7.59-7.64 (m, 1H), 7.50-7.58 (m, 1H), 7.08-7.18 (m, J=8.31 Hz, 2H), 6.50-6.58 (m, J=8.56 Hz, 2H), 4.27 (s, 2H), 3.54 (q, J=6.60 Hz, 2H), 2.54-2.58 (m, 2H); MS m/z 622 (M+H).

Example 42

3-(5-(2-(((2,2'-dichloro-4'-(trifluoromethyl)-[1,1'-biphenyl]-4-yl)amino)methyl)-5-(trifluoromethyl)phenyl)picolinamido)propanoic acid

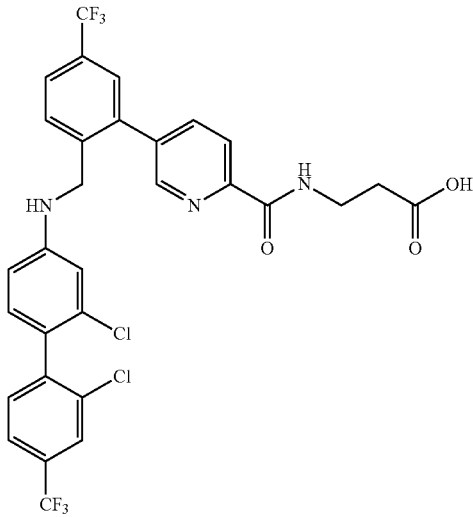

The title compound was prepared as described in Example 31 substituting (2-chloro-4-(trifluoromethyl)phenyl)boronic acid for (4-fluoro-3-(trifluoromethyl)phenyl)boronic acid.

$^1$H NMR (400 MHz, DMSO-$d_6$) δ 8.90 (t, J=5.87 Hz, 1H), 8.79 (s, 1H), 8.10-8.21 (m, 2H), 7.94 (s, 1H), 7.88 (d, J=8.31 Hz, 1H), 7.79 (d, J=8.31 Hz, 1H), 7.70-7.76 (m, 2H), 7.51 (d, J=7.83 Hz, 1H), 7.00 (d, J=8.31 Hz, 1H), 6.62 (d, J=1.96 Hz, 1H), 6.51 (dd, J=2.08, 8.44 Hz, 1H), 4.28 (s, 2H), 3.54 (q, J=6.85 Hz, 2H), 2.52-2.59 (m, 2H); MS m/z 656 (M+H).

Example 43

3-(5-(2-(((2-chloro-2'-methyl-4'-(trifluoromethyl)-[1,1'-biphenyl]-4-yl)amino)methyl)-5-(trifluoromethyl)phenyl)picolinamido)propanoic acid

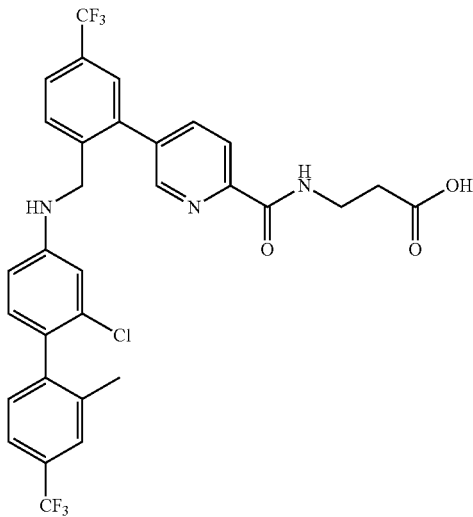 [SMILES: Cc1cc(C(F)(F)F)ccc1-c1ccc(NCc2ccc(C(F)(F)F)cc2-c2ccc(C(=O)NCCC(=O)O)nc2)cc1Cl]

STEP A: 2-chloro-2'-methyl-4'-(trifluoromethyl)-[1,1'-biphenyl]-4-amine

3-Chloro-4-iodoaniline (3.0 g, 11.8 mmol), (2-methyl-4-(trifluoromethyl)phenyl)boronic acid (2.9 g, 14.2 mmol), Pd(dppf)Cl$_2$ (1.0 g, 1.2 mmol), and K$_2$CO$_3$ (3.3 g, 23.7 mmol) were dissolved in 1,4-dioxane (40 mL) and water (10 mL) and the resulting mixture was heated to 80° C. After 16 h the resulting mixture was cooled to room temperature, diluted with EtOAc, washed with water and brine, dried (Na$_2$SO$_4$), and dry packed onto silica gel. Column chromatography yielded the title compound.

STEP B: N-(2-bromo-4-(trifluoromethyl)benzyl)-2-chloro-2'-methyl-4'-(trifluoromethyl)-[1,1'-biphenyl]-4-amine 2-Bromo-1-(bromomethyl)-4-(trifluoromethyl)benzene, prepared as described in Example 34 (2.5 g, 7.9 mmol), 2-chloro-2'-methyl-4'-(trifluoromethyl)-[1,1'-biphenyl]-4-amine (2.5 g, 8.7 mmol), and K$_2$CO$_3$ (1.6 g, 11.8 mmol) were diluted with DMF (20 mL) and heated to 80° C. After 3 h the resulting mixture was diluted with EtOAc, washed with water and brine, dried (Na2SO4), and dry packed onto silica gel. Column chromatography yielded the title compound.

STEP C: ethyl 3-(5-(2-(((2-chloro-2'-methyl-4'-(trifluoromethyl)-[1,1'-biphenyl]-4-yl)amino)methyl)-5-(trifluoromethyl)phenyl)picolinamido)propanoate N-(2-bromo-4-(trifluoromethyl)benzyl)-2-chloro-2'-methyl-4'-(trifluoromethyl)-[1,1'-biphenyl]-4-amine (3.9 g, 7.5 mmol), ethyl 3-(5-(4,4,5,5-tetramethyl-1,3,2-dioxaborolan-2-yl)picolinamido)propanoate, prepared as in STEP A above, (3.2 g, 6.6 mmol), Pd(dppf)Cl$_2$ (611 mg, 0.7 mmol), and K$_2$CO$_3$ (2.1 g, 14.9 mmol) were dissolved in 1,4-dioxane (60 mL) and water (15 mL) and the resulting mixture was heated to 80° C. After 16 h the resulting mixture was cooled to room temperature, diluted with EtOAc, washed with water and brine, dried (Na$_2$SO$_4$), and dry packed onto silica gel. Column chromatography yielded the title compound.

STEP D: 3-(5-(2-(((2-chloro-2'-methyl-4'-(trifluoromethyl)-[1,1'-biphenyl]-4-yl)amino)methyl)-5-(trifluoromethyl)phenyl)picolinamido)propanoic acid A 3M aqueous solution of NaOH (7.2 mL, 21.7 mmol) was added to a THF (20 mL) and MeOH (10 mL) solution of ethyl ethyl 3-(5-(2-(((2-chloro-2'-methyl-4'-(trifluoromethyl)-[1,1'-biphenyl]-4-yl)amino)methyl)-5-(trifluoromethyl)phenyl)picolinamido)propanoate (4.8 g, 7.2 mmol) and the resulting homogeneous mixture was stirred at room temperature. After 16 h the resulting mixture was concentrated in vacuo, suspended in water, and acidified with 2 M HCl. The resulting precipitate was filtered off, dried in vacuo, and purified via HPLC to yield the title compound.

$^1$H NMR (400 MHz, DMSO-$d_6$) δ 8.91 (t, J=5.99 Hz, 1H), 8.78 (s, 1H), 8.08-8.20 (m, 2H), 7.88 (d, J=8.31 Hz, 1H), 7.79 (d, J=8.07 Hz, 1H), 7.73 (s, 1H), 7.64 (s, 1H), 7.54 (d, J=8.07 Hz, 1H), 7.27 (d, J=8.07 Hz, 1H), 6.94 (d, J=8.31 Hz, 1H), 6.67-6.77 (m, 1H), 6.60 (d, J=2.20 Hz, 1H), 6.49 (dd, J=2.20, 8.31 Hz, 1H), 4.27 (d, J=5.14 Hz, 2H), 3.53 (q, J=6.60 Hz, 2H), 2.52-2.58 (m, 2H), 2.11 (s, 3H); MS m/z 636 (M+H).

Example 44

3-(5-(2-(((4'-chloro-[1,1'-biphenyl]-4-yl)amino)methyl)-5-(trifluoromethyl)phenyl)picolinamido)propanoic acid

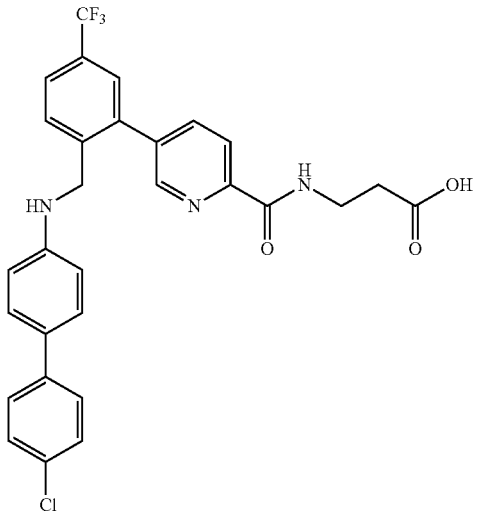

STEP A: N-(2-bromo-4-(trifluoromethyl)benzyl)-4'-chloro-[1,1'-biphenyl]-4-amine

Solid NaBH(OAc)₃ (1.4 g, 6.8 mmol) was added to a DCE solution (10 mL) of 2-bromo-4-(trifluoromethyl)benzaldehyde (860 mg, 3.4 mmol), 4'-chloro-[1,1'-biphenyl]-4-amine (761 mg, 3.7 mmol), and AcOH (0.78 mL, 13.6 mmol) and the resulting mixture was stirred at room temperature. After 16 h the resulting mixture diluted with EtOAc washed with water and brine, dried (Na₂SO₄), dry-packed onto silica gel and purified via column chromatography to yield the title compound.

STEP B: ethyl 3-(5-(2-(((4'-chloro-[1,1'-biphenyl]-4-yl)amino)methyl)-5-(trifluoromethyl)phenyl)picolinamido)propanoate N-(2-bromo-4-(trifluoromethyl)benzyl)-4'-chloro-[1,1'-biphenyl]-4-amine (1.4 g, 3.1 mmol), ethyl 3-(5-(4,4,5,5-tetramethyl-1,3,2-dioxaborolan-2-yl)picolinamido)propanoate, prepared as in step a, (1.6 g, 4.7 mmol), Pd(dppf)Cl₂ (255 mg, 0.3 mmol), and K₂CO₃ (859 mg, 6.2 mmol) were dissolved in 1,4-dioxane (24 mL) and water (6 mL) and the resulting mixture was heated to 80° C. After 16 h the resulting mixture was cooled to room temperature, diluted with EtOAc, washed with water and brine, dried (Na₂SO₄), and dry packed onto silica gel. Column chromatography yielded the title compound.

STEP C: 3-(5-(2-(((4'-chloro-[1,1'-biphenyl]-4-yl)amino)methyl)-5-(trifluoromethyl)phenyl)picolinamido)propanoic acid A 3M aqueous solution of NaOH (3.2 mL, 9.5 mmol) was added to a THF (10 mL) and MeOH (5 mL) solution of ethyl 345-(2-(((4'-chloro-[1,1'-biphenyl]-4-yl)amino)methyl)-5-(trifluoromethyl)phenyl)picolinamido)propanoate (1.9 g, 3.2 mmol) and the resulting homogeneous mixture was stirred at room temperature. After 16 h the resulting mixture was concentrated in vacuo, suspended in water, and acidified with 2 M HCl. The resulting precipitate was filtered off and dried in vacuo to yield the title compound.

¹H NMR (400 MHz, DMSO-d₆) δ 8.89 (t, J=5.99 Hz, 1H), 8.79 (s, 1H), 8.10-8.21 (m, 2H), 7.83 (d, J=8.07 Hz, 1H), 7.75 (d, J=8.31 Hz, 1H), 7.71 (s, 1H), 7.53 (d, J=8.31 Hz, 2H), 7.36 (d, J=8.56 Hz, 2H), 7.39 (d, J=8.31 Hz, 2H), 6.52 (d, J=8.56 Hz, 3H), 4.26 (s, 2H), 3.54 (q, J=6.85 Hz, 2H), 2.54-2.58 (m, 2H); MS m/z 554 (M+H).

Example 45

3-(5-(2-(((4'-chloro-[1,1'-biphenyl]-4-yl)amino)methyl)-5-methoxyphenyl)picolinamido)propanoic acid

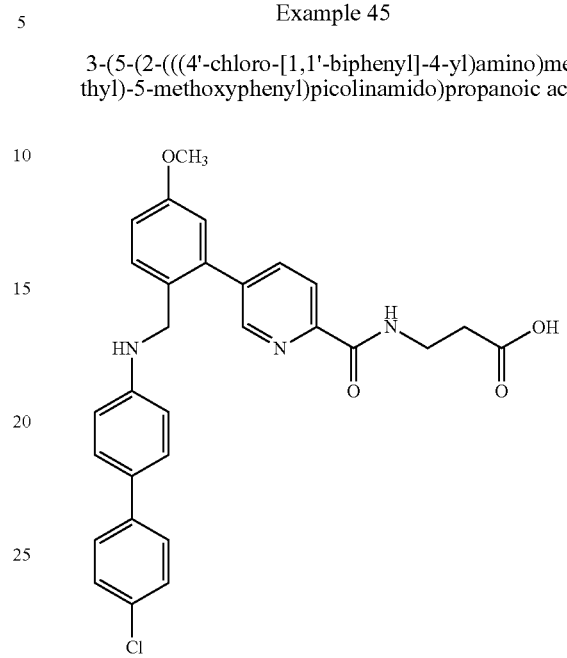

The title compound was prepared as described in Example 6 substituting (2-formyl-5-methoxyphenyl)boronic acid for (5-chloro-2-formylphenyl)boronic acid.

¹H NMR (400 MHz, DMSO-d₆) δ 8.81 (t, J=5.87 Hz, 1H), 8.73 (s, 1H), 8.08 (d, J=1.47 Hz, 2H), 7.52-7.59 (m, J=8.56 Hz, 2H), 7.35-7.47 (m, 6H), 7.15 (d, J=8.80 Hz, 1H), 6.64-6.74 (m, J=8.80 Hz, 2H), 4.32 (s, 2H), 3.79 (s, 3H), 3.53 (q, J=6.85 Hz, 2H), 2.54-2.59 (m, 2H); MS m/z 516 (M+H).

Example 46

3-(5-(2-(((2',4'-dichloro-[1,1'-biphenyl]-4-yl)amino)methyl)-5-methoxyphenyl)picolinamido)propanoic acid

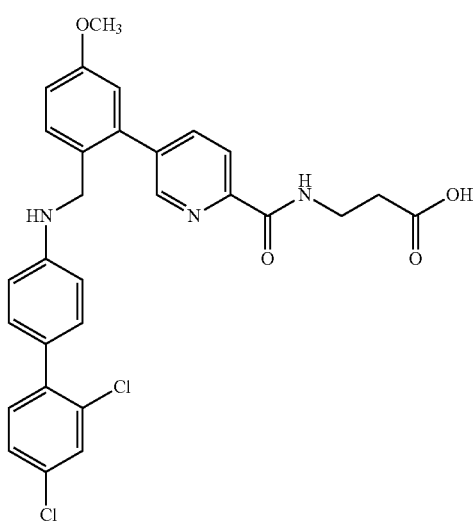 [SMILES: COc1ccc(CNc2ccc(-c3ccc(Cl)cc3Cl)cc2)c(-c2ccc(C(=O)NCCC(=O)O)nc2)c1]

The title compound was prepared as described in Example 6 substituting (2-formyl-5-methoxyphenyl)boronic acid and 2',4'-dichloro-[1,1'-biphenyl]-4-amine for (5-chloro-2-formylphenyl)boronic acid and 4'-chloro-[1,1'-biphenyl]-4-amine, respectively.

$^1$H NMR (400 MHz, DMSO-$d_6$) δ 8.81 (t, J=6.11 Hz, 1H), 8.75 (s, 1H), 8.04-8.11 (m, 2H), 7.64 (d, J=1.96 Hz, 1H), 7.40-7.48 (m, 3H), 7.32-7.37 (m, 1H), 7.16 (d, J=8.56 Hz, 3H), 6.68 (d, J=8.56 Hz, 2H), 4.31 (s, 2H), 3.79 (s, 3H), 3.49-3.58 (m, 2H), 2.54-2.58 (m, 2H); MS m/z 550 (M+H).

Example 47

3-(5-(5-methoxy-2-(((4'-(trifluoromethyl)-[1,1'-biphenyl]-4-yl)amino)methyl)phenyl)picolinamido)propanoic acid

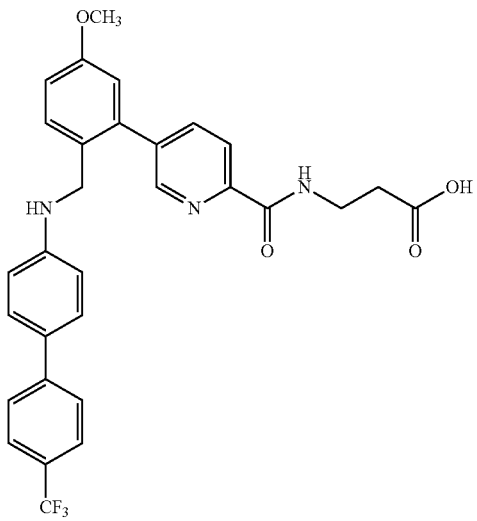 [SMILES: COc1ccc(CNc2ccc(-c3ccc(C(F)(F)F)cc3)cc2)c(-c2ccc(C(=O)NCCC(=O)O)nc2)c1]

STEP A: ethyl 3-(5-(2-formyl-5-methoxyphenyl)picolinamido)propanoate

Ethyl 3-(5-bromopicolinamido)propanoate (1.0 g, 3.3 mmol), (2-formyl-5-methoxyphenyl)boronic acid (777 mg, 4.3 mmol), Pd(dppf)Cl$_2$ (364 mg, 0.5 mmol), and K$_2$CO$_3$ (918 mg, 6.6 mmol) were dissolved in 1,4-dioxane (20 mL) and water (5 mL) and heated to 80° C. After 2 h the resulting mixture was cooled to room temperature, diluted with EtOAc washed with water and brine, dried (Na$_2$SO$_4$), concentrated and purified via column chromatography to yield the title compound.

STEP B: ethyl 3-(5-(2-(((4-bromophenyl)amino)methyl)-5-methoxyphenyl)picolinamido)propanoate Solid NaBH(OAc)$_3$ (1.3 g, 6.0 mmol) was added to a DCE solution (5 mL) of ethyl 3-(5-(2-formyl-5-methoxyphenyl)picolinamido)propanoate (1.4 g, 4.0 mmol), 4-bromoaniline (1.0 g, 6.0 mmol), and AcOH (0.23 mL, 4.0 mmol) and the resulting mixture was stirred at room temperature. After 16 h the resulting mixture diluted with EtOAc washed with water and brine, dried (Na$_2$SO$_4$), concentrated and purified via column chromatography to yield the title compound.

STEP C: ethyl 3-(5-(5-methoxy-2-(((4'-(trifluoromethyl)-[1,1-biphenyl]-4-yl)amino)methyl)phenyl)picolinamido)propanoate Ethyl 3-(5-(2-(((4-bromophenyl)amino)methyl)-5-methoxyphenyl)picolinamido)propanoate (200 mg, 0.39 mmol), (4-(trifluoromethyl)phenyl)boronic acid (111 mg, 0.59 mmol), Pd(dppf)Cl$_2$ (43 mg, 0.06 mmol), and K$_2$CO$_3$ (108 mg, 0.78 mmol) were dissolved in 1,4-dioxane (4 mL) and water (1 mL) and the resulting mixture was heated to 80° C. After 2 h the resulting mixture was cooled to room temperature, diluted with EtOAc, washed with water and brine, dried (Na$_2$SO$_4$), and dry packed onto silica gel. Column chromatography yielded the title compound.

STEP D: 3-(5-(5-methoxy-2-(((4'-(trifluoromethyl)-[1,1'-biphenyl]-4-yl)amino)methyl)phenyl)picolinamido)propanoic acid A 3M aqueous solution of NaOH (0.15 mL, 0.44 mmol) was added to a THF (1.8 mL) and MeOH (2 mL) solution of ethyl 3-(5-(5-methoxy-2-(((4'-(trifluoromethyl)-[1,1'-biphenyl]-4-yl)amino)methyl)phenyl)picolinamido)propanoate (85 mg, 0.15 mmol) and the resulting mixture was stirred at room temperature. After 2 h the resulting mixture was concentrated in vacuo, suspended in water, and acidified with 2 M HCl. The resulting precipitate was filtered off and dried in vacuo to yield the title compound.

$^1$H NMR (400 MHz, DMSO-$d_6$) δ 8.73-8.80 (m, 1H), 8.69 (s, 1H), 7.98-8.07 (m, 2H), 7.75 (d, J=7.58 Hz, 2H), 7.68 (d, J=7.58 Hz, 2H), 7.59 (d, J=7.34 Hz, 2H), 7.52 (s, 1H), 7.39-7.47 (m, 1H), 7.00-7.16 (m, 3H), 4.37 (s, 2H), 3.72 (s, 3H), 3.41-3.51 (m, 2H), 2.45-2.52 (m, 2H); MS m/z 550 (M+H).

Example 48

3-(5-(5-methoxy-2-(((4'-(trifluoromethoxy)-[1,1'-biphenyl]-4-yl)amino)methyl)phenyl)picolinamido)propanoic acid

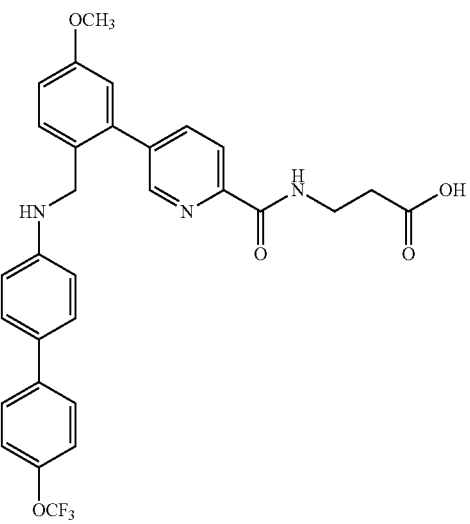 [SMILES: COc1ccc(CNc2ccc(-c3ccc(OC(F)(F)F)cc3)cc2)c(-c2ccc(C(=O)NCCC(=O)O)nc2)c1]

The title compound was prepared as described in Example 46 substituting (4-(trifluoromethoxy)phenyl)boronic acid for (4-(trifluoromethyl)phenyl)boronic acid.

$^1$H NMR (400 MHz, DMSO-$d_6$) δ 8.78-8.87 (m, 1H), 8.76 (s, 1H), 8.05-8.12 (m, 2H), 7.71 (d, J=7.83 Hz, 2H), 7.55-7.62 (m, 3H), 7.46-7.53 (m, 1H), 7.40 (d, J=7.83 Hz, 2H), 7.06-7.19 (m, 3H), 4.42 (s, 2H), 3.79 (s, 3H), 3.48-3.57 (m, 2H), 2.52-2.60 (m, 2H); MS m/z 566 (M+H).

Example 49

3-(5-(2-(((4'-(tert-butyl)-[1,1'-biphenyl]-4-yl)amino)methyl)-5-methoxyphenyl)picolinamido)propanoic acid

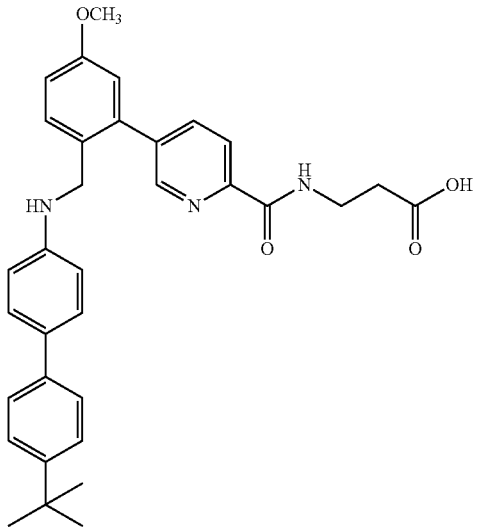 [SMILES: COc1ccc(CNc2ccc(-c3ccc(C(C)(C)C)cc3)cc2)c(-c2ccc(C(=O)NCCC(=O)O)nc2)c1]

The title compound was prepared as described in Example 47 substituting (4-(tert-butyl)phenyl)boronic acid for (4-(trifluoromethyl)phenyl)boronic acid.

$^1$H NMR (400 MHz, DMSO-d$_6$) δ 8.82-8.88 (m, 1H), 8.78 (s, 1H), 8.02-8.14 (m, 2H), 7.64-7.73 (m, 3H), 7.52-7.59 (m, 3H), 7.42-7.50 (m, 4H), 7.16 (d, J=8.07 Hz, 1H), 4.50 (s, 2H), 3.80 (s, 3H), 3.48-3.56 (m, 2H), 2.52-2.59 (m, 1H), 1.30 (s, 9H); MS m/z 538 (M+H).

Example 50

3-(5-(5-methoxy-2-(((3'-(trifluoromethoxy)-[1,1'-biphenyl]-4-yl)amino)methyl)phenyl)picolinamido)propanoic acid

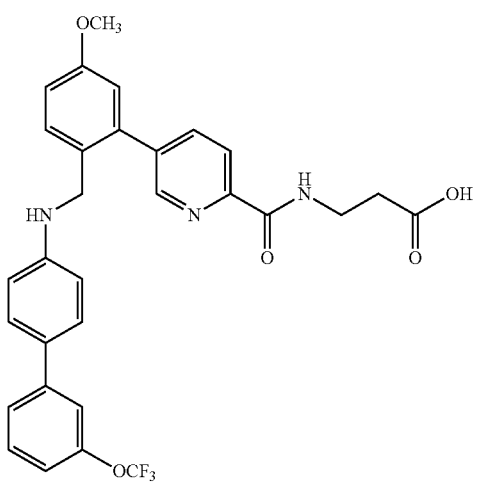 [SMILES: COc1ccc(CNc2ccc(-c3cccc(OC(F)(F)F)c3)cc2)c(-c2ccc(C(=O)NCCC(=O)O)nc2)c1]

The title compound was prepared as described in Example 47 substituting (3-(trifluoromethoxy)phenyl)boronic acid for (4-(trifluoromethyl)phenyl)boronic acid.

$^1$H NMR (400 MHz, DMSO-d$_6$) δ 8.80-8.86 (m, 1H), 8.76 (s, 1H), 8.04-8.13 (m, 2H), 7.71 (d, J=8.31 Hz, 2H), 7.56-7.62 (m, 3H), 7.46-7.53 (m, 1H), 7.36-7.44 (m, 2H), 7.07-7.19 (m, 3H), 4.42 (s, 2H), 3.48-3.57 (m, 2H), 2.53-2.59 (m, 2H); MS m/z 566 (M+H).

Example 51

3-(5-(5-chloro-2-(((2,2',4'-trichloro-[1,1'-biphenyl]-4-yl)amino)methyl)phenyl)picolinamido)propanoic acid

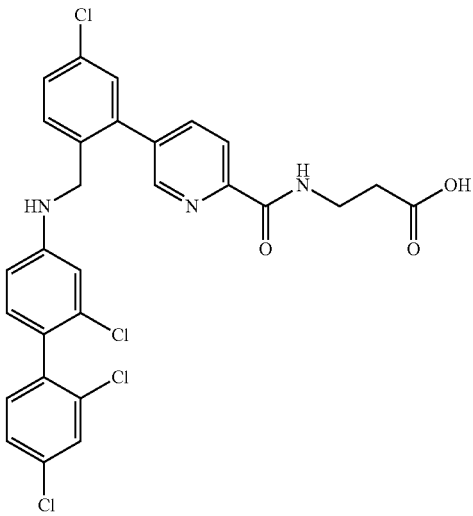 [SMILES: O=C(O)CCNC(=O)c1ccc(-c2cc(Cl)ccc2CNc2ccc(-c3ccc(Cl)cc3Cl)c(Cl)c2)cn1]

The title compound was prepared as described in Example 11 substituting 4-bromo-3-chloroaniline for 4-bromo-2-fluoroaniline.

$^1$H NMR (400 MHz, DMSO-d$_6$) δ 8.84-8.93 (m, 1H), 8.74 (s, 1H), 8.11 (s, 2H), 7.68 (d, J=1.96 Hz, 1H), 7.54-7.61 (m, 2H), 7.42-7.49 (m, 2H), 7.29 (d, J=8.31 Hz, 1H), 6.95 (d, J=8.31 Hz, 1H), 6.56 (d, J=2.20 Hz, 1H), 6.47 (dd, J=2.20, 8.56 Hz, 1H), 4.16 (s, 2H), 3.44-3.58 (m, 2H), 2.54-2.58 (m, 2H); MS m/z 590 (M+H).

Example 52

3-(5-(5-chloro-2-(((2-chloro-4'-fluoro-[1,1'-biphenyl]-4-yl)amino)methyl)phenyl)picolinamido)propanoic acid

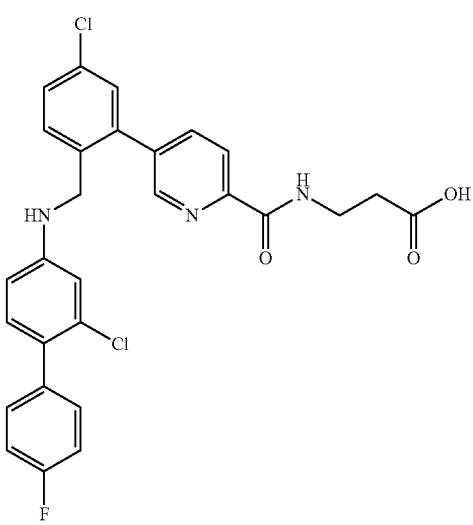 [SMILES: O=C(O)CCNC(=O)c1ccc(-c2cc(Cl)ccc2CNc2ccc(-c3ccc(F)cc3)c(Cl)c2)cn1]

The title compound was prepared as described in Example 11 substituting 4-bromo-3-chloroaniline and (4-fluorophenyl)boronic acid for 4-bromo-2-fluoroaniline and (2,4-dichlorophenyl)boronic acid, respectively.

¹H NMR (400 MHz, DMSO-d₆) δ 8.84-8.92 (m, 1H), 8.74 (s, 1H), 8.10-8.13 (m, 2H), 7.56 (s, 2H), 7.47 (s, 1H), 7.33-7.38 (m, 2H), 7.21 (t, J=8.93 Hz, 2H), 7.05 (d, J=8.56 Hz, 1H), 6.55 (d, J=2.45 Hz, 1H), 6.47 (dd, J=2.20, 8.31 Hz, 1H), 4.16 (s, 2H), 3.53 (q, J=6.85 Hz, 2H), 2.54-2.57 (m, 2H); MS m/z 538 (M+H).

Example 53

3-(5-(2-(((3',4'-dichloro-2-fluoro-[1,1'-biphenyl]-4-yl)amino)methyl)-5-fluorophenyl)picolinamido)propanoic acid

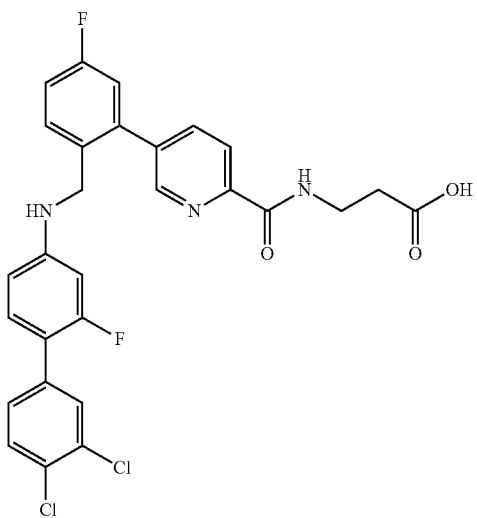 [SMILES: O=C(O)CCNC(=O)c1ccc(-c2cc(F)ccc2CNc2ccc(-c3ccc(Cl)c(Cl)c3)c(F)c2)cn1]

STEP A: methyl 5-(5-fluoro-2-formylphenyl)picolinate 2-bromo-4-fluorobenzaldehyde (800 mg, 3.9 mmol), methyl 5-(4,4,5,5-tetramethyl-1,3,2-dioxaborolan-2-yl)picolinate (1.2 g, 4.7 mmol), Pd(dppf)Cl₂ (433 mg, 0.6 mmol), and K₂CO₃ (1.1 g, 7.9 mmol) were dissolved in 1,4-dioxane (40 mL) and water (10 mL) and the resulting mixture was heated to 65° C. After 1.5 h the resulting mixture was cooled to room temperature, diluted with EtOAc, washed with water and brine, dried (Na₂SO₄), and dry packed onto silica gel. Column chromatography yielded the title compound.

STEP B: methyl 5-(2-(((4-bromo-3-fluorophenyl)amino)methyl)-5-fluorophenyl)picolinate Solid NaBH(OAc)₃ (491 mg, 2.3 mmol) was added to a DCE solution (4 mL) of methyl 5-(5-fluoro-2-formylphenyl)picolinate (300 mg, 1.2 mmol), 4-bromo-3-fluoroaniline (242 mg, 1.3 mmol), and AcOH (0.27 mL, 4.6 mmol) and the resulting mixture was stirred at room temperature. After 16 h the resulting mixture diluted with EtOAc washed with water and brine, dried (Na₂SO₄), concentrated and purified via column chromatography to yield the title compound.

STEP C: 5-(2-(((4-bromo-3-fluorophenyl)amino)methyl)-5-fluorophenyl)picolinic acid A 3M aqueous solution of NaOH (0.81 mL, 2.4 mmol) was added to a THF solution (13.7 mL) of methyl 5-(2-(((4-bromo-3-fluorophenyl)amino)methyl)-5-fluorophenyl)picolinate (350 mg, 0.8 mmol) and the resulting mixture was stirred at room temperature. After 2 h the resulting mixture was concentrated in vacuo, suspended in water, and acidified with 2 M HCl. The resulting precipitate was filtered off and dried in vacuo to yield the title compound.

STEP D: ethyl 3-(5-(2-(((4-bromo-3-fluorophenyl)amino)methyl)-5-fluorophenyl)picolinamido)propanoate Solid HATU (227 mg, 0.60 mmol) was added to a THF solution (4.8 mL) of 5-(2-(((4-bromo-3-fluorophenyl)amino)methyl)-5-fluorophenyl)picolinic acid (250 mg, 0.60 mmol), i-Pr₂NEt (0.31 mL, 1.79 mmol), and β-alanine ethyl ester hydrochloride (96 mg, 0.63) and the resulting mixture was stirred at room temperature. After 16 h the resulting mixture was diluted with EtOAc, washed with water and brine, dried (Na₂SO₄), concentrated and purified via column chromatography to yield the title compound.

STEP E: ethyl 3-(5-(2-(((3',4'-dichloro-2-fluoro-[1,1'-biphenyl]-4-yl)amino)methyl)-5-fluorophenyl)picolinamido)propanoate Ethyl 3-(5-(2-(((4-bromo-3-fluorophenyl)amino)methyl)-5-fluorophenyl)picolinamido)propanoate (100 mg, 0.19 mmol), (3,4-dichlorophenyl)boronic acid (44 mg, 0.23 mmol), Pd(dppf)Cl₂ (21 mg, 0.03 mmol), and K₂CO₃ (53 mg, 0.39 mmol) were dissolved in 1,4-dioxane (4 mL) and water (1 mL) and the resulting mixture was heated to 80° C. After 16 h the resulting mixture was cooled to room temperature, diluted with EtOAc, washed with water and brine, dried (Na₂SO₄), concentrated and purified via column chromatography to yield the title compound.

STEP F: 3-(5-(2-(((3',4'-dichloro-2-fluoro-[1,1'-biphenyl]-4-yl)amino)methyl)-5-fluorophenyl)picolinamido)propanoic acid A 3M aqueous solution of NaOH (0.10 mL, 0.31 mmol) was added to a THF solution (3 mL) of ethyl 3-(5-(2-(((3',4'-dichloro-2-fluoro-[1,1'-biphenyl]-4-yl)amino)methyl)-5-fluorophenyl)picolinamido)propanoate (60 mg, 0.10 mmol) and the resulting mixture was stirred at room temperature. After 16 h the resulting mixture was concentrated in vacuo, suspended in water, and acidified with 2 M HCl. The resulting precipitate was filtered off and dried in vacuo to yield the title compound.

¹H NMR (400 MHz, DMSO-d₆) δ 8.86 (t, J=6.11 Hz, 1H), 8.73 (d, J=1.71 Hz, 1H), 8.10 (s, 2H), 7.61-7.67 (m, 2H), 7.53-7.59 (m, 1H), 7.38-7.44 (m, 1H), 7.20-7.35 (m, 3H), 6.40 (dd, J=2.20, 8.56 Hz, 1H), 6.32 (dd, J=2.20, 14.18 Hz, 1H), 4.15 (s, 2H), 3.52 (q, J=6.77 Hz, 2H), 2.51-2.57 (m, 2H); MS m/z 556 (M+H).

Example 54

3-(5-(5-chloro-2-(((2-methoxy-4'-(trifluoromethyl)-[1,1'-biphenyl]-4-yl)amino)methyl)phenyl)picolinamido)propanoic acid

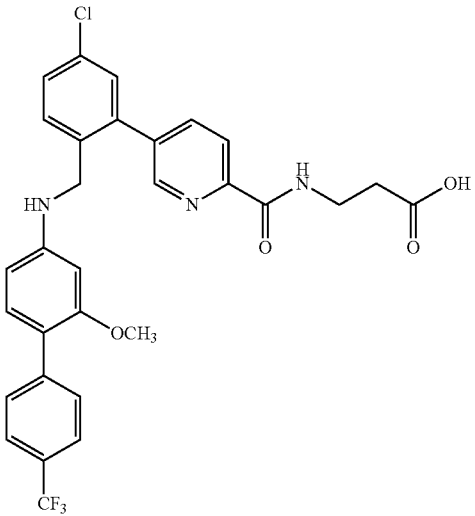 [SMILES: COc1cc(NCc2ccc(Cl)cc2-c2ccc(C(=O)NCCC(=O)O)nc2)ccc1-c1ccc(C(F)(F)F)cc1]

The title compound was prepared as described in Example 11 substituting 4-bromo-3-methoxyaniline and (4-(trifluoromethyl)phenyl)boronic acid for 4-bromo-2-fluoroaniline and (2,4-dichlorophenyl)boronic acid, respectively.

$^1$H NMR (400 MHz, DMSO-d$_6$) δ 8.85-8.90 (m, 1H), 8.75 (s, 1H), 8.10-8.14 (m, 2H), 7.51-7.68 (m, 6H), 7.46 (d, J=1.96 Hz, 1H), 6.99-7.06 (m, 1H), 6.21 (d, J=1.96 Hz, 1H), 6.10 (dd, J=1.83, 8.44 Hz, 1H), 4.19 (s, 2H), 3.64 (s, 3H), 3.53 (q, J=6.68 Hz, 2H), 2.52-2.58 (m, 2H); MS m/z 584 (M+H).

Example 55

3-(5-(5-chloro-2-(((3',4'-dichloro-2-(trifluoromethyl)-[1,1'-biphenyl]-4-yl)amino)methyl)phenyl)picolinamido)propanoic acid

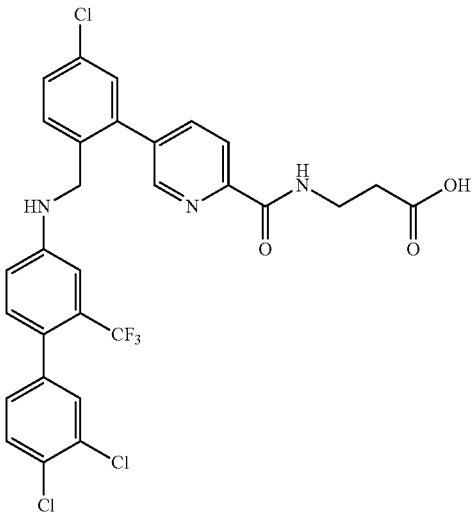

The title compound was prepared as described in Example 11 substituting 4-bromo-3-(trifluoromethyl)aniline and (3,4-dichlorophenyl)boronic acid for 4-bromo-2-fluoroaniline and (2,4-dichlorophenyl)boronic acid, respectively.

$^1$H NMR (400 MHz, DMSO-d$_6$) δ 8.86 (t, J=5.99 Hz, 1H), 8.72 (d, J=1.47 Hz, 1H), 8.09 (s, 2H), 7.61-7.64 (m, 1H), 7.54-7.57 (m, 2H), 7.45-7.48 (m, 2H), 7.21 (dd, J=2.20, 8.31 Hz, 1H), 7.05 (d, J=8.56 Hz, 1H), 6.84 (d, J=2.45 Hz, 1H), 6.61-6.67 (m, 1H), 4.22 (s, 2H), 3.49-3.57 (m, 2H), 2.52-2.59 (m, 2H); MS m/z 622 (M+H).

Example 56

3-(5-(5-fluoro-2-(((2-fluoro-4'-(trifluoromethyl)-[1,1'-biphenyl]-4-yl)amino)methyl)phenyl)picolinamido)propanoic acid

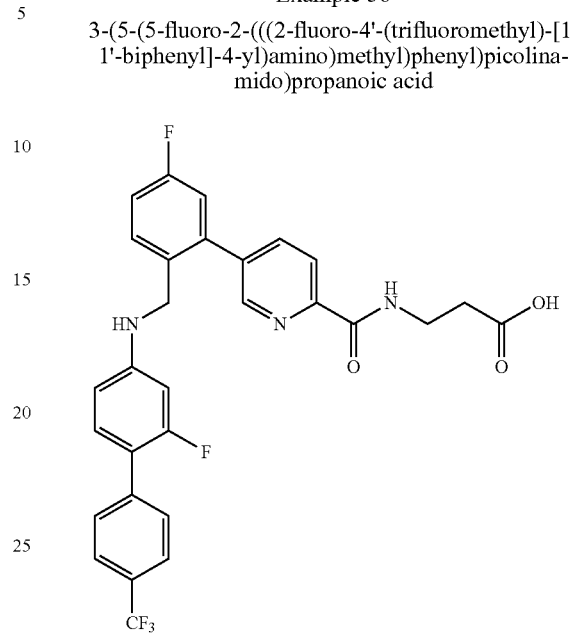

The title compound was prepared as described in Example 53 substituting (4-(trifluoromethyl)phenyl)boronic acid for (3,4-dichlorophenyl)boronic acid.

$^1$H NMR (400 MHz, DMSO-d$_6$) δ 8.87 (t, J=5.99 Hz, 1H), 8.74 (d, J=1.22 Hz, 1H), 8.06-8.15 (m, 2H), 7.70-7.76 (m, J=8.31 Hz, 2H), 7.62-7.68 (m, J=8.07 Hz, 2H), 7.58 (dd, J=6.11, 8.56 Hz, 1H), 7.22-7.37 (m, 3H), 6.44 (dd, J=2.20, 8.56 Hz, 1H), 6.34 (dd, J=2.08, 14.31 Hz, 1H), 4.16 (s, 2H), 3.52 (q, J=6.85 Hz, 2H), 2.51-2.58 (m, 2H); MS m/z 556 (M+H).

Example 57

3-(5-(2-(((2',4'-dichloro-2-fluoro-[1,1'-biphenyl]-4-yl)amino)methyl)-5-fluorophenyl)picolinamido)propanoic acid

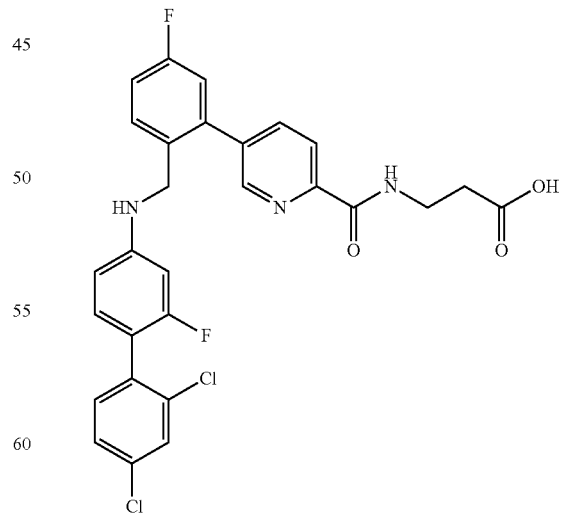

The title compound was prepared as described in Example 53 substituting (2,4-dichlorophenyl)boronic acid for (3,4-dichlorophenyl)boronic acid.

$^1$H NMR (400 MHz, DMSO-d$_6$) δ 8.88 (t, J=6.11 Hz, 1H), 8.74 (s, 1H), 8.06-8.15 (m, 2H), 7.67 (d, J=2.20 Hz, 1H), 7.60

(dd, J=5.87, 8.56 Hz, 1H), 7.45 (dd, J=2.20, 8.31 Hz, 1H), 7.24-7.38 (m, 3H), 6.99 (t, J=8.56 Hz, 1H), 6.39 (dd, J=2.20, 8.56 Hz, 1H), 6.31 (dd, J=1.96, 13.20 Hz, 1H), 4.14 (s, 2H), 3.53 (q, J=6.85 Hz, 2H), 2.51-2.58 (m, 2H); MS m/z 556 (M+H).

Example 58

3-(5-(5-chloro-2-(((3',4'-dichloro-[1,1'-biphenyl]-4-yl)amino)methyl)phenyl)picolinamido)propanoic acid

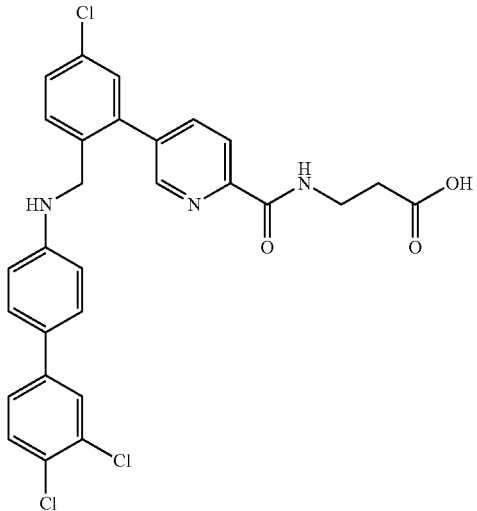 [SMILES: O=C(O)CCNC(=O)c1ccc(-c2cc(Cl)ccc2CNc2ccc(-c3ccc(Cl)c(Cl)c3)cc2)cn1]

The title compound was prepared as described in Example 11 substituting 4-bromoaniline and (3,4-dichlorophenyl)boronic acid for 4-bromo-2-fluoroaniline and (2,4-dichlorophenyl)boronic acid, respectively.

$^1$H NMR (400 MHz, DMSO-$d_6$) δ 8.87 (t, J=5.99 Hz, 1H), 8.74 (s, 1H), 8.07-8.13 (m, 2H), 7.75 (d, J=1.96 Hz, 1H), 7.57-7.61 (m, 1H), 7.49-7.55 (m, 3H), 7.46 (d, J=1.96 Hz, 1H), 7.41 (d, J=8.56 Hz, 2H), 6.51 (d, J=8.56 Hz, 2H), 4.16 (s, 2H), 3.53 (q, J=6.68 Hz, 2H), 2.52-2.58 (m, 2H); MS m/z 554 (M+H).

Example 59

3-(5-(2-(((4'-(tert-butyl)-[1,1'-biphenyl]-4-yl)amino)methyl)-5-chlorophenyl)picolinamido)propanoic acid

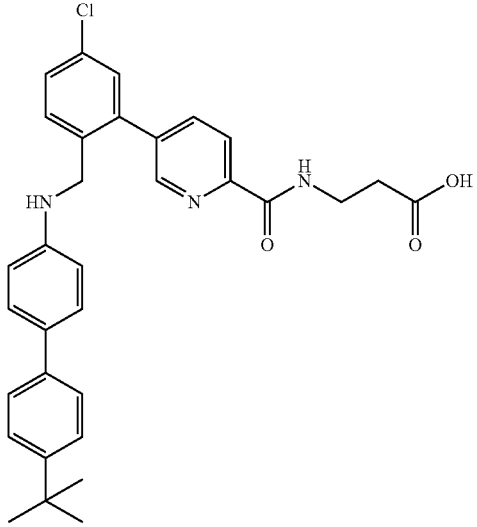 [SMILES: CC(C)(C)c1ccc(-c2ccc(NCc3ccc(Cl)cc3-c3ccc(C(=O)NCCC(=O)O)nc3)cc2)cc1]

The title compound was prepared as described in Example 11 substituting 4-bromoaniline and (4-(tert-butyl)phenyl)boronic acid for 4-bromo-2-fluoroaniline and (2,4-dichlorophenyl)boronic acid, respectively.

$^1$H NMR (400 MHz, DMSO-$d_6$) δ 8.88 (t, J=6.11 Hz, 1H), 8.76 (s, 1H), 8.08-8.16 (m, 2H), 7.50-7.59 (m, 2H), 7.35-7.47 (m, 5H), 7.29-7.35 (m, J=8.56 Hz, 2H), 6.48-6.54 (m, J=8.56 Hz, 2H), 4.14 (s, 2H), 3.53 (q, J=6.85 Hz, 2H), 2.52-2.58 (m, 2H), 1.28 (s, 9H); MS m/z 542 (M+H).

Example 60

3-(5-(2-(((2',4'-dichloro-[1,1'-biphenyl]-4-yl)amino)methyl)-4-methoxyphenyl)picolinamido)propanoic acid

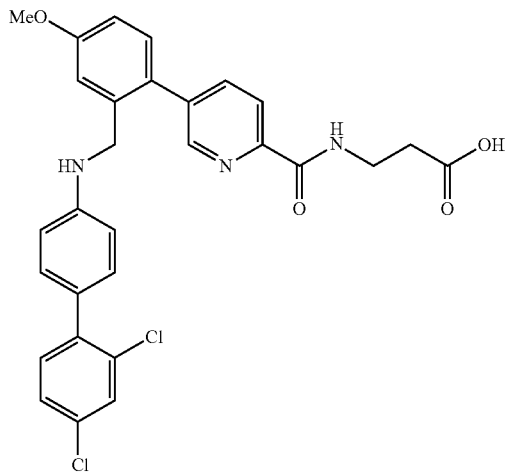 [SMILES: COc1ccc(-c2ccc(C(=O)NCCC(=O)O)nc2)c(CNc2ccc(-c3ccc(Cl)cc3Cl)cc2)c1]

STEP A: ethyl 3-(5-(2-formyl-4-methoxyphenyl)picolinamido)propanoate

Ethyl 3-(5-bromopicolinamido)propanoate (1.0 g, 3.3 mmol), (2-formyl-4-methoxyphenyl)boronic acid (896 mg, 5.0 mmol), Pd(dppf)Cl$_2$ (364 mg, 0.5 mmol), and K$_2$CO$_3$ (918 mg, 6.6 mmol) were dissolved in 1,4-dioxane (20 mL) and water (5 mL) and heated to 80° C. After 16 h the resulting mixture was cooled to room temperature, diluted with EtOAc washed with water and brine, dried (Na$_2$SO$_4$), concentrated and purified via column chromatography to yield the title compound.

STEP B: ethyl 3-(5-(2-(((2',4'-dichloro-[1,1'-biphenyl]-4-yl)amino)methyl)-4-methoxyphenyl)picolinamido)propanoate Solid NaBH(OAc)$_3$ (89 mg, 0.42 mmol) was added to a DCE solution (1 mL) of ethyl 3-(5-(2-formyl-4-methoxyphenyl)picolinamido)propanoate (100 mg, 0.28 mmol), 2',4'-dichloro-[1,1'-biphenyl]-4-amine (100 mg, 0.42 mmol), and AcOH (0.02 mL, 0.28 mmol) and the resulting mixture was stirred at room temperature. After 16 h the resulting mixture diluted with EtOAc washed with water and brine, dried (Na$_2$SO$_4$), concentrated and purified via column chromatography to yield the title compound.

STEP C: 3-(5-(2-(((2',4'-dichloro-[1,1'-biphenyl]-4-yl)amino)methyl)-4-methoxyphenyl)picolinamido) propanoic acid A 3M aqueous solution of NaOH (0.20 mL, 0.60 mmol) was added to a THF solution (3 mL) of ethyl 3-(5-(2-(((2',4'- dichloro-[1,1'-biphenyl]-4-yl)amino)methyl)-4-methoxyphenyl)picolinamido)propanoate (116 mg, 0.20 mmol) and the resulting mixture was stirred at room temperature. After 16 h the resulting mixture was concentrated in vacuo, suspended in water, and acidified with 2 M HCl. The resulting precipitate was filtered off and dried in vacuo to yield the title compound.

$^1$H NMR (400 MHz, DMSO-d$_6$) δ 8.82-8.87 (m, 1H), 8.69 (d, J=1.47 Hz, 1H), 8.02-8.08 (m, 2H), 7.63 (d, J=2.20 Hz, 1H), 7.49-7.53 (m, 1H), 7.40-7.42 (m, 1H), 7.35 (s, 1H), 7.33 (d, J=1.71 Hz, 1H), 7.13-7.16 (m, 2H), 7.12 (s, 1H), 7.01 (dd, J=2.57, 8.44 Hz, 1H), 6.56 (d, J=8.56 Hz, 2H), 4.16 (s, 2H), 3.79 (s, 3H), 3.52 (q, J=6.93 Hz, 2H), 2.51-2.58 (m, 2H); MS m/z 550 (M+H).

Example 61

3-(5-(2-(((3',4'-dichloro-[1,1'-biphenyl]-4-yl)amino)methyl)-4-methoxyphenyl)picolinamido)propanoic acid

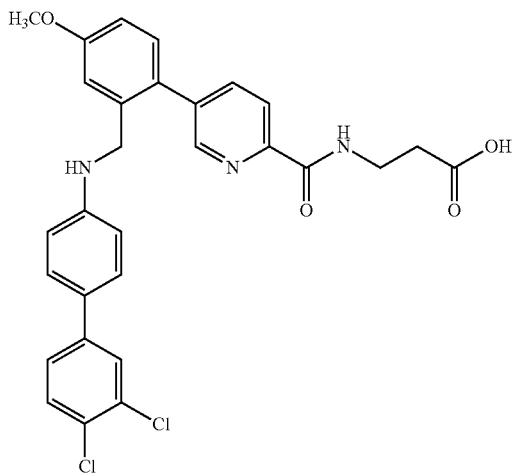 [SMILES: COc1ccc(-c2ccc(C(=O)NCCC(=O)O)nc2)c(CNc2ccc(-c3ccc(Cl)c(Cl)c3)cc2)c1]

STEP A: ethyl 3-(5-(2-(((4-bromophenyl)amino)methyl)-4-methoxyphenyl)picolinamido)propanoate Solid NaBH(OAc)$_3$ (446 mg, 2.1 mmol) was added to a DCE solution (7 mL) of ethyl 3-(5-(2-formyl-4-methoxyphenyl)picolinamido)propanoate, prepared as in Example 58 (500 mg, 1.4 mmol), 4-bromoaniline (362 mg, 2.1 mmol), and AcOH (0.08 mL, 1.4 mmol) and the resulting mixture was stirred at room temperature. After 16 h the resulting mixture diluted with EtOAc washed with water and brine, dried (Na$_2$SO$_4$), concentrated and purified via column chromatography to yield the title compound.

STEP B: ethyl 3-(5-(2-(((3',4'-dichloro-[1,1'-biphenyl]-4-yl)amino)methyl)-4-methoxyphenyl)picolinamido)propanoate Ethyl 3-(5-(2-(((4-bromophenyl)amino)methyl)-4-methoxyphenyl)picolinamido)propanoate (100 mg, 0.20 mmol), (2-formyl-4-methoxyphenyl)boronic acid (56 mg, 0.29 mmol), Pd(dppf)Cl$_2$ (21 mg, 0.03 mmol), and K$_2$CO$_3$ (54 mg, 0.39 mmol) were dissolved in 1,4-dioxane (4 mL) and water (1 mL) and heated to 80° C. After 16 h the resulting mixture was cooled to room temperature, diluted with EtOAc washed with water and brine, dried (Na$_2$SO$_4$), concentrated and purified via column chromatography to yield the title compound.

STEP C: 3-(5-(2-(((3',4'-dichloro-[1,1'-biphenyl]-4-yl)amino)methyl)-4-methoxyphenyl)picolinamido) propanoic acid A 3M aqueous solution of NaOH (0.20 mL, 0.60 mmol) was added to a THF solution (3 mL) of ethyl 3-(5-(2-(((3',4'-dichloro-[1,1'-biphenyl]-4-yl)amino)methyl)-4-methoxyphenyl)picolinamido)propanoate (116 mg, 0.20 mmol) and the resulting mixture was stirred at room temperature. After 16 h the resulting mixture was concentrated in vacuo, suspended in water, and acidified with 2 M HCl. The resulting precipitate was filtered off and dried in vacuo to yield the title compound.

$^1$H NMR (400 MHz, DMSO-d$_6$) δ 8.83 (t, J=5.99 Hz, 1H), 8.68 (d, J=1.22 Hz, 1H), 8.01-8.11 (m, 2H), 7.76 (d, J=2.20 Hz, 1H), 7.58 (d, J=8.56 Hz, 1H), 7.49-7.54 (m, 1H), 7.42 (d, J=8.80 Hz, 2H), 7.31 (d, J=8.56 Hz, 1H), 7.11 (d, J=2.69 Hz, 1H), 7.00 (dd, J=2.57, 8.44 Hz, 1H), 6.54 (d, J=8.56 Hz, 2H), 4.17 (s, 2H), 3.78 (s, 3H), 3.47-3.57 (m, 2H), 2.52-2.58 (m, 2H); MS m/z 550 (M+H).

Example 62

3-(5-(2-(((3'-fluoro-[1,1'-biphenyl]-4-yl)amino)methyl)-5-(trifluoromethyl)phenyl)picolinamido)propanoic acid

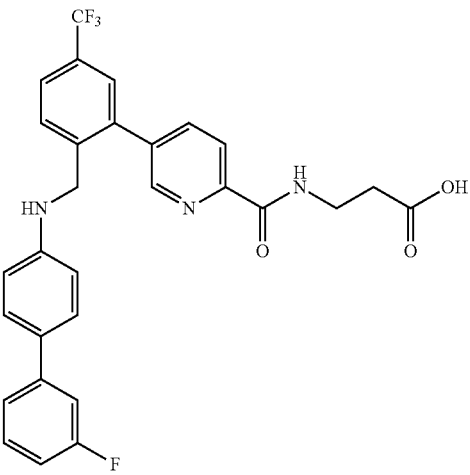 [SMILES: O=C(O)CCNC(=O)c1ccc(-c2cc(C(F)(F)F)ccc2CNc2ccc(-c3cccc(F)c3)cc2)cn1]

The title compound was prepared as described in Example 22 substituting 3'-fluoro-[1,1'-biphenyl]-4-amine for 4-iodoaniline.

$^1$H NMR (400 MHz, DMSO-d$_6$) δ 8.88 (t, J=5.99 Hz, 1H), 8.79 (d, J=1.22 Hz, 1H), 8.10-8.20 (m, 2H), 7.80-7.87 (m, 1H), 7.73-7.78 (m, 1H), 7.71 (s, 1H), 7.40 (d, J=8.80 Hz, 2H), 7.36-7.39 (m, 2H), 7.33 (dd, J=1.96, 12.47 Hz, 1H), 6.97-7.05 (m, 1H), 6.52 (d, J=8.56 Hz, 2H), 4.27 (s, 2H), 3.54 (q, J=6.85 Hz, 2H), 2.52-2.57 (m, 2H); MS m/z 538 (M+H).

Example 63

3-(5-(5-chloro-2-(((2-chloro-2',4'-difluoro-[1,1'-biphenyl]-4-yl)amino)methyl)phenyl)picolinamido)propanoic acid

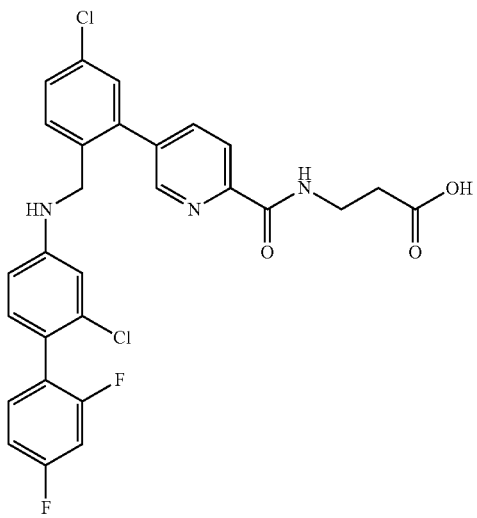 [SMILES: O=C(O)CCNC(=O)c1ccc(-c2cc(Cl)ccc2CNc2ccc(-c3ccc(F)cc3F)c(Cl)c2)cn1]

The title compound was prepared as described in Example 11 substituting 4-bromo-3-chloroaniline and (2,4-difluorophenyl)boronic acid for 4-bromo-2-fluoroaniline and (2,4-dichlorophenyl)boronic acid, respectively.

$^1$H NMR (400 MHz, DMSO-d$_6$) δ 8.86-8.92 (m, 1H), 8.74 (s, 1H), 8.12 (d, J=1.47 Hz, 2H), 7.56 (s, 2H), 7.47 (s, 1H), 7.24-7.36 (m, 2H), 7.07-7.16 (m, 1H), 7.01 (d, J=8.31 Hz, 1H), 6.58 (d, J=2.20 Hz, 1H), 6.48 (dd, J=2.20, 8.56 Hz, 1H), 4.16 (s, 2H), 3.53 (q, J=6.77 Hz, 2H), 2.52-2.58 (m, 2H); MS m/z 556 (M+H).

Example 64

3-(5-(2-(((4'-chloro-[1,1'-biphenyl]-4-yl)amino)methyl)-6-(trifluoromethyl)phenyl)picolinamido)propanoic acid

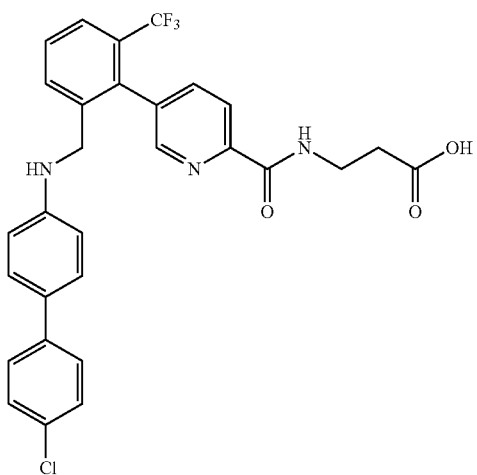 [SMILES: O=C(O)CCNC(=O)c1ccc(-c2c(CNc3ccc(-c4ccc(Cl)cc4)cc3)cccc2C(F)(F)F)cn1]

STEP A: ethyl 3-(5-(2-formyl-6-(trifluoromethyl)phenyl)picolinamido)propanoate 2-Chloro-3-(trifluoromethyl)benzaldehyde (199 mg, 0.96 mmol), ethyl 3-(5-(4,4,5,5-tetramethyl-1,3,2-dioxaborolan-2-yl)picolinamido)propanoate (410 mg, 1.2 mmol), Pd$_2$(dba)$_3$ (26 mg, 0.03 mmol), and 2M K$_3$PO$_4$ (aq) (1.0 mL, 2.0 mmol) were dissolved in 1,4-dioxane (2.9 mL) and heated to 100° C. After 2.5 h the resulting mixture was concentrated, taken up in DCM and the aqueous layer was extracted with DCM. The combined organics were dried (Na$_2$SO$_4$), concentrated and purified via column chromatography to yield the title compound.

STEP B: ethyl 3-(5-(2-(((4'-chloro-[1,1'-biphenyl]-4-yl)amino)methyl)-6-(trifluoromethyl)phenyl)picolinamido)propanoate Solid NaBH(OAc)$_3$ (68 mg, 0.32 mmol) was added to a DCM solution (0.4 mL) of ethyl 3-(5-(2-formyl-6-(trifluoromethyl)phenyl)picolinamido)propanoate (50.8 mg, 0.13 mmol) and 4'-chloro-[1,1'-biphenyl]-4-amine (28.9 mg, 0.14 mmol), and AcOH (0.07 mL) and the resulting mixture was warmed to 40° C. After 45 min 5M aqueous K$_2$CO$_3$ was added and the resulting mixture was extracted with DCM. The combined organics were dried (Na$_2$SO$_4$), concentrated and purified via column chromatography to yield the title compound.

STEP C: 3-(5-(2-(((4'-chloro-[1,1'-biphenyl]-4-yl)amino)methyl)-6-(trifluoromethyl)phenyl)picolinamido)propanoic acid A 1M aqueous solution of NaOH (0.30 mL, 0.30 mmol) was added to a THF (0.6 mL) and MeOH (0.3 mL) solution of ethyl 3-(5-(2-(((4'-chloro-[1,1'-biphenyl]-4-yl)amino)methyl)-6-(trifluoromethyl)phenyl)picolinamido)propanoate (57.5 mg, 0.10 mmol) and the resulting homogeneous mixture was stirred at room temperature. After 45 min the resulting mixture was acidified with 1M HCl (0.31 mL, 0.31 mmol) and then extracted with DCM. The combined organics were dried (Na$_2$SO$_4$), concentrated and purified via column chromatography to yield the title compound.

$^1$H NMR (400 MHz, CHLOROFORM-d) δ 8.50 (t, J=6.36 Hz, 1H), 8.45 (s, 1H), 8.26 (d, J=8.56 Hz, 1H), 7.69-7.80 (m, 3H), 7.52 (t, J=7.83 Hz, 1H), 7.35-7.42 (m, 2H), 7.31 (d, J=8.56 Hz, 4H), 6.47 (d, J=8.56 Hz, 2H), 3.95 (s, 2H), 3.77 (q, J=6.28 Hz, 2H), 2.73 (t, J=6.11 Hz, 2H); MS m/z 554 (M+H).

Example 65

3-(5-(2-(((4'-chloro-[1,1'-biphenyl]-4-yl)amino)methyl)-3-methylphenyl)picolinamido)propanoic acid

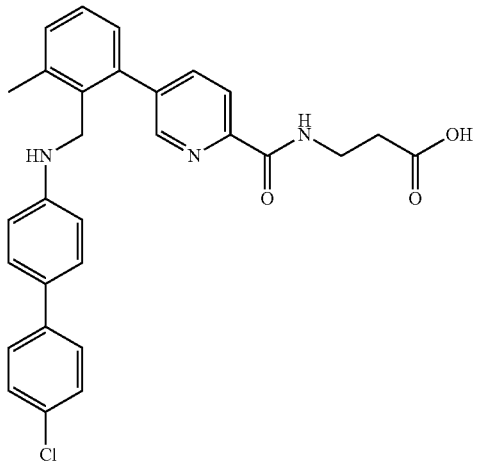 [SMILES: Cc1cccc(-c2ccc(C(=O)NCCC(=O)O)nc2)c1CNc1ccc(-c2ccc(Cl)cc2)cc1]

STEP A: ethyl 3-(5-(2-formyl-3-methylphenyl)picolinamido)propanoate 2-chloro-6-methylbenzaldehyde (156 mg, 1.01 mmol), ethyl 3-(5-(4,4,5,5-tetramethyl-1,3,2-dioxaborolan-2-yl)picolinamido)propanoate (434 mg, 1.25 mmol), Pd(PPh$_3$)$_4$ (58 mg, 0.05 mmol), and 2M K$_3$PO$_4$ (aq) (1.0 mL, 2.00 mmol) were dissolved in 1,4-dioxane (3.0 mL) and heated to 100° C. After 4 h the resulting mixture was cooled to room temperature, diluted with DCM, dried (Na$_2$SO$_4$), concentrated and purified via column chromatography to yield the title compound.

STEP B: 3-(5-(2-(((4'-chloro-[1,1'-biphenyl]-4-yl)amino)methyl)-3-methylphenyl)picolinamido)propanoic acid The title compound was prepared as described in Example 64, substituting ethyl 3-(5-(2-formyl-3-methylphenyl)picolinamido)propanoate for ethyl 3-(5-(2-formyl-6-(trifluoromethyl)phenyl)picolinamido)propanoate.

$^1$H NMR (400 MHz, CHLOROFORM-d) δ 8.52 (s, 1H), 8.37 (t, J=5.62 Hz, 1H), 8.08 (d, J=8.07 Hz, 1H), 7.83 (d, J=8.07 Hz, 1H), 7.32-7.38 (m, J=8.31 Hz, 2H), 7.29 (d, J=8.31 Hz, 2H), 7.20-7.27 (m, 4H), 7.02-7.10 (m, 1H), 6.49-6.58 (m, J=8.31 Hz, 2H), 4.00 (s, 2H), 3.65 (q, J=5.95 Hz, 2H), 2.60 (t, J=5.99 Hz, 2H), 2.39 (s, 3H); MS m/z 500 (M+H).

Example 66

3-(5-(2-(((4'-chloro-[1,1'-biphenyl]-4-yl)amino)methyl)-6-cyanophenyl)picolinamido)propanoic acid

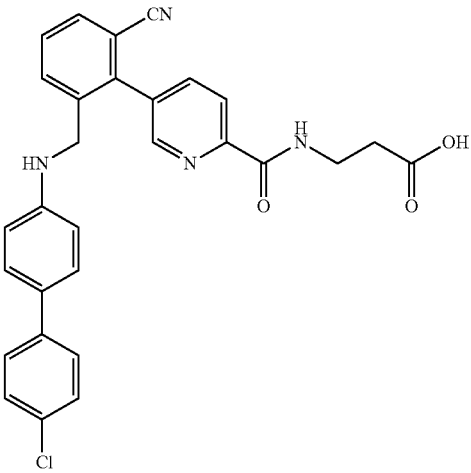 [SMILES: N#Cc1cccc(CNc2ccc(-c3ccc(Cl)cc3)cc2)c1-c1ccc(C(=O)NCCC(=O)O)nc1]

The title compound was prepared as described in Example 64, substituting 2-chloro-3-formylbenzonitrile for 2-chloro-3-(trifluoromethyl)benzaldehyde.

$^1$H NMR (400 MHz, CHLOROFORM-d) δ 8.57 (d, J=1.96 Hz, 1H), 8.51 (t, J=6.24 Hz, 1H), 8.31 (d, J=8.07 Hz, 1H), 7.87 (dd, J=1.96, 8.07 Hz, 1H), 7.80 (d, J=7.83 Hz, 1H), 7.70 (d, J=7.58 Hz, 1H), 7.51 (t, J=7.83 Hz, 1H), 7.36-7.43 (m, 2H), 7.31 (d, J=6.85 Hz, 4H), 6.47 (d, J=8.56 Hz, 2H), 4.13 (s, 2H), 3.77 (q, J=6.11 Hz, 2H), 2.73 (t, J=6.11 Hz, 2H); MS m/z 511 (M+H).

Example 67

3-(5-(3-chloro-2-(((4'-chloro-[1,1'-biphenyl]-4-yl)amino)methyl)-5-(trifluoromethyl)phenyl)picolinamido)propanoic acid

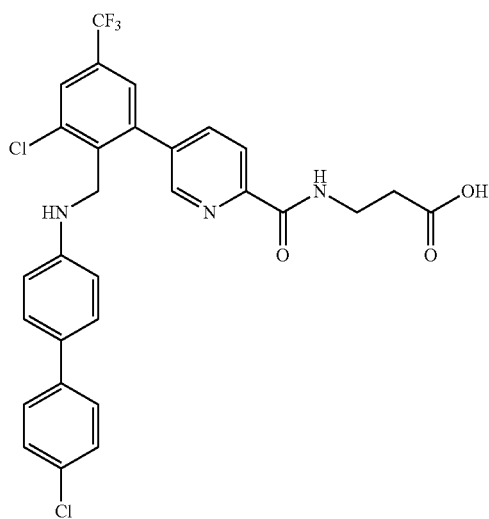 [SMILES: O=C(O)CCNC(=O)c1ccc(-c2cc(C(F)(F)F)cc(Cl)c2CNc2ccc(-c3ccc(Cl)cc3)cc2)cn1]

The title compound was prepared as described in Example 65, substituting 2,6-dichloro-4-(trifluoromethyl)benzaldehyde (prepared as described in U.S. Pat. No. 5,739,083 A) for 2-chloro-6-methylbenzaldehyde.

$^1$H NMR (400 MHz, CHLOROFORM-d) δ 8.61 (d, J=1.96 Hz, 1H), 8.44 (t, J=6.24 Hz, 1H), 8.24 (d, J=8.07 Hz, 1H), 7.95 (dd, J=1.96, 8.07 Hz, 1H), 7.79 (s, 1H), 7.47 (s, 1H), 7.38-7.44 (m, 2H), 7.29-7.38 (m, 4H), 6.55 (d, J=8.56 Hz, 2H), 4.30 (s, 2H), 3.75 (q, J=6.11 Hz, 2H), 2.71 (t, J=5.99 Hz, 2H); MS m/z 588 (M+H).

Example 68

3-(5-(2-(((4'-chloro-[1,1'-biphenyl]-4-yl)amino)methyl)-5-methylphenyl)picolinamido)propanoic acid

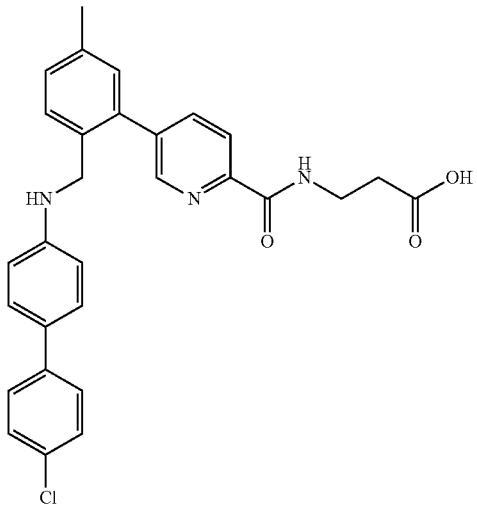 [SMILES: Cc1ccc(CNc2ccc(-c3ccc(Cl)cc3)cc2)c(-c2ccc(C(=O)NCCC(=O)O)nc2)c1]

The title compound was prepared as described in Example 65, substituting 2-bromo-4-methylbenzaldehyde for 2-chloro-6-methylbenzaldehyde.

¹H NMR (400 MHz, CHLOROFORM-d) δ 8.57 (s, 1H), 8.50 (t, J=5.99 Hz, 1H), 8.21 (d, J=8.07 Hz, 1H), 7.87 (d, J=8.07 Hz, 1H), 7.36-7.47 (m, 3H), 7.27-7.36 (m, 4H), 7.23 (d, J=8.31 Hz, 1H), 7.08 (s, 1H), 6.53 (d, J=8.31 Hz, 2H), 4.15 (s, 2H), 3.76 (q, J=5.87 Hz, 2H), 2.71 (t, J=5.87 Hz, 2H), 2.38 (s, 3H); MS m/z 500 (M+H).

Example 69

3-(5-(2-(((4'-chloro-[1,1'-biphenyl]-4-yl)amino)methyl)-6-methylphenyl)picolinamido)propanoic acid

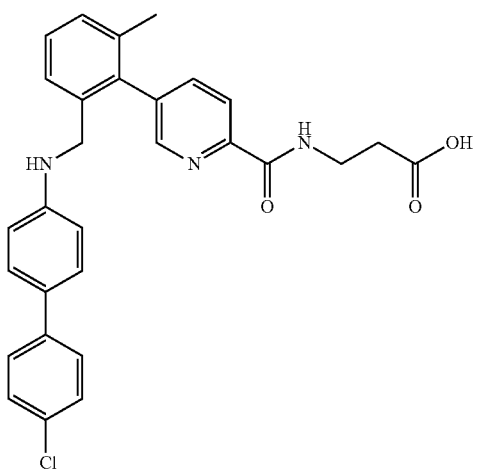 [SMILES: Cc1cccc(CNc2ccc(-c3ccc(Cl)cc3)cc2)c1-c1ccc(C(=O)NCCC(=O)O)nc1]

STEP A: 2-formyl-6-methylphenyl 1,1,2,2,3,3,4,4,4-nonafluorobutane-1-sulfonate

A 1.04 M THF solution of t-BuOK (3.7 mL, 3.9 mmol) was added to a THF solution (0.5 mL) of 2-hydroxy-3-methylbenzaldehyde (500 mg, 3.7 mmol) and 1,1,2,2,3,3,4,4,4-nonafluorobutane-1-sulfonyl fluoride (1.16 g, 3.9 mmol) and the reaction was stirred at room temperature. After 30 min the temperature was increased to 40° C. After 5 min the resulting mixture was partitioned with DCM and water, and the aqueous layer was extracted with DCM. The combined organic layers were dried (Na₂SO₄) and concentrated to yield a 4:1 w/w mixture of the title compound and starting material, which mixture was used in the next step without further purification.

STEP B: 3-(5-(2-(((4'-chloro-[1,1'-biphenyl]-4-yl)amino)methyl)-6-methylphenyl)picolinamido)propanoic acid The title compound was prepared as described in Example 64, substituting 2-formyl-6-methylphenyl 1,1,2,2,3,3,4,4,4-nonafluorobutane-1-sulfonate for 2-chloro-3-(trifluoromethyl)benzaldehyde.

¹H NMR (400 MHz, CHLOROFORM-d) δ 8.50 (t, J=6.24 Hz, 1H), 8.38-8.44 (m, 1H), 8.25 (d, J=7.82 Hz, 1H), 7.72 (dd, J=1.96, 8.07 Hz, 1H), 7.34-7.42 (m, 3H), 7.26-7.34 (m, 5H), 7.20-7.26 (m, 1H), 6.47 (d, J=8.56 Hz, 2H), 3.97 (s, 2H), 3.70-3.83 (m, 2H), 2.72 (t, J=6.11 Hz, 2H), 2.01 (s, 3H); MS m/z 500 (M+H).

Example 70

3-(5-(2-(((4'-chloro-[1,1'-biphenyl]-4-yl)amino)methyl)-5-(methylsulfonyl)phenyl)picolinamido)propanoic acid

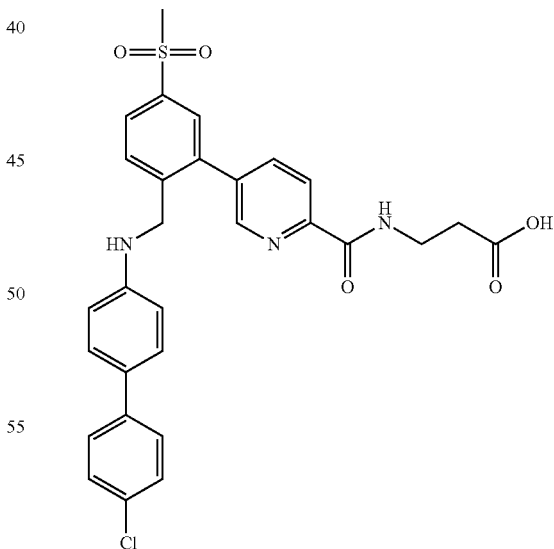

The title compound was prepared as described in Example 65, substituting 2-chloro-4-(methylsulfonyl)benzaldehyde for 2-chloro-6-methyl benzaldehyde.

¹H NMR (400 MHz, CHLOROFORM-d) δ 8.57 (s, 1H), 8.50 (t, J=6.11 Hz, 1H), 8.27 (d, J=7.82 Hz, 1H), 7.95 (d, J=8.07 Hz, 1H), 7.88 (d, J=8.07 Hz, 1H), 7.76-7.85 (m, 2H), 7.36-7.44 (m, 2H), 7.29-7.36 (m, 4H), 6.47-6.55 (m, J=8.31

Hz, 2H), 4.30 (s, 2H), 3.78 (q, J=6.03 Hz, 2H), 3.09 (s, 3H), 2.74 (t, J=5.87 Hz, 2H); MS m/z 564 (M+H).

Example 71

3-(5-(2-(((4'-chloro-[1,1'-biphenyl]-4-yl)amino)methyl)-3,5-bis(trifluoromethyl)phenyl)picolinamido)propanoic acid

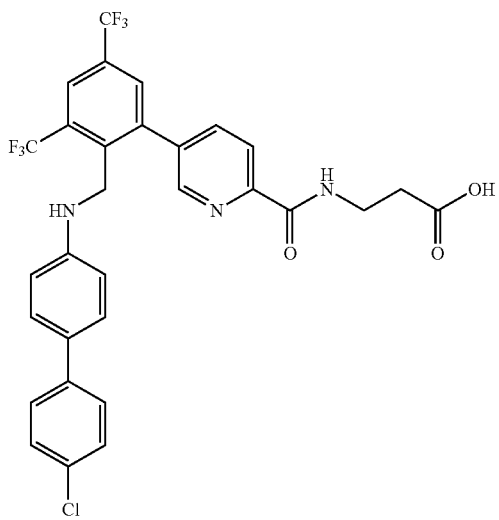 [SMILES: O=C(O)CCNC(=O)c1ccc(-c2cc(C(F)(F)F)cc(C(F)(F)F)c2CNc2ccc(-c3ccc(Cl)cc3)cc2)cn1]

STEP A:
2-bromo-4,6-bis(trifluoromethyl)benzaldehyde

A 2.59 M hexanes solution of n-BuLi (1.13 mL, 2.92 mmol) was added dropwise to a, 0° C., THF solution (4 mL) of 2,2,6,6-tetramethylpiperidine (0.50 mL, 2.92 mmol). After 5 min at 0° C., the solution was cooled to −78° C. and 1-bromo-3,5-bis(trifluoromethyl)benzene was added dropwise over 2 min. The resulting brown amber colored solution was stirred at −78° C. for an additional 20 min. Ethyl formate (0.587 mL, 7.30 mmol) was then added dropwise at −78° C. over 1 min. After 30 min at −78° C., 1 M aqueous HCl was added, the layers were separated and the organic layer was washed with 0.1 M aqueous HCl and 1 M aqueous. The organic layer was dried (Na$_2$SO$_4$), concentrated, and short path vacuum distilled to provide the title compound.

STEP B: ethyl 3-(5-(2-formyl-3,5-bis(trifluoromethyl)phenyl)picolinamido)propanoate 2-bromo-4,6-bis(trifluoromethyl)benzaldehyde (100 mg, 0.31 mmol), ethyl 3-(5-(4,4,5,5-tetramethyl-1,3,2-dioxaborolan-2-yl)picolinamido)propanoate (119 mg, 0.34 mmol), Pd(dppf)Cl$_2$ (23 mg, 0.03 mmol), and 2M K$_2$CO$_3$ (0.31 mL, 0.62 mmol), were dissolved in 1,4-dioxane (1.0 mL) and heated to 100° C. After 70 min the resulting mixture was cooled to room temperature, diluted with DCM, dried (Na$_2$SO$_4$), concentrated and purified via column chromatography to yield the title compound.

STEP C: ethyl 3-(5-(2-(((4'-chloro-[1,1'-biphenyl]-4-yl)amino)methyl)-3,5-bis(trifluoromethyl)phenyl)picolinamido)propanoate Ethyl 3-(5-(2-formyl-3,5-bis(trifluoromethyl)phenyl)picolinamido)propanoate (76 mg, 0.16 mmol) and 4'-chloro-[1,1'-biphenyl]-4-amine (40 mg, 0.20 mmol) in DMSO (0.16 mL) was stirred at 100° C. After 30 min EtOH (0.16 mL) was added and the resulting homogeneous solution was stirred at 100° C. After 1 h the resulting homogeneous solution was cooled to room temperature, and NaBH$_4$ (20 mg, 0.53 mmol), EtOH (1 mL), and DMSO (0.5 mL) were added and the resulting mixture was stirred. After 30 min, additional NaBH$_4$ (20 mg, 0.53 mmol) was added and the resulting homogeneous solution was stirred. After 20 min the resulting mixture was diluted with DCM (5 mL) and 1 M NaH$_2$PO$_4$ (4 mL) was carefully added. Water was added and the aqueous phase was extracted with DCM. The combined organic layers were dried (Na$_2$SO$_4$), concentrated, and purified via column chromatography to yield the title compound.

STEP D: 3-(5-(2-(((4'-chloro-[1,1'-biphenyl]-4-yl)amino)methyl)-3,5-bis(trifluoromethyl)phenyl)picolinamido)propanoic acid The title compound was prepared as described in Example 64, STEP C, substituting ethyl 3-(5-(2-(((4'-chloro-[1,1'-biphenyl]-4-yl)amino)methyl)-3,5-bis(trifluoromethyl)phenyl)picolinamido)propanoate for ethyl 3-(5-(2-(((4'-chloro-[1,1'-biphenyl]-4-yl)amino)methyl)-6-(trifluoromethyl)phenyl)picolinamido)propanoate.
$^1$H NMR (400 MHz, CHLOROFORM-d) δ 8.59 (d, J=1.71 Hz, 1H), 8.38 (t, J=6.24 Hz, 1H), 8.20 (d, J=8.07 Hz, 1H), 8.08 (s, 1H), 7.99 (dd, J=1.96, 8.07 Hz, 1H), 7.74 (s, 1H), 7.38-7.45 (m, 2H), 7.28-7.38 (m, 4H), 6.45 (d, J=8.56 Hz, 2H), 4.30 (s, 2H), 3.74 (q, J=6.11 Hz, 2H), 2.70 (t, J=6.11 Hz, 2H); MS m/z 622 (M+H).

Example 72

3-(5-(3-chloro-2-(((2',4'-dichloro-[1,1'-biphenyl]-4-yl)amino)methyl)-5-(trifluoromethyl)phenyl)picolinamido)propanoic acid

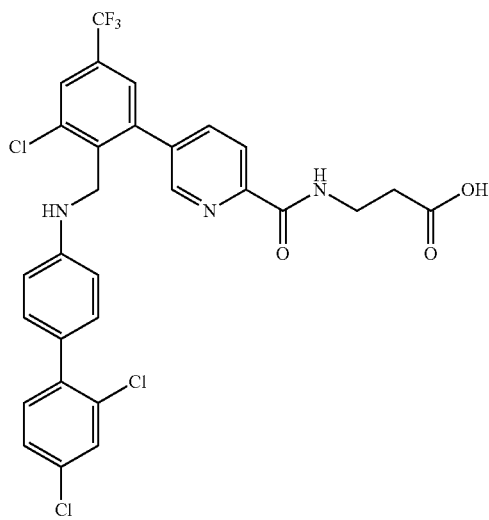 [SMILES: O=C(O)CCNC(=O)c1ccc(-c2cc(C(F)(F)F)cc(Cl)c2CNc2ccc(-c3ccc(Cl)cc3Cl)cc2)cn1]

STEP A:
1-bromo-3-chloro-2-iodo-5-(trifluoromethyl)benzene

A CH$_3$CN solution (70 mL) of 2-bromo-6-chloro-4-(trifluoromethyl)aniline (12.0 g, 43.7 mmol) was added dropwise over 5 min to a 4° C. solution of H$_2$SO$_4$ (70 mL) and water (70 mL) via pressure equalizing addition funnel under air, and the homogeneous solution was stirred in a −20° C. bath for 15 minutes until the internal temperature rose to 4° C. A 4° C.

water solution (40 mL) of NaNO$_2$ (5.4 g, 78.7 mmol) was added dropwise over 5 min, and after 8 min additional stirring in the −20° C. bath, the resulting 5° C. homogeneous solution was poured onto an ice bath-chilled water solution (70 mL) of KI (25.4 g, 153 mmol) (internal temperature rose to 13° C.). The resulting dark solution was stirred on the ice bath. After 45 min CHCl$_3$ (145 mL) was added and the layers were separated. The aqueous layer was extracted with CHCl$_3$ and the combined organic layers were washed with 2 M Na$_2$CO$_3$, 1 M sodium thiosulfate, dried (Na$_2$SO$_4$), and concentrated to yield the title compound, which was used in the next step without further purification.

STEP B: 2-bromo-6-chloro-4-(trifluoromethyl)benzonitrile 1-bromo-3-chloro-2-iodo-5-(trifluoromethyl)benzene (8.0 g, 20.6 mmol) and CuCN (1.9 g, 20.6 mmol) were dissolved in DMF (20 mL) and heated 100° C. After 2 h the temperature was increased to 110° C. After 3 h the reaction was cooled to room temperature, diluted with DCM, filtered, concentrated, and purified via column chromatography to yield the title compound.

STEP C: 2-bromo-6-chloro-4-(trifluoromethyl)benzaldehyde

A 1.1 M DCM solution of DIBAL (14.2 mL, 15.6 mmol) was added over 2 min to a 0° C. DCM solution of 2-bromo-6-chloro-4-(trifluoromethyl)benzonitrile (3.69 g, 13.0 mmol) in DCM (40 mL) and the ice bath was immediately removed. After 1 h the reaction was placed in an ice bath and 6 M HCl (aq) (15 mL) was added, the ice bath was removed and the resulting mixture was stirred vigorously. After 30 min the layers were separated and the aqueous layer was extracted with DCM. The combined organic layers were washed with 0.75 M tetrasodium EDTA, dried (Na$_2$SO$_4$), and concentrated to yield the title compound, which was used in the next step without further purification.

STEP D: 2',4'-dichloro-[1,1'-biphenyl]-4-amine

4-Iodoaniline (6.9 g, 31.7 mmol), (2,4-dichlorophenyl)boronic acid (7.3 g, 38.0 mmol), Pd(dppf)Cl$_2$ (1.3 g, 1.6 mmol), and 2M aqueous K$_2$CO$_3$ (31.7, 63.4 mmol) were dissolved in 1,4-dioxane (127 mL) and the resulting mixture was heated to 70° C. After 2.5 d the resulting mixture was cooled to room temperature, concentrated, diluted with EtOAc and 4M aqueous NaCl, and the layers were separated. The aqueous layer was extracted with EtOAc and the combined organics were dried (Na$_2$SO$_4$), concentrated, and purified via column chromatography to yield the title compound.

STEP E: N-(2-bromo-6-chloro-4-(trifluoromethyl)benzyl)-2',4'-dichloro-[1,1'-biphenyl]-4-amine A DCE solution (33 mL) of 2-bromo-6-chloro-4-(trifluoromethyl)benzaldehyde (3.7 g, 12.9 mmol), 2',4'-dichloro-[1,1'-biphenyl]-4-amine (3.4 g, 14.4 mmol), and HOAc (3.0 mL) was heated to 70° C. After 10 min the homogeneous solution was cooled to room temperature and solid NaBH(OAc)$_3$ (5.46 g, 25.8 mmol) was added and the resulting mixture was warmed to 40° C. After 30 min, EtOAc and 2 M K$_2$CO$_3$ were added and the layers were separated. The aqueous layer was extracted with EtOAc. The combined organic layers were washed with 4 M NaCl, dried (Na$_2$SO$_4$), concentrated, and purified via column chromatography to yield the title compound.

STEP F: ethyl 3-(5-(3-chloro-2-(((2',4'-dichloro-[1,1'-biphenyl]-4-yl)amino)methyl)-5-(trifluoromethyl)phenyl)picolinamido)propanoate N-(2-bromo-6-chloro-4-(trifluoromethyl)benzyl)-2',4'-dichloro-[1,1'-biphenyl]-4-amine (4.5 g, 8.8 mmol) and ethyl 3-(5-(4,4,5,5-tetramethyl-1,3,2-dioxaborolan-2-yl)picolinamido)propanoate (3.1 g, 8.8 mmol), Pd(dppf)Cl$_2$ (321 mg, 0.4 mmol), and 2 M K$_2$CO$_3$ (aq) (8.8 mL, 17.6 mmol) were dissolved in 1,4-dioxane (35 mL) and heated to 80° C. After 1 h the reaction was cooled to room temperature diluted with EtOAc and 4M aqueous NaCl, and the layers were separated. The aqueous layer was extracted with EtOAc and the combined organics were dried (Na$_2$SO$_4$), concentrated, and purified via column chromatography to yield the title compound.

STEP G: 3-(5-(3-chloro-2-(((2',4'-dichloro-[1,1'-biphenyl]-4-yl)amino)methyl)-5-(trifluoromethyl)phenyl)picolinamido)propanoic acid A 3M aqueous solution of NaOH (3.1 mL, 9.3 mmol) was added to a THF (12.6 mL) and MeOH (6.3 mL) solution of ethyl 3-(5-(3-chloro-2-(((2',4'-dichloro-[1,1'-biphenyl]-4-yl)amino)methyl)-5-(trifluoromethyl)phenyl)picolinamido)propanoate (4.1 g, 6.3 mmol) and the resulting homogeneous mixture was heated to 40° C. After 30 min the resulting mixture was acidified with 6M aqueous HCl (1.6 mL, 9.6 mmol) diluted with EtOAc and 4M aqueous NaCl, and the layers were separated. The aqueous layer was extracted with EtOAc and the combined organics were washed with 4M NaCl, dried (Na$_2$SO$_4$), concentrated, and purified via HPLC to yield the title compound.

$^1$H NMR (400 MHz, DMSO-d$_6$) δ 9.05 (t, J=5.62 Hz, 1H), 8.79 (s, 1H), 8.03-8.17 (m, 3H), 7.80 (s, 1H), 7.64 (s, 1H), 7.43 (d, J=8.31 Hz, 1H), 7.36 (d, J=8.31 Hz, 1H), 7.10-7.20 (m, J=8.31 Hz, 2H), 6.56-6.66 (m, J=8.31 Hz, 2H), 6.29-6.37 (m, 1H), 4.08-4.17 (m, 2H), 3.44 (q, J=6.36 Hz, 2H), 2.31 (t, J=6.60 Hz, 2H); MS m/z 624 (M+H).

Example 73

3-(5-(3-chloro-2-(((4'-chloro-2'-methyl-[1,1'-biphenyl]-4-yl)amino)methyl)-5-(trifluoromethyl)phenyl)picolinamido)propanoic acid

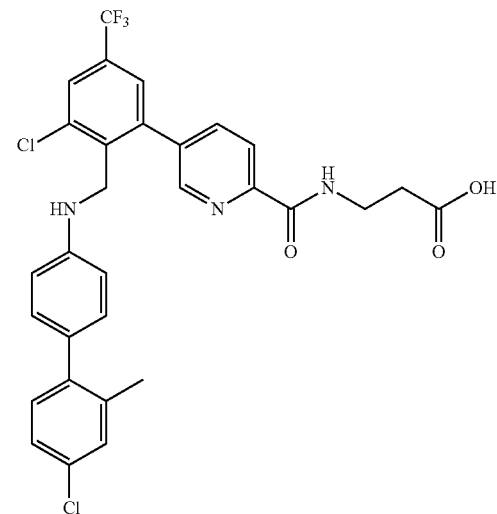 [SMILES: Cc1cc(Cl)ccc1-c1ccc(NCc2c(Cl)cc(C(F)(F)F)cc2-c2ccc(C(=O)NCCC(=O)O)nc2)cc1]

STEP A: ethyl 3-(5-(3-chloro-2-formyl-5-(trifluoromethyl)phenyl)picolinamido)propanoate The title compound was prepared as described in Example 6, STEP A substituting 2,6-dichloro-4-(trifluoromethyl)benzaldehyde (prepared as described in U.S. Pat. No. 5,739,083 A) for 2-chloro-6-methylbenzaldehyde.

STEP B: 4'-chloro-2'-methyl-[1,1'-biphenyl]-4-amine

The title compound was prepared as described in Example 72, STEP D, substituting 2-methyl-4-chlorophenylboronic acid for 2,4-dichlorophenylboronic acid, and substituting microwave heating at 160° C. for 15 min for 70° C. thermal heating for 2.5 days.

STEP C: ethyl 3-(5-(3-chloro-2-(((4'-chloro-2'-methyl-[1,1'-biphenyl]-4-yl)amino)methyl)-5-(trifluoromethyl)phenyl)picolinamido)propanoate The title compound was prepared as described in Example 64, STEP B substituting ethyl 3-(5-(3-chloro-2-formyl-5-(trifluoromethyl)phenyl)picolinamido)propanoate and 4'-chloro-2'-methyl-[1,1'-biphenyl]-4-amine for ethyl 3-(5-(2-formyl-6-(trifluoromethyl)phenyl)picolinamido)propanoate and 4'-chloro-[1,1'-biphenyl]-4-amine, and stirring at 50° C. rather than 40° C.

STEP D: 3-(5-(3-chloro-2-(((4'-chloro-2'-methyl-[1,1'-biphenyl]-4-yl)amino)methyl)-5-(trifluoromethyl)phenyl)picolinamido)propanoic acid The title compound was prepared as described in Example 64, STEP C, substituting ethyl 3-(5-(3-chloro-2-(((4'-chloro-2'-methyl-[1,1'-biphenyl]-4-yl)amino)methyl)-5-(trifluoromethyl)phenyl)picolinamido)propanoate for ethyl 3-(5-(2-(((4'-chloro-[1,1'-biphenyl]-4-yl)amino)methyl)-6-(trifluoromethyl)phenyl)picolinamido)propanoate.
$^1$H NMR (400 MHz, CHLOROFORM-d) δ 8.63 (s, 1H), 8.45 (t, J=5.99 Hz, 1H), 8.25 (d, J=8.07 Hz, 1H), 7.95-8.04 (m, 1H), 7.80 (s, 1H), 7.48 (s, 1H), 7.21 (s, 1H), 7.13-7.19 (m, 1H), 7.02-7.13 (m, 3H), 6.54 (d, J=8.56 Hz, 2H), 4.30 (s, 2H), 3.77 (d, J=5.87 Hz, 2H), 2.72 (t, J=5.50 Hz, 2H), 2.24 (s, 3H); MS m/z 602 (M+H).

Example 74

3-(5-(3-chloro-2-(((2,4'-dichloro-[1,1'-biphenyl]-4-yl)amino)methyl)-5-(trifluoromethyl)phenyl)picolinamido)propanoic acid

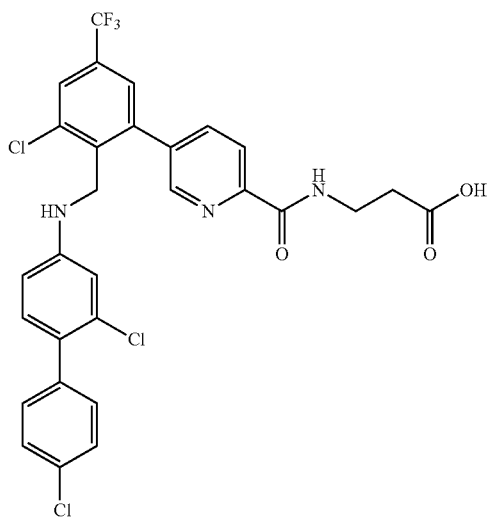 [SMILES: O=C(O)CCNC(=O)c1ccc(-c2cc(C(F)(F)F)cc(Cl)c2CNc2ccc(-c3ccc(Cl)cc3)c(Cl)c2)cn1]

The title compound was prepared as described in Example 72, substituting 2,4'-dichloro-[1,1'-biphenyl]-4-amine, prepared as in Example 27, for 2',4'-dichloro-[1,1'-biphenyl]-4-amine.

$^1$H NMR (400 MHz, MeOH) δ 8.70 (d, J=1.47 Hz, 1H), 8.11 (d, J=7.83 Hz, 1H), 8.03 (dd, J=2.20, 8.07 Hz, 1H), 7.91 (d, J=1.22 Hz, 1H), 7.63 (s, 1H), 7.29-7.40 (m, 4H), 7.02 (d, J=8.56 Hz, 1H), 6.54 (d, J=2.45 Hz, 1H), 6.46 (dd, J=2.45, 8.56 Hz, 1H), 4.28 (s, 2H), 3.65 (t, J=6.72 Hz, 2H), 2.61 (t, J=6.72 Hz, 2H); MS m/z 622 (M+H).

Example 75

3-(5-(3-chloro-2-(((4'-chloro-2-methyl-[1,1'-biphenyl]-4-yl)amino)methyl)-5-(trifluoromethyl)phenyl)picolinamido)propanoic acid

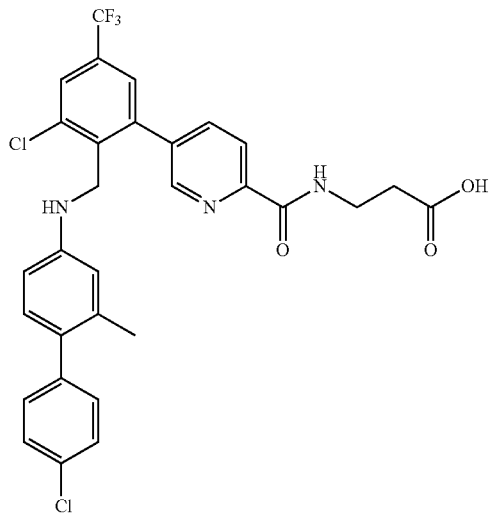 [SMILES: Cc1cc(NCc2c(Cl)cc(C(F)(F)F)cc2-c2ccc(C(=O)NCCC(=O)O)nc2)ccc1-c1ccc(Cl)cc1]

STEP A: ethyl 3-(5-(3-chloro-2-formyl-5-(trifluoromethyl)phenyl)picolinamido)propanoate 2-Bromo-6-chloro-4-(trifluoromethyl)benzaldehyde (3.4 g, 11.9 mmol) (as described in Example 72, STEP C), ethyl 3-(5-(4,4,5,5-tetramethyl-1,3,2-dioxaborolan-2-yl)picolinamido)propanoate (5.0 g, 14.3 mmol), Pd(dppf)Cl$_2$ (435 mg, 0.6 mmol), and 2 M K$_2$CO$_3$ (aq) (11.9 mL, 23.8 mmol) were dissolved in 1,4-dioxane (48 mL) and heated to 90° C. After 2 h the temperature was lowered to 80° C. After 14 h the resulting mixture was concentrated, diluted with EtOAc and 4M aqueous NaCl, and the layers were separated. The aqueous layer was extracted with EtOAc and the combined organics were dried (Na$_2$SO$_4$), concentrated, and purified via column chromatography to yield the title compound.

STEP B: 4'-chloro-2-methyl-[1,1'-biphenyl]-4-amine 4-bromo-3-methylaniline (5.1 g, 27.4 mmol), 4-chlorophenylboronic acid (5.1 g, 32.9 mmol), Pd(dppf)Cl$_2$ (1.1 g, 1.4 mmol), and 2M aqueous K$_2$CO$_3$ (27.4 mL, 54.8 mmol) were dissolved in 1,4-dioxane (110 mL) and the resulting mixture was heated to 100° C. After 2 h the resulting mixture was cooled to room temperature, concentrated, diluted with EtOAc and 4M aqueous NaCl, and the layers were separated. The aqueous layer was extracted with EtOAc and the combined organics were dried (Na$_2$SO$_4$), concentrated, and purified via column chromatography to yield the title compound.

STEP C: ethyl 3-(5-(3-chloro-2-(((4'-chloro-2-methyl-[1,1'-biphenyl]-4-yl)amino)methyl)-5-(trifluoromethyl)phenyl)picolinamido)propanoate Solid NaBH(OAc)$_3$ (2.6 g, 12.1 mmol) was added to a DCE solution (16 mL) of ethyl 3-(5-(3-chloro-2-formyl-5-(trifluoromethyl)phenyl)picolinamido)propanoate (2.6 g, 6.1 mmol) and 4'-chloro-2-methyl-[1,1'-biphenyl]-4-amine (1.6 g, 7.3 mmol), and AcOH (1.4 mL, 1.2 mmol) and the resulting mixture was stirred at room temperature. After 2 h additional NaBH(OAc)₃ (2.6 g, 12.1 mmol) was added. After 4 h the resulting mixture was diluted with EtOAc and 2M aqueous K₂CO₃ and the layers were separated. The aqueous phase was added was extracted with EtOAc and the combined organics were dried (Na₂SO₄), concentrated and purified via column chromatography to yield the title compound.

STEP D: 3-(5-(3-chloro-2-(((4% chloro-2-methyl-[1,1'-biphenyl]-4-yl)amino)methyl)-5-(trifluoromethyl)phenyl)picolinamido)propanoic acid A 3M aqueous solution of NaOH (1.9 mL, 5.7 mmol) was added to a THF (7.6 mL) and MeOH (3.8 mL) solution of ethyl 3-(5-(3-chloro-2-(((4'-chloro-2-methyl-[1,1'-biphenyl]-4-yl)amino)methyl)-5-(trifluoromethyl)phenyl)picolinamido)propanoate (2.4 g, 3.8 mmol) and the resulting homogeneous mixture was stirred at room temperature. After 30 min the resulting mixture concentrated and then acidified with 1M aqueous HCl. The resulting mixture was diluted with EtOAc and the layers were separated. The aqueous phase was extracted with EtOAc and the combined organics were washed with 4M NaCl, dried (Na₂SO₄), and concentrated. The resulting material was dissolved in diethyl ether, 1M diethyl ether solution of HCl (5.7 mL, 5.7 mmol) was added and the resulting precipitate was filtered, washed with diethyl ether, and dried in vacuo to yield the title compound.

¹H NMR (400 MHz, MeOD) δ 8.39 (s, 1H), 8.05-8.12 (m, 2H), 7.88 (dd, J=1.71, 8.07 Hz, 1H), 7.66 (s, 1H), 7.41-7.49 (m, J=8.31 Hz, 2H), 7.28-7.36 (m, J=8.31 Hz, 2H), 7.06 (d, J=8.07 Hz, 1H), 6.56-6.65 (m, 2H), 4.70 (s, 2H), 3.65 (t, J=6.48 Hz, 2H), 2.60 (t, J=6.60 Hz, 2H), 2.08 (s, 3H); MS m/z 602 (M+H).

Example 76

3-(5-(2-(((2,4'-dichloro-[1,1'-biphenyl]-4-yl)amino)methyl)-3,5-bis(trifluoromethyl)phenyl)picolinamido)propanoic acid

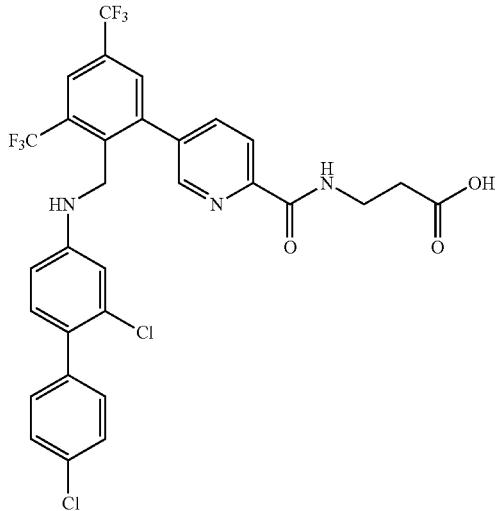 [SMILES: O=C(O)CCNC(=O)c1ccc(-c2cc(C(F)(F)F)cc(C(F)(F)F)c2CNc2ccc(-c3ccc(Cl)cc3)c(Cl)c2)cn1]

STEP A: 2,4'-dichloro-[1,1'-biphenyl]-4-amine

The title compound was prepared as described in Example 75, STEP B, substituting 3-chloro-4-iodoaniline for 4-bromo-3-methylaniline.

STEP B: 3-(5-(2-(((2,4'-dichloro-[1,1'-biphenyl]-4-yl)amino)methyl)-3,5-bis(trifluoromethyl)phenyl)picolinamido)propanoic acid The title compound was prepared as described in Example 71, substituting 2,4'-dichloro-[1,1'-biphenyl]-4-amine for 4'-chloro-[1,1'-biphenyl]-4-amine.

¹H NMR (400 MHz, CHLOROFORM-d) δ 8.59 (d, J=1.71 Hz, 1H), 8.42 (s, 1H), 8.22 (d, J=8.07 Hz, 1H), 8.09 (s, 1H), 7.95 (dd, J=2.08, 8.19 Hz, 1H), 7.76 (s, 1H), 7.34 (q, J=8.56 Hz, 4H), 7.04 (d, J=8.31 Hz, 1H), 6.43 (d, J=2.20 Hz, 1H), 6.34 (dd, J=2.32, 8.44 Hz, 1H), 4.29 (s, 2H), 3.76 (q, J=5.99 Hz, 2H), 2.72 (t, J=5.99 Hz, 2H); MS m/z 656 (M+H).

Example 77

3-(5-(4-chloro-2-(((4'-chloro-2'-methyl-[1,1'-biphenyl]-4-yl)amino)methyl)-5-(trifluoromethyl)phenyl)picolinamido)propanoic acid

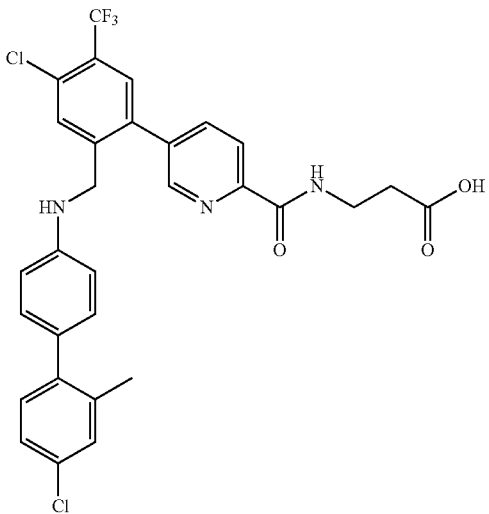 [SMILES: Cc1cc(Cl)ccc1-c1ccc(NCc2cc(Cl)c(C(F)(F)F)cc2-c2ccc(C(=O)NCCC(=O)O)nc2)cc1]

STEP A:
5-chloro-2-methoxy-4-(trifluoromethyl)benzaldehyde

A 1.61 M hexanes solution of n-BuLi (18.7 mL, 30.1 mmol) was added to a −78° C. diethyl ether solution (45 mL) of 1-chloro-4-methoxy-2-(trifluoromethyl)benzene (5.3 g, 25.1 mmol) and TMEDA (4.5 mL, 30.1 mmol). After 30 min at −78° C. the reaction was transferred to an ice bath and stirred at 0° C. After 5 min DMF (5.0 mL, 65.0 mmol) was added and the reaction was maintained in the ice bath. After 2 hrs at 0° C. 6 M aqueous HCl (aq) (17.0 mL, 102 mmol) was added and the aqueous layer was extracted with EtOAc. The combined organic layers were washed with 4 M NaCl and 5 M K₂CO₃, dried (Na₂SO₄), and concentrated to yield the title compound, which was used in the next step without further purification.

STEP B:
5-chloro-2-hydroxy-4-(trifluoromethyl)benzaldehyde

A 1M DCM solution of BBr₃ (24.0 mL, 24.0 mmol) was added to neat 5-chloro-2-methoxy-4-(trifluoromethyl)benzaldehyde (3.4 g, 14.4 mmol) and the resulting mixture was heated to 50° C. After 1 h the resulting mixture was diluted with DCM and ice and the layers were separated. The aqueous phase was added was extracted with DCM and the combined organics were dried (Na₂SO₄), concentrated and purified via column chromatography to yield the title compound.

STEP C:
4-chloro-2-formyl-5-(trifluoromethyl)phenyl 1,1,2,2,3,3,4,4,4-nonafluorobutane-1-sulfonate A 1.04 M THF solution of t-BuOK (4.9 mL, 5.1 mmol) was added to a 0° C., THF solution (4 mL) of 5-chloro-2-hydroxy- 4-(trifluoromethyl)benzaldehyde (1.0 g, 4.6 mmol). After 4 min, neat 1,1,2,2,3,3,4,4,4-nonafluorobutane-1-sulfonyl fluoride (1.7 mL, 9.3 mmol) was added and the ice bath was removed. After 1 h at room temperature, AcOH (1 mL) was added and the resulting mixture was concentrated. The resulting material was diluted with DCM and 1M aqueous HCl, the layers were separated, and the organic layer was washed with 1 M NaHCO$_3$, dried (Na$_2$SO$_4$), and concentrated to yield the title compound that was used without further purification.

STEP D: ethyl 3-(5-(4-chloro-2-formyl-5-(trifluoromethyl)phenyl)picolinamido)propanoate The title compound was prepared as described in Example 65, STEP A, substituting 4-chloro-2-formyl-5-(trifluoromethyl)phenyl 1,1,2,2,3,3,4,4,4-nonafluorobutane-1-sulfonate for 2-chloro-6-methylbenzaldehyde.

STEP E: 3-(5-(4-chloro-2-(((4'-chloro-2'-methyl-[1,1'-biphenyl]-4-yl)amino)methyl)-5-(trifluoromethyl)phenyl)picolinamido)propanoic acid The title compound was prepared as described in Example 64, STEP B, substituting ethyl 3-(5-(4-chloro-2-formyl-5-(trifluoromethyl)phenyl)picolinamido)propanoate and 4'-chloro-2'-methyl-[1,1'-biphenyl]-4-amine (as described in Example 73, STEP B) for ethyl 3-(5-(2-formyl-6-(trifluoromethyl)phenyl)picolinamido)propanoate and 4'-chloro-[1,1'-biphenyl]-4-amine, and then as described in Example 75, STEP C.

$^1$H NMR (400 MHz, CHLOROFORM-d) δ 8.57 (d, J=1.47 Hz, 1H), 8.48 (t, J=6.24 Hz, 1H), 8.27 (d, J=8.07 Hz, 1H), 7.88 (dd, J=1.96, 8.07 Hz, 1H), 7.79 (s, 1H), 7.58 (s, 1H), 7.19-7.23 (m, 1H), 7.12-7.19 (m, 1H), 7.02-7.12 (m, 3H), 6.50 (d, J=8.31 Hz, 2H), 4.25 (s, 2H), 3.79 (q, J=6.03 Hz, 2H), 2.74 (t, J=5.99 Hz, 2H), 2.22 (s, 3H); MS m/z 602 (M+H).

Example 78

3-(5-(4-chloro-2-(((2,4'-dichloro-[1,1'-biphenyl]-4-yl)amino)methyl)-5-(trifluoromethyl)phenyl)picolinamido)propanoic acid

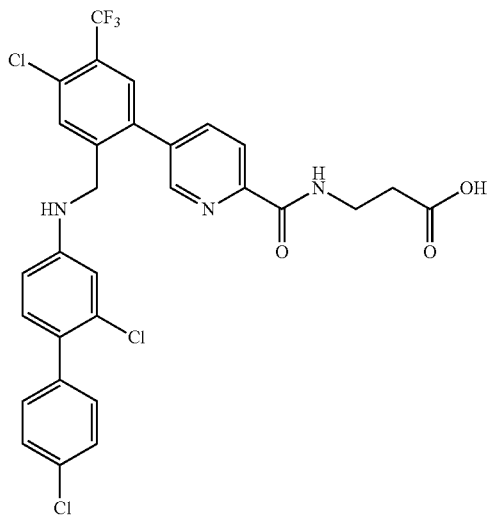 [SMILES: O=C(O)CCNC(=O)c1ccc(-c2cc(C(F)(F)F)c(Cl)cc2CNc2ccc(-c3ccc(Cl)cc3)c(Cl)c2)cn1]

The title compound was prepared as described in Example 77 substituting 2,4'-dichloro-[1,1'-biphenyl]-4-amine (see Example 74) for 4'-chloro-2'-methyl-[1,1'-biphenyl]-4-amine.

$^1$H NMR (400 MHz, CHLOROFORM-d) δ 8.56 (d, J=1.71 Hz, 1H), 8.48 (t, J=6.24 Hz, 1H), 8.27 (d, J=8.07 Hz, 1H), 7.86 (dd, J=2.08, 7.95 Hz, 1H), 7.73 (s, 1H), 7.58 (s, 1H), 7.24-7.38 (m, 4H), 7.06 (d, J=8.31 Hz, 1H), 6.52 (d, J=2.45 Hz, 1H), 6.39 (dd, J=2.32, 8.44 Hz, 1H), 4.23 (s, 2H), 3.78 (q, J=6.28 Hz, 2H), 2.74 (t, J=6.11 Hz, 2H); MS m/z 622 (M+H).

Example 79

3-(5-(4-chloro-2-(((4'-chloro-2-methyl-[1,1'-biphenyl]-4-yl)amino)methyl)-5-(trifluoromethyl)phenyl)picolinamido)propanoic acid

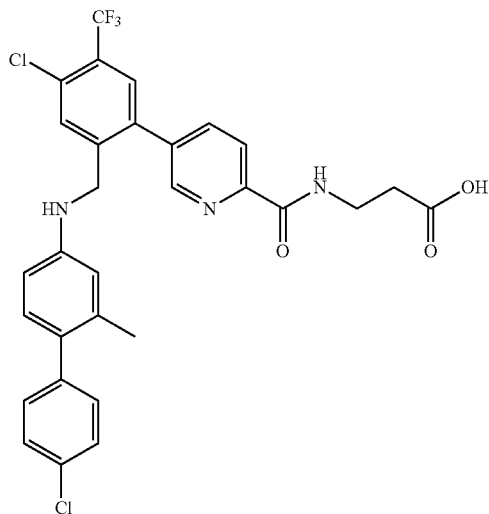 [SMILES: Cc1cc(NCc2cc(Cl)c(C(F)(F)F)cc2-c2ccc(C(=O)NCCC(=O)O)nc2)ccc1-c1ccc(Cl)cc1]

The title compound was prepared as described in Example 77 substituting 4'-chloro-2-methyl-[1,1'-biphenyl]-4-amine (see Example 76, STEP B) for 4'-chloro-2'-methyl-[1,1'-biphenyl]-4-amine.

$^1$H NMR (400 MHz, CHLOROFORM-d) δ 8.57 (d, J=1.96 Hz, 1H), 8.47 (t, J=6.36 Hz, 1H), 8.28 (d, J=8.07 Hz, 1H), 7.88 (dd, J=2.20, 8.07 Hz, 1H), 7.77 (s, 1H), 7.58 (s, 1H), 7.29-7.36 (m, 2H), 7.14-7.22 (m, J=8.56 Hz, 2H), 6.97 (d, J=8.31 Hz, 1H), 6.37 (d, J=2.20 Hz, 1H), 6.33 (dd, J=2.45, 8.31 Hz, 1H), 4.23 (s, 2H), 3.79 (q, J=6.28 Hz, 2H), 2.75 (t, J=6.11 Hz, 2H), 2.15 (s, 3H); MS m/z 602 (M+H).

Example 80

3-(5-(4-chloro-2-(((4'-chloro-[1,1'-biphenyl]-4-yl)amino)methyl)-5-(trifluoromethyl)phenyl)picolinamido)propanoic acid

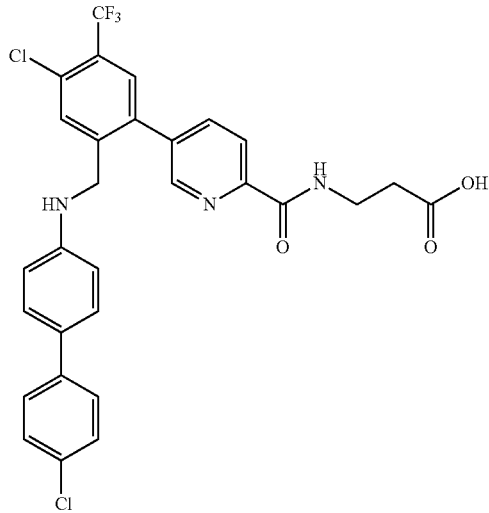 [SMILES: O=C(O)CCNC(=O)c1ccc(-c2cc(C(F)(F)F)c(Cl)cc2CNc2ccc(-c3ccc(Cl)cc3)cc2)cn1]

The title compound was prepared as described in Example 77 substituting 4'-chloro-[1,1'-biphenyl]-4-amine for 4'-chloro-2'-methyl-[1,1'-biphenyl]-4-amine.

¹H NMR (400 MHz, CHLOROFORM-d) δ 8.53-8.60 (m, 1H), 8.46 (t, J=6.24 Hz, 1H), 8.28 (d, J=8.07 Hz, 1H), 7.86 (dd, J=2.08, 7.95 Hz, 1H), 7.75 (s, 1H), 7.58 (s, 1H), 7.38-7.46 (m, J=8.56 Hz, 2H), 7.30-7.38 (m, 4H), 6.47-6.56 (m, J=8.56 Hz, 2H), 4.25 (s, 2H), 3.78 (q, J=6.11 Hz, 2H), 2.74 (t, J=6.11 Hz, 2H); MS m/z 588 (M+H).

Example 81

3-(5-(2-(((4'-chloro-2'-methyl-[1,1'-biphenyl]-4-yl)amino)methyl)-3,5-bis(trifluoromethyl)phenyl)picolinamido)propanoic acid

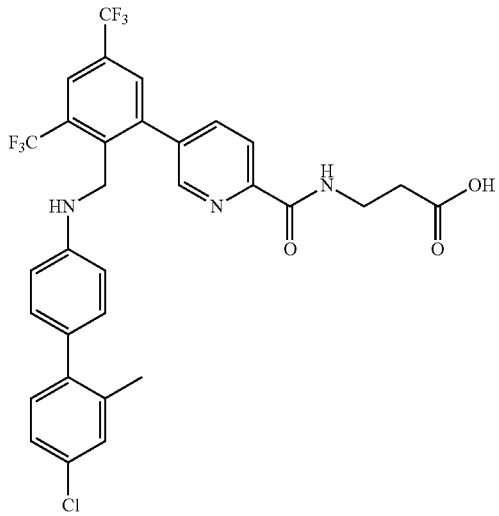 [SMILES: Cc1cc(Cl)ccc1-c1ccc(NCc2c(-c3ccc(C(=O)NCCC(=O)O)nc3)cc(C(F)(F)F)cc2C(F)(F)F)cc1]

The title compound was prepared as described in Example 71 substituting 4'-chloro-2'-methyl-[1,1'-biphenyl]-4-amine for 4'-chloro-[1,1'-biphenyl]-4-amine.

¹H NMR (400 MHz, CHLOROFORM-d) δ 8.61 (d, J=1.71 Hz, 1H), 8.36-8.46 (m, 1H), 8.21 (d, J=8.07 Hz, 1H), 8.09 (s, 1H), 8.03 (dd, J=2.20, 8.07 Hz, 1H), 7.76 (s, 1H), 7.22 (s, 1H), 7.17 (dd, J=1.83, 8.19 Hz, 1H), 7.11 (d, J=8.07 Hz, 1H), 7.00-7.08 (m, J=8.31 Hz, 2H), 6.40-6.48 (m, J=8.56 Hz, 2H), 4.30 (s, 2H), 3.76 (q, J=6.28 Hz, 2H), 2.72 (t, J=6.11 Hz, 2H), 2.24 (s, 3H); MS m/z 636 (M+H).

Example 82

3-(5-(4-chloro-2-(((2',4'-dichloro-[1,1'-biphenyl]-4-yl)amino)methyl)-5-(trifluoromethyl)phenyl)picolinamido)propanoic acid

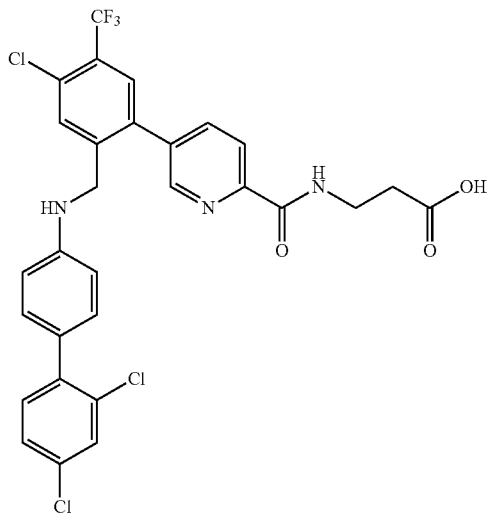 [SMILES: O=C(O)CCNC(=O)c1ccc(-c2cc(C(F)(F)F)c(Cl)cc2CNc2ccc(-c3ccc(Cl)cc3Cl)cc2)cn1]

The title compound was prepared as described in Example 77 substituting 2',4'-dichloro-[1,1'-biphenyl]-4-amine for 4'-chloro-2'-methyl-[1,1'-biphenyl]-4-amine.

¹H NMR (400 MHz, CHLOROFORM-d) δ 8.54-8.61 (m, 1H), 8.47 (t, J=6.24 Hz, 1H), 8.28 (d, J=8.07 Hz, 1H), 7.87 (dd, J=2.08, 7.95 Hz, 1H), 7.77 (s, 1H), 7.58 (s, 1H), 7.43 (d, J=1.71 Hz, 1H), 7.16-7.25 (m, 4H), 6.51 (d, J=8.56 Hz, 2H), 4.26 (s, 2H), 3.79 (q, J=6.19 Hz, 2H), 2.75 (t, J=5.99 Hz, 2H); MS m/z 622 (M+H).

Example 83

3-(5-(2-(((2'-methyl-4'-(trifluoromethyl)-[1,1'-biphenyl]-4-yl)amino)methyl)-3,5-bis(trifluoromethyl)phenyl)picolinamido)propanoic acid

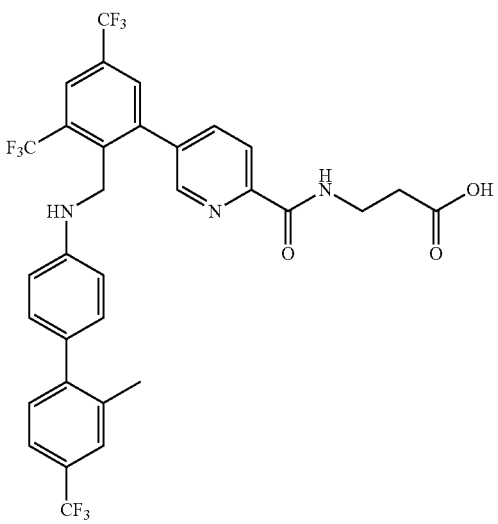 [SMILES: Cc1cc(C(F)(F)F)ccc1-c1ccc(NCc2c(-c3ccc(C(=O)NCCC(=O)O)nc3)cc(C(F)(F)F)cc2C(F)(F)F)cc1]

STEP A: 2'-methyl-4'-(trifluoromethyl)-[1,1'-biphenyl]-4-amine

The title compound was prepared as described in Example 76, STEP B, substituting 4-iodoaniline and 2-methyl-4-(trifluoromethylphenylboronic acid for 4-bromo-3-methylaniline and 4-chlorophenylboronic acid.

STEP B: 3-(5-(2-(((2'-methyl-4'-(trifluoromethyl)-[1,1'-biphenyl]-4-yl)amino)methyl)-3,5-bis(trifluoromethyl)phenyl)picolinamido)propanoic acid The title compound was prepared as described in Example 71 substituting 2'-methyl-4'-(trifluoromethyl)-[1,1'-biphenyl]-4-amine for 4'-chloro-[1,1'-biphenyl]-4-amine.

¹H NMR (400 MHz, CHLOROFORM-d) δ 8.61 (d, J=1.47 Hz, 1H), 8.41 (t, J=6.48 Hz, 1H), 8.21 (d, J=8.07 Hz, 1H), 8.09 (s, 1H), 8.02 (dd, J=2.20, 8.07 Hz, 1H), 7.76 (s, 1H), 7.41-7.51 (m, 2H), 7.29 (d, J=8.07 Hz, 1H), 7.02-7.10 (m, 2H), 6.43-6.49 (m, 2H), 4.31 (s, 2H), 3.76 (q, J=6.19 Hz, 2H), 2.72 (t, J=6.11 Hz, 2H), 2.32 (s, 3H); MS m/z 670 (M+H).

Example 84

3-(5-(2-(((2',3'-dichloro-[1,1'-biphenyl]-4-yl)amino)methyl)-3,5-bis(trifluoromethyl)phenyl)picolinamido)propanoic acid

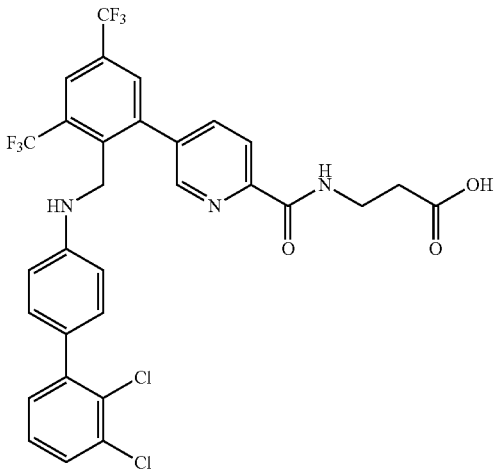 [SMILES: O=C(O)CCNC(=O)c1ccc(-c2cc(C(F)(F)F)cc(C(F)(F)F)c2CNc2ccc(-c3cccc(Cl)c3Cl)cc2)cn1]

STEP A: 2',3'-dichloro-[1,1'-biphenyl]-4-amine

The title compound was prepared as described in Example 76, STEP B, substituting 4-iodoaniline and 2,3-dichlorophenylboronic acid for 4-bromo-3-methylaniline and 4-chlorophenylboronic acid.

STEP B: 3-(5-(2-(((2',3'-dichloro-[1,1'-biphenyl]-4-yl)amino)methyl)-3,5-bis(trifluoromethyl)phenyl)picolinamido)propanoic acid The title compound was prepared as described in Example 71 substituting 2',3'-dichloro-[1,1'-biphenyl]-4-amine for 4'-chloro-[1,1'-biphenyl]-4-amine.
$^1$H NMR (400 MHz, CHLOROFORM-d) δ 8.61 (d, J=1.71 Hz, 1H), 8.41 (t, J=6.36 Hz, 1H), 8.21 (d, J=8.07 Hz, 1H), 8.09 (s, 1H), 8.00 (dd, J=2.20, 8.07 Hz, 1H), 7.73-7.78 (m, 1H), 7.40 (dd, J=3.55, 5.99 Hz, 1H), 7.14-7.22 (m, 4H), 6.41-6.48 (m, 2H), 4.31 (s, 2H), 3.77 (q, J=6.19 Hz, 2H), 2.73 (t, J=6.11 Hz, 2H); MS m/z 656 (M+H).

Example 85

3-(5-(2-(((2',6'-dichloro-[1,1'-biphenyl]-4-yl)amino)methyl)-3,5-bis(trifluoromethyl)phenyl)picolinamido)propanoic acid

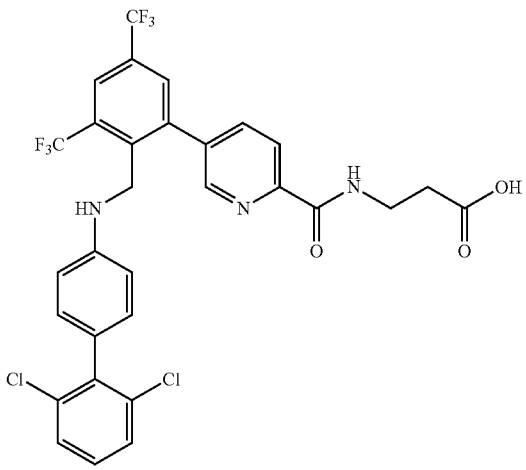 [SMILES: O=C(O)CCNC(=O)c1ccc(-c2cc(C(F)(F)F)cc(C(F)(F)F)c2CNc2ccc(-c3c(Cl)cccc3Cl)cc2)cn1]

STEP A: 2',6'-dichloro-[1,1'-biphenyl]-4-amine

The title compound was prepared as described in Example 76, STEP B, but heating at 90° C. for 14 hrs, substituting 4-iodoaniline and 2,6-dichlorophenylboronic acid for 4-bromo-3-methylaniline and 4-chlorophenylboronic acid.

STEP B: 3-(5-(2-(((2',6'-dichloro-[1,1'-biphenyl]-4-yl)amino)methyl)-3,5-bis(trifluoromethyl)phenyl)picolinamido)propanoic acid The title compound was prepared as described in Example 71 substituting 2',6'-dichloro-[1,1'-biphenyl]-4-amine for 4'-chloro-[1,1'-biphenyl]-4-amine.
$^1$H NMR (400 MHz, CHLOROFORM-d) δ 8.61 (d, J=1.47 Hz, 1H), 8.40 (s, 1H), 8.21 (d, J=8.07 Hz, 1H), 8.09 (s, 1H), 7.98 (dd, J=2.20, 8.07 Hz, 1H), 7.75 (s, 1H), 7.37 (d, J=8.07 Hz, 2H), 7.13-7.21 (m, 1H), 6.98-7.06 (m, 2H), 6.41-6.49 (m, 2H), 4.33 (s, 2H), 3.77 (q, J=6.36 Hz, 2H), 2.74 (t, J=6.24 Hz, 2H); MS m/z 656 (M+H).

Example 86

3-(5-(2-(((4'-chloro-2-methyl-[1,1'-biphenyl]-4-yl)amino)methyl)-3,5-bis(trifluoromethyl)phenyl)picolinamido)propanoic acid

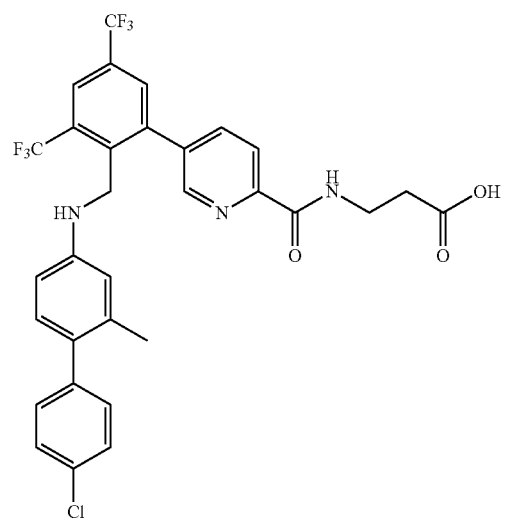 [SMILES: Cc1cc(NCc2c(-c3ccc(C(=O)NCCC(=O)O)nc3)cc(C(F)(F)F)cc2C(F)(F)F)ccc1-c1ccc(Cl)cc1]

The title compound was prepared as described in Example 71 substituting 4'-chloro-2-methyl-[1,1'-biphenyl]-4-amine (prepared as in Example 76, STEP B) for 4'-chloro-[1,1'-biphenyl]-4-amine.
$^1$H NMR (400 MHz, CHLOROFORM-d) δ 8.61 (d, J=1.47 Hz, 1H), 8.37-8.47 (m, 1H), 8.21 (d, J=7.83 Hz, 1H), 8.05-8.10 (m, 1H), 8.01 (dd, J=2.20, 8.07 Hz, 1H), 7.75 (s, 1H), 7.30-7.38 (m, 2H), 7.16-7.23 (m, 2H), 6.91-6.99 (m, 1H), 6.24-6.32 (m, 2H), 4.28 (s, 2H), 3.77 (q, J=6.36 Hz, 2H), 2.73 (t, J=6.11 Hz, 2H), 2.13 (s, 3H); MS m/z 636 (M+H).

Example 87

3-(5-(2-(((2',4'-dichloro-[1,1'-biphenyl]-4-yl)amino)methyl)-3,5-bis(trifluoromethyl)phenyl)picolinamido)propanoic acid

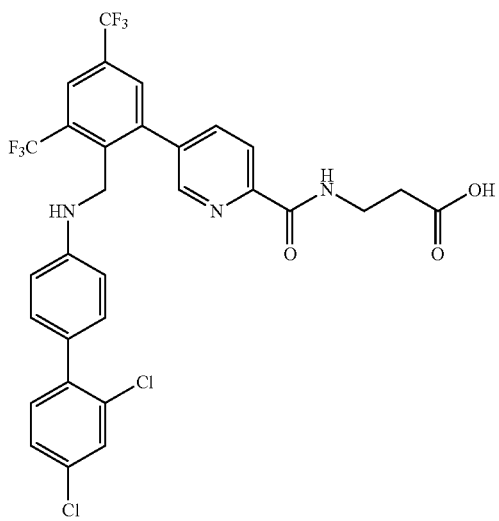 [SMILES: O=C(O)CCNC(=O)c1ccc(-c2cc(C(F)(F)F)cc(C(F)(F)F)c2CNc2ccc(-c3ccc(Cl)cc3Cl)cc2)cn1]

The title compound was prepared as described in Example 71 substituting 2',4'-dichloro-[1,1'-biphenyl]-4-amine (prepared as in Example 72, STEP D) for 4'-chloro-[1,1'-biphenyl]-4-amine.

$^1$H NMR (400 MHz, CHLOROFORM-d) δ 8.60 (d, J=1.96 Hz, 1H), 8.42 (t, J=6.24 Hz, 1H), 8.20 (d, J=8.07 Hz, 1H), 8.08 (s, 1H), 7.99 (dd, J=1.96, 8.07 Hz, 1H), 7.74 (s, 1H), 7.43 (d, J=1.71 Hz, 1H), 7.12-7.25 (m, 4H), 6.44 (d, J=8.56 Hz, 2H), 4.30 (s, 2H), 3.75 (q, J=6.11 Hz, 2H), 2.71 (t, J=6.11 Hz, 2H); MS m/z 656 (M+H).

Example 88

3-(5-(5-chloro-2-(((2,4'-difluoro-[1,1'-biphenyl]-4-yl)amino)methyl)phenyl)picolinamido)propanoic acid

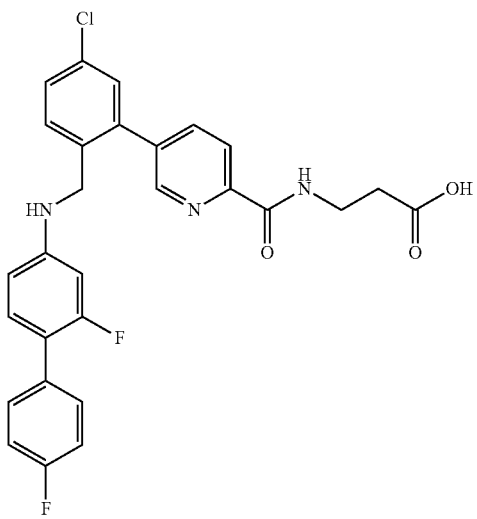

The title compound was prepared as described in Example 11 substituting 4-bromo-3-fluoroaniline and (4-fluorophenyl)boronic acid for 4-bromo-2-fluoroaniline and (2,4-dichlorophenyl)boronic acid, respectively.

$^1$H NMR (DMSO-d$_6$, 400 MHz): δ=8.82-8.93 (m, 1H), 8.74 (d, J=1.2 Hz, 1H), 8.06-8.18 (m, 2H), 7.65-7.81 (m, 1H), 7.53-7.63 (m, 2H), 7.47-7.53 (m, 1H), 7.40-7.47 (m, 2H), 7.07-7.35 (m, 3H), 6.16-6.44 (m, 1H), 4.16 (s, 2H), 3.43-3.69 (m, 2H), 2.55-2.62 ppm (m, 2H); MS m/z 523 (M+H).

Example 89

3-(5-(5-chloro-2-(((2,2',4'-trifluoro-[1,1'-biphenyl]-4-yl)amino)methyl)phenyl)picolinamido)propanoic acid

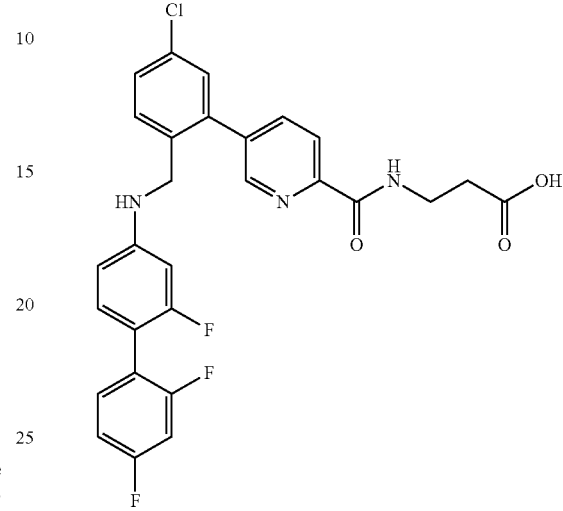

The title compound was prepared as described in Example 11 substituting 4-bromo-3-fluoroaniline and (2,4-difluorophenyl)boronic acid for 4-bromo-2-fluoroaniline and (2,4-dichlorophenyl)boronic acid, respectively.

$^1$H NMR (DMSO-d$_6$, 400 MHz): δ=8.82-8.93 (m, 1H), 8.74 (d, J=1.2 Hz, 1H), 8.06-8.18 (m, 2H), 7.65-7.81 (m, 1H), 7.53-7.63 (m, 2H), 7.47-7.53 (m, 1H), 7.40-7.47 (m, 2H), 7.07-7.35 (m, 3H), 6.16-6.44 (m, 1H), 4.16 (s, 2H), 3.43-3.69 (m, 2H), 2.55-2.62 ppm (m, 2H); MS m/z 541 (M+H).

Example 90

3-(5-(5-chloro-2-(((2-fluoro-4'-(trifluoromethyl)-[1,1'-biphenyl]-4-yl)amino)methyl)phenyl)picolinamido)propanoic acid

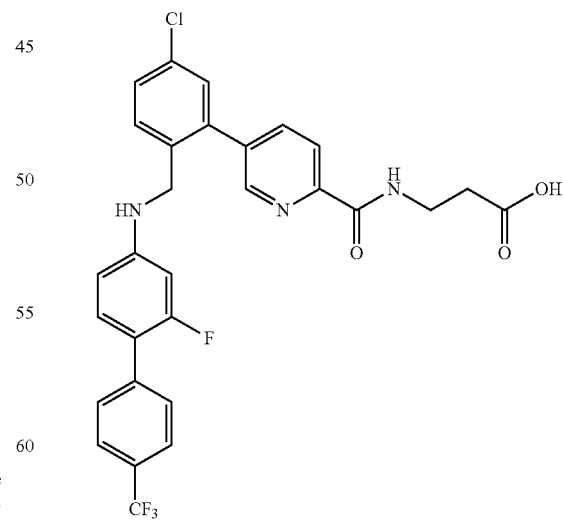

The title compound was prepared as described in Example 11 substituting 4-bromo-3-fluoroaniline and (4-(trifluoromethyl)phenyl)boronic acid for 4-bromo-2-fluoroaniline and (2,4-dichlorophenyl)boronic acid, respectively.

$^1$H NMR (DMSO-d$_6$, 400 MHz): δ=8.81-8.94 (m, 4H), 8.68-8.79 (m, 1H), 8.09-8.18 (m, 2H), 7.68-7.91 (m, 4H), 7.57-7.68 (m, 2H), 7.55 (d, J=1.2 Hz, 1H), 7.47 (s, 1H), 7.27 (t, J=8.9 Hz, 1H), 6.78 (s, 1H), 6.23-6.49 (m, 1H), 4.18 (d, J=5.4 Hz, 1H), 3.44-3.62 (m, 2H), 2.54-2.62 ppm (m, 2H); MS m/z 573 (M+H).

Example 91

3-(5-(5-chloro-2-(((4'-chloro-2-fluoro-[1,1'-biphenyl]-4-yl)amino)methyl)phenyl)picolinamido)propanoic acid

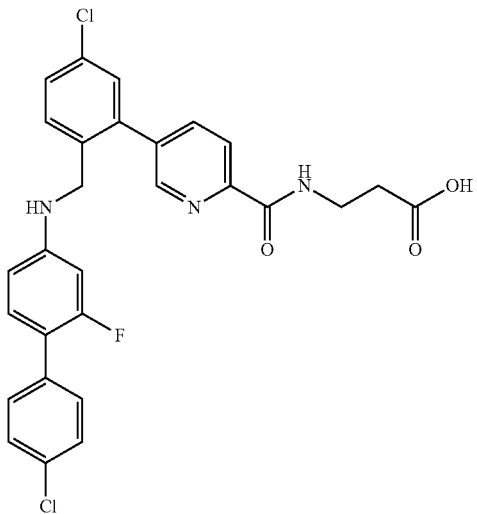

The title compound was prepared as described in Example 11 substituting 4-bromo-3-fluoroaniline and (4-chlorophenyl)boronic acid for 4-bromo-2-fluoroaniline and (2,4-dichlorophenyl)boronic acid, respectively.

$^1$H NMR (DMSO-d$_6$, 400 MHz): δ=12.28 (br. s., 4H), 8.87 (s, 4H), 8.69-8.81 (m, 4H), 8.07-8.19 (m, 8H), 7.66-7.83 (m, 5H), 7.54 (s, 12H), 7.37-7.49 (m, 12H), 7.18 (d, J=9.0 Hz, 4H), 6.20-6.46 (m, 1H), 4.17 (br. s., 1H), 3.53 (br. s., 2H), 2.56 ppm (br. s., 2H)); MS m/z 540 (M+H).

Example 92

3-(5-(5-chloro-2-(((2',4'-dichloro-2-fluoro-[1,1'-biphenyl]-4-yl)amino)methyl)phenyl)picolinamido)propanoic acid

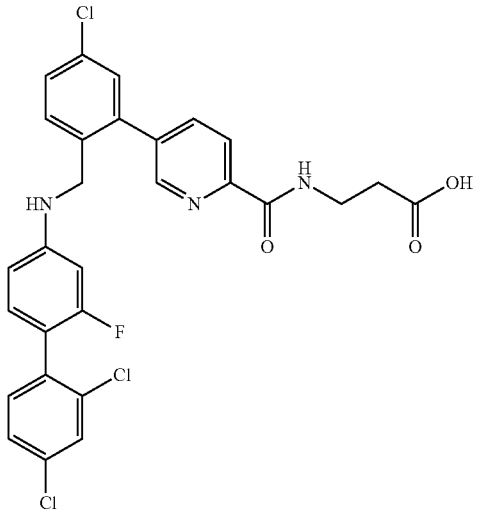 [SMILES: O=C(O)CCNC(=O)c1ccc(-c2cc(Cl)ccc2CNc2ccc(-c3ccc(Cl)cc3Cl)c(F)c2)cn1]

The title compound was prepared as described in Example 11 substituting 4-bromo-3-fluoroaniline for 4-bromo-2-fluoroaniline.

$^1$H NMR (DMSO-d$_6$, 400 MHz): δ=12.27 (br. s., 1H), 8.88 (s, 1H), 8.74 (s, 1H), 8.06-8.21 (m, 2H), 7.65-7.81 (m, 2H), 7.50-7.59 (m, 1H), 7.41-7.48 (m, 1H), 7.33 (d, J=8.3 Hz, 1H), 6.23-6.42 (m, 1H), 4.15 (d, J=5.1 Hz, 1H), 3.46-3.61 (m, 2H), 2.61-2.73 (m, 1H), 2.56 (s, 1H), 2.33 ppm (d, 1H)); MS m/z 574 (M+H).

Example 93

3-(5-(5-chloro-2-(((4'-chloro-2,3'-difluoro-[1,1'-biphenyl]-4-yl)amino)methyl)phenyl)picolinamido)propanoic acid

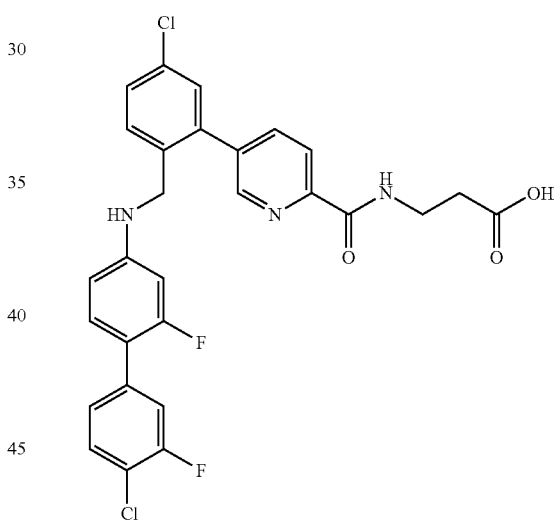

The title compound was prepared as described in Example 11 substituting 4-bromo-3-fluoroaniline and (4-chloro-3-fluorophenyl)boronic acid for 4-bromo-2-fluoroaniline and (2,4-dichlorophenyl)boronic acid, respectively.

$^1$H NMR (DMSO-d$_6$, 400 MHz): δ=12.28 (br. s., 1H), 8.83-8.94 (m, 1H), 8.70-8.78 (m, 1H), 8.06-8.19 (m, 2H), 8.02 (d, J=8.3 Hz, 2H), 7.65-7.82 (m, 1H), 7.50-7.65 (m, 2H), 7.38-7.50 (m, 2H), 7.16-7.34 (m, 1H), 6.25-6.43 (m, 1H), 4.17 (d, J=5.1 Hz, 1H), 3.46-3.64 (m, 2H), 2.56 ppm (d, J=2.4 Hz, 2H)); MS m/z 557 (M+H).

Example 94

3-(5-(2-((2',4'-dichloro-[1,1'-biphenyl]-4-yl)carbamoyl)-4,5-difluorophenyl)picolinamido)propanoic acid

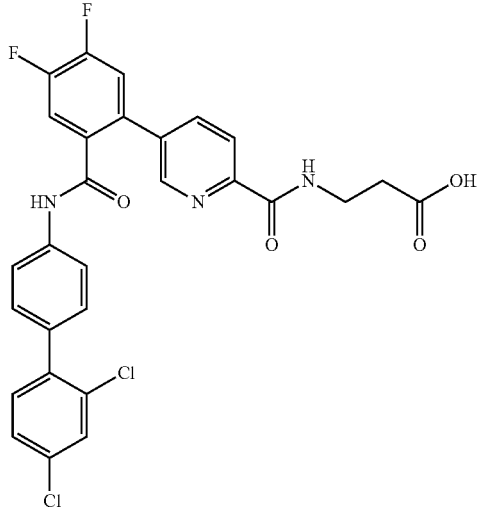 [SMILES: O=C(O)CCNC(=O)c1ccc(-c2cc(F)c(F)cc2C(=O)Nc2ccc(-c3ccc(Cl)cc3Cl)cc2)cn1]

STEP A: 2-bromo-N-(2',4'-dichloro-[1,1'-biphenyl]-4-yl)-4,5-difluorobenzamide Solid HATU (501 mg, 1.3 mmol) was added to a DMF solution (1 mL) of 2-bromo-4,5-difluorobenzoic acid (250 mg, 1.1 mmol), i-Pr$_2$NEt (0.5 mL, 3.2 mmol), and 2',4'-dichloro-[1,1'-biphenyl]-4-amine (251 mg, 1.1 mmol) and the resulting mixture was stirred at room temperature. After 2 h the resulting mixture was directly purified via column chromatography to yield the title compound.

STEP B: ethyl 3-(5-(2-((2',4'-dichloro-[1,1'-biphenyl]-4-yl)carbamoyl)-4,5-difluorophenyl)picolinamido)propanoate 2-Bromo-N-(2',4'-dichloro-[1,1'-biphenyl]-4-yl)-4,5-difluorobenzamide (100 mg, 0.22 mmol), ethyl 3-(5-(4,4,5,5-tetramethyl-1,3,2-dioxaborolan-2-yl)picolinamido)propanoate (114 mg, 0.33 mmol), Pd(dppf)Cl$_2$ (24 mg, 0.03 mmol), and K$_2$CO$_3$ (60 mg, 0.44 mmol) were dissolved in 1,4-dioxane (1 mL) and water (0.5 mL) and the resulting mixture was heated to 85° C. After 2 h the resulting mixture directly purified via column chromatography to yield the title compound.

STEP C: 3-(5-(2-((2',4'-dichloro-[1,1'-biphenyl]-4-yl)carbamoyl)-4,5-difluorophenyl)picolinamido)propanoic acid A 3M aqueous solution of NaOH (0.27 mL, 0.82 mmol) was added to a THF solution (0.9 mL) of ethyl 3-(5-(2-((2',4'-dichloro-[1,1'-biphenyl]-4-yl)carbamoyl)-4,5-difluorophenyl)picolinamido)propanoate (100 mg, 0.17 mmol) and the resulting mixture was stirred at room temperature. After 16 h the resulting mixture was concentrated and purified via HPLC to yield the title compound.

$^1$H NMR (DMSO-d$_6$, 400 MHz): δ=12.26 (br. s., 1H), 10.68 (s, 1H), 8.79-8.92 (m, 1H), 8.67 (s, 1H), 8.02-8.10 (m, 2H), 7.90-7.98 (m, 1H), 7.78-7.86 (m, 1H), 7.73 (d, J=2.0 Hz, 1H), 7.63 (d, J=8.6 Hz, 2H), 7.48-7.53 (m, 1H), 7.35-7.45 (m, 3H), 3.49 ppm (q, 2H); MS m/z 571 (M+H).

Example 95

3-(5-(4,5-difluoro-2-((4'-fluoro-[1,1'-biphenyl]-4-yl)carbamoyl)phenyl)picolinamido)propanoic acid

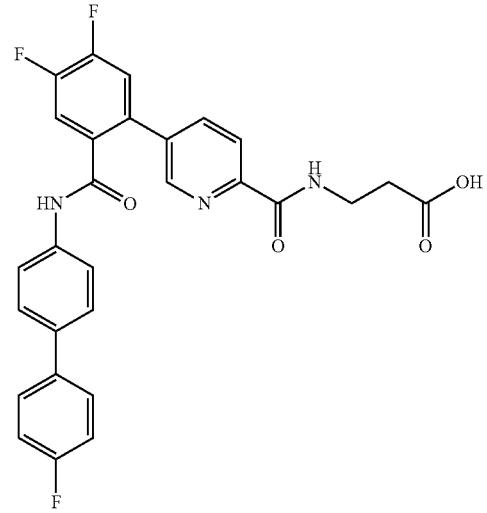 [SMILES: O=C(O)CCNC(=O)c1ccc(-c2cc(F)c(F)cc2C(=O)Nc2ccc(-c3ccc(F)cc3)cc2)cn1]

The title compound was prepared as described in Example 94 substituting 4'-fluoro-[1,1'-biphenyl]-4-amine for 2',4'-dichloro-[1,1'-biphenyl]-4-amine.

$^1$H NMR (DMSO-d$_6$, 400 MHz): δ=10.65 (s, 1H), 8.77-8.93 (m, 1H), 8.66 (s, 1H), 8.04 (s, 2H), 7.89-7.99 (m, 1H), 7.82 (dd, J=11.2, 7.6 Hz, 1H), 7.57-7.71 (m, 6H), 7.27 (t, J=8.8 Hz, 2H), 4.26 (t, J=7.0 Hz, 1H), 3.48 (q, J=6.5 Hz, 2H), 2.38-2.44 ppm (m, 1H)); MS m/z 521 (M+H).

Example 96

3-(5-(4,5-difluoro-2-((4'-(trifluoromethyl)-[1,1'-biphenyl]-4-yl)carbamoyl)phenyl)picolinamido)propanoic acid

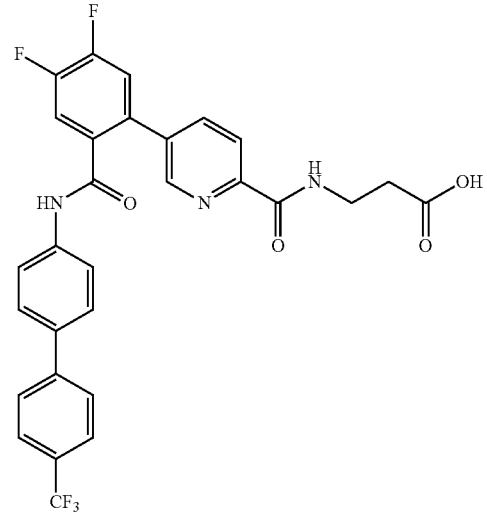 [SMILES: O=C(O)CCNC(=O)c1ccc(-c2cc(F)c(F)cc2C(=O)Nc2ccc(-c3ccc(C(F)(F)F)cc3)cc2)cn1]

The title compound was prepared as described in Example 94 substituting 4'-(trifluoromethyl)[1,1'-biphenyl]-4-amine for 2',4'-dichloro-[1,1'-biphenyl]-4-amine.

$^1$H NMR (DMSO-d$_6$ $^1$H NMR (DMSO-d$_6$, 400 MHz): δ=10.65 (s, 5H), 8.85 (t, J=5.5 Hz, 5H), 8.66 (s, 6H), 8.04 (s, 11H), 7.92 (d, J=8.3 Hz, 3H), 7.95 (d, J=8.1 Hz, 3H), 7.80 (d, J=7.6 Hz, 3H), 7.83 (d, J=7.6 Hz, 3H), 7.55-7.72 (m, 36H), 7.27 (t, J=8.8 Hz, 12H), 3.48 (d, J=6.4 Hz, 8H), 3.48 ppm (d, J=19.3 Hz, 4H)); MS m/z 570 (M+H).

Example 97

3-(5-(2-((4'-chloro-[1,1'-biphenyl]-4-yl)carbamoyl)-4,5-difluorophenyl)picolinamido)propanoic acid

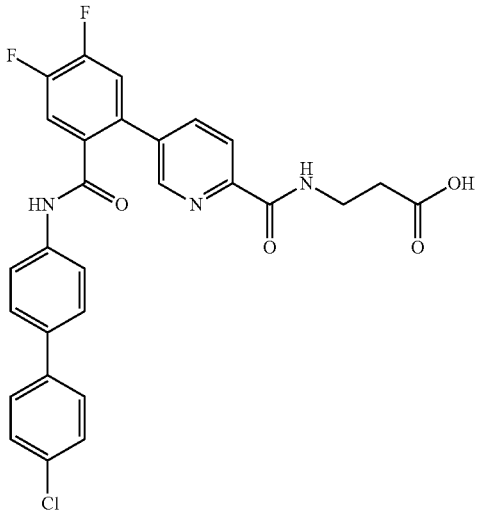 [SMILES: O=C(O)CCNC(=O)c1ccc(-c2cc(F)c(F)cc2C(=O)Nc2ccc(-c3ccc(Cl)cc3)cc2)cn1]

The title compound was prepared as described in Example 94 substituting 4'-chloro-[1,1'-biphenyl]-4-amine for 2',4'-dichloro-[1,1'-biphenyl]-4-amine.

$^1$H NMR (DMSO-d$_6$ $^1$H NMR (DMSO-d$_6$, 400 MHz): δ=10.62 (br. s., 1H), 8.83 (br. s., 1H), 8.66 (br. s., 1H), 8.04 (br. s., 2H), 7.75-7.99 (m, 2H), 7.57-7.72 (m, 6H), 7.49 (d, J=8.1 Hz, 2H), 3.49 ppm (br. s., 4H)); MS m/z 537 (M+H).

Example 98

3-(5-(5-chloro-2-(((4'-chloro-2-cyano-3'-(trifluoromethyl)-[1,1'-biphenyl]-4-yl)amino)methyl)phenyl)picolinamido)propanoic acid

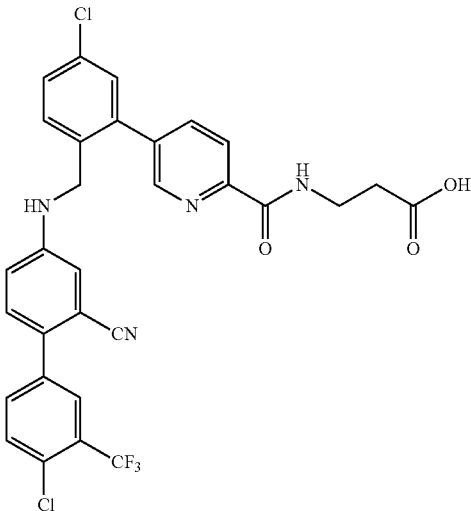 [SMILES: N#Cc1cc(NCc2ccc(Cl)cc2-c2ccc(C(=O)NCCC(=O)O)nc2)ccc1-c1ccc(Cl)c(C(F)(F)F)c1]

The title compound was prepared as described in Example 11 substituting 5-amino-2-bromobenzonitrile and (4-chloro-3-(trifluoromethyl)phenyl)boronic acid for 4-bromo-2-fluoroaniline and (2,4-dichlorophenyl)boronic acid, respectively.

$^1$H NMR (DMSO-d$_6$, 400 MHz): δ=8.85 (s, 1H), 8.68 (s, 1H), 8.02-8.22 (m, 2H), 7.83 (d, J=5.9 Hz, 2H), 7.40-7.69 (m, 4H), 7.34 (d, J=8.6 Hz, 1H), 6.74-6.98 (m, 2H), 4.40 (br. s., 2H), 3.46-3.67 ppm (m, 4H)); MS m/z 614 (M+H).

Example 99

3-(5-(5-chloro-2-(((2',4'-dichloro-2-cyano-[1,1'-biphenyl]-4-yl)amino)methyl)phenyl)picolinamido)propanoic acid

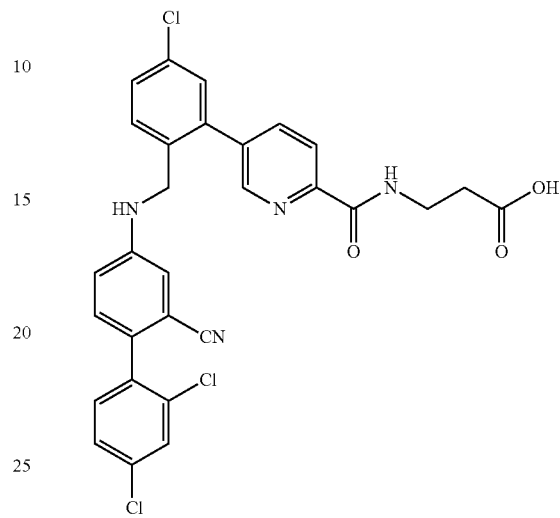

The title compound was prepared as described in Example 11 substituting 5-amino-2-bromobenzonitrile and (2,4-dichlorophenyl)boronic acid for 4-bromo-2-fluoroaniline and (2,4-dichlorophenyl)boronic acid, respectively.

$^1$H NMR (DMSO-d$_6$, 400 MHz): δ=12.01 (br. s., 1H), 8.61 (t, J=5.9 Hz, 1H), 8.48 (s, 1H), 8.05-8.16 (m, 2H), 7.83 (d, J=7.8 Hz, 1H), 7.67-7.75 (m, 1H), 7.60-7.67 (m, 1H), 7.57 (s, 2H), 7.44 (s, 1H), 7.15 (d, J=8.6 Hz, 1H), 6.92 (d, J=2.4 Hz, 1H), 6.80-6.91 (m, 2H), 4.21 (d, J=5.1 Hz, 2H), 3.73-3.87 (m, 1H), 3.47-3.66 ppm (m, 3H)); MS m/z 581 (M+H).

Example 100

3-(5-(5-chloro-2-(((2-cyano-4'-fluoro-3'-(trifluoromethyl)-[1,1'-biphenyl]-4-yl)amino)methyl)phenyl)picolinamido)propanoic acid

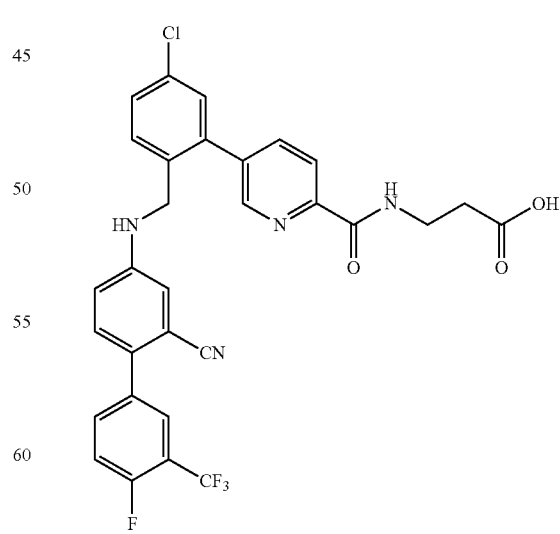

The title compound was prepared as described in Example 11 substituting 5-amino-2-bromobenzonitrile and (4-fluoro-3-(trifluoromethyl)phenyl)boronic acid for 4-bromo-2-fluoroaniline and (2,4-dichlorophenyl)boronic acid, respectively.

¹H NMR (CHLOROFORM-d, 400 MHz): δ=8.80-8.91 (m, 1H), 8.73 (s, 1H), 8.02-8.17 (m, 3H), 7.76-7.90 (m, 3H), 7.61 (t, J=9.7 Hz, 1H), 7.55 (s, 2H), 7.48 (s, 1H), 7.34 (d, J=8.8 Hz, 1H), 6.75-6.96 (m, 3H), 4.23 (br. s., 2H), 3.48-3.58 ppm (m, 4H)); MS m/z 598 (M+H).

Example 101

3-(5-(5-chloro-2-(((2'-chloro-2-cyano-3'-(trifluoromethyl)-[1,1'-biphenyl]-4-yl)amino)methyl)phenyl)picolinamido)propanoic acid

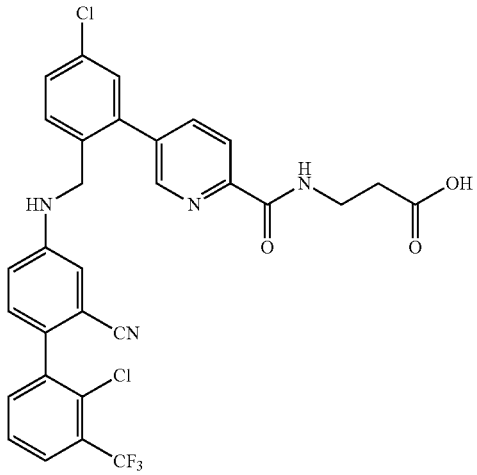 [SMILES: N#Cc1cc(NCc2ccc(Cl)cc2-c2ccc(C(=O)NCCC(=O)O)nc2)ccc1-c1cccc(C(F)(F)F)c1Cl]

The title compound was prepared as described in Example 11 substituting 5-amino-2-bromobenzonitrile and (2-chloro-3-(trifluoromethyl)phenyl)boronic acid for 4-bromo-2-fluoroaniline and (2,4-dichlorophenyl)boronic acid, respectively.
¹H NMR (DMSO-d₆, 400 MHz): δ=12.28 (br. s., 1H), 8.87 (t, J=5.9 Hz, 1H), 8.74 (s, 1H), 8.05-8.20 (m, 2H), 7.93 (d, J=7.8 Hz, 1H), 7.53-7.74 (m, 4H), 7.48 (s, 1H), 7.19 (d, J=8.6 Hz, 1H), 6.76-6.96 (m, 3H), 4.21 (d, J=5.1 Hz, 2H), 3.67-3.89 (m, 1H), 3.45-3.67 ppm (m, 4H)); MS m/z 614 (M+H).

Example 102

3-(5-(2-(((2-chloro-4'-fluoro-3'-(trifluoromethyl)-[1,1'-biphenyl]-4-yl)amino)methyl)-4,5-difluorophenyl)picolinamido)propanoic acid

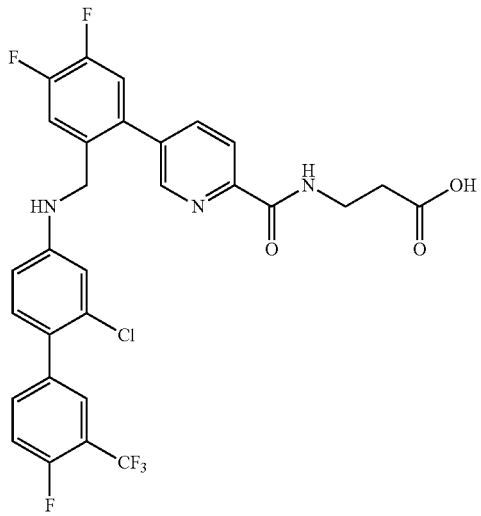 [SMILES: O=C(O)CCNC(=O)c1ccc(-c2cc(F)c(F)cc2CNc2ccc(-c3ccc(F)c(C(F)(F)F)c3)c(Cl)c2)cn1]

STEP A: (2-bromo-4,5-difluorophenyl)methanol

Solid CDI (4.3 g, 26.4 mmol) was added to a THF solution (130 mL) of 2-bromo-4,5-difluorobenzoic acid and the solution was refluxed. After 3 h the resulting mixture was cooled to room temperature and a water solution (26 mL) of NaBH₄ (666 mg, 17.6 mmol) was added. After 10 min the resulting mixture was diluted with EtOAc and 10% aqueous NaHCO₃ and the layers were separated. The organic layer was washed with water and brine, dried (Na₂SO₄), concentrated, and purified via column chromatography to yield the title compound.

STEP B: ethyl 3-(5-(4,5-difluoro-2-(hydroxymethyl)phenyl)picolinamido)propanoate (2-bromo-4,5-difluorophenyl)methanol (2.8 g, 12.5 mmol), ethyl 3-(5-(4,4,5,5-tetramethyl-1,3,2-dioxaborolan-2-yl)picolinamido)propanoate (4.8 g, 13.7 mmol), Pd(dppf)Cl₂ (1.4 g, 1.9 mmol), and K₂CO₃ (3.4 g, 24.9 mmol) were dissolved in 1,4-dioxane (28 mL) and water (15 mL) and the resulting mixture was heated to 85° C. After 2 h the resulting mixture was diluted with EtOAc and the layers were separated. The organic layer was dried (Na₂SO₄), concentrated, and purified via column chromatography to yield the title compound.

STEP C: ethyl 3-(5-(2-(bromomethyl)-4,5-difluorophenyl)picolinamido)propanoate

Neat CBr₄ (4.6 g, 13.7 mmol) was added to a 0° C., DCM solution (66 mL) of ethyl 3-(5-(4,5-difluoro-2-(hydroxymethyl)phenyl)picolinamido)propanoate (4.2 g, 11.4 mmol) and PPh₃ (3.6 g, 13.7 mmol), the cold bath was removed, and the resulting mixture was allowed to warm to room temperature. After 2 h the resulting mixture was diluted with diethyl ether, filtered through a pad of CELITE, concentrated and purified via column chromatography to yield the title compound.

STEP D: ethyl 3-(5-(2-(((3-chloro-4-iodophenyl)amino)methyl)-4,5-difluorophenyl)picolinamido)propanoate Ethyl 3-(5-(2-(bromomethyl)-4,5-difluorophenyl)picolinamido)propanoate (1.0 g, 2.3 mmol), 3-chloro-4-iodoaniline (1.2 g, 4.7 mmol), and K₂CO₃ (647 mg, 4.7 mmol) were diluted with DMF (2.4 mL) and the resulting mixture was stirred at room temperature. After 2 h the resulting mixture directly purified via column chromatography to yield the title compound.

STEP E: ethyl 3-(5-(2-(((2-chloro-4'-fluoro-3'-(trifluoromethyl)-[1,1'-biphenyl]-4-yl)amino)methyl)-4,5-difluorophenyl)picolinamido)propanoate Ethyl 3-(5-(2-(((3-chloro-4-iodophenyl)amino)methyl)-4,5-difluorophenyl)picolinamido)propanoate (123 mg, 0.21 mmol), (4-fluoro-3-(trifluoromethyl)phenyl)boronic acid (85 mg, 0.41 mmol), Pd(dppf)Cl₂ (23 mg, 0.03 mmol), and K₂CO₃ (85 mg, 0.62 mmol) were dissolved in 1,4-dioxane (1 mL) and water (0.3 mL) and the resulting mixture was heated to 70° C. After 1 h the resulting mixture directly purified via column chromatography to yield the title compound.

STEP F: 3-(5-(2-(((2-chloro-4'-fluoro-3'-(trifluoromethyl)-[1,1'-biphenyl]-4-yl)amino)methyl)-4,5-difluorophenyl)picolinamido)propanoic acid A 3M aqueous solution of NaOH (0.28 mL, 0.84 mmol) was added to a THF solution (0.9 mL) of ethyl 3-(5-(2-(((2-chloro-4'-fluoro-3'-(trifluoromethyl)-[1,1'-biphenyl]-4-yl)amino)methyl)-4,5-difluorophenyl)picolinamido)propanoate (100 mg, 0.17 mmol) and the resulting mixture was stirred at room temperature. After 16 h the resulting mixture was concentrated and purified via HPLC to yield the title compound.

¹H NMR (DMSO-d₆, 400 MHz): δ=8.84-8.96 (m, 1H), 8.69-8.77 (m, 1H), 8.08-8.16 (m, 2H), 7.50-7.62 (m, 2H), 7.39-7.50 (m, 3H), 7.31-7.39 (m, 2H), 7.07 (d, J=8.6 Hz, 1H), 6.56 (d, J=2.0 Hz, 1H), 6.48 (dd, 1H), 4.15 (s, 1H), 3.53 (q, J=6.7 Hz, 2H), 2.54-2.59 ppm (m, 2H)); MS m/z 609 (M+H).

Example 103

3-(5-(2-(((2,4'-dichloro-[1,1'-biphenyl]-4-yl)amino)methyl)-4,5-difluorophenyl)picolinamido)propanoic acid

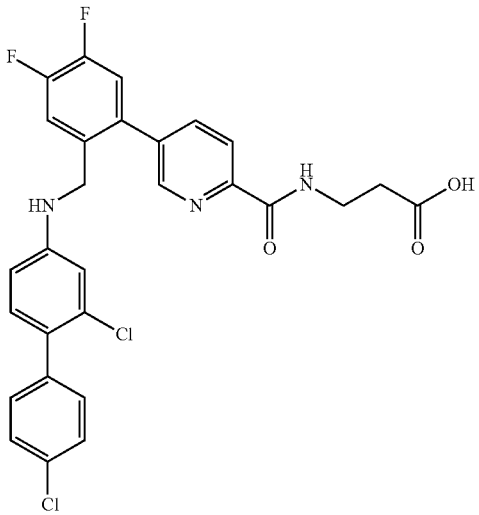 [SMILES: O=C(O)CCNC(=O)c1ccc(-c2cc(F)c(F)cc2CNc2ccc(-c3ccc(Cl)cc3)c(Cl)c2)cn1]

The title compound was prepared as described in Example 102 substituting (4-chlorophenyl)boronic acid for (4-fluoro-3-(trifluoromethyl)phenyl)boronic acid.

¹H NMR (DMSO-d₆, 400 MHz): δ=8.84-8.96 (m, 1H), 8.69-8.77 (m, 1H), 8.08-8.16 (m, 2H), 7.50-7.62 (m, 2H), 7.42-7.50 (m, 2H), 7.31-7.39 (m, 2H), 7.07 (d, J=8.6 Hz, 1H), 6.56 (d, J=2.0 Hz, 1H), 6.48 (dd, 1H), 4.15 (s, 1H), 3.53 (q, J=6.7 Hz, 2H), 2.54-2.59 ppm (m, 2H)); MS m/z 557 (M+H).

Example 104

3-(5-(2-(((2,4'-dichloro-2'-fluoro-[1,1'-biphenyl]-4-yl)amino)methyl)-4,5-difluorophenyl)picolinamido)propanoic acid

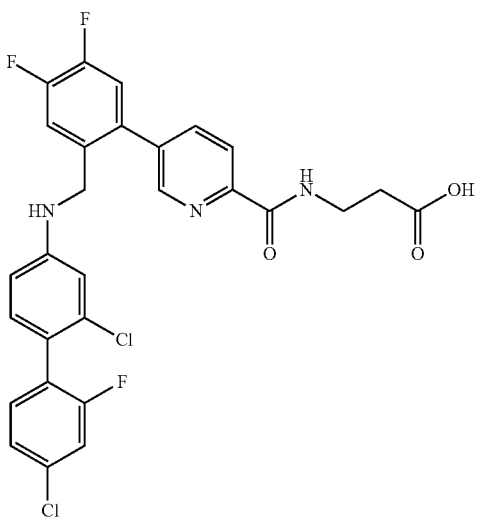 [SMILES: O=C(O)CCNC(=O)c1ccc(-c2cc(F)c(F)cc2CNc2ccc(-c3ccc(Cl)cc3F)c(Cl)c2)cn1]

The title compound was prepared as described in Example 102 substituting (4-chloro-2-fluorophenyl)boronic acid for (4-fluoro-3-(trifluoromethyl)phenyl)boronic acid.

¹H NMR (DMSO-d₆, 400 MHz): δ=8.89 (t, J=6.1 Hz, 1H), 8.73 (d, J=6.6 Hz, 1H), 8.08-8.16 (m, 2H), 7.58 (dd, J=11.1, 8.1 Hz, 2H), 7.37-7.50 (m, 2H), 7.28-7.37 (m, 2H), 6.99-7.06 (m, 2H), 6.57-6.64 (m, 2H), 6.48 (dd, J=8.3, 2.3 Hz, 1H), 4.15 (s1H), 2.54-2.59 ppm (m, 2H)); MS m/z 575 (M+H).

Example 105

3-(5-(2-(((2-chloro-2'-fluoro-4'-methyl-[1,1'-biphenyl]-4-yl)amino)methyl)-4,5-difluorophenyl)picolinamido)propanoic acid

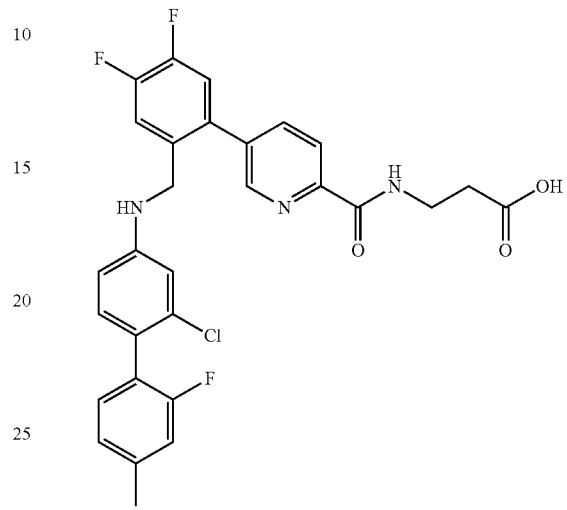

The title compound was prepared as described in Example 102 substituting (2-fluoro-4-methylphenyl)boronic acid for (4-fluoro-3-(trifluoromethyl)phenyl)boronic acid.

¹H NMR (DMSO-d₆, 400 MHz): δ=8.82-8.98 (m, 1H), 8.74 (d, J=5.1 Hz, 1H), 8.07-8.19 (m, 2H), 7.49-7.64 (m, 1H), 6.90-7.30 (m, 5H), 6.41-6.57 (m, 1H), 3.40-3.64 (m, 3H), 2.55-2.63 (m, 2H), 2.35 ppm (s, 3H); MS m/z 555 (M+H).

Example 106

3-(5-(2-(((2,4'-dichloro-3'-(trifluoromethyl)-[1,1'-biphenyl]-4-yl)amino)methyl)-4,5-difluorophenyl)picolinamido)propanoic acid

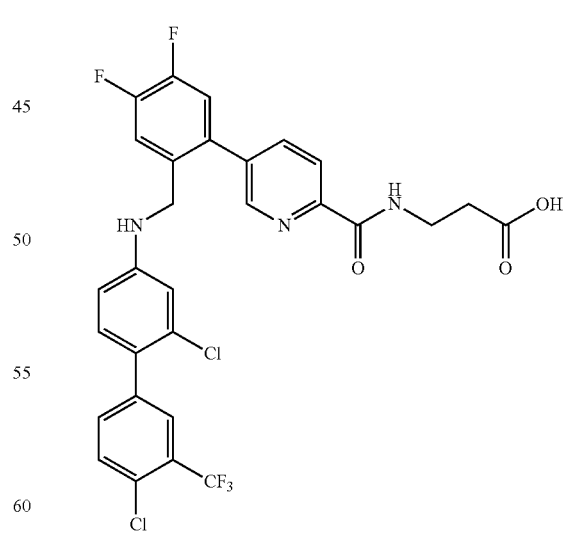

The title compound was prepared as described in Example 102 substituting (4-chloro-3-(trifluoromethyl)phenyl)boronic acid for (4-fluoro-3-(trifluoromethyl)phenyl)boronic acid.

¹H NMR (DMSO-d₆, 400 MHz): δ=8.82-8.98 (m, 1H), 8.74 (d, J=5.1 Hz, 1H), 8.07-8.19 (m, 2H), 7.49-7.64 (m, 1H), 7.18-7.32 (m, 3H) 6.90-7.10 (m, 2H), 6.41-6.57 (m, 1H), 3.40-3.64 (m, 3H), 2.55-2.63 (m, 2H); MS m/z 625 (M+H).

Example 107

3-(5-(2-(((2,2'-dichloro-3'-(trifluoromethyl)-[1,1'-biphenyl]-4-yl)amino)methyl)-4,5-difluorophenyl)picolinamido)propanoic acid

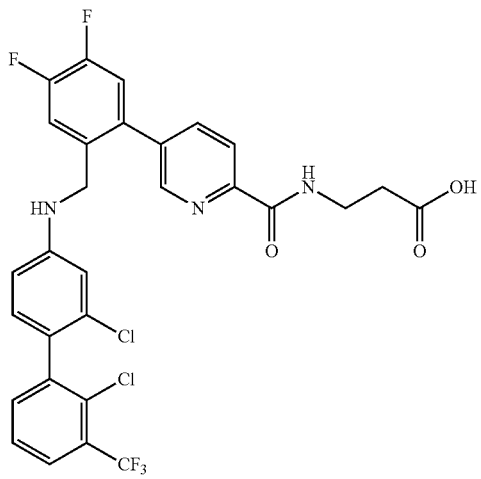 [SMILES: O=C(O)CCNC(=O)c1ccc(-c2cc(F)c(F)cc2CNc2ccc(-c3cccc(C(F)(F)F)c3Cl)c(Cl)c2)cn1]

The title compound was prepared as described in Example 102 substituting (2-chloro-3-(trifluoromethyl)phenyl)boronic acid for (4-fluoro-3-(trifluoromethyl)phenyl)boronic acid.

$^1$H NMR (DMSO-$d_6$, 400 MHz): δ=8.83-8.96 (m, 1H), 8.69-8.76 (m, 1H), 8.07-8.16 (m, 2H), 7.50-7.60 (m, 2H), 7.39-7.50 (m, 3H), 7.31-7.39 (m, 2H), 7.07 (d, J=8.6 Hz, 1H), 6.56 (d, J=2.0 Hz, 1H), 6.48 (m, 1H), 4.15 (s, 1H), 3.53 (q, J=6.7 Hz, 2H), 2.54-2.59 ppm (m, 2H); MS m/z 625 (M+H).

Example 108

3-(5-(4,5-difluoro-2-(((2,2',4'-trichloro-[1,1'-biphenyl]-4-yl)amino)methyl)phenyl)picolinamido)propanoic acid

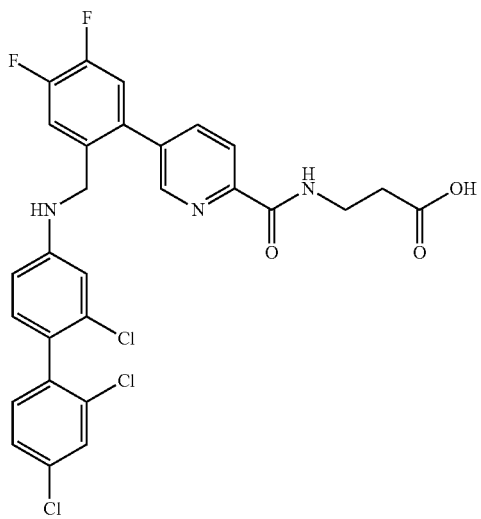 [SMILES: O=C(O)CCNC(=O)c1ccc(-c2cc(F)c(F)cc2CNc2ccc(-c3ccc(Cl)cc3Cl)c(Cl)c2)cn1]

The title compound was prepared as described in Example 102 substituting (2,4-dichlorophenyl)boronic acid for (4-fluoro-3-(trifluoromethyl)phenyl)boronic acid.

$^1$H NMR (DMSO-$d_6$, 400 MHz): δ=8.89 (t, J=6.1 Hz, 1H), 8.73 (d, J=6.6 Hz, 1H), 8.08-8.16 (m, 2H), 7.58 (dd, J=11.1, 8.1 Hz, 2H), 7.37-7.50 (m, 2H), 7.28-7.37 (m, 2H), 6.99-7.06 (m, 2H), 6.57-6.64 (m, 2H), 6.48 (dd, J=8.3, 2.3 Hz, 1H), 4.15 (s 1H), 2.54-2.59 ppm (m, 2H); MS m/z 592 (M+H).

Example 109

3-(5-(2-(((2-cyano-4'-fluoro-3'-(trifluoromethyl)-[1,1'-biphenyl]-4-yl)amino)methyl)-4,5-difluorophenyl)picolinamido)propanoic acid

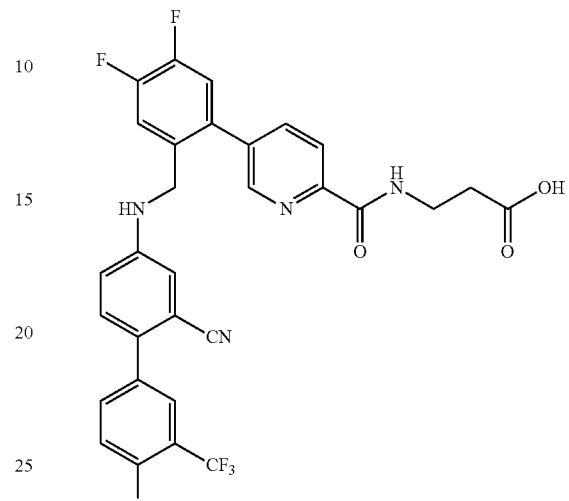

The title compound was prepared as described in Example 102 substituting 5-amino-2-iodobenzonitrile for 3-chloro-4-iodoaniline.

$^1$H NMR (DMSO-$d_6$, 400 MHz): δ=8.81-9.01 (m, 2H), 8.65-8.81 (m, 2H), 8.00-8.23 (m, 3H), 7.90 (d, J=6.1 Hz, 2H), 7.51-7.67 (m, 2H), 7.45 (br. s., 1H), 7.33 (dd, J=18.1, 8.6 Hz, 2H), 6.78-6.97 (m, 2H), 6.76 (br. s., 1H), 6.64 (d, J=8.6 Hz, 1H), 4.38 (br. s., 1H), 4.22 ppm (br. s., 2H); MS m/z 600 (M+H).

Example 110

3-(5-(2-(((4'-chloro-2-cyano-[1,1'-biphenyl]-4-yl)amino)methyl)-4,5-difluorophenyl)picolinamido)propanoic acid

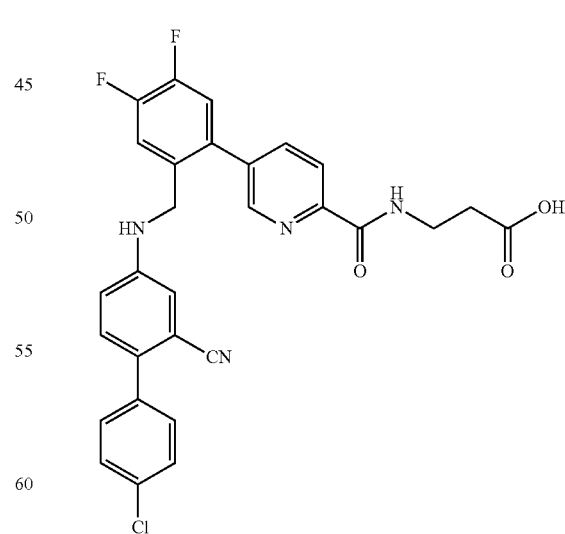

The title compound was prepared as described in Example 102 substituting 5-amino-2-iodobenzonitrile and (4-chlorophenyl)boronic acid for 3-chloro-4-iodoaniline and (4-fluoro-3-(trifluoromethyl)phenyl)boronic acid, respectively.

¹H NMR (DMSO-d₆, 400 MHz): δ=8.88 (t, J=6.0 Hz, 1H), 8.68-8.78 (m, 1H), 8.08-8.18 (m, 2H), 7.87-7.95 (m, 3H), 7.76-7.86 (m, 3H), 7.53-7.64 (m, 2H), 7.38 (d, J=8.6 Hz, 2H), 6.94 (d, J=2.4 Hz, 1H), 6.86 (dd, J=8.7, 2.3 Hz, 1H), 4.23 (s, 2H), 3.46-3.60 ppm (m, 2H); MS m/z 548 (M+H).

Example 111

3-(5-(2-(((4'-chloro-2-cyano-2'-fluoro-[1,1'-biphenyl]-4-yl)amino)methyl)-4,5-difluorophenyl)picolinamido)propanoic acid

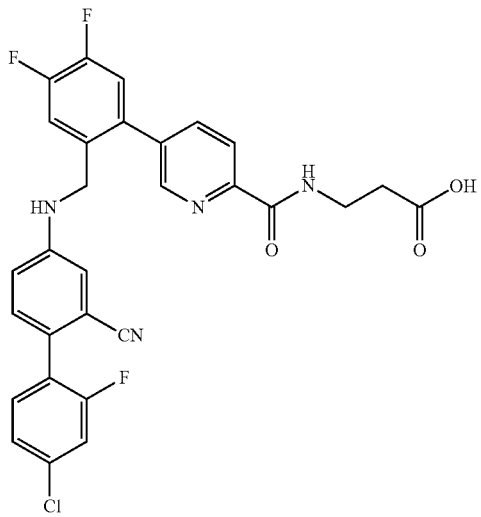 [SMILES: N#Cc1cc(NCc2cc(F)c(F)cc2-c2ccc(C(=O)NCCC(=O)O)nc2)ccc1-c1ccc(Cl)cc1F]

The title compound was prepared as described in Example 102 substituting 5-amino-2-iodobenzonitrile and (4-chloro-2-fluorophenyl)boronic acid for 3-chloro-4-iodoaniline and (4-fluoro-3-(trifluoromethyl)phenyl)boronic acid, respectively.

¹H NMR (DMSO-d₆, 400 MHz): δ=8.90 (dd, J=10.6, 5.7 Hz, 2H), 8.74 (d, J=7.8 Hz, 1H), 8.07-8.17 (m, 3H), 8.03 (dd, J=10.8, 8.3 Hz, 1H), 7.77-7.89 (m, 1H), 7.52-7.64 (m, 3H), 7.34-7.52 (m, 3H), 7.17-7.28 (m, 1H), 4.16-4.31 (m, 2H), 3.48-3.60 (m, 4H), 2.54-2.60 ppm (m, 2H); MS m/z 566 (M+H).

Example 112

3-(5-(2-(((2-cyano-2'-fluoro-4'-methyl-[1,1'-biphenyl]-4-yl)amino)methyl)-4,5-difluorophenyl)picolinamido)propanoic acid

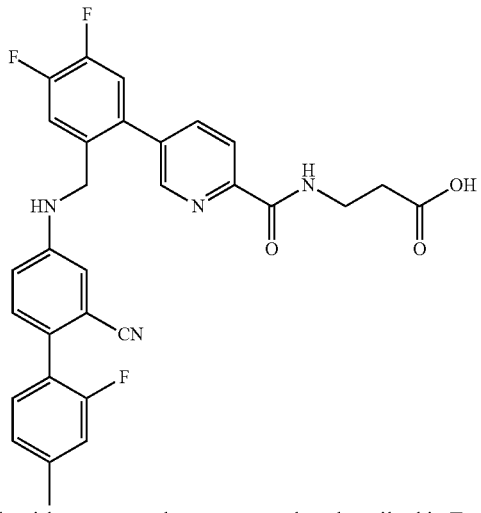

The title compound was prepared as described in Example 102 substituting 5-amino-2-iodobenzonitrile and (2-fluoro-4-methylphenyl)boronic acid for 3-chloro-4-iodoaniline and (4-fluoro-3-(trifluoromethyl)phenyl)boronic acid, respectively.

¹H NMR (DMSO-d₆, 400 MHz): δ=8.91 (br. s., 1H), 8.75 (s, 1H), 7.91-8.31 (m, 3H), 7.81 (br. s., 1H), 7.42-7.72 (m, 2H), 7.03-7.42 (m, 4H), 6.90 (s, 1H), 4.20 (s, 1H), 3.32-3.68 (m, 3H), 2.56 (s, 1H), 2.36 ppm (s, 3H); MS m/z 546 (M+H).

Example 113

3-(5-(2-(((4'-chloro-2-cyano-3'-(trifluoromethyl)-[1,1'-biphenyl]-4-yl)amino)methyl)-4,5-difluorophenyl)picolinamido)propanoic acid

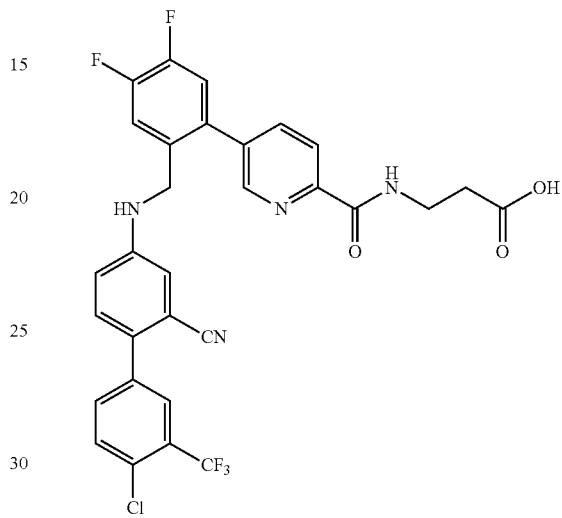

The title compound was prepared as described in Example 102 substituting 5-amino-2-iodobenzonitrile and (4-chloro-3-(trifluoromethyl)phenyl)boronic acid for 3-chloro-4-iodoaniline and (4-fluoro-3-(trifluoromethyl)phenyl)boronic acid, respectively.

¹H NMR (DMSO-d₆, 400 MHz): δ=8.88 (t, J=6.0 Hz, 1H), 8.68-8.78 (m, 1H), 8.08-8.18 (m, 2H), 7.87-7.95 (m, 2H), 7.76-7.86 (m, 3H), 7.53-7.64 (m, 2H), 7.38 (d, J=8.6 Hz, 2H), 6.94 (d, J=2.4 Hz, 1H), 6.86 (dd, J=8.7, 2.3 Hz, 1H), 4.23 (s, 2H), 3.46-3.60 ppm (m, 2H); MS m/z 616 (M+H).

Example 114

3-(5-(2-(((2',4'-dichloro-2-cyano-[1,1'-biphenyl]-4-yl)amino)methyl)-4,5-difluorophenyl)picolinamido)propanoic acid

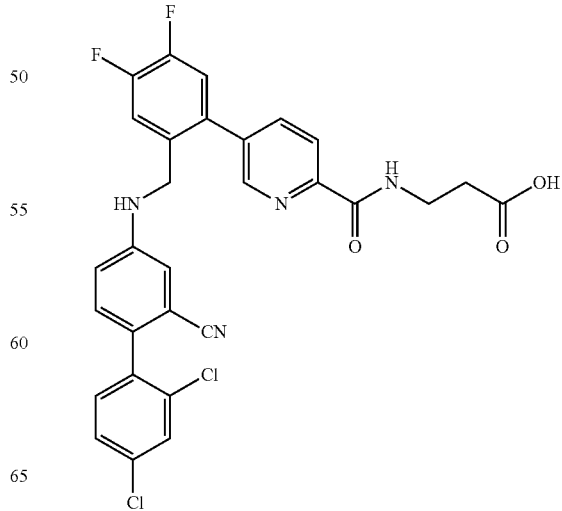

The title compound was prepared as described in Example 102 substituting 5-amino-2-iodobenzonitrile and (2,4-dichlorophenyl)boronic acid for 3-chloro-4-iodoaniline and (4-fluoro-3-(trifluoromethyl)phenyl)boronic acid, respectively.

$^1$H NMR (DMSO-$d_6$, 400 MHz): δ=8.88 (s, 1H), 8.73 (s, 1H), 8.10 (s, 2H), 7.76 (s, 1H), 7.47-7.65 (m, 4H), 7.41 (d, J=8.3 Hz, 1H), 7.15 (s, 1H), 4.20 (s, 2H), 3.53 (d, J=9.3 Hz, 3H), 2.56 ppm (m, 2H); MS m/z 582 (M+H).

Example 115

3-(5-(2-(((2-cyano-4'-fluoro-3'-methyl-[1,1'-biphenyl]-4-yl)amino)methyl)-4,5-difluorophenyl)picolinamido)propanoic acid

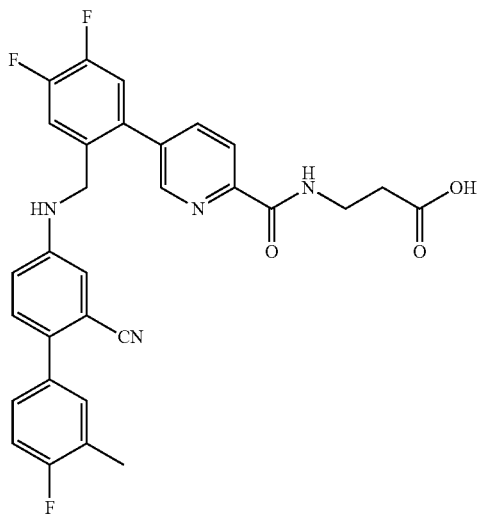 [SMILES: Cc1cc(-c2ccc(NCc3cc(F)c(F)cc3-c3ccc(C(=O)NCCC(=O)O)nc3)cc2C#N)ccc1F]

The title compound was prepared as described in Example 102 substituting 5-amino-2-iodobenzonitrile and (4-fluoro-3-methylphenyl)boronic acid for 3-chloro-4-iodoaniline and (4-fluoro-3-(trifluoromethyl)phenyl)boronic acid, respectively.

$^1$H NMR (DMSO-$d_6$, 400 MHz): δ=8.83-9.03 (m, 1H), 8.74 (d, J=9.5 Hz, 1H), 8.13 (d, J=10.5 Hz, 1H), 7.92-8.07 (m, 1H), 7.74-7.90 (m, 1H), 7.16-7.68 (m, 4H), 4.37 (br. s., 1H), 4.27 (t, J=7.1 Hz, 1H), 4.20 (br. s., 1H), 3.49-3.63 (m, 2H), 2.27 ppm (br. s., 3H); MS m/z 546 (M+H).

Example 116

3-(5-(2-(((2-cyano-3'-fluoro-5'-(trifluoromethyl)-[1,1'-biphenyl]-4-yl)amino)methyl)-4,5-difluorophenyl)picolinamido)propanoic acid

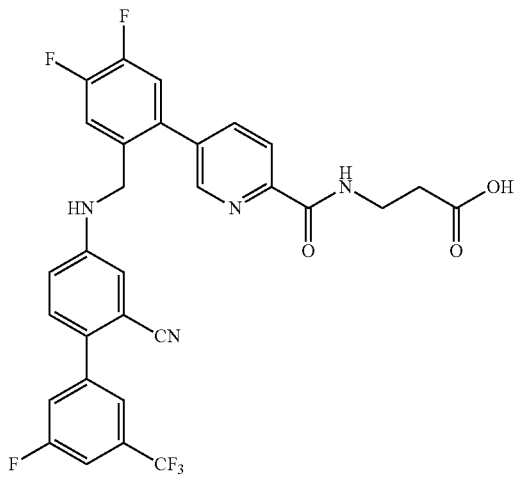 [SMILES: N#Cc1cc(NCc2cc(F)c(F)cc2-c2ccc(C(=O)NCCC(=O)O)nc2)ccc1-c1cc(F)cc(C(F)(F)F)c1]

The title compound was prepared as described in Example 102 substituting 5-amino-2-iodobenzonitrile and (3-fluoro-5-(trifluoromethyl)phenyl)boronic acid for 3-chloro-4-iodoaniline and (4-fluoro-3-(trifluoromethyl)phenyl)boronic acid, respectively.

$^1$H NMR (DMSO-$d_6$, 400 MHz): δ=9.80 (d, J=2.4 Hz, 1H), 8.88 (t, J=5.9 Hz, 1H), 8.72 (s, 1H), 8.07-8.19 (m, 3H), 7.64-7.78 (m, 4H), 7.59 (dd, J=11.0, 8.1 Hz, 2H), 7.34-7.45 (m, 1H), 6.93 (d, J=2.4 Hz, 1H), 6.85 (d, J=11.0 Hz, 1H), 4.24 (s, 2H), 3.55 (dq, J=12.7, 6.5 Hz, 4H), 2.54-2.60 ppm (m, 2H); MS m/z 600 (M+H).

Example 117

3-(5-(2-(((4'-chloro-[1,1'-biphenyl]-4-yl)amino)methyl)-4,5-difluorophenyl)picolinamido)propanoic acid

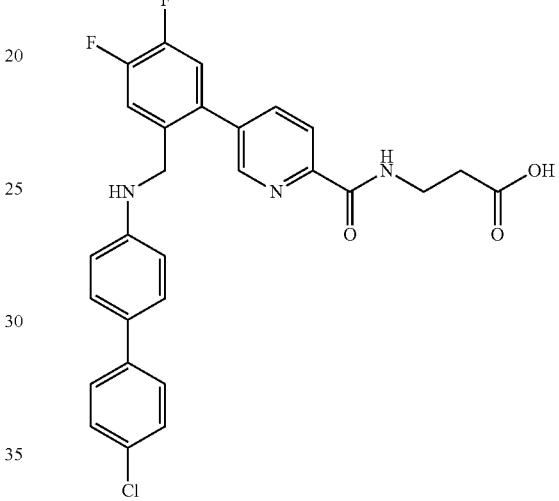

STEP A: ethyl 3-(5-(2-(((4'-chloro-[1,1'-biphenyl]-4-yl)amino)methyl)-4,5-difluorophenyl)picolinamido)propanoate Ethyl 3-(5-(2-(bromomethyl)-4,5-difluorophenyl)picolinamido)propanoate (115 mg, 0.27 mmol), 4'-chloro-[1,1'-biphenyl]-4-amine (110 mg, 0.54 mmol), and $K_2CO_3$ (74 mg, 0.54 mmol) were diluted with DMF (0.3 mL) and the resulting mixture was stirred at room temperature. After 2 h the resulting mixture directly purified via column chromatography to yield the title compound.

STEP B: 3-(5-(2-(((4'-chloro-[1,1'-biphenyl]-4-yl)amino)methyl)-4,5-difluorophenyl)picolinamido)propanoic acid A 3M aqueous solution of NaOH (0.34 mL, 1.03 mmol) was added to a THF solution (1.1 mL) of ethyl 3-(5-(2-(((4'-chloro-[1,1'-biphenyl]-4-yl)amino)methyl)-4,5-difluorophenyl)picolinamido)propanoate (115 mg, 0.21 mmol) and the resulting mixture was stirred at room temperature. After 16 h the resulting mixture was concentrated and purified via HPLC to yield the title compound.

$^1$H NMR (DMSO-$d_6$, 400 MHz): δ=8.92 (t, J=6.1 Hz, 1H), 8.74 (s, 1H), 8.09-8.18 (m, 2H), 7.78-7.87 (m, 1H), 7.76 (d, J=8.6 Hz, 1H), 7.66-7.73 (m, 3H), 7.48-7.57 (m, 3H), 7.35-7.42 (m, 1H), 7.28 (d, J=8.6 Hz, 1H), 3.54 (quin, J=6.7 Hz, 3H), 2.54-2.59 ppm (m, 2H); MS m/z 523 (M+H).

Example 118

3-(5-(2-(((2',4'-dichloro-[1,1'-biphenyl]-4-yl)amino)methyl)-4,5-difluorophenyl)picolinamido)propanoic acid

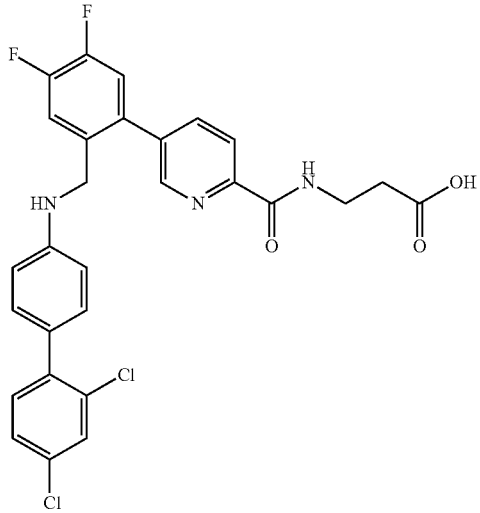 [SMILES: O=C(O)CCNC(=O)c1ccc(-c2cc(F)c(F)cc2CNc2ccc(-c3ccc(Cl)cc3Cl)cc2)cn1]

The title compound was prepared as described in Example 117 substituting 2',4'-dichloro-[1,1'-biphenyl]-4-amine for 4'-chloro-[1,1'-biphenyl]-4-amine.

$^1$H NMR (DMSO-$d_6$, 400 MHz): δ=8.82-8.99 (m, 1H), 8.75 (s, 1H), 8.09-8.17 (m, 2H), 7.71-7.87 (m, 1H), 7.48-7.66 (m, 2H), 7.39-7.48 (m, 2H), 7.30-7.39 (m, 1H), 7.27 (d, J=8.6 Hz, 1H), 7.14 (d, J=8.6 Hz, 1H), 6.52 (d, 1H), 4.15 (s, 1H), 3.43-3.59 (m, 2H), 2.54-2.60 ppm (m, 2H); MS m/z 557 (M+H).

Example 119

3-(5-(2-(((4'-chloro-2'-methyl-2-(trifluoromethyl)-[1,1'-biphenyl]-4-yl)amino)methyl)-5-(trifluoromethyl)phenyl)picolinamido)propanoic acid

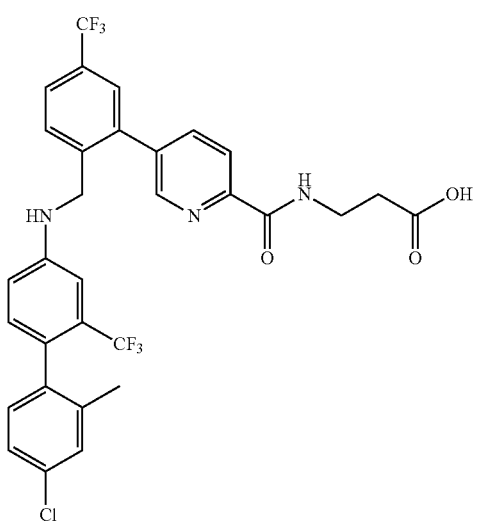 [SMILES: Cc1cc(Cl)ccc1-c1ccc(NCc2ccc(C(F)(F)F)cc2-c2ccc(C(=O)NCCC(=O)O)nc2)cc1C(F)(F)F]

The title compound was prepared as described in Example 22 substituting 4-iodo-3-(trifluoromethyl)aniline for 4-iodoaniline.

$^1$H NMR (ACETONE-$d_6$, 400 MHz): δ=8.78 (br. s., 1H), 8.20-8.38 (m, 3H), 7.81-8.00 (m, 3H), 7.69-7.81 (m, 3H), 7.63 (d, J=8.8 Hz, 1H), 7.34-7.51 (m, 2H), 7.28 (d, J=2.0 Hz, 1H), 7.20 (dd, J=8.3, 2.2 Hz, 2H), 7.08 (d, J=8.3 Hz, 1H), 7.02 (d, J=2.4 Hz, 1H), 6.97 (d, J=8.3 Hz, 1H), 6.84 (dd, J=8.3, 2.2 Hz, 1H), 4.54 (s, 3H), 3.73 (t, J=6.8 Hz, 4H), 2.71 (t, J=6.7 Hz, 2H), 1.99 ppm (s, 3H); MS m/z 637 (M+H).

Example 120

3-(5-(2-(((2'-methyl-2,4'-bis(trifluoromethyl)-[1,1'-biphenyl]-4-yl)amino)methyl)-5-(trifluoromethyl)phenyl)picolinamido)propanoic acid

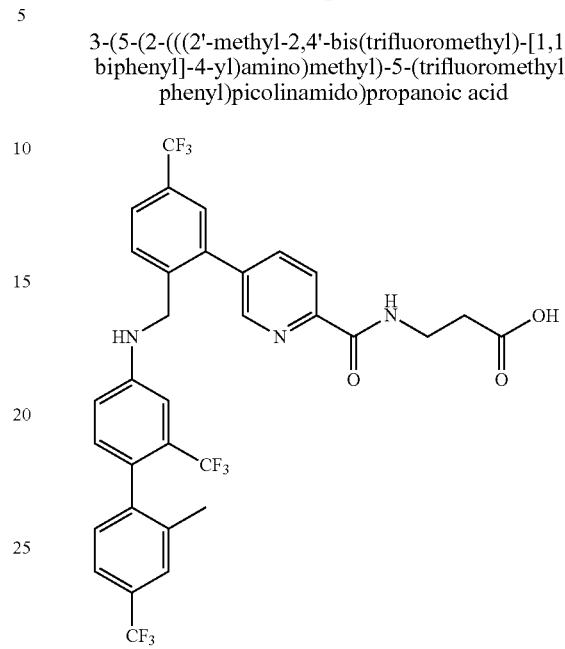

The title compound was prepared as described in Example 22 substituting 4-iodo-3-(trifluoromethyl)aniline and (2-methyl-4-(trifluoromethyl)phenyl)boronic acid for 4-iodoaniline and (4-chloro-2-methylphenyl)boronic acid, respectively.

$^1$H NMR (Aceton, 400 MHz): δ=8.76 (s, 2H), 8.17-8.34 (m, 4H), 7.88-7.97 (m, 2H), 7.85 (s, 2H), 7.74 (s, 3H), 7.58 (s, 2H), 7.50 (s, 3H), 7.30 (d, J=8.1 Hz, 2H), 6.93-7.06 (m, 3H), 6.85 (d, J=2.4 Hz, 2H), 4.53 (s, 3H), 3.72 (t, J=6.7 Hz, 4H), 2.70 (t, J=6.7 Hz, 4H), 2.08-2.12 ppm (m, 3H); MS m/z 671 (M+H).

Example 121

3-(5-(2-(((4'-fluoro-2,3'-bis(trifluoromethyl)-[1,1'-biphenyl]-4-yl)amino)methyl)-5-(trifluoromethyl)phenyl)picolinamido)propanoic acid

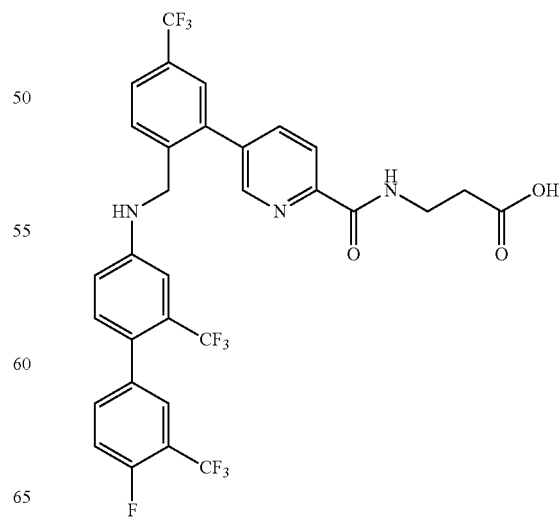

The title compound was prepared as described in Example 22 substituting 4-iodo-3-(trifluoromethyl)aniline and (4-fluoro-3-(trifluoromethyl)phenyl)boronic acid for 4-iodoaniline and (4-chloro-2-methylphenyl)boronic acid, respectively.

¹H NMR (Acetone, 400 MHz): δ=8.76 (br. s., 1H), 8.17-8.33 (m, 2H), 7.79-7.95 (m, 2H), 7.74 (s, 1H), 7.54-7.67 (m, 2H), 7.43 (dd, J=10.8, 8.6 Hz, 1H), 7.12 (d, J=8.3 Hz, 1H), 7.00 (d, J=2.2 Hz, 1H), 6.81 (dd, J=8.3, 2.2 Hz, 1H), 4.54 (s, 2H), 3.72 (t, J=6.7 Hz, 2H), 2.70 ppm (t, J=6.7 Hz, 2H); MS m/z 675 (M+H).

Example 122

3-(5-(2-(((2',4'-dichloro-2-(trifluoromethyl)-[1,1'-biphenyl]-4-yl)amino)methyl)-5-(trifluoromethyl)phenyl)picolinamido)propanoic acid

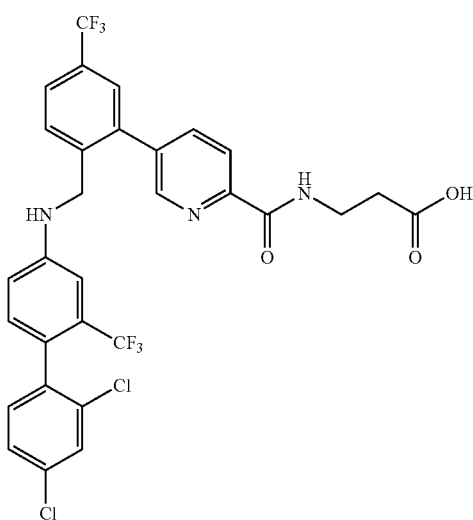 [SMILES: O=C(O)CCNC(=O)c1ccc(-c2cc(C(F)(F)F)ccc2CNc2ccc(-c3ccc(Cl)cc3Cl)c(C(F)(F)F)c2)cn1]

The title compound was prepared as described in Example 22 substituting 4-iodo-3-(trifluoromethyl)aniline and (2,4-dichlorophenyl)boronic acid for 4-iodoaniline and (4-chloro-2-methylphenyl)boronic acid, respectively.

¹H NMR (Acetone, 400 MHz): δ=8.77 (s, 1H), 8.18-8.32 (m, 2H), 7.80-7.95 (m, 2H), 7.74 (d, J=1.2 Hz, 1H), 7.55 (d, J=2.2 Hz, 1H), 7.39 (dd, J=8.2, 2.1 Hz, 1H), 7.29 (d, J=8.3 Hz, 1H), 6.94-7.05 (m, 2H), 6.81 (dd, J=8.3, 2.4 Hz, 1H), 4.52 (s, 2H), 3.72 (t, J=6.7 Hz, 2H), 2.70 ppm (t, 2H); MS m/z 657 (M+H).

Example 123

3-(5-(2-(((4'-chloro-2-(trifluoromethyl)-[1,1'-biphenyl]-4-yl)amino)methyl)-5-(trifluoromethyl)phenyl)picolinamido)propanoic acid

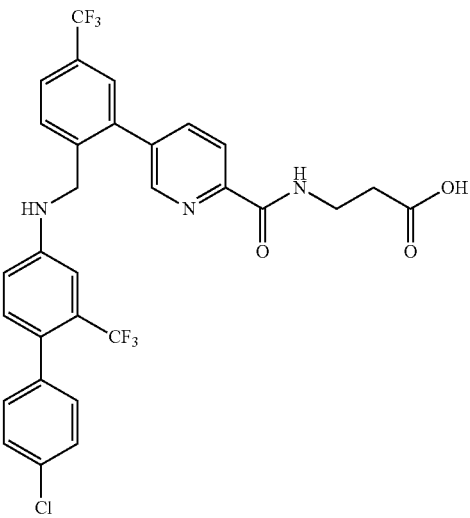 [SMILES: O=C(O)CCNC(=O)c1ccc(-c2cc(C(F)(F)F)ccc2CNc2ccc(-c3ccc(Cl)cc3)c(C(F)(F)F)c2)cn1]

The title compound was prepared as described in Example 22 substituting 4-iodo-3-(trifluoromethyl)aniline and (4-chlorophenyl)boronic acid for 4-iodoaniline and (4-chloro-2-methylphenyl)boronic acid, respectively.

¹H NMR (Acetone, 400 MHz): δ=8.70 (br. s., 1H), 8.20-8.37 (m, 2H), 7.90-7.96 (m, 1H), 7.84 (d, J=8.6 Hz, 1H), 7.74 (s, 1H), 7.35-7.43 (m, 2H), 7.27 (d, J=8.3 Hz, 2H), 7.07 (d, J=8.3 Hz, 1H), 7.00 (d, J=2.4 Hz, 1H), 6.82 (dd, J=8.3, 2.2 Hz, 1H), 4.54 (s, 2H), 3.72 (t, J=6.7 Hz, 2H), 2.70 ppm (t, 2H); MS m/z 623 (M+H).

Example 124

3-(5-(2-(((4'-(tert-butyl)-2-(trifluoromethyl)-[1,1'-biphenyl]-4-yl)amino)methyl)-5-(trifluoromethyl)phenyl)picolinamido)propanoic acid

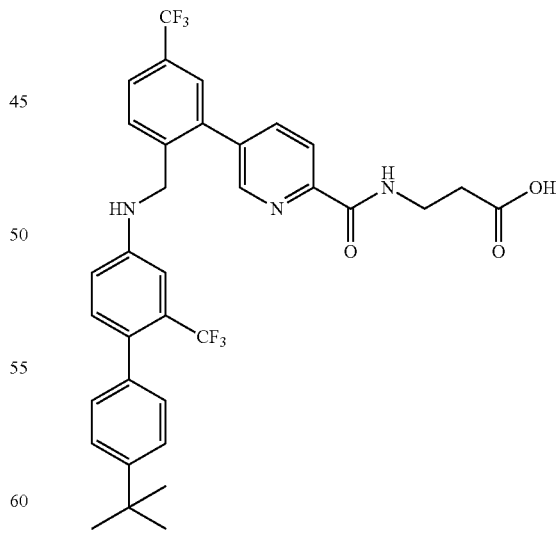

The title compound was prepared as described in Example 22 substituting 4-iodo-3-(trifluoromethyl)aniline and (4-(tert-butyl)phenyl)boronic acid for 4-iodoaniline and (4-chloro-2-methylphenyl)boronic acid, respectively.

¹H NMR (Acetone, 400 MHz): δ=8.74 (br. s., 1H), 8.18-8.35 (m, 2H), 7.95 (d, J=8.3 Hz, 1H), 7.80-7.89 (m, 1H), 7.74

(s, 1H), 7.38-7.46 (m, 2H), 7.19 (d, J=8.1 Hz, 2H), 7.07 (d, J=8.3 Hz, 1H), 7.01 (d, J=2.4 Hz, 1H), 6.83 (dd, J=8.4, 2.3 Hz, 1H), 4.53 (s, 2H), 3.72 (t, J=6.7 Hz, 2H), 2.70 (t, J=6.7 Hz, 2H), 1.34 ppm (s, 9H); MS m/z 645 (M+H).

Example 125

3-(5-(2-(((2',4'-difluoro-2-(trifluoromethyl)-[1,1'-biphenyl]-4-yl)amino)methyl)-5-(trifluoromethyl)phenyl)picolinamido)propanoic acid

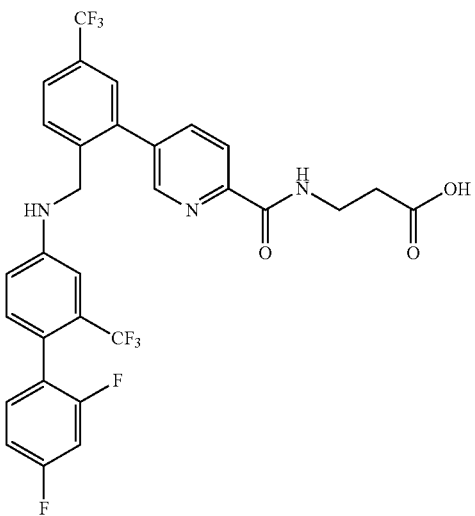 [SMILES: O=C(O)CCNC(=O)c1ccc(-c2cc(C(F)(F)F)ccc2CNc2ccc(-c3ccc(F)cc3F)c(C(F)(F)F)c2)cn1]

The title compound was prepared as described in Example 22 substituting 4-iodo-3-(trifluoromethyl)aniline and (2,4-difluorophenyl)boronic acid for 4-iodoaniline and (4-chloro-2-methylphenyl)boronic acid, respectively.

$^1$H NMR (Acetone, 400 MHz): δ=8.64 (s, 1H), 8.04-8.20 (m, 2H), 7.67-7.85 (m, 2H), 7.61 (d, J=1.2 Hz, 1H), 7.42 (d, J=2.2 Hz, 2H), 7.27 (dd, J=8.2, 2.1 Hz, 2H), 7.16 (d, J=8.3 Hz, 2H), 6.81-6.92 (m, 3H), 6.68 (dd, J=8.3, 2.4 Hz, 1H), 4.39 (s, 3H), 3.59 (t, J=6.7 Hz, 2H), 2.57 ppm (t, 2H); MS m/z 625 (M+H).

Example 126

3-(5-(2-(((4'-chloro-2'-fluoro-2-(trifluoromethyl)-[1,1'-biphenyl]-4-yl)amino)methyl)-5-(trifluoromethyl)phenyl)picolinamido)propanoic acid

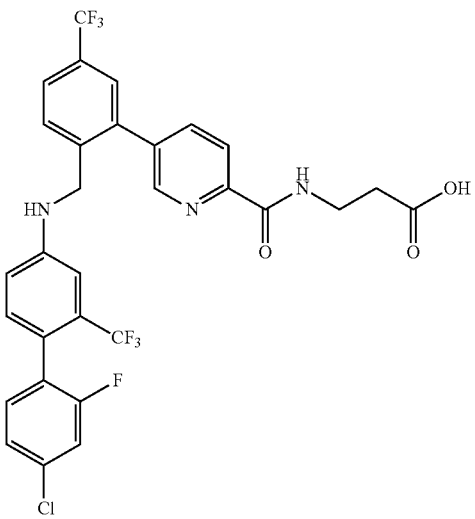

The title compound was prepared as described in Example 221 substituting 4-iodo-3-(trifluoromethyl)aniline and (4-chloro-2-fluorophenyl)boronic acid for 4-iodoaniline and (4-chloro-2-methylphenyl)boronic acid, respectively.

$^1$H NMR (Acetone, 400 MHz): δ=8.64 (s, 1H), 8.02-8.21 (m, 2H), 7.66-7.87 (m, 3H), 7.61 (d, J=1.2 Hz, 1H), 7.42 (d, J=2.2 Hz, 1H), 7.27 (dd, J=8.2, 2.1 Hz, 1H), 7.16 (d, J=8.3 Hz, 1H), 6.79-6.93 (m, 2H), 6.68 (dd, J=8.3, 2.4 Hz, 1H), 4.39 (s, 2H), 3.59 (t, J=6.7 Hz, 2H), 2.57 ppm (t, 2H); MS m/z 641 (M+H).

Example 127

3-(5-(2-(((2,4'-bis(trifluoromethyl)-[1,1'-biphenyl]-4-yl)amino)methyl)-5-(trifluoromethyl)phenyl)picolinamido)propanoic acid

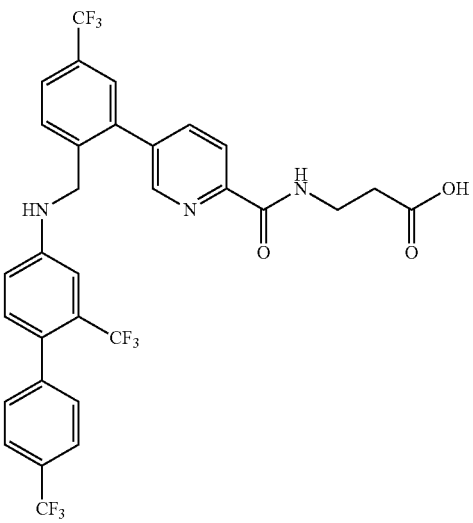 [SMILES: O=C(O)CCNC(=O)c1ccc(-c2cc(C(F)(F)F)ccc2CNc2ccc(-c3ccc(C(F)(F)F)cc3)c(C(F)(F)F)c2)cn1]

The title compound was prepared as described in Example 22 substituting 4-iodo-3-(trifluoromethyl)aniline and (4-(trifluoromethyl)phenyl)boronic acid for 4-iodoaniline and (4-chloro-2-methylphenyl)boronic acid, respectively.

$^1$H NMR (Acetone, 400 MHz): δ=8.64 (s, 1H), 8.14 (s, 1H), 8.04-8.12 (m, 1H), 7.80 (d, J=8.1 Hz, 1H), 7.67-7.76 (m, 1H), 7.61 (d, J=1.2 Hz, 1H), 7.42 (d, J=2.2 Hz, 1H), 7.27 (dd, J=8.2, 2.1 Hz, 1H), 7.16 (d, J=8.3 Hz, 1H), 6.83-6.91 (m, 2H), 6.68 (dd, J=8.3, 2.4 Hz, 1H), 4.39 (s, 2H), 3.59 (t, J=6.7 Hz, 2H), 2.57 ppm (t, 2H); MS m/z 657 (M+H).

Example 128

3-(5-(2-(((2'-chloro-2,4'-bis(trifluoromethyl)-[1,1'-biphenyl]-4-yl)amino)methyl)-5-(trifluoromethyl)phenyl)picolinamido)propanoic acid

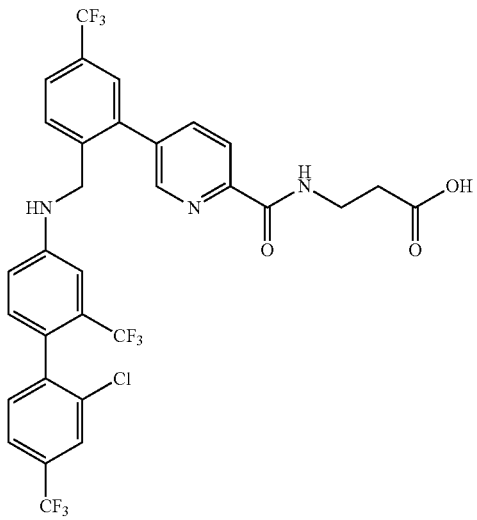

The title compound was prepared as described in Example 22 substituting 4-iodo-3-(trifluoromethyl)aniline and (2-chloro-4-(trifluoromethyl)phenyl)boronic acid for 4-iodoaniline and (4-chloro-2-methylphenyl)boronic acid, respectively.

$^1$H NMR (Acetone, 400 MHz): δ=8.53-8.72 (m, 2H), 8.75 (s, 2H), 8.14 (s, 1H), 8.02-8.13 (m, 2H), 7.66-7.84 (m, 3H), 7.61 (d, J=1.2 Hz, 1H), 7.42 (d, J=2.2 Hz, 2H), 7.09-7.31 (m, 3H), 6.79-6.91 (m, 3H), 6.68 (dd, J=8.3, 2.4 Hz, 1H), 4.39 (s, 2H), 3.59 (t, J=6.7 Hz, 2H), 2.57 ppm (t, J=6.6 Hz, 2H); MS m/z 691 (M+H).

Example 129

3-(5-(5-chloro-2-(((3'-(trifluoromethoxy)-[1,1'-biphenyl]-4-yl)amino)methyl)phenyl)picolinamido)propanoic acid

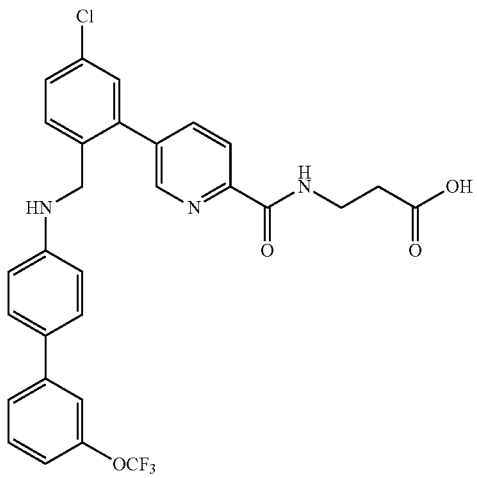 [SMILES: O=C(O)CCNC(=O)c1ccc(-c2cc(Cl)ccc2CNc2ccc(-c3cccc(OC(F)(F)F)c3)cc2)cn1]

STEP A: tert-butyl 3-(5-(5-chloro-2-formylphenyl)picolinamido)propanoate tert-Butyl 3-(5-bromopicolinamido)propanoate (3.4 g, 10.3 mmol), (5-chloro-2-formylphenyl)boronic acid (2.1 g, 11.3 mmol), Pd(dppf)Cl$_2$ (840 mg, 1.0 mmol), and K$_2$CO$_3$ (3.1 g, 22.6 mmol) were dissolved in 1,4-dioxane (35 mL) and water (9 mL) and heated to 90° C. After 3 h the resulting mixture was cooled to room temperature, diluted with EtOAc and water and the layers were separated. The combined organics were washed dried (Na$_2$SO$_4$), concentrated, and purified via column chromatography to yield the title compound.

STEP B: tert-butyl 3-(5-(2-(((4-bromophenyl)amino)methyl)-5-chlorophenyl)picolinamido)propanoate Solid NaBH(OAc)$_3$ (1.4 g, 6.8 mmol) was added to a DCM solution (10 mL) of tert-butyl 3-(5-(5-chloro-2-formylphenyl)picolinamido)propanoate (1.3 g, 3.4 mmol) and 4-bromoaniline (882 mg, 5.1 mmol), and the resulting mixture was stirred at room temperature. After 40 h the resulting mixture diluted with DCM and saturated aqueous Na$_2$CO$_3$ and stirred vigorously. After 5 min, the layers were separated and the aqueous phase was extracted with DCM. The combined organics were washed with water and brine, dried (Na$_2$SO$_4$), concentrated and purified via column chromatography to yield the title compound.

STEP C: tert-butyl 3-(5-(5-chloro-2-(((3'-(trifluoromethoxy)-[1,1'-biphenyl]-4-yl)amino)methyl)phenyl)picolinamido)propanoate tert-Butyl 3-(5-(5-chloro-2-(((4-bromophenyl)amino)methyl)phenyl)picolinamido)propanoate (82 mg, 0.15 mmol), (3-(trifluoromethoxy)phenyl)boronic acid (41 mg, 0.20 mmol), Pd(dppf)Cl$_2$ (18 mg, 0.02 mmol), and K$_2$CO$_3$ (55 mg, 0.40 mmol) were dissolved in 1,4-dioxane (1.5 mL) and water (0.5 mL) and heated to 120° C. in the microwave. After 1 h the resulting mixture was diluted with DCM, dried (Na$_2$SO$_4$), filtered through CELITE, and purified via column chromatography to yield the title compound.

STEP D: 3-(5-(5-chloro-2-(((3'-(trifluoromethoxy)-[1,1'-biphenyl]-4-yl)amino)methyl)phenyl)picolinamido)propanoic acid A 4M HCl solution in 1,4-dioxane (3 mL, 12 mmol) was added to a tert-butyl 3-(5-(5-chloro-2-(((3'-(trifluoromethoxy)-[1,1'-biphenyl]-4-yl)amino)methyl)phenyl)picolinamido)propanoate (49 mg, 0.08 mmol) and the resulting mixture was stirred at room temperature. After 1.5 h the resulting mixture was concentrated in vacuo, triturated with MeOH (0.5 mL) and diethyl ether (5 mL), and filtered to yield the title compound.

$^1$H NMR (400 MHz, CD$_3$OD): δ 8.35 (s, 1H), 8.06 (d, J=8 Hz, 1H), 7.76 (d, J=8 Hz, 2H), 7.47-7.66 (m, 7H), 7.41 (br s, 1H), 7.30 (d, J=8 Hz, 1H), 6.90 (d, J=8 Hz, 2H), 4.61 (s, 2H), 3.66 (t, J=6.8 Hz, 2H), 2.62 (t, J=6.8 Hz, 2H); MS m/z 570 (M+H).

Example 130

3-(5-(5-chloro-2-(((3'-(trifluoromethyl)-[1,1'-biphenyl]-4-yl)amino)methyl)phenyl)picolinamido)propanoic acid

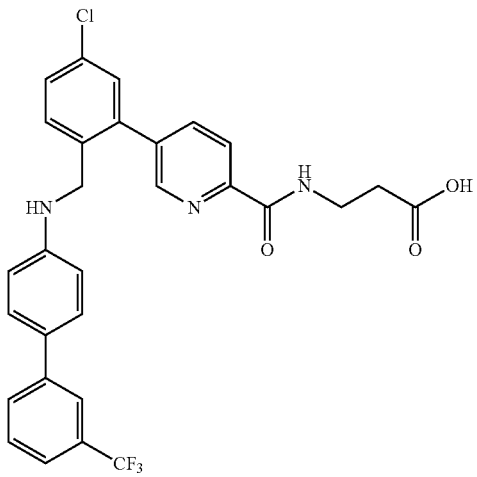 [SMILES: O=C(O)CCNC(=O)c1ccc(-c2cc(Cl)ccc2CNc2ccc(-c3cccc(C(F)(F)F)c3)cc2)cn1]

The title compound was prepared as described in Example 129 substituting (3-(trifluoromethyl)phenyl)boronic acid for (3-(trifluoromethoxy)phenyl)boronic acid.

$^1$H NMR (400 MHz, CD$_3$OD): δ 8.34 (s, 1H), 8.07 (d, J=8 Hz, 1H), 7.86-7.94 (m, 2H), 7.75-7.83 (m, 2H), 7.64-7.73 (m, 3H), 7.60 (d, J=8 Hz, 2H), 7.42 (br s, 1H), 6.97 (d, J=8 Hz, 2H), 4.66 (s, 2H), 3.65 (t, J=6.4 Hz, 2H), 2.61 (t, J=6.4 Hz, 2H); MS m/z 554 (M+H).

Example 131

3-(5-(5-chloro-2-(((2'-(trifluoromethyl)-[1,1'-biphenyl]-4-yl)amino)methyl)phenyl)picolinamido)propanoic acid

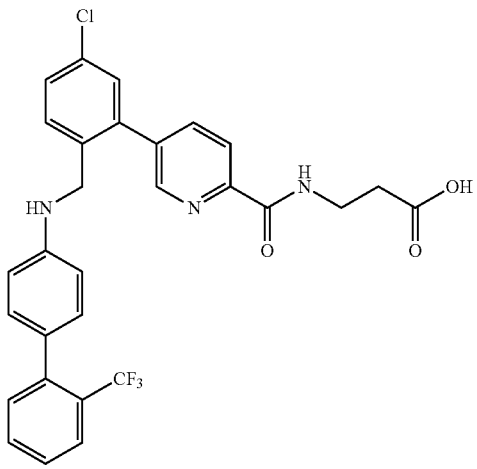 [SMILES: O=C(O)CCNC(=O)c1ccc(-c2cc(Cl)ccc2CNc2ccc(-c3ccccc3C(F)(F)F)cc2)cn1]

The title compound was prepared as described in Example 129 substituting (2-(trifluoromethyl)phenyl)boronic acid for (3-(trifluoromethoxy)phenyl)boronic acid.

$^1$H NMR (400 MHz, CD$_3$OD): δ 8.38 (s, 1H), 8.13 (d, J=8 Hz, 1H), 7.71-7.84 (m, 4H), 7.55-7.66 (m, 2H), 7.48 (d, J=8 Hz, 1H), 7.43 (s, 1H), 7.25 (d, J=8.3 Hz, 2H), 6.91 (d, J=8.3 Hz, 2H), 4.61 (s, 2H), 3.67 (t, J=6.6 Hz, 2H), 2.62 (t, J=6.6 Hz, 2H); MS m/z 554 (M+H).

Example 132

3-(5-(5-chloro-2-(((2'-(trifluoromethoxy)-[1,1'-biphenyl]-4-yl)amino)methyl)phenyl)picolinamido)propanoic acid

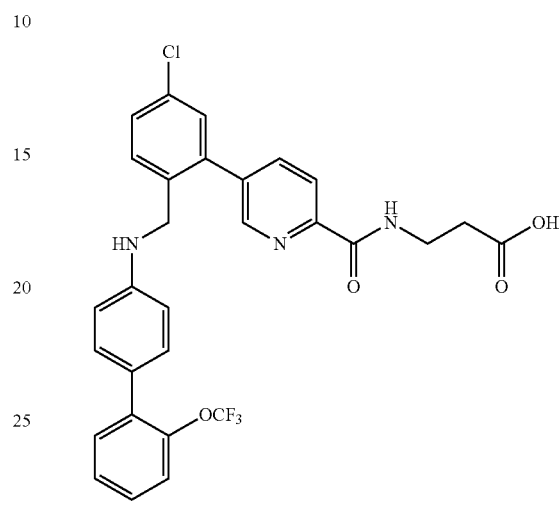

The title compound was prepared as described in Example 129 substituting 4-iodoaniline and (2-(trifluoromethoxy)phenyl)boronic acid for 4-bromoaniline and (3-(trifluoromethoxy)phenyl)boronic acid, respectively.

$^1$H NMR (400 MHz, CD$_3$OD): δ 8.35 (s, 1H), 8.11 (d, J=8 Hz, 1H), 7.81 (d, J=8 Hz, 1H), 7.77 (dd, J=8, 2 Hz, 1H), 7.66 (dd, J=8, 2 Hz, 1H), 7.49-7.60 (m, 3H), 7.40-7.46 (m, 4H), 7.01 (d, J=8 Hz, 2H), 4.68 (s, 2H), 3.66 (t, J=6.6 Hz, 2H), 2.62 (t, J=6.6 Hz, 2H); MS m/z 570 (M+H).

Example 133

3-(5-(5-chloro-2-(((2'-fluoro-[1,1'-biphenyl]-4-yl)amino)methyl)phenyl)picolinamido)propanoic acid

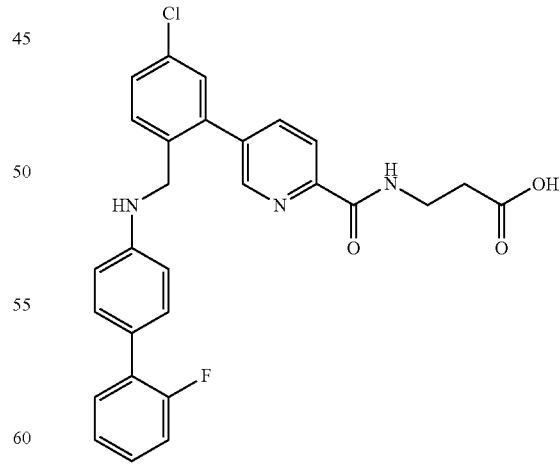

The title compound was prepared as described in Example 129 substituting 4-iodoaniline and (2-fluorophenyl)boronic acid for 4-bromoaniline and (3-(trifluoromethoxy)phenyl) boronic acid, respectively.

$^1$H NMR (400 MHz, CD$_3$OD): δ 8.30 (s, 1H), 8.06 (d, J=8 Hz, 1H), 7.81 (d, J=8 Hz, 1H), 7.67 (dd, J=8, 2 Hz, 2H), 7.39-7.55 (m, 5H), 7.32 (t, J=8 Hz, 1H), 7.23 (dd, J=10.8, 8 Hz, 1H), 6.92-6.98 (m, 2H), 4.68 (s, 2H), 3.65 (t, J=6.4 Hz, 2H), 2.61 (t, J=6.4 Hz, 2H); MS m/z 504 (M+H).

Example 134

3-(5-(5-chloro-2-(((3'-fluoro-[1,1'-biphenyl]-4-yl)amino)methyl)phenyl)picolinamido)propanoic acid

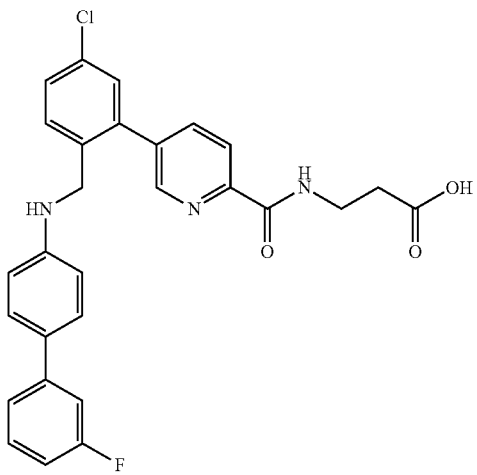

The title compound was prepared as described in Example 129 substituting 4-iodoaniline and (3-fluorophenyl)boronic acid for 4-bromoaniline and (3-(trifluoromethoxy)phenyl) boronic acid, respectively.

$^1$H NMR (400 MHz, CD$_3$OD): δ 8.29 (s, 1H), 8.04 (d, J=8 Hz, 1H), 7.80 (d, J=8 Hz, 1H), 7.64-7.74 (m, 2H), 7.55 (d, J=8 Hz, 2H), 7.35-7.54 (m, 4H), 7.11-7.18 (m, 1H), 6.94 (d, J=8 Hz, 2H), 4.67 (s, 2H), 3.66 (t, J=6.6 Hz, 2H), 2.62 (t, J=6.6 Hz, 2H); MS m/z 504 (M+H).

Example 135

3-(5-(5-chloro-2-(((2'-chloro-[1,1'-biphenyl]-4-yl)amino)methyl)phenyl)picolinamido)propanoic acid

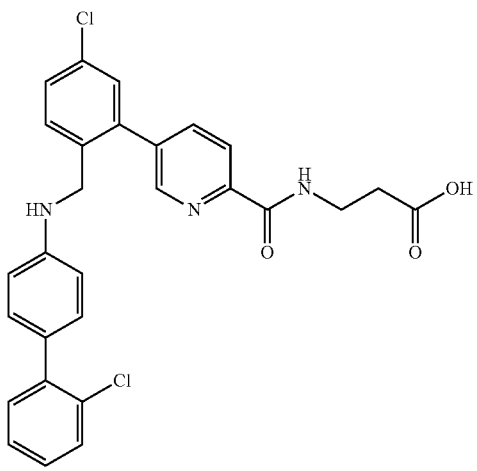 [SMILES: O=C(O)CCNC(=O)c1ccc(-c2cc(Cl)ccc2CNc2ccc(-c3ccccc3F)cc2)cn1]

The title compound was prepared as described in Example 129 substituting 4-iodoaniline and (2-chlorophenyl)boronic acid for 4-bromoaniline and (3-(trifluoromethoxy)phenyl) boronic acid, respectively.

$^1$H NMR (400 MHz, CD$_3$OD): δ 8.32 (br s, 1H), 8.09 (br s, 1H), 7.61-7.85 (m, 3H), 7.33-7.55 (m, 5H), 6.96 (d, J=8 Hz, 2H), 4.67 (s, 2H), 3.65 (m, 2H), 2.61 (m, 2H); MS m/z 520 (M+H).

Example 136

3-(5-(5-chloro-2-(((3',4'-difluoro-[1,1'-biphenyl]-4-yl)amino)methyl)phenyl)picolinamido)propanoic acid

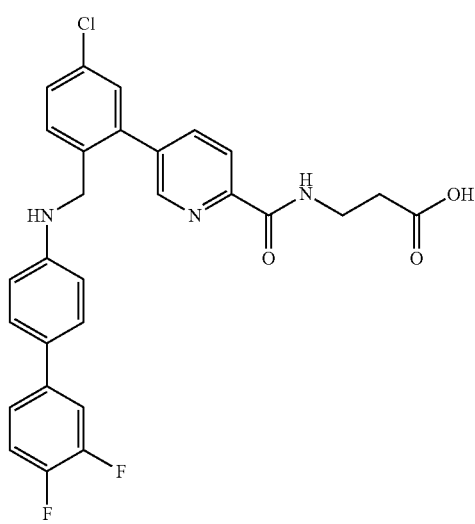 [SMILES: O=C(O)CCNC(=O)c1ccc(-c2cc(Cl)ccc2CNc2ccc(-c3ccc(F)c(F)c3)cc2)cn1]

STEP A: 3',4'-difluoro-[1,1'-biphenyl]-4-amine

4-Iodoaniline (800 mg, 3.7 mmol), (3,4-difluorophenyl) boronic acid (1.2 g, 7.3 mmol), Pd(dppf)Cl$_2$ (267 mg, 0.4 mmol), and 2M aqueous K$_2$CO$_3$ (3.7 mL, 7.3 mmol) were dissolved in 1,4-dioxane (15 mL) and heated to 80° C. After 2 h the resulting mixture was cooled to room temperature and the layers were separated. The organic phase was concentrated and purified via column chromatography to yield the title compound.

STEP B: ethyl 3-(5-(5-chloro-2-(((3',4'-difluoro-[1,1'-biphenyl]-4-yl)amino)methyl)phenyl)picolinamido)propanoate Solid NaBH(OAc)$_3$ (116 mg, 0.55 mmol) was added to a DCM solution (1 mL) of ethyl 3-(5-(5-chloro-2-formylphenyl)picolinamido)propanoate (95 mg, 0.27 mmol), 3',4'-difluoro-[1,1'-biphenyl]-4-amine (73 mg, 0.36 mmol), and 1 drop of AcOH and the resulting mixture was stirred at room temperature. After 3 h the resulting mixture diluted with DCM and saturated aqueous NaHCO$_3$ and the layers were separated. The organic phase was washed with brine, dried (Na$_2$SO$_4$), concentrated and purified via column chromatography to yield the title compound.

STEP C: 3-(5-(5-chloro-2-(((3',4'-difluoro-[1,1'-biphenyl]-4-yl)amino)methyl)phenyl)picolinamido) propanoic acid A 1M aqueous solution of NaOH (2.0 mL, 2.0 mmol) was added to a THF (1 mL) and MeOH (5 mL) solution of ethyl 3-(5-(5-chloro-2-(((3',4'-difluoro-[1,1'-biphenyl]-4-yl)amino)methyl)phenyl)picolinamido)propanoate (50 mg, 0.09 mmol) and the resulting mixture was heated to 55° C. After 10 min the resulting mixture was neutralized with 2M aqueous HCl, concentrated and extracted with EtOAc. The combined extracts were concentrated and purified via column chromatography to yield the title compound.

$^1$H NMR (CDCl$_3$): δ 8.56 (s, 1H), 8.50 (t, 1H), 8.28 (br, 1H), 8.23 (d, 1H), 7.86 (d, 1H), 7.50 (d, 1H), 7.39 (d, 1H), 7.22-7.31 (4H), 7.09-7.19 (2H), 6.51 (d, 2H), 4.18 (s, 2H), 3.77 (dt, 2H), 2.73 (t, 2H); MS m/z 522 (M+H).

Example 137

3-(5-(5-chloro-2-(((3',5'-difluoro-[1,1'-biphenyl]-4-yl)amino)methyl)phenyl)picolinamido)propanoic acid

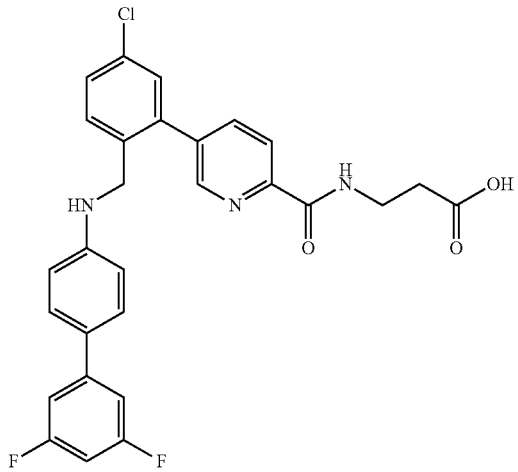 [SMILES: O=C(O)CCNC(=O)c1ccc(-c2cc(Cl)ccc2CNc2ccc(-c3cc(F)cc(F)c3)cc2)cn1]

The title compound was prepared as described in Example 136 substituting (3,5-difluorophenyl)boronic acid for (3,4-difluorophenyl)boronic acid.

$^1$H NMR (CDCl$_3$): δ 8.55 (br, 2H), 8.51 (t, 1H), 8.23 (d, 1H), 7.85 (dd, 1H), 7.49 (d, 1H), 7.38 (dd, 1H), 7.32 (d, 2H), 7.25 (t, 1H), 6.98 (d, 1H), 6.65 (t, 1H), 6.51 (d, 2H), 4.18 (s, 2H), 3.77 (dt, 2H), 2.72 (t, 2H); MS m/z 522 (M+H).

Example 138

3-(5-(5-chloro-2-(((2,2'-dichloro-4'-fluoro-[1,1'-biphenyl]-4-yl)amino)methyl)phenyl)picolinamido) propanoic acid The title compound was prepared as described in Example 136 substituting 4-bromo-3-chloroaniline and (2-chloro-4-fluorophenyl)boronic acid for 4-iodoaniline and (3,4-difluorophenyl)boronic acid, respectively.

$^1$H NMR (CDCl$_3$): δ 8.57 (s, 1H), 8.49 (t, 1H), 8.25 (d, 1H), 7.87 (dd, 1H), 7.51 (d, 1H), 7.42 (dd, 1H), 7.28 (d, 1H), 7.16-7.23 (2H), 6.99 (dt, 1H), 6.97 (d, 1H), 6.56 (d, 1H), 6.41 (dd, 1H), 4.16 (s, 2H), 3.79 (dt, 2H), 2.75 (t, 2H); MS m/z 572 (M+H).

Example 139

3-(5-(5-chloro-2-(((2-chloro-4'-fluoro-3'-methyl-[1,1'-biphenyl]-4-yl)amino)methyl)phenyl)picolinamido)propanoic acid

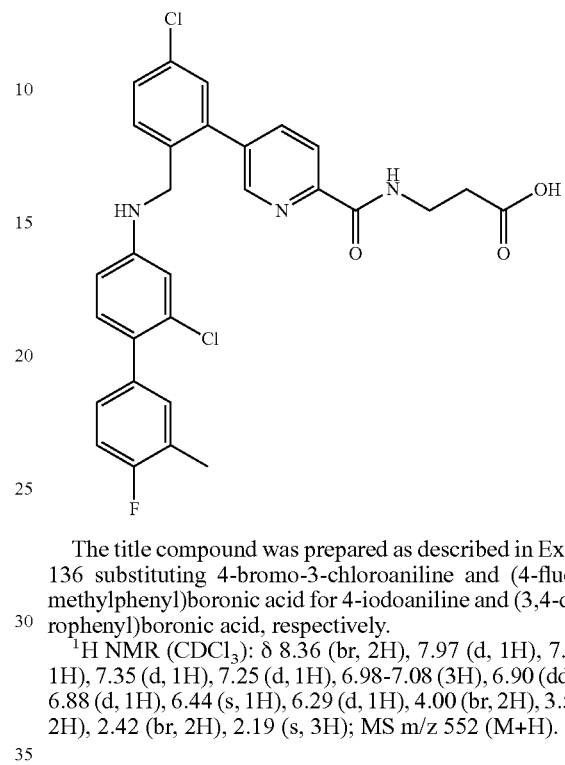

The title compound was prepared as described in Example 136 substituting 4-bromo-3-chloroaniline and (4-fluoro-3-methylphenyl)boronic acid for 4-iodoaniline and (3,4-difluorophenyl)boronic acid, respectively.

$^1$H NMR (CDCl$_3$): δ 8.36 (br, 2H), 7.97 (d, 1H), 7.60 (d, 1H), 7.35 (d, 1H), 7.25 (d, 1H), 6.98-7.08 (3H), 6.90 (dd, 1H), 6.88 (d, 1H), 6.44 (s, 1H), 6.29 (d, 1H), 4.00 (br, 2H), 3.54 (br, 2H), 2.42 (br, 2H), 2.19 (s, 3H); MS m/z 552 (M+H).

Example 140

3-(5-(5-chloro-2-(((2-chloro-4'-(trifluoromethoxy)-[1,1'-biphenyl]-4-yl)amino)methyl)phenyl)picolinamido)propanoic acid

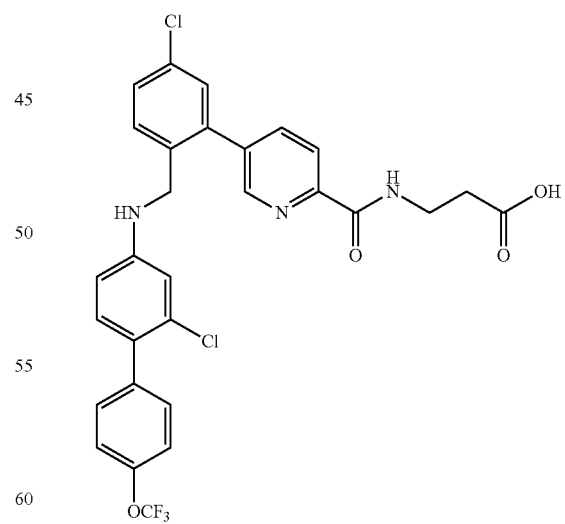

The title compound was prepared as described in Example 136 substituting 4-bromo-3-chloroaniline and (4-(trifluoromethoxy)phenyl)boronic acid for 4-iodoaniline and (3,4-difluorophenyl)boronic acid, respectively.

$^1$H NMR (CD$_3$OD): δ 8.65 (s, 1H), 8.14 (d, 1H), 7.99 (d, 1H), 7.56 (d, 1H), 7.45 (dd, 1H), 7.41 (d, 2H), 7.35 (d, 1H), 7.24 (d, 2H), 7.01 (d, 1H), 6.51 (dd, 1H), 6.42 (dd, 1H), 4.17 (s, 2H), 3.67 (br, 2H), 2.54 (br, 2H); MS m/z 604 (M+H).

Example 141

3-(5-(5-chloro-2-(((2'-chloro-6'-fluoro-[1,1'-biphenyl]-4-yl)amino)methyl)phenyl)picolinamido)propanoic acid

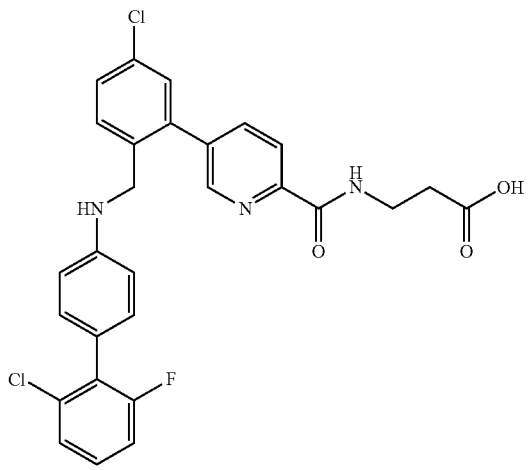 [SMILES: O=C(O)CCNC(=O)c1ccc(-c2cc(Cl)ccc2CNc2ccc(-c3c(F)cccc3Cl)cc2)cn1]

The title compound was prepared as described in Example 136 substituting (2-chloro-6-fluorophenyl)boronic acid for (3,4-difluorophenyl)boronic acid.

$^1$H NMR (CDCl$_3$): δ 8.55 (d, 1H), 8.52 (t, 1H), 8.23 (d, 1H), 8.03 (br, 1H), 7.85 (dd, 1H), 7.48 (d, 1H), 7.37 (dd, 1H), 7.32 (d, 1H), 7.27-7.31 (2H), 7.24 (d, 1H), 7.13 (m, 1H), 7.00 (t, 1H), 6.51 (d, 2H), 4.16 (s, 2H), 3.77 (dt, 2H), 2.73 (t, 2H); MS m/z 538 (M+H).

Example 142

3-(5-(5-chloro-2-(((2-chloro-4'-fluoro-2'-(trifluoromethyl)-[1,1'-biphenyl]-4-yl)amino)methyl)phenyl)picolinamido)propanoic acid

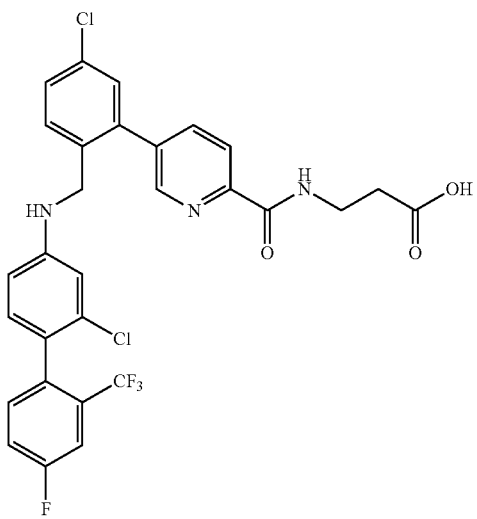 [SMILES: O=C(O)CCNC(=O)c1ccc(-c2cc(Cl)ccc2CNc2ccc(-c3ccc(F)cc3C(F)(F)F)c(Cl)c2)cn1]

The title compound was prepared as described in Example 136 substituting 4-bromo-3-chloroaniline and (4-fluoro-2-(trifluoromethyl)phenyl)boronic acid for 4-iodoaniline and (3,4-difluorophenyl)boronic acid, respectively.

$^1$H NMR (CD$_3$OD): δ 8.66 (s, 1H), 8.13 (d, 1H), 7.99 (dd, 1H), 7.57 (d, 1H), 7.46 (m, 2H), 7.35 (m, 2H), 7.27 (m, 1H), 6.88 (d, 1H), 6.50 (d, 1H), 6.39 (dd, 1H), 4.18 (s, 2H), 3.69 (t, 2H), 2.65 (t, 2H); MS m/z 606 (M+H).

Example 143

3-(5-(5-chloro-2-(((2'-chloro-4'-methoxy-[1,1'-biphenyl]-4-yl)amino)methyl)phenyl)picolinamido)propanoic acid

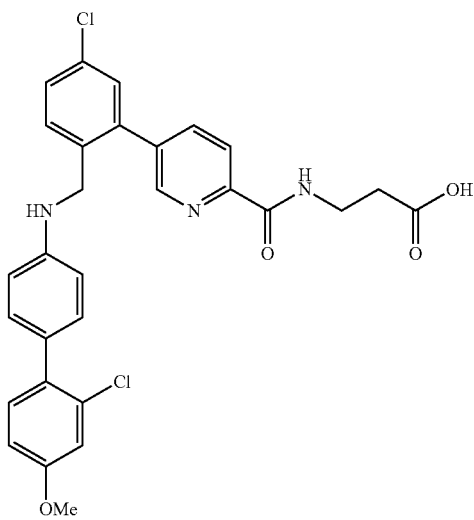 [SMILES: COc1ccc(-c2ccc(NCc3ccc(Cl)cc3-c3ccc(C(=O)NCCC(=O)O)nc3)cc2)c(Cl)c1]

The title compound was prepared as described in Example 136 substituting (2-chloro-4-methoxyphenyl)boronic acid for (3,4-difluorophenyl)boronic acid.

$^1$H NMR (CDCl$_3$): δ 8.58 (d, 1H), 8.49 (t, 1H), 8.24 (d, 1H), 7.88 (dd, 1H), 7.52 (d, 1H), 7.40 (dd, 1H), 7.27 (d, 1H), 7.17-7.22 (3H), 6.97 (d, 1H), 6.82 (dd, 1H), 6.52 (d, 2H), 4.17 (s, 2H), 3.81 (s, 3H), 3.78 (dt, 2H), 2.74 (t, 2H); MS m/z 550 (M+H).

Example 144

3-(5-(5-chloro-2-(((2-chloro-4'-fluoro-3'-(trifluoromethyl)-[1,1'-biphenyl]-4-yl)amino)methyl)phenyl)picolinamido)propanoic acid

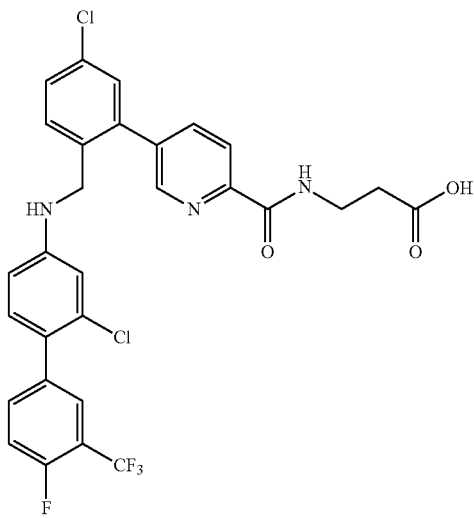 [SMILES: O=C(O)CCNC(=O)c1ccc(-c2cc(Cl)ccc2CNc2ccc(-c3ccc(F)c(C(F)(F)F)c3)c(Cl)c2)cn1]

The title compound was prepared as described in Example 136 substituting 4-bromo-3-chloroaniline and (4-fluoro-3-(trifluoromethyl)phenyl)boronic acid for 4-iodoaniline and (3,4-difluorophenyl)boronic acid, respectively.

$^{1}$H NMR (CDCl$_{3}$): δ 8.57 (d, 1H), 8.46 (t, 1H), 8.26 (d, 1H), 7.87 (dd, 1H), 7.60 (dd, 1H), 7.55 (m, 1H), 7.49 (d, 1H), 7.43 (dd, 1H), 7.30 (d, 1H), 7.20 (t, 1H), 7.05 (d, 1H), 6.55 (d, 1H), 6.42 (dd, 1H), 4.18 (s, 2H), 3.80 (dt, 2H), 2.76 (t, 2H); MS m/z 606 (M+H).

Example 145

3-(5-(2-((4'-chloro-[1,1'-biphenyl]-4-yl)carbamoyl)-5-methylphenyl)picolinamido)propanoic acid

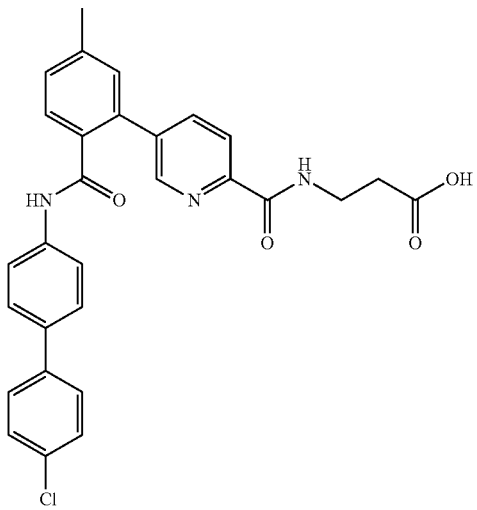 [SMILES: Cc1ccc(C(=O)Nc2ccc(-c3ccc(Cl)cc3)cc2)c(-c2ccc(C(=O)NCCC(=O)O)nc2)c1]

STEP A: 2-bromo-N-(4'-chloro-[1,1'-biphenyl]-4-yl)-4-methylbenzamide

4'-chloro-[1,1'-biphenyl]-4-amine (159 mg, 0.78 mmol), 2-bromo-4-methylbenzoic acid (140 mg, 0.65 mmol), EDC (125 mg, 0.65 mmol), HOBt (100 mg, 0.65 mmol), and diisopropylethyl amine (0.22 mL, 1.30 mmol) were dissolved in THF (2.6 mL) and stirred at room temperature. After 3 h the resulting mixture directly purified via column chromatography to yield the title compound.

STEP B: ethyl 3-(5-(2-((4'-chloro-[1,1'-biphenyl]-4-yl)carbamoyl)-5-methylphenyl)picolinamido)propanoate 2-bromo-N-(4'-chloro-[1,1'-biphenyl]-4-yl)-4-methylbenzamide (50 mg, 0.13 mmol), ethyl 3-(5-(4,4,5,5-tetramethyl-1,3,2-dioxaborolan-2-yl)picolinamido)propanoate (68 g, 0.16 mmol), Pd(dppf)Cl$_{2}$ (9 mg, 0.01 mmol), and 2M aqueous K$_{2}$CO$_{3}$ (0.13 mL g, 0.25 mmol) were dissolved in 1,4-dioxane (2 mL) and the resulting mixture was heated to 85° C. After 16 h the resulting mixture was cooled to room temperature and purified directly via column chromatography to yield the title compound.

STEP C: 3-(5-(2-((4'-chloro-[1,1'-biphenyl]-4-yl)carbamoyl)-5-methylphenyl)picolinamido)propanoic acid A 1M aqueous solution of NaOH (2.0 mL, 2.0 mmol) was added to a THF (1 mL) and MeOH (5 mL) solution of ethyl 3-(5-(2-((4'-chloro-[1,1'-biphenyl]-4-yl)carbamoyl)-5-methylphenyl)picolinamido)propanoate (50 mg, 0.09 mmol) and the resulting mixture was heated to 55° C. After 10 min the resulting mixture was neutralized with 2M aqueous HCl, concentrated and extracted with EtOAc. The combined extracts were concentrated and purified via column chromatography to yield the title compound.

$^{1}$H NMR (CD$_{3}$OD): δ 8.68 (s, 1H), 8.09 (d, 1H), 8.01 (dd, 1H), 7.52-7.64 (7H), 7.38-7.43 (4H), 3.65 (t, 2H), 2.61 (t, 2H), 2.48 (s, 3H); MS m/z 514 (M+H).

Example 146

3-(5-(5-chloro-2-(((4'-fluoro-3'-methyl-[1,1'-biphenyl]-4-yl)amino)methyl)phenyl)picolinamido)propanoic acid

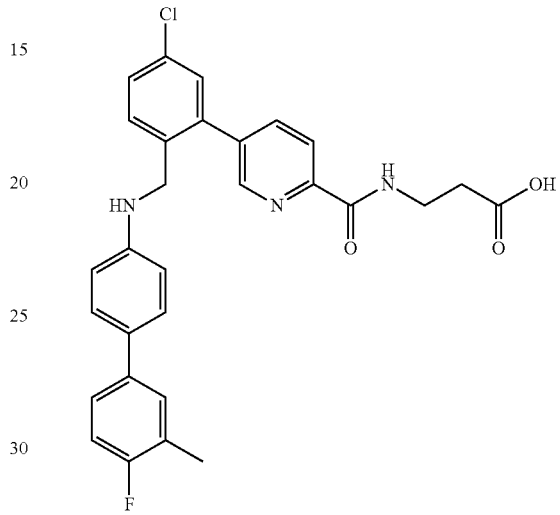

STEP A: methyl 3-(5-bromopicolinamido)propanoate

Neat Et$_{3}$N (5.2 mL, 37.5 mmol) was added to a DCM mixture (50 mL) of 5-bromopicolinic acid (5.1 g, 25.0 mmol), beta-alanine mether ester hydrochloride (4.2 g, 30.0 mmol), and EDCI (5.8 g, 30 mmol) and the resulting mixture was stirred at room temperature. After 24 h the resulting mixture was poured into CH$_{2}$Cl$_{2}$/H$_{2}$O (50 mL/50 mL). The aqueous layer was extracted with CH$_{2}$Cl$_{2}$ (50 mL). The combined organic layers were dried (Na$_{2}$SO$_{4}$), concentrated, and purified via column chromatography to yield the title compound.

STEP B: methyl 3-(5-(5-chloro-2-formylphenyl)picolinamido)propanoate

Methyl 3-(5-bromopicolinamido)propanoate (2.0 g, 7.0 mmol), (5-chloro-2-formylphenyl)boronic acid (1.4 g, 7.7 mmol), Pd(dppf)Cl$_{2}$ (572 mg, 0.7 mmol), and K$_{2}$CO$_{3}$ (2.1 g, 15.4 mmol) were dissolved in 1,4-dioxane (24 mL) and water (6 mL) and heated to 90° C. After 3 h the resulting mixture was poured into EtOAc/H$_{2}$O (30 mL/30 mL) and the layers were separated. The aqueous layer was extracted with EtOAc and the combined organic layers were dried (Na$_{2}$SO$_{4}$), concentrated, and purified via column chromatography to yield the title compound.

STEP C: methyl 3-(5-(5-chloro-2-(((4-iodophenyl)amino)methyl)phenyl)picolinamido)propanoate Solid NaBH(OAc)$_{3}$ (1.3 g, 6.0 mmol) was added to a DCM solution (6 mL) of methyl 3-(5-(5-chloro-2-formylphenyl)picolinamido)propanoate (1.0 g, 3.0 mmol) and 4-iodoaniline (723 mg, 3.3 mmol), and the resulting mixture was stirred at room temperature. After 3 h the resulting mixture diluted with DCM and saturated aqueous Na$_{2}$CO$_{3}$ and the layers were separated. The aqueous phase was extracted with DCM and the combined organics were dried ($Na_2SO_4$), concentrated and purified via column chromatography to yield the title compound.

STEP D: methyl 3-(5-(5-chloro-2-(((4'-fluoro-3'-methyl-[1,1'-biphenyl]-4-yl)amino)methyl)phenyl)picolinamido)propanoate Methyl 3-(5-(5-chloro-2-(((4-iodophenyl)amino)methyl)phenyl)picolinamido)propanoate (83 mg, 0.15 mmol), (4-fluoro-3-methylphenyl)boronic acid (31 mg, 0.20 mmol), Pd(dppf)$Cl_2$ (12 mg, 0.02 mmol), and $K_2CO_3$ (55 mg, 0.40 mmol) were dissolved in 1,4-dioxane (1.5 mL) and water (0.5 mL) and heated to 90° C. After 1.5 h the resulting mixture was diluted with DCM, dried ($Na_2SO_4$), concentrated, and purified via column chromatography to yield the title compound.

STEP E: 3-(5-(5-chloro-2-(((4'-fluoro-3'-methyl-[1,1'-biphenyl]-4-yl)amino)methyl)phenyl)picolinamido)propanoic acid A 1M aqueous solution of LiOH (2.0 mL, 2.0 mmol) was added to a THF (2.0 mL) and MeOH (0.5 mL) solution of ethyl 3-(5-(5-chloro-2-(((3',4'-difluoro-[1,1'-biphenyl]-4-yl)amino)methyl)phenyl)picolinamido)propanoate (32 mg, 0.06 mmol) and the resulting mixture was stirred at room temperature. After 1 h the resulting mixture was neutralized with 2M aqueous HCl, diluted with DCM and water and the layers were separated. The aqueous layer was extracted with DCM and the combined extracts were dried ($Na_2SO_4$), and concentrated. The product was dissolved in $Et_2O$ (5-7 mL) and then added to heptane (25 mL). The resulting mixture was contracted slowly to about half volume (15 mL). The solid was collected by filtration, washed with heptane (3 mL×2) and dried in vacuo to yield the title compound.

$^1$H NMR (400 MHz, CHLOROFORM-d) δ=8.57-8.60 (br s, 1H), 8.45 (t, J=6.4 Hz, 1H), 8.25 (d, J=8.1 Hz, 1H), 7.89 (dd, J=2.1, 7.9 Hz, 1H), 7.52 (d, J=8.3 Hz, 1H), 7.41 (dd, J=2.0, 8.3 Hz, 1H), 7.22-7.35 (m, 7H), 6.97-7.03 (m, 1H), 6.53 (d, J=8.3 Hz, 2H), 4.18 (s, 2H), 3.79 (q, J=6.2 Hz, 2H), 2.75 (t, J=6.1 Hz, 2H), 2.30 (s, 3H); MS m/z 519 (M+H).

Example 147

3-(5-(5-chloro-2-(((2'-chloro-4'-(trifluoromethyl)-[1,1'-biphenyl]-4-yl)amino)methyl)phenyl)picolinamido)propanoic acid

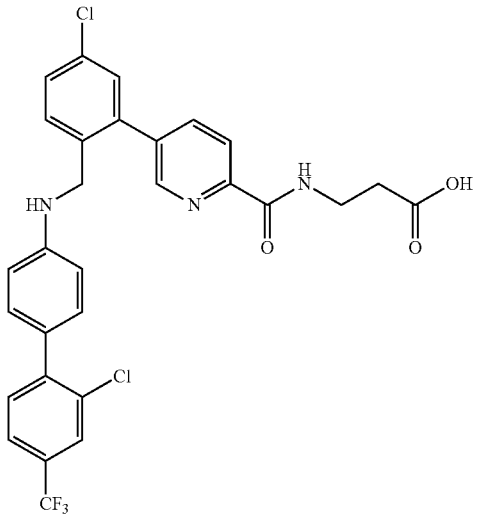 [SMILES: O=C(O)CCNC(=O)c1ccc(-c2cc(Cl)ccc2CNc2ccc(-c3ccc(C(F)(F)F)cc3Cl)cc2)cn1]

The title compound was prepared as described in Example 146 substituting (2-chloro-4-(trifluoromethyl)phenyl)boronic acid for (4-fluoro-3-methylphenyl)boronic acid.

$^1$H NMR (400 MHz, CHLOROFORM-d) δ=8.59 (s, 1H), 8.46 (t, J=6.1 Hz, 1H), 8.26 (d, J=8.1 Hz, 1H), 7.87-7.92 (m, 1H), 7.69 (s, 1H), 7.48-7.55 (m, 2H), 7.37-7.46 (m, 2H), 7.20-7.32 (m, 4H), 6.55 (d, J=8.3 Hz, 2H), 4.20 (s, 2H), 3.80 (q, J=6.3 Hz, 2H), 2.76 (t, J=6.1 Hz, 2H); MS m/z 589 (M+H).

Example 148

3-(5-(5-chloro-2-(((4'-chloro-2'-methyl-[1,1'-biphenyl]-4-yl)amino)methyl)phenyl)picolinamido)propanoic acid

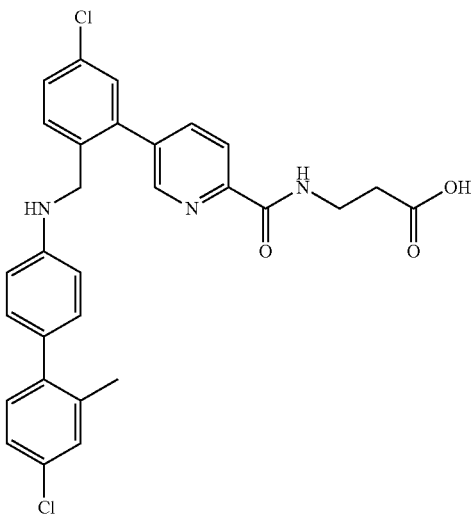 [SMILES: Cc1cc(Cl)ccc1-c1ccc(NCc2ccc(Cl)cc2-c2ccc(C(=O)NCCC(=O)O)nc2)cc1]

The title compound was prepared as described in Example 146 substituting (4-chloro-2-methylphenyl)boronic acid for (4-fluoro-3-methylphenyl)boronic acid.

$^1$H NMR (400 MHz, CHLOROFORM-d) δ=8.57-8.60 (m, 1H), 8.46 (t, J=5.9 Hz, 1H), 8.25 (d, J=8.1 Hz, 1H), 7.90 (dd, J=2.0, 8.1 Hz, 1H), 7.54 (d, J=8.3 Hz, 1H), 7.42 (dd, J=2.0, 8.3 Hz, 1H), 7.20-7.31 (m, 3H), 7.04-7.18 (m, 4H), 6.52 (d, J=8.3 Hz, 2H), 4.18 (s, 2H), 3.79 (d, J=6.4 Hz, 2H), 2.76 (t, J=6.0 Hz, 2H), 2.24 (s, 3H); MS m/z 535 (M+H).

Example 149

3-(5-(5-chloro-2-(((4'-fluoro-2'-(trifluoromethyl)-[1,1'-biphenyl]-4-yl)amino)methyl)phenyl)picolinamido)propanoic acid

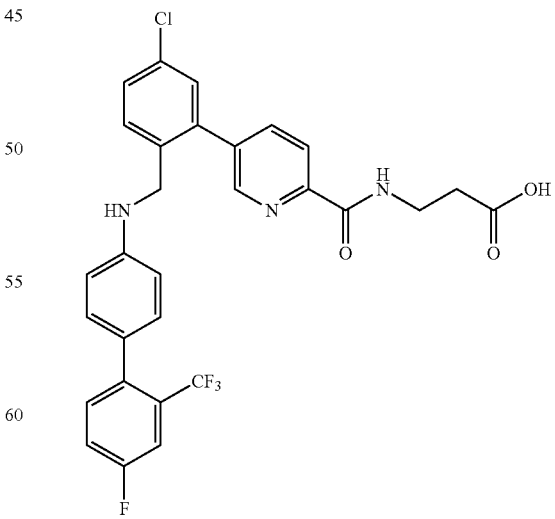

The title compound was prepared as described in Example 146 substituting (4-fluoro-2-(trifluoromethyl)phenyl)boronic acid for (4-fluoro-3-methylphenyl)boronic acid.

¹H NMR (400 MHz, CHLOROFORM-d) δ=8.55-8.62 (m, 1H), 8.46 (t, J=6.4 Hz, 1H), 8.25 (d, J=7.8 Hz, 1H), 7.89 (dd, J=2.1, 7.9 Hz, 1H), 7.54 (d, J=8.3 Hz, 1H), 7.42 (td, J=2.2, 8.3 Hz, 2H), 7.16-7.32 (m, 4H), 7.02-7.11 (m, J=8.3 Hz, 2H), 6.44-6.54 (m, J=8.6 Hz, 2H), 4.19 (s, 2H), 3.80 (q, J=6.3 Hz, 2H), 2.76 (t, J=6.0 Hz, 2H); MS m/z 573 (M+H).

Example 150

3-(5-(5-chloro-2-(((3'-chloro-4'-fluoro-[1,1'-biphenyl]-4-yl)amino)methyl)phenyl)picolinamido)propanoic acid

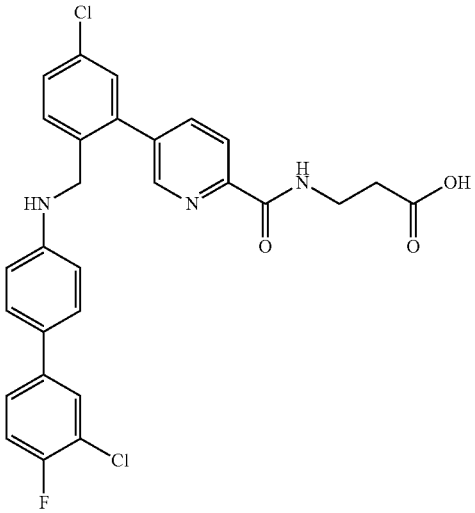 [SMILES: O=C(O)CCNC(=O)c1ccc(-c2cc(Cl)ccc2CNc2ccc(-c3ccc(F)c(Cl)c3)cc2)cn1]

The title compound was prepared as described in Example 146 substituting (3-chloro-4-fluorophenyl)boronic acid for (4-fluoro-3-methylphenyl)boronic acid.
¹H NMR (400 MHz, CHLOROFORM-d) δ=8.58 (s, 1H), 8.46 (t, J=6.1 Hz, 1H), 8.25 (d, J=7.8 Hz, 1H), 7.88 (dd, J=1.5, 8.1 Hz, 1H), 7.46-7.54 (m, 2H), 7.38-7.44 (m, 1H), 7.23-7.35 (m, 5H), 7.13 (t, J=8.7 Hz, 1H), 6.53 (d, J=8.6 Hz, 2H), 4.19 (s, 2H), 3.79 (q, J=6.1 Hz, 2H), 2.75 (t, J=6.0 Hz, 2H); MS m/z 539 (M+H).

Example 151

3-(5-(5-chloro-2-(((4'-fluoro-2'-methyl-[1,1'-biphenyl]-4-yl)amino)methyl)phenyl)picolinamido)propanoic acid

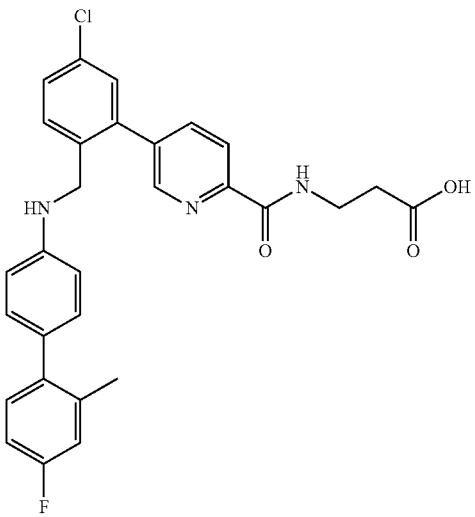 [SMILES: Cc1cc(F)ccc1-c1ccc(NCc2ccc(Cl)cc2-c2ccc(C(=O)NCCC(=O)O)nc2)cc1]

The title compound was prepared as described in Example 146 substituting (4-fluoro-2-methylphenyl)boronic acid for (4-fluoro-3-methylphenyl)boronic acid.
¹H NMR (400 MHz, CHLOROFORM-d) δ=8.59 (s, 1H), 8.46 (t, J=6.1 Hz, 1H), 8.25 (d, J=8.1 Hz, 1H), 7.91 (dd, J=1.8, 7.9 Hz, 1H), 7.54 (d, J=8.3 Hz, 1H), 7.42 (dd, J=1.7, 8.3 Hz, 1H), 7.23-7.33 (m, 2H), 7.12 (dd, J=6.1, 8.3 Hz, 1H), 7.01-7.08 (d, J=8.3 Hz, 2H), 6.82-6.96 (m, 2H), 6.48-6.56 (d, J=8.3 Hz, 2H), 4.18 (s, 2H), 3.79 (q, J=6.1 Hz, 2H), 2.76 (t, J=6.0 Hz, 2H), 2.24 (s, 3H); MS m/z 519 (M+H).

Example 152

3-(5-(5-chloro-2-(((2'-chloro-4'-fluoro-[1,1'-biphenyl]-4-yl)amino)methyl)phenyl)picolinamido)propanoic acid

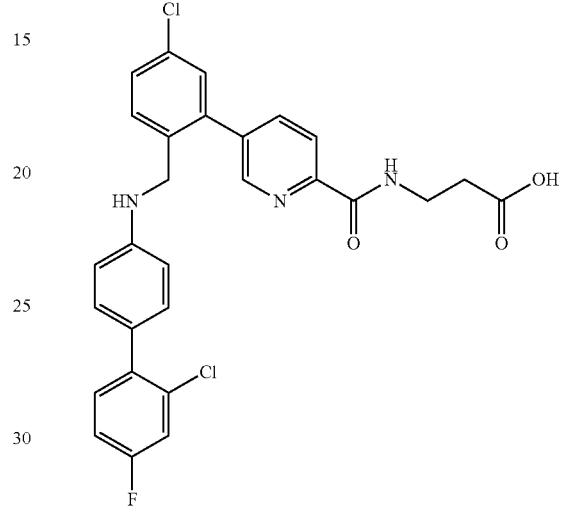

The title compound was prepared as described in Example 146 substituting (2-chloro-4-fluorophenyl)boronic acid for (4-fluoro-3-methylphenyl)boronic acid.
¹H NMR (400 MHz, CHLOROFORM-d) δ=8.58 (s, 1H), 8.46 (t, J=6.0 Hz, 1H), 8.25 (d, J=8.1 Hz, 1H), 7.88 (d, J=7.3 Hz, 1H), 7.55 (d, J=8.3 Hz, 1H), 7.42 (dd, J=2.0, 8.3 Hz, 1H), 7.14-7.33 (m, 6H), 6.99 (td, J=2.6, 8.3 Hz, 1H), 6.55 (d, J=8.3 Hz, 2H), 4.19 (s, 2H), 3.79 (q, J=6.1 Hz, 2H), 2.76 (t, J=6.0 Hz, 2H); MS m/z 539 (M+H).

Example 153

3-(5-(5-chloro-2-((4'-chloro-2'-methyl-[1,1'-biphenyl]-4-yl)carbamoyl)phenyl)picolinamido)propanoic acid

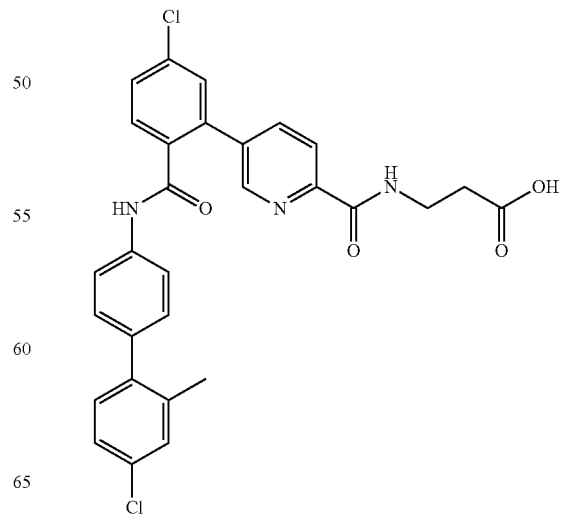

STEP A: 4'-chloro-2'-methyl-[1,1'-biphenyl]-4-amine 4-iodoaniline (3.3 g, 15.0 mmol), (4-chloro-2-methylphenyl)boronic acid (3.3 g, 19.5 mmol), Pd(dppf)Cl$_2$ (1.22 g, 1.5 mmol), and K$_2$CO$_3$ (4.1 g, 30 mmol) were dissolved in 1,4-dioxane (60 mL) and water (15 mL) and heated to 90° C. After 3 h the resulting mixture was diluted EtOAc and water and the layers were separated. The organic layer was dried (Na$_2$SO$_4$), concentrated, and purified via column chromatography to yield the title compound.

STEP B: ethyl 3-(5-(5-chloro-2-((4'-chloro-2'-methyl-[1,1'-biphenyl]-4-yl)carbamoyl)phenyl)picolinamido)propanoate Neat Et$_3$N (0.14 mL, 1.0 mmol) was added to a DCM mixture (5 mL) of 2-(6-((2-carboxyethyl)carbamoyl)pyridin-3-yl)-4-chlorobenzoic acid (226 mg, 0.6 mmol), 4'-chloro-2'-methyl-[1,1'-biphenyl]-4-amine (109 mg, 0.5 mmol), and EDCI (192 mg, 1.0 mmol) and the resulting mixture was stirred at room temperature. After 3 h the resulting mixture was directly purified via column chromatography to yield the title compound.

STEP C: 3-(5-(5-chloro-2-((4'-chloro-2'-methyl-[1,1'-biphenyl]-4-yl)carbamoyl)phenyl)picolinamido)propanoic acid A 1M aqueous solution of LiOH (2.0 mL, 2.0 mmol) was added to a THF (4.0 mL) and MeOH (1.0 mL) solution of ethyl 3-(5-(5-chloro-2-((4'-chloro-2'-methyl-[1,1'-biphenyl]-4-yl)carbamoyl)phenyl)picolinamido)propanoate (100 mg, 0.17 mmol) and the resulting mixture was stirred at room temperature. After 1 h the resulting mixture was neutralized with 2M aqueous HCl, diluted with EtOAc and water and the layers were separated. The aqueous layer was extracted with EtOAc and the combined extracts were dried (Na$_2$SO$_4$), and concentrated. The title compound was re-solidified from CH$_2$Cl$_2$/heptane (ca. 1/9) and dried in vacuo.

$^1$H NMR (400 MHz, DMSO-d$_6$) δ=10.60 (s, 1H), 8.87 (br. s., 1H), 8.69 (s, 1H), 8.07 (s, 2H), 7.65-7.81 (m, 3H), 7.61 (d, J=7.8 Hz, 2H), 7.38 (br. s., 1H), 7.23-7.34 (m, 3H), 7.20 (s, 1H), 3.48 (br. s., 3H), 2.54 (br s, 2H), 2.22 (s, 3H); MS m/z 549 (M+H).

Example 154

3-(5-(2-((4'-chloro-2'-methyl-[1,1'-biphenyl]-4-yl)carbamoyl)-5-(trifluoromethyl)phenyl)picolinamido)propanoic acid

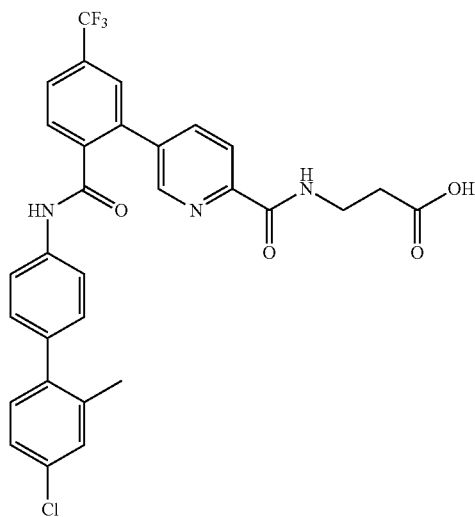 [SMILES: Cc1cc(Cl)ccc1-c1ccc(NC(=O)c2ccc(C(F)(F)F)cc2-c2ccc(C(=O)NCCC(=O)O)nc2)cc1]

STEP A: 2-(6-((3-ethoxy-3-oxopropyl)carbamoyl)pyridin-3-yl)-4-(trifluoromethyl)benzoic acid 2-bromo-4-(trifluoromethyl)benzoic acid (538 mg, 2.0 mmol), ethyl 3-(5-(4,4,5,5-tetramethyl-1,3,2-dioxaborolan-2-yl)picolinamido)propanoate (1.0 g, 3.0 mmol), Pd(dppf)Cl$_2$ (163 mg, 0.2 mmol), and K$_2$CO$_3$ (1.1 g, 8.0 mmol) were dissolved in 1,4-dioxane (12 mL) and water (4 mL) and heated to 90° C. After 3 h the resulting mixture was diluted EtOAc and water and 2N aqueous HCl was added until the pH of the aqueous layer was ca. 3-4. The layers were separated and the aqueous layer was extracted with EtOAc. The combined organic layers were dried (Na$_2$SO$_4$) and concentrated to yield the title compound, which was used in the next step without further purification.

STEP B: ethyl 3-(5-(2-((4'-chloro-2'-methyl-[1,1'-biphenyl]-4-yl)carbamoyl)-5-(trifluoromethyl)phenyl)picolinamido)propanoate Neat Et$_3$N (0.28 mL, 2.0 mmol) was added to a DCM mixture (3 mL) of 2-(6-((3-ethoxy-3-oxopropyl)carbamoyl)pyridin-3-yl)-4-(trifluoromethyl)benzoic acid (~40% pure) (616 mg, 0.6 mmol), 4'-chloro-2'-methyl-[1,1'-biphenyl]-4-amine (109 mg, 0.5 mmol), and EDCI (383 mg, 2.0 mmol) and the resulting mixture was stirred at room temperature. After 3 h the resulting mixture was directly purified via column chromatography to yield the title compound.

STEP C: 3-(5-(2-((4'-chloro-2'-methyl-[1,1'-biphenyl]-4-yl)carbamoyl)-5-(trifluoromethyl)phenyl)picolinamido)propanoic acid A 1M aqueous solution of LiOH (1.0 mL, 1.0 mmol) was added to a THF (2.0 mL) and MeOH (0.5 mL) solution of ethyl 3-(5-(2-((4'-chloro-2'-methyl-[1,1'-biphenyl]-4-yl)carbamoyl)-5-(trifluoromethyl)phenyl)picolinamido)propanoate (85 mg, 0.14 mmol) and the resulting mixture was stirred at room temperature. After 1 h the resulting mixture was neutralized with 2M aqueous HCl, diluted with EtOAc and water and the layers were separated. The aqueous layer was extracted with EtOAc and the combined extracts were dried (Na$_2$SO$_4$), and concentrated. The title compound was re-solidified from CH$_2$Cl$_2$/heptane (ca. 1/19) and dried in vacuo.

$^1$H NMR (400 MHz, DMSO-d$_6$) δ=12.28 (br. s., 1H), 10.70 (s, 1H), 8.87 (t, J=6.0 Hz, 1H), 8.73 (d, J=1.5 Hz, 1H), 8.11-8.17 (m, 1H), 8.09 (d, J=8.1 Hz, 1H), 7.97-8.03 (m, 2H), 7.90-7.97 (m, 1H), 7.61 (d, J=8.6 Hz, 2H), 7.38 (d, J=2.0 Hz, 1H), 7.24-7.33 (m, 3H), 7.20 (d, J=8.3 Hz, 1H), 3.50 (q, J=6.8 Hz, 2H), 2.51-2.55 (m, 2H), 2.22 (s, 3H); MS m/z 583 (M+H).

Example 155

3-(5-(5-chloro-2-(1-((4'-fluoro-[1,1'-biphenyl]-4-yl)amino)ethyl)phenyl)picolinamido)propanoic acid

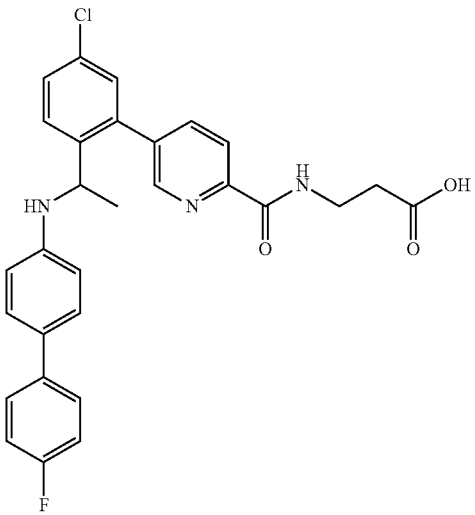 [SMILES: CC(Nc1ccc(-c2ccc(F)cc2)cc1)c1ccc(Cl)cc1-c1ccc(C(=O)NCCC(=O)O)nc1]

STEP A: 1-(2-bromo-4-chlorophenyl)ethanol

Solid NaBH$_4$ (354 mg, 9.4 mmol) was added to a 0° C., THF (5 mL) and MeOH (15 mL) solution of 1-(2-bromo-4-chlorophenyl)ethanone (1.8 g, 7.8 mmol). After 30 min 2N aqueous HCl was slowly added, and the resulting mixture was extracted with EtOAc. The combined organic extracts were dried (Na$_2$SO$_4$), concentrated, and purified via column chromatography to yield the title compound.

STEP B: N-(1-(2-bromo-4-chlorophenyl)ethyl)-4'-fluoro-[1,1'-biphenyl]-4-amine

Neat methanesulfonyl chloride (0.18 mL, 2.4 mmol) was added to a 0° C., DCM solution (20 mL) of 1-(2-bromo-4-chlorophenyl)ethanol (558 mg, 2.4 mmol) and Et$_3$N (0.36 mL, 2.6 mmol) and the resulting mixture was allowed to warm to room temperature gradually. After 30 min Et$_3$N (0.36 mL, 2.6 mmol) and 4'-fluoro-[1,1'-biphenyl]-4-amine (444 g, 2.4 mmol) were added sequentially and stirred at room temperature. After 16 h the resulting mixture was concentrated and purified via column chromatography to yield the title compound.

STEP C: ethyl 3-(5-(5-chloro-2-(1-((4'-fluoro-[1,1'-biphenyl]-4-yl)amino)ethyl)phenyl)picolinamido)propanoate N-(1-(2-bromo-4-chlorophenyl)ethyl)-4'-fluoro-[1,1'-biphenyl]-4-amine (138 mg, 0.34 mmol), ethyl 3-(5-(4,4,5,5-tetramethyl-1,3,2-dioxaborolan-2-yl)picolinamido)propanoate (142 mg, 0.41 mmol), Pd(dppf)Cl$_2$ (37 mg, 0.05 mmol), and K$_2$CO$_3$ (108 g, 0.78 mmol) were dissolved in wet DMF (3 mL) and water (4 mL) and heated to 90° C. After 16 h the resulting mixture was cooled to room temperature, filtered through CELITE and the filtrate was diluted with EtOAc, washed with water and sat. aqueous NaHCO$_3$. The organic layer was dried (Na$_2$SO$_4$), concentrated and purified via column chromatography to yield the title compound.

STEP D: 3-(5-(5-chloro-2-(1-((4'-fluoro-[1,1'-biphenyl]-4-yl)amino)ethyl)phenyl)picolinamido)propanoic acid A 3M aqueous NaOH solution (0.20 mL, 0.60 mmol) was added to a THF (1.0 mL) and MeOH (1.5 mL) solution of ethyl 3-(5'-chloro-2'-(1-((4'-chloro-[1,1'-biphenyl]-4-yl)amino)ethyl)-[1,1'-biphenyl]-4-ylcarboxamido)propanoate (56 mg, 0.10 mmol) and the resulting mixture was stirred at room temperature. After 2 h the resulting mixture was acidified with 1N aqueous HCl and extracted with EtOAc. The combined organics were dried (Na$_2$SO$_4$) and concentrated to yield the title compound.

$^1$H NMR (400 MHz, CHLOROFORM-d) δ=8.58 (br.s., 1H), 8.47 (t, J=6.1 Hz, 1H), 8.29 (d, J=8.1 Hz, 1H), 7.87 (dd, J=2.0, 8.1 Hz, 1H), 7.56 (d, J=8.6 Hz, 1H), 7.34-7.45 (m, 3H), 7.22-7.31 (m, 3H), 7.19 (d, J=2.2 Hz, 1H), 7.04 (t, J=8.7 Hz, 2H), 6.37 (d, J=8.6 Hz, 2H), 4.44 (q, J=6.6 Hz, 1H), 3.80 (q, J=6.1 Hz, 2H), 2.76 (t, J=6.0 Hz, 2H), 1.40 ppm (d, J=6.6 Hz, 3H). MS m/z 518 (M+H).

Example 156

3-(5-(2-(((4'-acetyl-[1,1'-biphenyl]-4-yl)amino)methyl)-5-chlorophenyl)picolinamido)propanoic acid

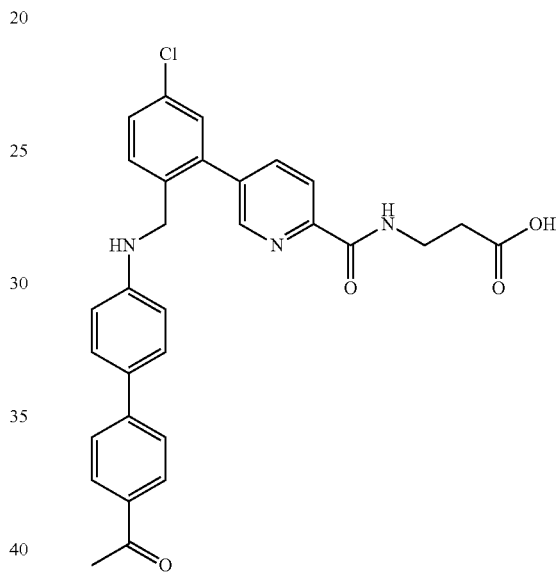

STEP A: Ethyl 3-(5-(5-chloro-2-formylphenyl)picolinamido)propanoate

Ethyl 3-(5-bromopicolinamido)propanoate (2.2 g, 7.3 mmol), (5-chloro-2-formylphenyl)boronic acid (1.4 g, 7.7 mmol), Pd(dppf)Cl$_2$ (810 mg, 1.1 mmol), and K$_2$CO$_3$ (2.3 g, 16.9 mmol) and PdCl$_2$(dppf) were dissolved in wet DMF (10 mL) and the resulting mixture was heated to 90° C. After 16 h the resulting mixture was cooled to room temperature, filtered through CELITE and the filtrate was diluted with EtOAc, washed with water and sat. aqueous NaHCO$_3$. The organic layer was dried (Na$_2$SO$_4$), concentrated and purified via column chromatography to yield the title compound.

STEP B: Ethyl 3-(5-(2-(((4-bromophenyl)amino)methyl)-5-chlorophenyl)picolinamido)propanoate Solid NaBH(OAc)$_3$ (709 mg, 3.3 mmol) was added to a DCE solution (8 mL) of ethyl 3-(5-(5-chloro-2-formylphenyl)picolinamido)propanoate (603 mg, 1.7 mmol), 4-bromoaniline (287.6 mg, 1.67 mmol) and HOAc (0.10 mL, 1.7 mmol) the resulting mixture was stirred at room temperature. After 16 h the resulting mixture diluted with DCM and washed with saturated aqueous NaHCO$_3$ and water. The organic layer was dried (Na$_2$SO$_4$), concentrated and purified via column chromatography to yield the title compound.

STEP C: 3-(5-(2-(((4'-acetyl-[1,1'-biphenyl]-4-yl)amino)methyl)-5-chlorophenyl)picolinamido)propanoic acid Ethyl 3-(5-(2-(((4-bromophenyl)amino)methyl)-5-chlorophenyl)picolinamido)propanoate (84 mg, 0.16 mmol), (4-acetylphenyl)boronic acid (32 mg, 0.20 mmol), Pd(dppf)Cl₂ (18 mg, 0.02 mmol), 2M aqueous Na₂CO₃ (0.22 mL, 0.44 mmol) were dissolved in 1,4-dioxane (1.2 mL) and the resulting mixture was heated to 90° C. After 16 h the resulting mixture was cooled to room temperature, acidified with 2N HCl, filtered through CELITE and the filtrate was diluted with EtOAc, washed with water and saturated aqueous NaHCO₃. The organic layer was dried (Na₂SO₄), concentrated and purified via column chromatography to yield the title compound.

¹H NMR (400 MHz, CHLOROFORM-d) δ=8.54-8.59 (m, 1H), 8.47 (t, J=6.1 Hz, 1H), 8.24 (d, J=8.1 Hz, 1H), 7.96 (d, J=8.3 Hz, 2H), 7.87 (dd, J=2.0, 8.1 Hz, 1H), 7.57 (d, J=8.3 Hz, 2H), 7.50 (d, J=8.3 Hz, 1H), 7.43 (d, J=8.6 Hz, 2H), 7.37-7.42 (m, 1H), 7.26 (m, 1H), 6.54 (d, J=8.6 Hz, 2H), 4.19 (s, 2H), 3.77 (q, J=6.0 Hz, 2H), 2.73 (t, J=6.0 Hz, 2H), 2.60 (s, 3H), 2.02-2.07 ppm (m, 2H). MS m/z 528 (M+H).

Example 157

3-(5-(2-(((4'-fluoro-[1,1'-biphenyl]-4-yl)amino)methyl)-5-(prop-1-en-2-yl)phenyl)picolinamido)propanoic acid

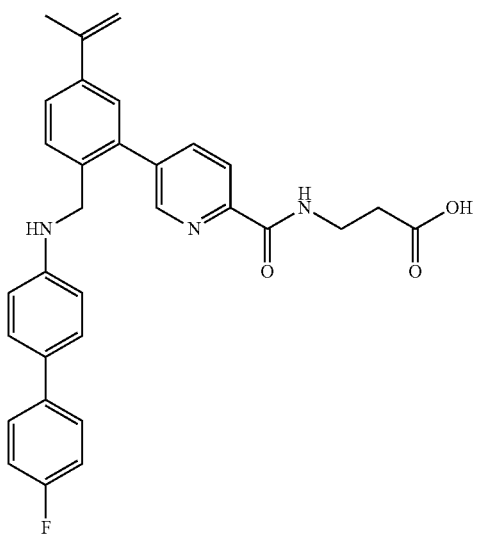 [SMILES: C=C(C)c1ccc(CNc2ccc(-c3ccc(F)cc3)cc2)c(-c2ccc(C(=O)NCCC(=O)O)nc2)c1]

STEP A: ethyl 3-(5-(2-formyl-5-(prop-1-en-2-yl)phenyl)picolinamido)propanoate Ethyl 3-(5-(5-chloro-2-formylphenyl)picolinamido)propanoate (180 mg, 0.50 mmol), 4,4,5,5-tetramethyl-2-(prop-1-en-2-yl)-1,3,2-dioxaborolane (126 mg, 0.75 mmol), Pd(OAc)₂ (11 mg, 0.05 mmol), S-PHOS (41 mg, 0.10) K₃PO₃ (318 mg, 1.50 mmol) were dissolved in toluene (2 mL) and the resulting mixture was heated to 90° C. After 16 h the resulting mixture was cooled to room temperature, diluted with EtOAc, washed with water and brine, dried (Na₂SO₄), concentrated and purified via column chromatography to yield the title compound.

STEP B: ethyl 3-(5-(2-(((4'-fluoro-[1,1'-biphenyl]-4-yl)amino)methyl)-5-(prop-1-en-2-yl)phenyl)picolinamido)propanoate Solid NaBH(OAc)₃ (114 mg, 0.54 mmol) was added to a DCE solution (8 mL) of ethyl 3-(5-(2-(((4'-fluoro-[1,1'-biphenyl]-4-yl)amino)methyl)-5-(prop-1-en-2-yl)phenyl)picolinamido)propanoate (99 mg, 0.27 mmol), 4'-fluoro-[1,1'-biphenyl]-4-amine (50 mg, 0.27 mmol) and HOAc (0.02 mL, 0.27 mmol) the resulting mixture was stirred at room temperature. After 16 h the resulting mixture diluted with DCM and washed with saturated aqueous NaHCO₃ and water. The organic layer was dried (Na₂SO₄), concentrated and purified via column chromatography to yield the title compound.

STEP C: 3-(5-(2-(((4'-fluoro-[1,1'-biphenyl]-4-yl)amino)methyl)-5-(prop-1-en-2-yl)phenyl)picolinamido)propanoic acid A 3M aqueous NaOH solution (0.32 mL, 0.97 mmol) was added to a THF (1.0 mL) and MeOH (1.5 mL) solution of ethyl 3-(5-(2-(((4'-fluoro-[1,1'-biphenyl]-4-yl)amino)methyl)-5-(prop-1-en-2-yl)phenyl)picolinamido)propanoate (87 mg, 0.16 mmol) and the resulting mixture was stirred at room temperature. After 2 h the resulting mixture was acidified with 1N aqueous HCl and extracted with EtOAc. The combined organics were dried (Na₂SO₄), concentrated and purified via column chromatography to give the title compound.

¹H NMR (400 MHz, CHLOROFORM-d) δ=8.61 (br. s., 1H), 8.47 (m, 1H), 8.24 (m, 1H), 7.92 (m, 1H), 7.53 (m, 2H), 7.43 (m, 2H), 7.33 (m, 3H), 7.05 (m, 2H), 6.56 (m, 2H), 5.42 (br. s., 1H), 5.14 (br. s., 1H), 4.20 (br. s., 2H), 3.78 (m, 2H), 2.74 (m, 2H), 2.17 ppm (s, 3H). MS m/z 510 (M+H).

Example 158

3-(5-(2-(((4'-fluoro-[1,1'-biphenyl]-4-yl)amino)methyl)-5-isopropylphenyl)picolinamido)propanoic acid

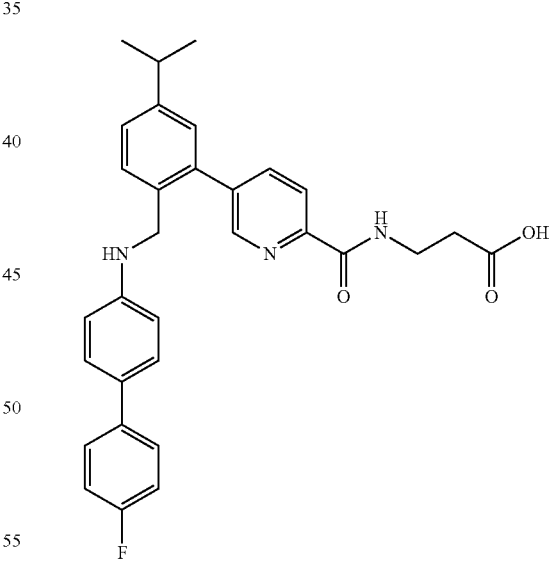

A mixture of 3-(5-(2-(((4'-fluoro-[1,1'-biphenyl]-4-yl)amino)methyl)-5-(prop-1-en-2-yl)phenyl)picolinamido)propanoic acid (46 mg, 0.09 mmol), ammonium formate (57 mg, 0.91 mmol) and 10% Pd—C (10 mg, 0.01 mmol) in MeOH (5 mL) was refluxed. After 1 h, the resulting mixture was filtered through celite and washed with DCM-MeOH. The filtrate was concentrated and purified via column chromatography to yield the title compound.

¹H NMR (400 MHz, CHLOROFORM-d) δ=8.61 (br. s., 1H), 8.47 (m, 1H), 8.23 (m, 1H), 7.92 (m, 1H), 7.39-7.60 (m, 3H), 7.32 (m, 3H), 7.14 (br. s., 1H), 7.06 (m, 2H), 6.57 (m,

2H), 4.18 (br. s., 2H), 3.77 (m, 2H), 2.96 (m, 1H), 2.74 (m, 2H), 1.28 ppm (s, 6H). MS m/z 512 (M+H).

Example 159

3-(5-(2-(((2,4'-dichloro-[1,1'-biphenyl]-4-yl)amino)methyl)-3-methoxy-5-(trifluoromethyl)phenyl)picolinamido)propanoic acid

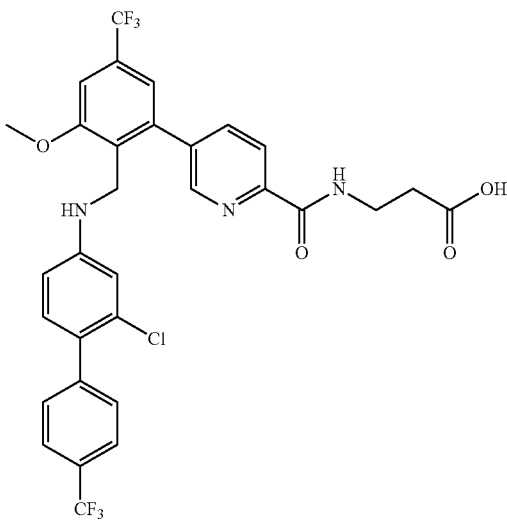 [SMILES: COc1cc(C(F)(F)F)cc(-c2ccc(C(=O)NCCC(=O)O)nc2)c1CNc1ccc(-c2ccc(C(F)(F)F)cc2)c(Cl)c1]

STEP A: 2-chloro-4'-(trifluoromethyl)-[1,1'-biphenyl]-4-amine 4-bromo-3-chloroaniline (2.1 g, 10.2 mmol), (4-(trifluoromethyl)phenyl)boronic acid (2.7 g, 14.2 mmol), Pd(dppf)Cl$_2$ (744 mg, 1.0 mmol), 2M aqueous Na$_2$CO$_3$ (15.3 mL, 30.5 mmol) were dissolved in 1,4-dioxane (30 mL) and the resulting mixture was heated to 90° C. After 16 h the resulting mixture was cooled to room temperature, was diluted with EtOAc, washed with water and brine. The organic layer was dried (Na$_2$SO$_4$), concentrated and diethyl ether was added. The resulting precipitate was filtered and dried in vacuo to yield the title compound.

STEP B: 2-chloro-6-methoxy-4-(trifluoromethyl)benzaldehyde

A 2M BuLi solution (2.07 mL, 4.3 mmol) was added to a −78° C. THF solution (20 mL) of 1-chloro-3-methoxy-5-(trifluoromethyl)benzene (870 mg, 4.1 mmol). After 45 min neat DMF (0.39 mL, 5.0 mmol) was added, and the resulting solution was allowed to warm to 0° C. gradually, quenched with NH$_4$Cl solution, and extracted with diethyl ether. The combined extracts were dried (Na$_2$SO$_4$), concentrated, and purified via column chromatography to yield the title compound.

STEP C: Ethyl 3-(5-(2-formyl-3-methoxy-5-(trifluoromethyl)phenyl)picolinamido)propanoate 2-Chloro-6-methoxy-4-(trifluoromethyl)benzaldehyde (272.1 mg, 1.14 mmol), ethyl 3-(5-(4,4,5,5-tetramethyl-1,3,2-dioxaborolan-2-yl)picolinamido)propanoate (516.2 mg, 1.48 mmol), SPhos (140.5 mg, 0.34 mmol), Pd(OAc)$_2$ (38.4 mg, 0.17 mmol) and K$_3$PO$_4$ (726.3 mg, 3.42 mmol) were dissolved in wet PhMe (8 mL) and the resulting mixture was heated to 90° C. After 16 h the resulting mixture was diluted with water and extracted with EtOAc. The combined organic extracts were dried (Na$_2$SO$_4$), concentrated, and purified via column chromatography to yield the title compound.

STEP D: ethyl 3-(5-(2-(((2-chloro-4'-(trifluoromethyl)-[1,1'-biphenyl]-4-yl)amino)methyl)-3-methoxy-5-(trifluoromethyl)phenyl)picolinamido)propanoate Solid NaBH(OAc)$_3$ (74 mg, 0.35 mmol) was added to a DCE solution (1 mL) of ethyl 3-(5-(2-formyl-3-methoxy-5-(trifluoromethyl)phenyl)picolinamido)propanoate (98 mg, 0.23 mmol), 2-chloro-4'-(trifluoromethyl)-[1,1-biphenyl]-4-amine (63 mg, 0.23 mmol) and HOAc (0.01 mL, 0.23 mmol) the resulting mixture was stirred at room temperature. After 16 h the resulting mixture diluted with DCM and washed with saturated aqueous NaHCO$_3$ and water. The organic layer was dried (Na$_2$SO$_4$), concentrated and purified via column chromatography to yield the title compound.

STEP E: 3-(5-(2-(((2-chloro-4'-(trifluoromethyl)-[1,1'-biphenyl]-4-yl)amino)methyl)-3-methoxy-5-(trifluoromethyl)phenyl)picolinamido)propanoic acid A 3M aqueous NaOH solution (0.16 mL, 0.49 mmol) was added to a THF (1.0 mL) and MeOH (1.5 mL) solution of ethyl 3-(5-(2-(((2-chloro-4'-(trifluoromethyl)-[1,1'-biphenyl]-4-yl)amino)methyl)-3-methoxy-5-(trifluoromethyl)phenyl)picolinamido)propanoate (56 mg, 0.08 mmol) and the resulting mixture was stirred at room temperature. After 2 h the resulting mixture was acidified with 1N aqueous HCl and extracted with EtOAc. The combined organics were dried (Na$_2$SO$_4$), concentrated and purified via column chromatography to give the title compound.

$^1$H NMR (400 MHz, CHLOROFORM-d) δ=8.60 (s, 1H), 8.41-8.52 (m, 1H), 8.27 (t, J=8.1 Hz, 1H), 7.92 (d, J=7.8 Hz, 1H), 7.57-7.69 (m, J=8.1 Hz, 2H), 7.46-7.56 (m, J=7.8 Hz, 2H), 7.22 (s, 1H), 7.19 (s, 1H), 7.07 (d, J=8.6 Hz, 1H), 6.54 (s, 1H), 6.41 (d, J=8.6 Hz, 1H), 4.21 (s, 2H), 4.01 (s, 3H), 3.79 (q, J=6.0 Hz, 2H), 2.75 ppm (t, J=5.9 Hz, 2H). MS m/z 652 (M+H).

Example 160

3-(5-(3-methoxy-2-(((2,4',6-trichloro-[1,1'-biphenyl]-4-yl)amino)methyl)-5-(trifluoromethyl)phenyl)picolinamido)propanoic acid

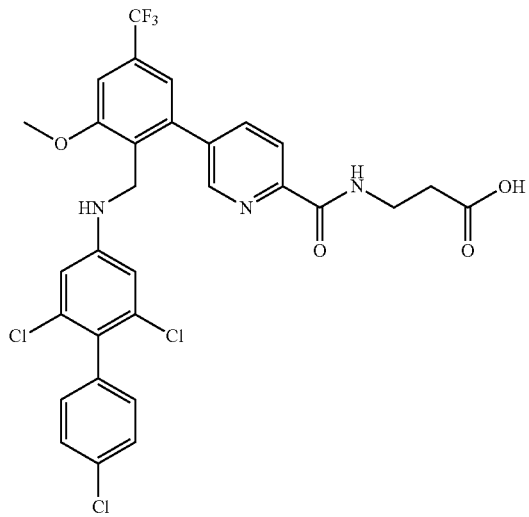 [SMILES: COc1cc(C(F)(F)F)cc(-c2ccc(C(=O)NCCC(=O)O)nc2)c1CNc1cc(Cl)c(-c2ccc(Cl)cc2)c(Cl)c1]

STEP A: 2,4',6-trichloro-[1,1'-biphenyl]-4-amine

The title compound was prepared as described in Example 159 substituting 4-bromo-3,5-dichloroaniline and (4-chlorophenyl)boronic acid for 4-bromo-3-chloroaniline and (4-(trifluoromethyl)phenyl)boronic acid, respectively.

STEP B: 3-(5-(3-methoxy-2-(((2,4',6-trichloro-[1,1'-biphenyl]-4-yl)amino)methyl)-5-(trifluoromethyl)phenyl)picolinamido)propanoic acid The title compound was prepared as described in Example 159 substituting 2,4',6-trichloro-[1,1'-biphenyl]-4-amine for 2-chloro-4'-(trifluoromethyl)-[1,1'-biphenyl]-4-amine.

$^1$H NMR (400 MHz, CHLOROFORM-d) δ=8.58 (s, 1H), 8.47 (m, 1H), 8.29 (d, J=8.1 Hz, 1H), 7.90 (d, J=7.8 Hz, 1H), 7.38 (d, J=7.8 Hz, 2H), 7.22 (s, 1H), 7.10-7.21 (m, 3H), 6.44 (s, 2H), 4.19 (s, 2H), 4.01 (s, 3H), 3.79 (q, J=6.1 Hz, 2H), 2.75 ppm (t, J=5.5 Hz, 2H). MS m/z 652 (M+H).

Example 161

3-(5-(2-(((2'-chloro-4'-(trifluoromethyl)-[1,1'-biphenyl]-4-yl)amino)methyl)-3-methoxy-5-(trifluoromethyl)phenyl)picolinamido)propanoic acid

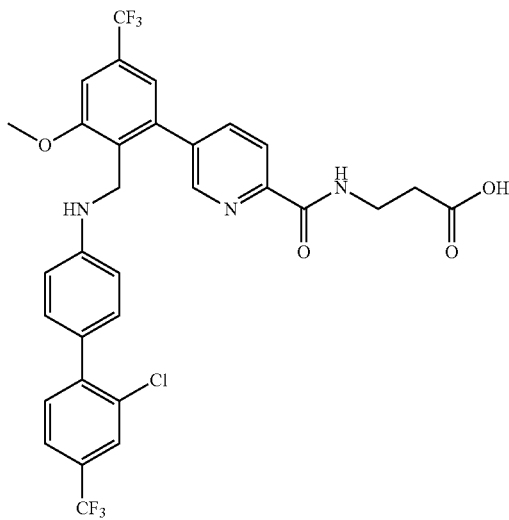 [SMILES: COc1cc(C(F)(F)F)cc(-c2ccc(C(=O)NCCC(=O)O)nc2)c1CNc1ccc(-c2ccc(C(F)(F)F)cc2Cl)cc1]

STEP A: 2'-chloro-4'-(trifluoromethyl)-[1,1'-biphenyl]-4-amine

The title compound was prepared as described in Example 159 substituting 4-bromoaniline and (2-chloro-4-(trifluoromethyl)phenyl)boronic acid for 4-bromo-3-chloroaniline and (4-(trifluoromethyl)phenyl)boronic acid, respectively.

STEP B: 3-(5-(2-(((2'-chloro-4'-(trifluoromethyl)-[1,1'-biphenyl]-4-yl)amino)methyl)-3-methoxy-5-(trifluoromethyl)phenyl)picolinamido)propanoic acid The title compound was prepared as described in Example 159 substituting 2'-chloro-4'-(trifluoromethyl)-[1,1'-biphenyl]-4-amine for 2-chloro-4'-(trifluoromethyl)-[1,1'-biphenyl]-4-amine.

$^1$H NMR (400 MHz, CHLOROFORM-d) δ=8.62 (d, J=1.5 Hz, 1H), 8.46 (t, J=6.2 Hz, 1H), 8.25 (d, J=8.6 Hz, 1H), 7.94 (dd, J=2.2, 8.1 Hz, 1H), 7.70 (m, 1H), 7.48-7.56 (m, 1H), 7.42 (d, J=8.1 Hz, 1H), 7.24 (s, 1H), 7.17-7.23 (m, 2H), 6.50-6.59 (m, 2H), 4.22 (s, 2H), 4.00 (s, 3H), 3.79 (q, J=6.2 Hz, 2H), 2.75 ppm (t, J=6.1 Hz, 2H). MS m/z 652 (M+H).

Example 162

3-(5-(2-(((2,4'-dichloro-[1,1'-biphenyl]-4-yl)amino)methyl)-3-methoxy-5-(trifluoromethyl)phenyl)picolinamido)propanoic acid

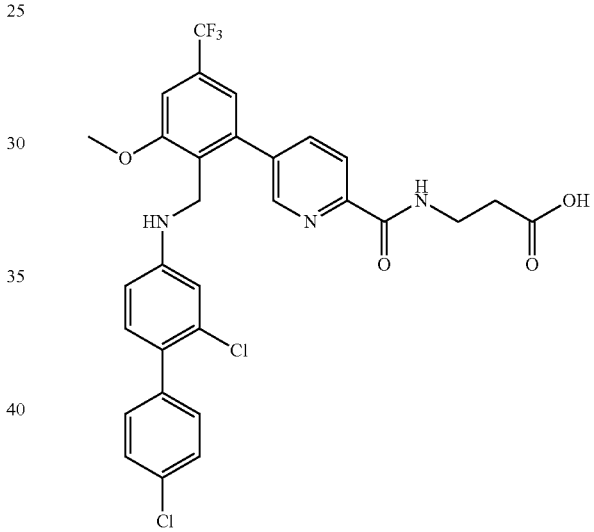

STEP A: 2,4'-dichloro-[1,1'-biphenyl]-4-amine

The title compound was prepared as described in Example 159 (4-chlorophenyl)boronic acid for (4-(trifluoromethyl)phenyl)boronic acid.

STEP B: -(5-(2-(((2,4'-dichloro-[1,1'-biphenyl]-4-yl)amino)methyl)-3-methoxy-5-(trifluoromethyl)phenyl)picolinamido)propanoic acid The title compound was prepared as described in Example 159 substituting 2,4'-dichloro-[1,1'-biphenyl]-4-amine for 2-chloro-4'-(trifluoromethyl)-[1,1'-biphenyl]-4-amine.

$^1$H NMR (400 MHz, CHLOROFORM-d) δ=8.60 (s, 1H), 8.46 (t, J=5.9 Hz, 1H), 8.27 (d, J=8.1 Hz, 1H), 7.92 (d, J=8.1 Hz, 1H), 7.29-7.38 (m, 4H), 7.22 (s, 1H), 7.18 (s, 1H), 7.04 (d, J=8.3 Hz, 1H), 6.53 (s, 1H), 6.39 (d, J=8.3 Hz, 1H), 4.20 (s, 2H), 4.00 (s, 3H), 3.79 (q, J=6.0 Hz, 2H), 2.75 ppm (t, J=6.0 Hz, 2H). MS m/z 618 (M+H).

Example 163

3-(5-(2-(((2-chloro-4'-(trifluoromethyl-[1,1'-biphenyl]-4-yl)amino)methyl)-3-methyl-5-(trifluoromethyl)phenyl)picolinamido)propanoic acid

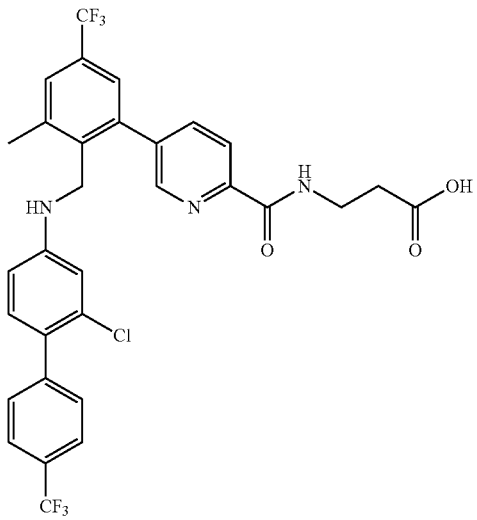 [SMILES: Cc1cc(C(F)(F)F)cc(-c2ccc(C(=O)NCCC(=O)O)nc2)c1CNc1ccc(-c2ccc(C(F)(F)F)cc2)c(Cl)c1]

STEP A: 2,6-dichloro-4-(trifluoromethyl)benzaldehyde

The title compound was prepared as described in Example 159 substituting 1,3-dichloro-5-(trifluoromethyl)benzene for 1-chloro-3-methoxy-5-(trifluoromethyl)benzene.

STEP B: Ethyl 3-(5-(3-chloro-2-formyl-5-(trifluoromethyl)phenyl)picolinamido)propanoate 2,6-Dichloro-4-(trifluoromethyl)benzaldehyde (3.2 g, 13.2 mmol), ethyl 3-(5-(4,4,5,5-tetramethyl-1,3,2-dioxaborolan-2-yl)picolinamido)propanoate (1.5 g, 4.4 mmol), Pd(dppf)Cl$_2$ (320 mg, 0.4 mmol) and K$_3$Pa$_4$hydrate (3.0 g, 13.2 mmol) were dissolved in 1,4-dioxane (200 mL) and the resulting mixture was heated to 90° C. After 10 h the resulting mixture was diluted with water and extracted with EtOAc. The combined organic extracts were dried (Na$_2$SO$_4$), concentrated, and purified via column chromatography to yield the title compound.

STEP C: Ethyl 3-(5-(2-formyl-3-methyl-5-(trifluoromethyl)phenyl)picolinamido)propanoate Ethyl 3-(5-(3-chloro-2-formyl-5-(trifluoromethyl)phenyl)picolinamido)propanoate (150 mg, 0.35 mmol), methylboronic acid (31 mg, 0.53 mmol), Pd(dppf)Cl$_2$ (34 mg, 0.05 mmol) and K$_3$Pa$_4$hydrate (322 mg, 1.40 mmol) were dissolved in 1,4-dioxane (2 mL) and the resulting mixture was heated to 90° C. After 10 h the resulting mixture was diluted with water and extracted with EtOAc. The combined organic extracts were dried (Na$_2$SO$_4$), concentrated, and purified via column chromatography to yield the title compound.

STEP D: Ethyl 3-(5-(2-(((2-chloro-4'-(trifluoromethyl)-[1,1'-biphenyl]-4-yl)amino)methyl)-3-methyl-5-(trifluoromethyl)phenyl)picolinamido)propanoate Ethyl 3-(5-(2-formyl-3-methyl-5-(trifluoromethyl)phenyl)picolinamido)propanoate (37 mg, 0.09 mmol), 2-chloro-4'-(trifluoromethyl)-[1,1-biphenyl]-4-amine (39 mg, 0.14 mmol) and HOAc (5 µL, 0.09 mmol) were dissolved in EtOH (2 mL) and the resulting mixture was heated to 80° C. After 5 h the resulting mixture was cooled to room temperature, solid NaCNBH$_3$ (28 mg, 0.45 mmol) was added and the resulting mixture was stirred at room temperature. After 2 h saturated aqueous NH$_4$Cl was added and the aqueous phase was extracted with EtOAc. The combined organics were dried (Na$_2$SO$_4$), concentrated and purified via column chromatography to yield the title compound.

STEP E: 3-(5-(2-(((2-chloro-4'-(trifluoromethyl)-[1,1'-biphenyl]-4-yl)amino)methyl)-3-methyl-5-(trifluoromethyl)phenyl)picolinamido)propanoic acid A 3M aqueous NaOH solution (0.13 mL, 0.39 mmol) was added to a THF (2.0 mL) and MeOH (1.0 mL) solution of ethyl 3-(5-(2-(((2-chloro-4'-(trifluoromethyl)-[1,1'-biphenyl]-4-yl)amino)methyl)-3-methyl-5-(trifluoromethyl)phenyl)picolinamido)propanoate (44 mg, 0.07 mmol) and the resulting mixture was stirred at room temperature. After 2 h the resulting mixture was acidified with 1N aqueous HCl and extracted with EtOAc. The combined organics were dried (Na$_2$SO$_4$), concentrated and purified via column chromatography to give the title compound.

$^1$H NMR (400 MHz, CHLOROFORM-d) δ=8.59 (s, 1H), 8.44 (t, J=6.4 Hz, 1H), 8.23 (d, J=7.8 Hz, 1H), 7.90 (dd, J=1.8, 7.9 Hz, 1H), 7.62-7.68 (m, J=8.1 Hz, 2H), 7.60 (s, 1H), 7.52 (d, J=8.1 Hz, 2H), 7.42 (s, 1H), 7.13 (d, J=8.3 Hz, 1H), 6.64 (d, J=2.2 Hz, 1H), 6.51 (dd, J=2.2, 8.3 Hz, 1H), 4.12 (s, 2H), 3.77 (q, J=6.1 Hz, 2H), 2.73 (t, J=6.0 Hz, 2H), 2.56 ppm (s, 3H). MS m/z 636 (M+H).

Example 164

3-(5-(2-(((2,4'-dichloro-[1,1'-biphenyl]-4-yl)amino)methyl)-3-hydroxy-5-(trifluoromethyl)phenyl)picolinamido)propanoic acid

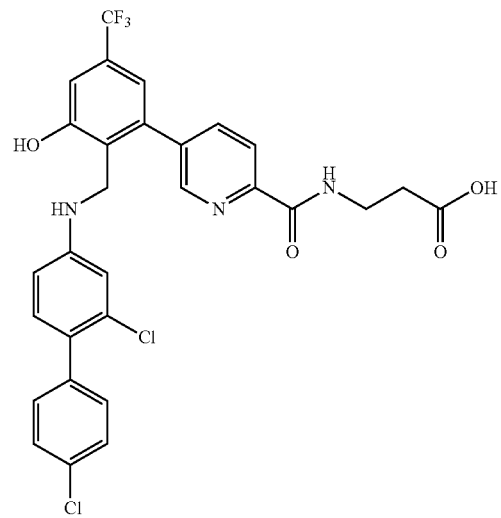 [SMILES: O=C(O)CCNC(=O)c1ccc(-c2cc(C(F)(F)F)cc(O)c2CNc2ccc(-c3ccc(Cl)cc3)c(Cl)c2)cn1]

STEP A: 2-chloro-6-(methoxymethoxy)-4-(trifluoromethyl)benzaldehyde

Neat chloro(methoxy)methane (1.8 mL, 23.8 mmol) was added to a MeCN solution (20 mL) of 3-chloro-5-(trifluoromethyl)phenol (3.6 g, 18.3 mmol) and Cs$_2$CO$_3$ and the resulting mixture was stirred at room temperature. After 5 h the resulting mixture was diluted with diethyl ether, filtered and concentrated. The resulting material was filtered through a short pad of silica gel, followed by concentration to yield 1-chloro-3-(methoxymethoxy)-5-(trifluoromethyl)benzene.

A 1.6M LDA solution (12.6 mL, 20.1 mmol) was added to a −78° C. THF solution (50 mL) of 1-chloro-3-(methoxymethoxy)-5-(trifluoromethyl)benzene (from above). After 30 min neat DMF (3.9 mL, 50.0 mmol) was added, and the resulting solution was allowed to warm to 0° C. gradually, quenched with NH$_4$Cl solution, and extracted with diethyl ether. The combined extracts were dried (Na$_2$SO$_4$), concentrated, and purified via column chromatography to yield the title compound.

STEP B: Ethyl 3-(5-(2-formyl-3-(methoxymethoxy)-5-(trifluoromethyl)phenyl)picolinamido)propanoate The title compound was prepared as described in Example 159 substituting 2-chloro-6-(methoxymethoxy)-4-(trifluoromethyl)benzaldehyde for 2-chloro-6-methoxy-4-(trifluoromethyl)benzaldehyde.

STEP C: Ethyl 3-(5-(2-formyl-3-hydroxy-5-(trifluoromethyl)phenyl)picolinamido)propanoate Neat TFA (1 mL) was added to a DCM solution (3 mL) of ethyl 3-(5-(2-formyl-3-(methoxymethoxy)-5-(trifluoromethyl)phenyl)picolinamido)propanoate (121 mg, 0.27 mmol) and the resulting mixture was stirred at room temperature. After 1 h the resulting mixture was concentrated to yield the title compound, which was used in the next step without further purification.

STEP D: 3-(5-(2-(((2,4'-dichloro-[1,1'-biphenyl]-4-yl)amino)methyl)-3-hydroxy-5-(trifluoromethyl)phenyl)picolinamido)propanoic acid The title compound was prepared as described in Example 159 substituting ethyl 3-(5-(2-formyl-3-hydroxy-5-(trifluoromethyl)phenyl)picolinamido)propanoate and 2,4'-dichloro-[1,1'-biphenyl]-4-amine for ethyl 3-(5-(2-formyl-3-methoxy-5-(trifluoromethyl)phenyl)picolinamido)propanoate and 2-chloro-4'-(trifluoromethyl)-[1,1'-biphenyl]-4-amine, respectively.

$^1$H NMR (400 MHz, CHLOROFORM-d) δ=8.53 (d, J=1.7 Hz, 1H), 8.46 (t, J=6.2 Hz, 1H), 8.28 (d, J=8.1 Hz, 1H), 7.83 (dd, J=2.2, 8.1 Hz, 1H), 7.33-7.39 (m, 2H), 7.30 (s, 1H), 7.25-7.29 (m, 2H), 7.14 (d, J=8.3 Hz, 1H), 7.09 (s, 1H), 6.79 (d, J=2.4 Hz, 1H), 6.66 (dd, J=2.4, 8.3 Hz, 1H), 4.35 (s, 2H), 3.79 (q, J=6.2 Hz, 2H), 2.75 ppm (t, J=6.1 Hz, 2H). MS m/z 632 (M+H).

Example 165

3-(5-(2-(((2,4'-dichloro-2'-methyl-[1,1'-biphenyl]-4-yl)amino)methyl)-3-methyl-5-(trifluoromethyl)phenyl)picolinamido)propanoic acid

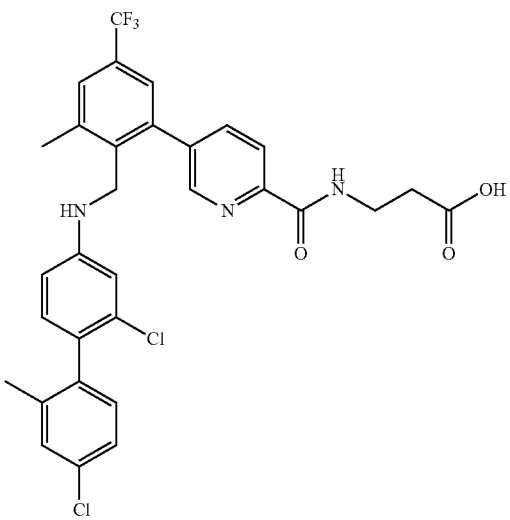 [SMILES: Cc1cc(Cl)ccc1-c1ccc(NCc2c(C)cc(C(F)(F)F)cc2-c2ccc(C(=O)NCCC(=O)O)nc2)cc1Cl]

The title compound was prepared as described in Example 163 substituting 2,4'-dichloro-2'-methyl-[1,1'-biphenyl]-4-amine for 2-chloro-4'-(trifluoromethyl)-[1,1'-biphenyl]-4-amine.

$^1$H NMR (400 MHz, CHLOROFORM-d) δ=8.60 (d, J=1.7 Hz, 1H), 8.45 (t, J=6.2 Hz, 1H), 8.23 (d, J=7.6 Hz, 1H), 7.92 (dd, J=2.2, 8.1 Hz, 1H), 7.60 (s, 1H), 7.41 (s, 1H), 7.24 (d, J=2.0 Hz, 1H), 7.18 (dd, J=2.0, 8.1 Hz, 1H), 7.05 (d, J=8.1 Hz, 1H), 6.96 (d, J=8.3 Hz, 1H), 6.62 (d, J=2.4 Hz, 1H), 6.48 (dd, J=2.4, 8.3 Hz, 1H), 4.11 (s, 2H), 3.78 (q, J=6.1 Hz, 2H), 2.74 (t, J=6.0 Hz, 2H), 2.57 ppm (s, 3H). MS m/z 616 (M+H).

Example 166

3-(5-(2-(((2-chloro-2'-methyl-4'-(trifluoromethyl)-[1,1'-biphenyl]-4-yl)amino)methyl)-3-methyl-5-(trifluoromethyl)phenyl)picolinamido)propanoic acid

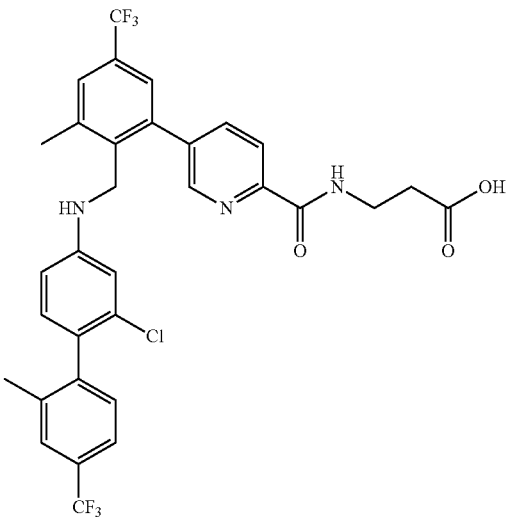 [SMILES: Cc1cc(C(F)(F)F)ccc1-c1ccc(NCc2c(C)cc(C(F)(F)F)cc2-c2ccc(C(=O)NCCC(=O)O)nc2)cc1Cl]

The title compound was prepared as described in Example 163 substituting 2-chloro-2'-methyl-4'-(trifluoromethyl)-[1,1'-biphenyl]-4-amine for 2-chloro-4'-(trifluoromethyl)-[1,1'-biphenyl]-4-amine.

$^1$H NMR (400 MHz, CHLOROFORM-d) δ=8.60 (d, J=1.7 Hz, 1H), 8.45 (t, J=5.7 Hz, 1H), 8.23 (d, J=8.1 Hz, 1H), 7.92 (dd, J=2.2, 8.1 Hz, 1H), 7.60 (s, 1H), 7.50 (s, 1H), 7.46 (d, J=8.3 Hz, 1H), 7.42 (s, 1H), 7.24 (d, J=7.6 Hz, 1H), 6.97 (d, J=8.3 Hz, 1H), 6.64 (d, J=2.4 Hz, 1H), 6.50 (dd, J=2.2, 8.3 Hz, 1H), 4.12 (s, 2H), 3.78 (q, J=6.3 Hz, 3H), 2.68-2.79 (m, 2H), 2.58 (s, 3H), 2.19 ppm (s, 3H). MS m/z 650 (M+H).

Example 167

3-(5-(2-(((2-chloro-2'-methyl-4'-(trifluoromethyl-[1,1'-biphenyl]-4-yl)amino)methyl)-3-isopropyl-5-(trifluoromethyl)phenyl)picolinamido)propanoic acid

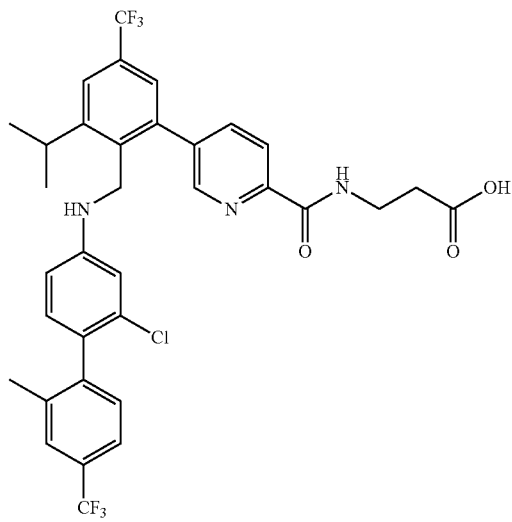 [SMILES: Cc1cc(C(F)(F)F)ccc1-c1ccc(NCc2c(-c3ccc(C(=O)NCCC(=O)O)nc3)cc(C(F)(F)F)cc2C(C)C)cc1Cl]

STEP A: Ethyl 3-(5-(2-formyl-3-(prop-1-en-2-yl)-5-(trifluoromethyl)phenyl)picolinamido)propanoate The title compound was prepared as described in Example 163 substituting 4,4,5,5-tetramethyl-2-(prop-1-en-2-yl)-1,3,2-dioxaborolane for methylboronic acid.

STEP B: Ethyl 3-(5-(2-(hydroxymethyl)-3-isopropyl-5-(trifluoromethyl)phenyl)picolinamido)propanoate A solution of ethyl 3-(5-(2-formyl-3-(prop-1-en-2-yl)-5-(trifluoromethyl)phenyl)picolinamido)propanoate (150.1 mg, 0.35 mmol) in THF (5 mL) and MeOH (25 mL) was hydrogenated substituting H-Cube (10 Bar $H_2$) at 40° C. at a flow rate of 1 mL/min. The resulting solution was concentrated to yield the title compound.

STEP C: Ethyl 3-(5-(2-(bromomethyl)-3-isopropyl-5-(trifluoromethyl)phenyl)picolinamido)propanoate Neat $CBr_4$ (57 mg, 0.17 mmol) was added to a DCM solution (5 mL) of ethyl 3-(5-(2-(hydroxymethyl)-3-isopropyl-5-(trifluoromethyl)phenyl)picolinamido)propanoate (75 mg, 0.17 mmol) and $PPh_3$ (45 mg, 0.17 mmol) and the resulting mixture was stirred at room temperature. After 16 h the resulting mixture was concentrated and purified via column chromatography to yield the title compound.

STEP D: Ethyl 3-(5-(2-(((2-chloro-2'-methyl-4'-(trifluoromethyl)-[1,1'-biphenyl]-4-yl)amino)methyl)-3-isopropyl-5-(trifluoromethyl)phenyl)picolinamido)propanoate Ethyl 3-(5-(2-(bromomethyl)-3-isopropyl-5-(trifluoromethyl)phenyl)picolinamido)propanoate (27 mg, 0.05 mmol), 2-chloro-2'-methyl-4'-(trifluoromethyl)-[1,1'-biphenyl]-4-amine (20 mg, 0.07 mmol) and $iPr_2NEt$ (27 μL, 0.16 mmol) were dissolved in toluene (3 mL) and the resulting mixture was heated at 100° C. After 16 h the resulting mixture was concentrated and purified via column chromatography to yield the title compound.

STEP E: 3-(5-(2-(((2-chloro-2'-methyl-4'-(trifluoromethyl)-[1,1'-biphenyl]-4-yl)amino)methyl)-3-isopropyl-5-(trifluoromethyl)phenyl)picolinamido)propanoic acid A 3M aqueous NaOH solution (0.04 mL, 0.11 mmol) was added to a THF (2.0 mL) and MeOH (1.0 mL) solution of ethyl 3-(5-(2-(((2-chloro-2'-methyl-4'-(trifluoromethyl)-[1,1'-biphenyl]-4-yl)amino)methyl)-3-isopropyl-5-(trifluoromethyl)phenyl)picolinamido)propanoate (13 mg, 0.02 mmol) and the resulting mixture was stirred at room temperature. After 2 h the resulting mixture was acidified with 1N aqueous HCl and extracted with EtOAc. The combined organics were dried ($Na_2SO_4$), concentrated and purified via column chromatography to yield the title compound.

$^1$H NMR (400 MHz, CHLOROFORM-d) δ=8.61 (d, J=1.5 Hz, 1H), 8.45 (t, J=6.4 Hz, 1H), 8.22 (d, J=7.3 Hz, 1H), 7.93 (dd, J=2.2, 8.1 Hz, 1H), 7.71 (br. s., 1H), 7.50 (s, 1H), 7.46 (d, J=8.1 Hz, 1H), 7.39 (d, J=1.2 Hz, 1H), 7.24 (d, J=8.1 Hz, 1H), 6.97 (d, J=8.3 Hz, 1H), 6.63 (d, J=2.2 Hz, 1H), 6.49 (dd, J=2.4, 8.3 Hz, 1H), 4.11 (s, 2H), 3.78 (q, J=6.1 Hz, 2H), 3.27-3.40 (m, 1H), 2.74 (t, J=6.1 Hz, 2H), 2.20 (s, 3H), 1.36 ppm (d, J=6.8 Hz, 6H). MS m/z 678 (M+H).

Example 168

3-(5-(2-(((4'-(tert-butyl)-2-chloro-[1,1'-biphenyl]-4-yl)amino)methyl)-5-chlorophenyl)picolinamido)propanoic acid

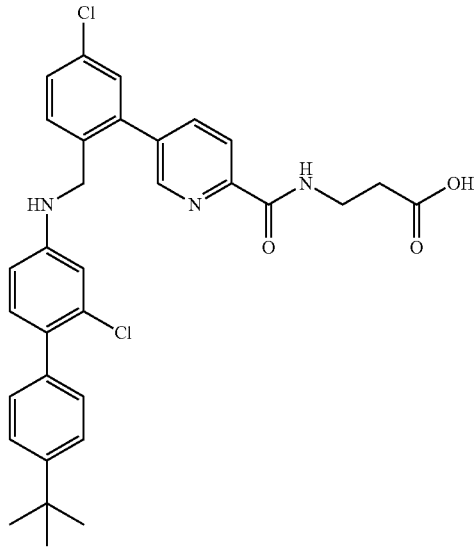 [SMILES: CC(C)(C)c1ccc(-c2ccc(NCc3ccc(Cl)cc3-c3ccc(C(=O)NCCC(=O)O)nc3)cc2Cl)cc1]

The title compound was prepared as described in Example 146 substituting 4-bromo-3-chloroaniline and (4-(tert-butyl)phenyl)boronic acid for 4-iodoaniline and (4-fluoro-3-methylphenyl)boronic acid, respectively.

$^1$H NMR (CDCl$_3$): δ 8.57 (d, 1H), 8.47 (t, 1H), 8.26 (d, 1H), 7.87 (dd, 1H), 7.50 (dd, 1H), 7.43-7.38 (m, 3H), 7.32 (d, 2H), 7.28 (d, 1H), 7.10 (d, 1H), 6.55 (d, 1H), 6.41 (dd, 1H), 4.15 (s, 2H), 3.78 (dt, 2H), 2.74 (t, 2H), 1.35 (s, 9H); MS m/z 576 (M+H).

Example 169

3-(5-(5-chloro-2-(((2,4'-dichloro-3'-(trifluoromethyl)-[1,1'-biphenyl]-4-yl)amino)methyl)phenyl)picolinamido)propanoic acid

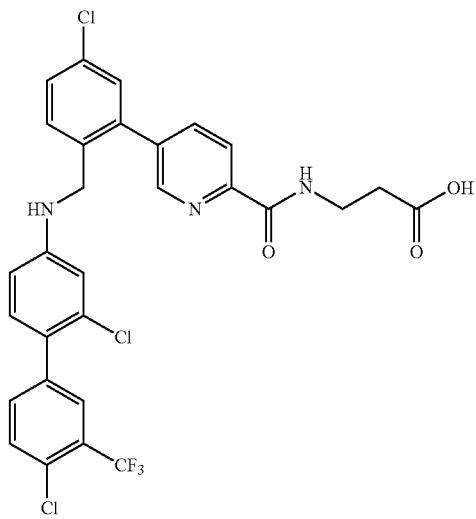 [SMILES: O=C(O)CCNC(=O)c1ccc(-c2cc(Cl)ccc2CNc2ccc(-c3ccc(Cl)c(C(F)(F)F)c3)c(Cl)c2)cn1]

The title compound was prepared as described in Example 146 substituting 4-bromo-3-chloroaniline and (4-chloro-3-(trifluoromethyl)phenyl)boronic acid for 4-iodoaniline and (4-fluoro-3-methylphenyl)boronic acid, respectively.

$^1$H NMR (CDCl$_3$): δ 8.56 (d, 1H), 8.48 (t, 1H), 8.26 (d, 1H), 7.87 (dd, 1H), 7.69 (d, 1H), 7.50-7.48 (m, 3H), 7.42 (d,

1H), 7.29 (d, 1H), 7.05 (d, 1H), 6.55 (d, 1H), 6.42 (dd, 1H), 4.18 (s, 2H), 3.79 (dt, 2H), 2.75 (t, 2H); MS m/z 622 (M+H).

Example 170

3-(5-(5-chloro-2-(((2-chloro-3'-(trifluoromethyl)-[1, 1'-biphenyl]-4-yl)amino)methyl)phenyl)picolinamido)propanoic acid

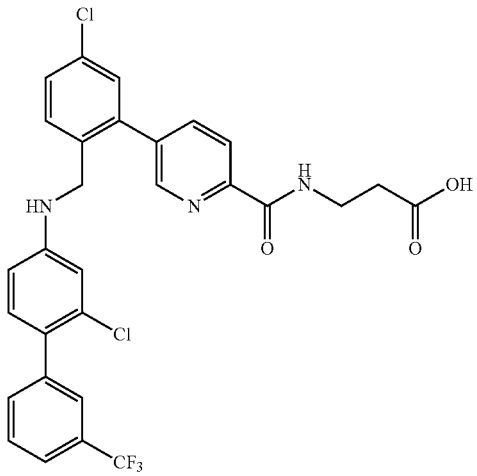 [SMILES: O=C(O)CCNC(=O)c1ccc(-c2cc(Cl)ccc2CNc2ccc(-c3cccc(C(F)(F)F)c3)c(Cl)c2)cn1]

The title compound was prepared as described in Example 146 substituting 3-chloro-4-iodoaniline and (3-(trifluoromethyl)phenyl)boronic acid for 4-iodoaniline and (4-fluoro-3-methylphenyl)boronic acid, respectively.

$^1$H NMR (CDCl$_3$): δ 8.57 (d, 1H), 8.47 (t, 1H), 8.26 (d, 1H), 7.88 (dd, 1H), 7.63 (d, 1H), 7.59-7.47 (m, 4H), 7.43 (dd, 1H), 7.29 (d, 1H), 7.09 (d, 1H), 6.56 (d, 1H), 6.43 (dd, 1H), 4.18 (s, 2H), 3.79 (dt, 2H), 2.75 (t, 2H); MS m/z 588 (M+H).

Example 171

3-(5-(5-chloro-2-(((2,3'-dichloro-4'-fluoro-[1,1'-biphenyl]-4-yl)amino)methyl)phenyl)picolinamido)propanoic acid

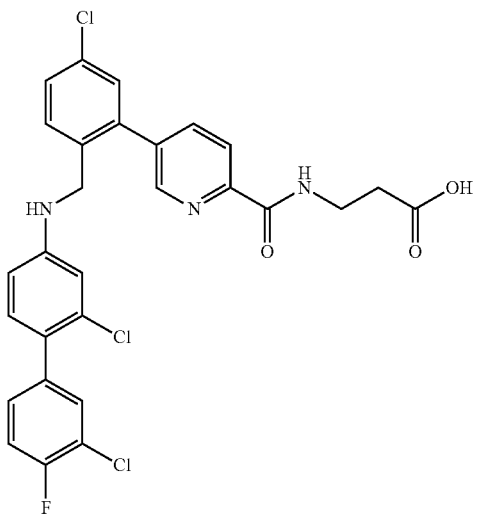 [SMILES: O=C(O)CCNC(=O)c1ccc(-c2cc(Cl)ccc2CNc2ccc(-c3ccc(F)c(Cl)c3)c(Cl)c2)cn1]

The title compound was prepared as described in Example 146 substituting 4-bromo-3-chloroaniline and (3-chloro-4-fluorophenyl)boronic acid for 4-iodoaniline and (4-fluoro-3-methylphenyl)boronic acid, respectively.

$^1$H NMR (CDCl$_3$): δ 8.56 (d, 1H), 8.48 (t, 1H), 8.25 (d, 1H), 7.86 (dd, 1H), 7.48 (d, 1H), 7.41 (m, 2H), 7.28 (d, 1H), 7.24-7.21 (d, 1H), 7.12 (t, 1H), 7.02 (d, 1H), 6.53 (d, 1H), 6.39 (dd, 1H), 4.18 (s, 2H), 3.80 (dt, 2H), 2.76 (t, 2H); MS m/z 572 (M+H).

Example 172

3-(5-(5-chloro-2-(((2-chloro-4'-methyl-[1,1'-biphenyl]-4-yl)amino)methyl)phenyl)picolinamido)propanoic acid

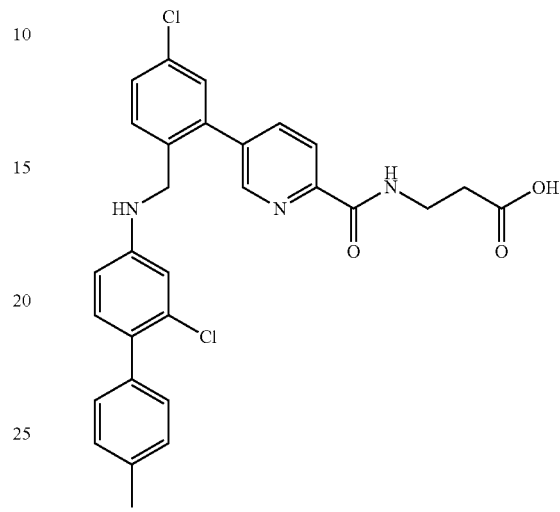

The title compound was prepared as described in Example 146 substituting 3-chloro-4-iodoaniline and p-tolylboronic acid for 4-iodoaniline and (4-fluoro-3-methylphenyl)boronic acid, respectively.

$^1$H NMR (CDCl$_3$): δ 8.56 (d, 1H), 8.48 (t, 1H), 8.25 (d, 1H), 7.86 (dd, 1H), 7.50 (dd, 1H), 7.41 (d, 1H), 7.28-7.25 (m, 3H), 7.19 (d, 2H), 7.07 (d, 1H), 6.55 (d, 1H), 6.41 (dd, 1H), 4.15 (s, 2H), 3.77 (dt, 2H), 2.74 (t, 2H), 2.37 (s, 3H); MS m/z 576 (M+H).

Example 173

3-(5-(4-(((2',4'-dichloro-[1,1'-biphenyl]-4-yl)amino)methyl)-[1,1'-biphenyl]-3-yl)picolinamido)propanoic acid

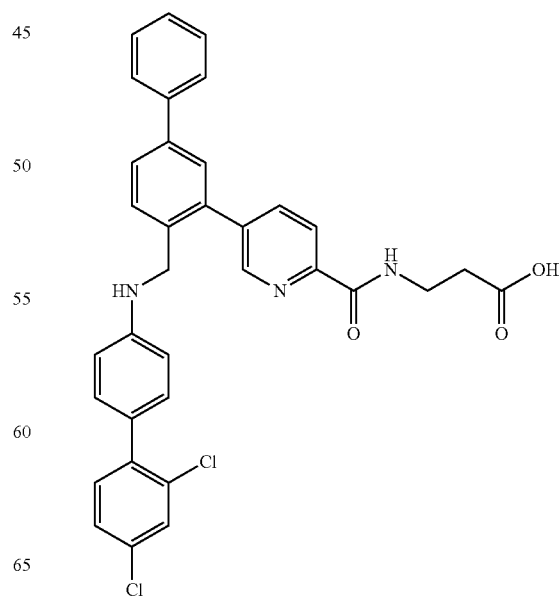

The title compound was prepared as described in Example 157 substituting phenylboronic acid and 2',4'-dichloro-[1,1'-biphenyl]-4-amine for 4,4,5,5-tetramethyl-2-(prop-1-en-2-yl)-1,3,2-dioxaborolane and 4'-fluoro-[1,1'-biphenyl]-4-amine, respectively.

$^1$H NMR (400 MHz, CHLOROFORM-d) δ=8.64 (s, 1H), 8.50 (t, J=5.9 Hz, 1H), 8.25 (d, J=8.1 Hz, 1H), 7.94 (d, J=7.1 Hz, 1H), 7.63-7.71 (m, 2H), 7.60 (d, J=7.3 Hz, 2H), 7.50 (s, 1H), 7.41-7.48 (m, 3H), 7.37 (t, J=7.2 Hz, 1H), 7.15-7.25 (m, 4H), 6.59 (d, J=8.3 Hz, 2H), 4.26 (s, 2H), 3.79 (q, J=5.5 Hz, 2H), 2.75 ppm (t, J=5.7 Hz, 2H). MS m/z 596 (M+H).

Example 174

3-(5-(4-(((4'-fluoro-[1,1'-biphenyl]-4-yl)amino)methyl)-2',3',4',5'-tetrahydro-[1,1'-biphenyl]-3-yl)picolinamido)propanoic acid

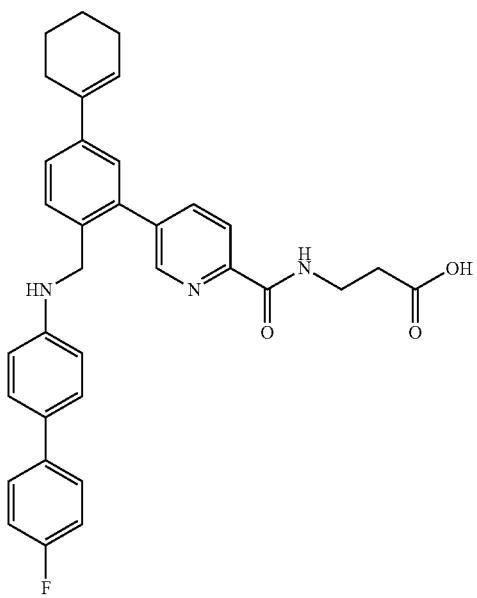 [SMILES: O=C(O)CCNC(=O)c1ccc(-c2cc(C3=CCCCC3)ccc2CNc2ccc(-c3ccc(F)cc3)cc2)cn1]

The title compound was prepared as described in Example 157 substituting cyclohex-1-en-1-ylboronic acid for 4,4,5,5-tetramethyl-2-(prop-1-en-2-yl)-1,3,2-dioxaborolane.

$^1$H NMR (400 MHz, CHLOROFORM-d) δ=8.58 (s, 1H), 8.47 (t, J=6.2 Hz, 1H), 8.21 (d, J=7.8 Hz, 1H), 7.86 (d, J=6.6 Hz, 1H), 7.53 (d, J=7.8 Hz, 1H), 7.38-7.49 (m, 3H), 7.29-7.37 (m, J=8.3 Hz, 2H), 7.26 (m, 1H), 7.06 (t, J=8.7 Hz, 2H), 6.53 (d, J=8.3 Hz, 2H), 6.18 (br. s., 1H), 4.20 (s, 2H), 3.78 (q, J=6.0 Hz, 2H), 2.74 (t, J=6.0 Hz, 2H), 2.40 (m, 2H), 2.15-2.30 (m, 2H), 1.73-1.85 (m, 2H), 1.59-1.73 ppm (m, 2H). MS m/z 550 (M+H).

Example 175

3-(5-(5-cyclohexyl-2-(((4'-fluoro-[1,1'-biphenyl]-4-yl)amino)methyl)phenyl)picolinamido)propanoic acid

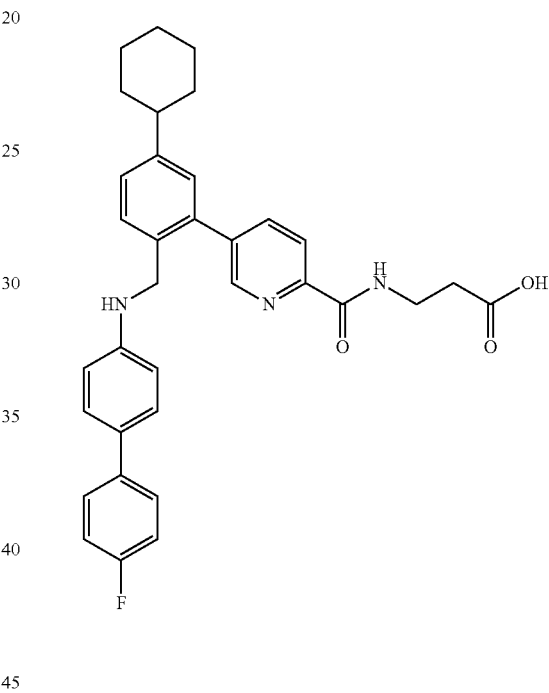

A mixture of 3-(5-(4-(((4'-fluoro-[1,1'-biphenyl]-4-yl)amino)methyl)-2',3',4',5'-tetrahydro-[1,1'-biphenyl]-3-yl)picolinamido)propanoic acid (47.6 mg, 0.087 mmol), ammonium formate (54.6 mg, 0.87 mmol) and 10% Pd—C (9.2 mg, 0.0087 mmol) in MeOH (5 mL) was refluxed for 1 h, then filtered through CELITE, washed with DCM-MeOH. The filtrate was concentrated and purified via column chromatography to give the title compound.

$^1$H NMR (400 MHz, CHLOROFORM-d) δ=8.61 (br. s., 1H), 8.46 (m, 1H), 8.22 (d, J=7.1 Hz, 1H), 7.92 (d, J=6.6 Hz, 1H), 7.46 (m, 3H), 7.25-7.38 (m, 3H), 7.13 (br. s., 1H), 7.06 (m, 2H), 6.57 (d, J=7.6 Hz, 2H), 4.17 (br. s., 2H), 3.77 (m, 2H), 2.74 (m, 2H), 2.55 (m, 1H), 1.80-1.96 (m, 4H), 1.71-1.79 (m, 1H), 1.31-1.50 (m, 4H), 1.15-1.31 ppm (m, 1H). MS m/z 552 (M+H).

Example 176

3-(5-(4-(((2',4'-dichloro-[1,1'-biphenyl]-4-yl)amino)methyl)-2',3',4',5'-tetrahydro-[1,1'-biphenyl]-3-yl)picolinamido)propanoic acid

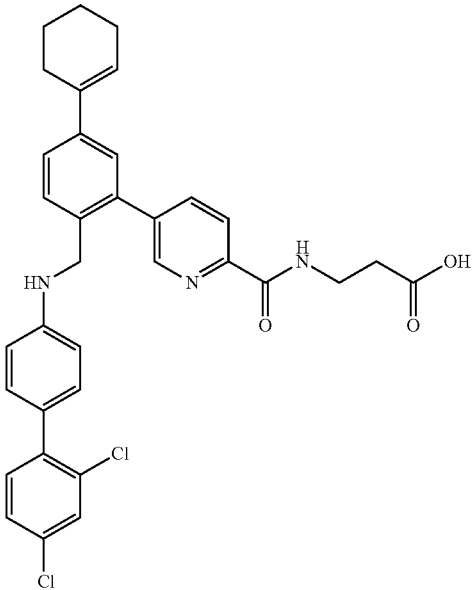 [SMILES: O=C(O)CCNC(=O)c1ccc(-c2cc(C3=CCCCC3)ccc2CNc2ccc(-c3ccc(Cl)cc3Cl)cc2)cn1]

The title compound was prepared as described in Example 157 substituting cyclohex-1-en-1-ylboronic acid and 2',4'-dichloro-[1,1'-biphenyl]-4-amine for 4,4,5,5-tetramethyl-2-(prop-1-en-2-yl)-1,3,2-dioxaborolane and 4'-fluoro-[1,1'-biphenyl]-4-amine, respectively.

$^1$H NMR (400 MHz, CHLOROFORM-d) δ=8.60 (br. s., 1H), 8.49 (m, 1H), 8.23 (d, J=8.1 Hz, 1H), 7.90 (d, J=7.8 Hz, 1H), 7.40-7.55 (m, 3H), 7.13-7.33 (m, 5H), 6.56 (d, J=8.1 Hz, 2H), 6.18 (br. s., 1H), 4.19 (br. s., 2H), 3.79 (m, 2H), 2.74 (m, 2H), 2.41 (m, 2H), 2.22 (m, 2H), 1.73-1.86 (m, 2H), 1.58-1.73 ppm (m, 2H). MS m/z 600 (M+H).

Example 177

3-(5-(2-(((2-chloro-2'-methyl-4'-(trifluoromethyl)-[1,1'-biphenyl]-4-yl)amino)methyl)-3-cyclopropyl-5-(trifluoromethyl)phenyl)picolinamido)propanoic acid

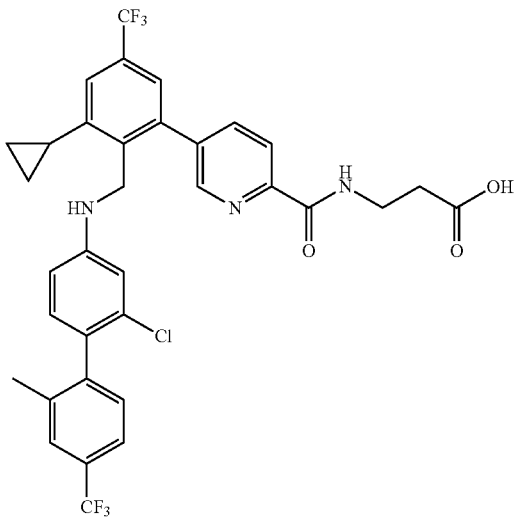 [SMILES: Cc1cc(C(F)(F)F)ccc1-c1ccc(NCc2c(-c3ccc(C(=O)NCCC(=O)O)nc3)cc(C(F)(F)F)cc2C2CC2)cc1Cl]

The title compound was prepared as described in Example 163 substituting cyclopropylboronic acid and 2-chloro-2'-methyl-4'-(trifluoromethyl)-[1,1'-biphenyl]-4-amine for methylboronic acid and 2-chloro-4'-(trifluoromethyl)-[1,1'-biphenyl]-4-amine, respectively.

$^1$H NMR (400 MHz, CHLOROFORM-d) δ=8.61 (s, 1H), 8.45 (t, J=6.2 Hz, 1H), 8.25 (d, J=8.1 Hz, 1H), 7.94 (dd, J=1.8, 7.9 Hz, 1H), 7.50 (s, 1H), 7.46 (d, J=8.3 Hz, 1H), 7.39 (s, 1H), 7.34 (s, 1H), 7.24 (d, J=8.1 Hz, 1H), 6.97 (d, J=8.3 Hz, 1H), 6.64 (d, J=2.0 Hz, 1H), 6.51 (dd, J=2.0, 8.3 Hz, 1H), 4.30 (s, 2H), 3.79 (q, J=6.3 Hz, 2H), 2.75 (t, J=6.0 Hz, 2H), 2.20 (s, 3H), 2.12-2.18 (m, 1H), 1.08-1.18 (m, 2H), 0.86 (q, J=5.4 Hz, 2H). MS m/z 676 (M+H).

Example 178

3-(5-(3-cyclopropyl-2-(((2,4'-dichloro-2'-methyl-[1,1'-biphenyl]-4-yl)amino)methyl)-5-(trifluoromethyl)phenyl)picolinamido)propanoic acid

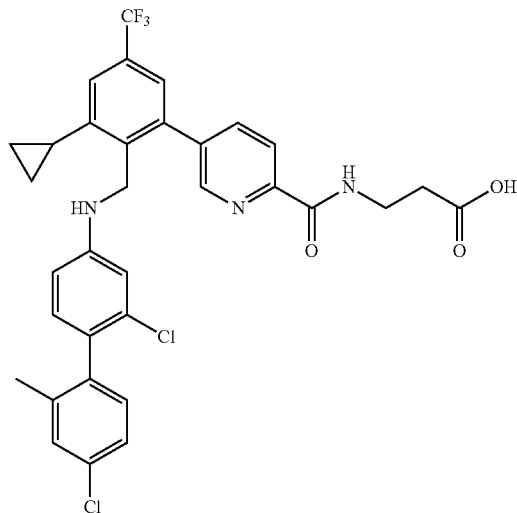 [SMILES: Cc1cc(Cl)ccc1-c1ccc(NCc2c(-c3ccc(C(=O)NCCC(=O)O)nc3)cc(C(F)(F)F)cc2C2CC2)cc1Cl]

The title compound was prepared as described in Example 163 substituting cyclopropylboronic acid and 2,4'-dichloro-2'-methyl-[1,1'-biphenyl]-4-amine for methylboronic acid and 2-chloro-4'-(trifluoromethyl)-[1,1'-biphenyl]-4-amine, respectively.

$^1$H NMR (400 MHz, CHLOROFORM-d) δ=8.61 (d, J=1.5 Hz, 1H), 8.45 (t, J=6.4 Hz, 1H), 8.23 (d, J=8.1 Hz, 1H), 7.93 (dd, J=2.1, 7.9 Hz, 1H), 7.38 (s, 1H), 7.33 (s, 1H), 7.23 (d, J=2.0 Hz, 1H), 7.17 (dd, J=2.1, 8.2 Hz, 1H), 7.04 (d, J=8.1 Hz, 1H), 6.95 (d, J=8.3 Hz, 1H), 6.63 (d, J=2.4 Hz, 1H), 6.48 (dd, J=2.4, 8.3 Hz, 1H), 4.29 (s, 2H), 3.78 (q, J=6.1 Hz, 2H), 2.74 (t, J=6.1 Hz, 2H), 2.13-2.22 (m, 1H), 2.11 (s, 3H), 1.03-1.17 (m, 2H), 0.77-0.92 ppm (m, 2H). MS m/z 642 (M+H).

Example 179

3-(5-(2-(((2-chloro-2'-methyl-4'-(trifluoromethyl)-[1,1'-biphenyl]-4-yl)amino)methyl)-5-(trifluoromethyl)-[1,1'-biphenyl]-3-yl)picolinamido)propanoic acid

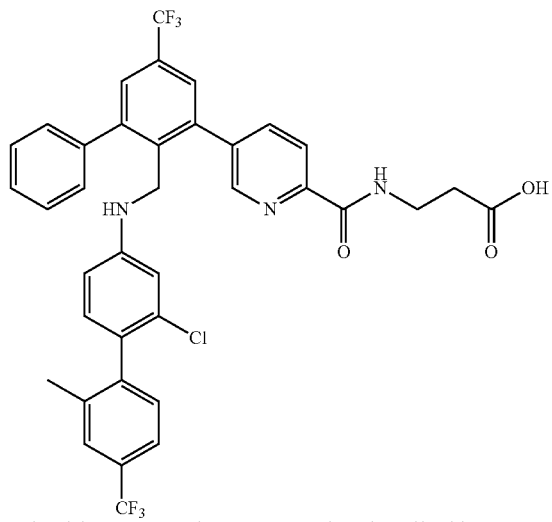 [SMILES: Cc1cc(C(F)(F)F)ccc1-c1ccc(NCc2c(-c3ccccc3)cc(C(F)(F)F)cc2-c2ccc(C(=O)NCCC(=O)O)nc2)cc1Cl]

The title compound was prepared as described in Example 163 substituting phenylboronic acid and 2-chloro-2'-methyl-4'-(trifluoromethyl)-[1,1'-biphenyl]-4-amine for methylboronic acid and 2-chloro-4'-(trifluoromethyl)-[1,1'-biphenyl]-4-amine, respectively.

$^1$H NMR (400 MHz, CHLOROFORM-d) δ=8.65 (s, 1H), 8.46 (t, J=6.1 Hz, 1H), 8.27 (d, J=8.1 Hz, 1H), 7.92-8.00 (m, 1H), 7.65 (s, 1H), 7.53 (s, 1H), 7.40-7.50 (m, 7H), 7.17 (d, J=8.1 Hz, 1H), 6.78 (d, J=8.3 Hz, 1H), 6.21 (d, J=2.2 Hz, 1H), 6.09 (dd, J=2.2, 8.3 Hz, 1H), 4.17 (s, 2H), 3.79 (q, J=6.1 Hz, 2H), 2.75 (t, J=6.0 Hz, 2H), 2.11 ppm (s, 3H). MS m/z 712 (M+H).

Example 180

3-(5-(2-(((4'-chloro-2-methoxy-2'-methyl-[1,1'-biphenyl]-4-yl)amino)methyl)-3-cyclopropyl-5-(trifluoromethyl)phenyl)picolinamido)propanoic acid

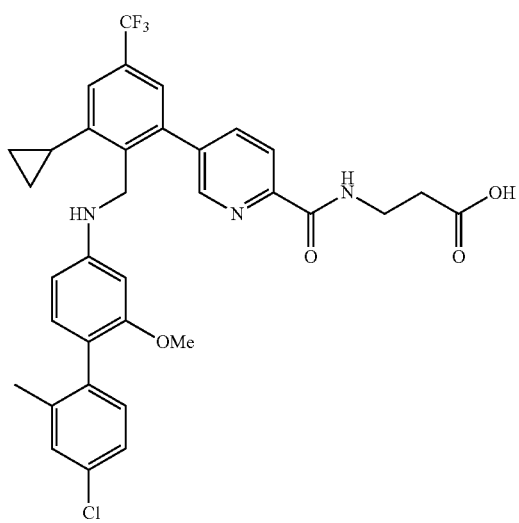 [SMILES: COc1cc(NCc2c(-c3ccc(C(=O)NCCC(=O)O)nc3)cc(C(F)(F)F)cc2C2CC2)ccc1-c1ccc(Cl)cc1C]

STEP A: 4'-chloro-2-methoxy-2'-methyl-[1,1'-biphenyl]-4-amine

The title compound was prepared as described in Example 159 substituting 4-bromo-3-methoxyaniline and (4-chloro-2-methylphenyl)boronic acid for 4-bromo-3-chloroaniline and (4-(trifluoromethyl)phenyl)boronic acid, respectively.

STEP B: 3-(5-(2-(((4'-chloro-2-methoxy-2'-methyl-[1,1'-biphenyl]-4-yl)amino)methyl)-3-cyclopropyl-5-(trifluoromethyl)phenyl)picolinamido)propanoic acid The title compound was prepared as described in Example 163 substituting cyclopropylboronic acid and 4'-chloro-2-methoxy-2'-methyl-[1,1'-biphenyl]-4-amine for methylboronic acid and 2-chloro-4'-(trifluoromethyl)-[1,1'-biphenyl]-4-amine, respectively.

$^1$H NMR (400 MHz, CHLOROFORM-d) δ 8.62 (s, 1H), 8.39-8.52 (m, 1H), 8.24 (d, J=8.07 Hz, 1H), 7.90-8.03 (m, 1H), 7.39 (s, 1H), 7.32 (s, 1H), 7.18-7.22 (m, 1H), 7.12-7.18 (m, 1H), 7.03-7.11 (m, 1H), 6.89 (d, J=8.07 Hz, 1H), 6.12-6.25 (m, 2H), 4.33 (s, 2H), 3.78 (q, J=5.95 Hz, 2H), 3.67 (s, 3H), 2.67-2.81 (m, 2H), 2.17-2.28 (m, 1H), 2.12 (s, 3H), 1.05-1.18 (m, 2H), 0.78-0.94 (m, 2H); MS m/z 638 (M+H).

Example 181

3-(5-(3-cyclopropyl-2-(((2-methoxy-2'-methyl-4'-(trifluoromethyl)-[1,1'-biphenyl]-4-yl)amino)methyl)-5-(trifluoromethyl)phenyl)picolinamido)propanoic acid

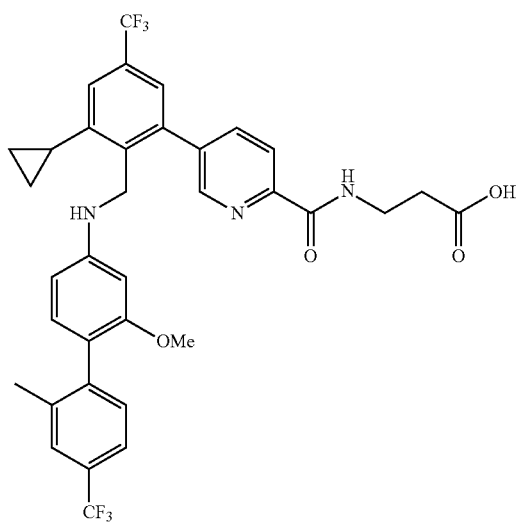

STEP A: 2-methoxy-2'-methyl-4'-(trifluoromethyl)-[1,1'-biphenyl]-4-amine

The title compound was prepared as described in Example 159 substituting 4-bromo-3-methoxyaniline and (2-methyl-4-(trifluoromethyl)phenyl)boronic acid for 4-bromo-3-chloroaniline and (4-(trifluoromethyl)phenyl)boronic acid, respectively.

STEP B: 3-(5-(3-cyclopropyl-2-(((2-methoxy-2'-methyl-4'-(trifluoromethyl)-[1,1'-biphenyl]-4-yl)amino)methyl)-5-(trifluoromethyl)phenyl)picolinamido)propanoic acid The title compound was prepared as described in Example 163 substituting cyclopropylboronic acid and 2-methoxy-2'-methyl-4'-(trifluoromethyl)-[1,1'-biphenyl]-4-amine for methylboronic acid and 2-chloro-4'-(trifluoromethyl)-[1,1'-biphenyl]-4-amine, respectively.

$^1$H NMR (400 MHz, CHLOROFORM-d) δ 8.63 (d, J=1.71 Hz, 1H), 8.45 (t, J=6.36 Hz, 1H), 8.24 (d, J=8.07 Hz, 1H), 7.97 (dd, J=2.08, 7.95 Hz, 1H), 7.47 (s, 1H), 7.43 (d, J=8.31 Hz, 1H), 7.39 (s, 1H), 7.32 (s, 1H), 7.24-7.28 (m, 1H), 6.91 (d, J=8.07 Hz, 1H), 6.22 (dd, J=2.08, 8.19 Hz, 1H), 6.17 (d, J=1.96 Hz, 1H), 4.33 (s, 2H), 3.78 (q, J=6.11 Hz, 2H), 3.69 (s, 3H), 2.74 (t, J=6.11 Hz, 2H), 2.21-2.24 (m, 1H), 2.20 (s, 3H), 1.08-1.16 (m, 2H), 0.86 (q, J=5.14 Hz, 2H); MS m/z 672 (M+H).

Example 182

3-(5-(3-cyclopropyl-2-(((2,2'-dichloro-4'-methoxy-[1,1'-biphenyl]-4-yl)amino)methyl)-5-(trifluoromethyl)phenyl)picolinamido)propanoic acid

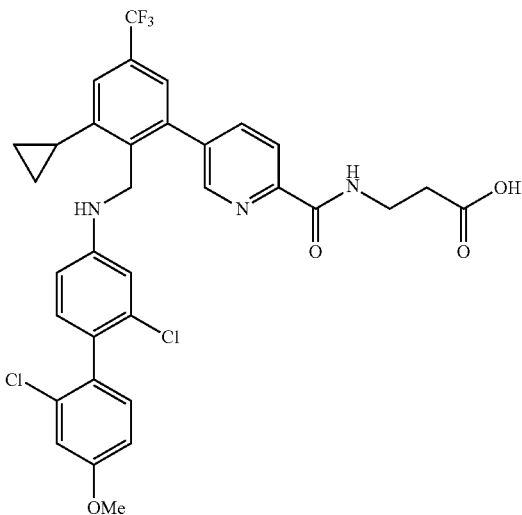 [SMILES: COc1ccc(-c2ccc(NCc3c(-c4ccc(C(=O)NCCC(=O)O)nc4)cc(C(F)(F)F)cc3C3CC3)cc2Cl)c(Cl)c1]

STEP A: 2,2'-dichloro-4'-methoxy-[1,1'-biphenyl]-4-amine

The title compound was prepared as described in Example 159 substituting 3-chloro-4-iodoaniline and (2-chloro-4-methoxyphenyl)boronic acid for 4-bromo-3-chloroaniline and (4-(trifluoromethyl)phenyl)boronic acid, respectively.

STEP B: 3-(5-(3-cyclopropyl-2-(((2,2'-dichloro-4'-methoxy-[1,1'-biphenyl]-4-yl)amino)methyl)-5-(trifluoromethyl)phenyl)picolinamido)propanoic acid The title compound was prepared as described in Example 163 substituting cyclopropylboronic acid and 2,2'-dichloro-4'-methoxy-[1,1'-biphenyl]-4-amine for methylboronic acid and 2-chloro-4'-(trifluoromethyl)-[1,1'-biphenyl]-4-amine, respectively.
$^1$H NMR (400 MHz, CHLOROFORM-d) δ 8.59-8.66 (m, 1H), 8.46 (t, J=6.24 Hz, 1H), 8.24 (d, J=7.83 Hz, 1H), 7.93 (dd, J=2.08, 7.95 Hz, 1H), 7.38 (s, 1H), 7.32 (s, 1H), 7.16 (d, J=8.56 Hz, 1H), 7.04 (d, J=8.31 Hz, 1H), 7.00 (d, J=2.45 Hz, 1H), 6.84 (dd, J=2.45, 8.56 Hz, 1H), 6.64 (d, J=2.20 Hz, 1H), 6.49 (dd, J=2.20, 8.31 Hz, 1H), 4.29 (s, 2H), 3.83 (s, 3H), 3.79 (q, J=6.19 Hz, 2H), 2.75 (t, J=6.11 Hz, 2H), 2.12-2.21 (m, 1H), 1.08-1.15 (m, 2H), 0.85 (q, J=5.30 Hz, 2H); MS m/z 658 (M+H).

BIOLOGICAL EXAMPLE 1

Inhibition $^{125}$I-Glucagon Binding to Membranes from HEK293 Cells Expressing the Human Glucagon Receptor (GCGR)

Full-length human GCGR (Accession Number: NM000160) subcloned into pcDNA3.1 was stably transfected into HEK293 cells (hGluc-1 HEK) and maintained under G418 selection (500 µg/mL). Cell cultures were maintained in DMEM/F12 media supplemented with 10% FBS and 1% GlutaMax. Membranes were prepared from these cells as follows: cells were harvested from T225 flasks and re-suspended in hypotonic lysis buffer, 50 mM HEPES pH 7.4 supplemented with Complete Protease inhibitors (Boehringer Mannheim, Indianapolis, Ind.). Cells were dounced 20 times on ice and spun at 700×g to remove nuclei and unlysed cells. The resulting pellet was re-suspended in hypotonic lysis buffer and the above step was repeated. Supernatants from the low speed centrifugation were combined and subsequently spun at 100K×g for 1 hr at 4° C. and the resulting pellet was re-suspended in buffer containing 50 mM HEPES pH 7.4 and 10% sucrose and the protein concentration was adjusted at 1 mg/mL as determined in the BCA assay. Membranes were aliquoted and stored at −80° C. The binding assay was performed by a filtration method in a 384 well format. Membranes at a final protein concentration of 6 µg/well were incubated with $^{125}$I-glucagon at 0.3 nM and in the presence of compound for 2 hours at room temperature in a total reaction volume of 40 µL per well. Assay buffer consisted of 50 mM HEPES, pH 7.4, 5 mM MgCl$_2$, 1 mM CaCl$_2$ and 0.2% BSA. 30 µL of the reaction was then transferred to PEI treated filter plates and followed by filter aspiration. Plates were then washed 5× and allowed to dry at room temperature overnight. The next day the bottom of the plate was covered with seal tape and scintillant was added. Total counts retained by the filters were quantified with a Top Count instrument. IC$_{50}$'s were generated by using a non-linear regression macro driven in Excel and converted to K's.

BIOLOGICAL EXAMPLE 2

IC$_{50}$ Values in Cellular Functional Assays: cAMP Readout

Full-length human GCGR (Accession Number: NM000160) subcloned into pcDNA3.1 was stably transfected into HEK293 cells (hGluc-1 HEK) and maintained under G418 selection (500 µg/mL). Cell cultures were maintained in DMEM/F12 media supplemented with 10% FBS and 1% GlutaMax. Glucagon stimulated cAMP was quantified using LANCE technology as per manufacturer instructions. On the day of the experiment, spent media was removed and cells were washed with Hank's Buffered Saline solution (HBSS) and cells were harvested with non-enzymatic cell dissociation solution, then washed once with HBSS. Cells were re-suspended in stimulation buffer at a concentration of 0.83×10$^6$ cells/ml and cAMP detection antibody was added. 6 µl/well of this solution was then dispensed in a 384 well plate (cell density 5000 cells/well). Test compound was serially diluted in DMSO and 50 nl were dispensed on top of the cell solution and allowed to incubate for 30 minutes. 6 µl of a 2× glucagon solution (final concentration in assay 100 µM) was then added and the reaction was terminated after 5 minutes with the addition of detection mix. The mixture was incubated, protected from light for 1.5 h. cAMP levels were quantified by TR-FRET in an EnVision instrument against a known standard. IC$_{50}$'s were generated by using a non-linear regression macro driven in Excel and converted to K, values.

Representative compounds of the present invention were tested according to the procedures as described in Biological Example 1 and Biological Example 2, with results as listed in Table 2, below. When a compound was tested more than one time, an average of the measured values is listed in the table below.

TABLE 2

Biological Assay Results

| ID No. | $^{125}$I-Glucagon Ki (μM) | cAMP Ki (μM) |
|---|---|---|
| 1 | >5.40008 | >10.3992 |
| 2 | 0.1873 | 0.5099 |
| 3 | >5.40008 | >10.3992 |
| 4 | 0.0649 | 0.2099 |
| 5 | 0.0671 | 0.1808 |
| 6 | 0.0401 | 0.0505 |
| 7 | 0.0224 | 0.0448 |
| 8 | 0.0943 | 0.5647 |
| 9 | 0.0957 | 0.5500 |
| 10 | 0.0312 | 0.1095 |
| 11 | 0.0412 | 0.2648 |
| 12 | 0.0530 | 0.5000 |
| 13 | 0.0393 | 0.3112 |
| 14 | 0.0651 | 0.0948 |
| 15 | 0.0339 | 0.0906 |
| 16 | 0.0438 | 0.0505 |
| 17 | 1.4781 | >10.3992 |
| 18 |  | 0.2800 |
| 19 | 0.0396 | 0.0458 |
| 20 | 0.0614 | 0.1577 |
| 21 | 0.0194 | 0.0566 |
| 22 | 0.0252 | 0.0224 |
| 23 | 0.0261 | 0.1300 |
| 24 | 0.0283 | 0.0324 |
| 25 | 0.0470 | 0.2200 |
| 26 | 0.0296 | 0.1750 |
| 27 | 0.0215 | 0.0173 |
| 28 | 0.0280 | 0.0316 |
| 29 | 0.0304 | 0.0620 |
| 30 | 0.0193 | 0.0194 |
| 31 | 0.0221 | 0.0194 |
| 32 | 0.0251 | 0.0725 |
| 33 | 0.0213 | 0.0598 |
| 34 | 0.0238 | 0.0171 |
| 35 | 0.0144 | 0.0350 |
| 36 | 0.0673 | 0.0951 |
| 37 | 0.0232 | 0.0300 |
| 38 | 0.0225 | 0.0224 |
| 39 | 0.0266 | 0.0474 |
| 40 | 0.0263 | 0.0642 |
| 41 | 0.0204 | 0.0283 |
| 42 | 0.0165 | 0.0200 |
| 43 | 0.0172 | 0.0219 |
| 44 | 0.0184 | 0.0601 |
| 45 |  | >20 |
| 46 |  | >20 |
| 47 |  | >20 |
| 48 |  | >20 |
| 49 |  | >20 |
| 50 |  | >20 |
| 51 | 0.0168 | 0.0341 |
| 52 | 0.0199 | 0.1098 |
| 53 | 0.1029 | 0.4950 |
| 54 | 0.0485 | 0.2199 |
| 55 | 0.1565 | 0.6500 |
| 56 | 0.0988 | 0.3089 |
| 57 | 0.0742 | 0.2047 |
| 58 | 0.0473 | 0.0584 |
| 59 | 0.0724 | 0.3196 |
| 60 | 0.1939 | 1.3747 |
| 61 | 0.0977 | 0.4791 |
| 62 | 0.0374 | 0.1750 |
| 63 | 0.0226 | 0.1881 |
| 64 | 0.0957 | 1.8501 |
| 65 | 0.1391 | 0.3900 |
| 66 | 0.0687 | 1.8501 |
| 67 | 0.0188 | 0.0122 |
| 68 | 0.0400 | 0.1512 |
| 69 | 0.0852 | 0.5000 |
| 70 | 0.0522 | >10.3992 |
| 71 | 0.0313 | 0.0173 |
| 72 | 0.0203 | 0.0135 |
| 73 | 0.0195 | 0.0037 |
| 74 | 0.0149 | 0.0071 |
| 75 | 0.0278 | 0.0067 |
| 76 |  | 0.0145 |
| 77 | 0.0242 | 0.0224 |
| 78 | 0.0240 | 0.0250 |
| 79 | 0.0240 | 0.0316 |
| 80 | 0.0286 | 0.0474 |
| 81 |  | 0.0100 |
| 82 | 0.0338 | 0.0346 |
| 83 |  | 0.0141 |
| 84 |  | 0.0367 |
| 85 |  | 0.0324 |
| 86 |  | 0.0350 |
| 87 |  | 0.0173 |
| 88 | 0.0443 | 0.3700 |
| 89 | 0.0606 | 0.5500 |
| 90 | 0.0336 | 0.2810 |
| 91 | 0.0334 | 0.2947 |
| 92 | 0.0194 | 0.1137 |
| 93 | 0.0534 | 0.2950 |
| 94 | 0.0335 | 0.0785 |
| 95 | 0.1391 | 0.5999 |
| 96 | 0.0338 | 0.1756 |
| 97 | 0.0574 | 0.2250 |
| 98 |  | 0.1950 |
| 99 |  | 0.0654 |
| 100 |  | 0.1350 |
| 101 |  | 0.0950 |
| 102 | 0.0213 | 0.0418 |
| 103 | 0.0229 | 0.0689 |
| 104 | 0.0254 | 0.0844 |
| 105 | 0.0330 | 0.2550 |
| 106 | 0.0261 | 0.3200 |
| 107 | 0.0237 | 0.0548 |
| 108 | 0.0239 | 0.0849 |
| 109 | 0.0304 | 0.1150 |
| 110 | 0.0435 | 0.1700 |
| 111 | 0.0696 | 0.1800 |
| 112 | 0.0765 | 0.2800 |
| 113 | 0.0583 | 0.6500 |
| 114 | 0.0404 | 0.0735 |
| 115 | 0.0957 | 0.5000 |
| 116 | 0.1826 | 1.6998 |
| 117 | 0.0435 | 0.1600 |
| 118 | 0.0678 | 0.1200 |
| 119 |  | 0.0600 |
| 120 |  | 0.0374 |
| 121 |  | 0.1000 |
| 122 |  | 0.0850 |
| 123 |  | 0.1100 |
| 124 |  | 0.2850 |
| 125 |  | 0.2050 |
| 126 |  | >5.19996 |
| 127 |  | 0.0700 |
| 128 |  | 0.0458 |
| 129 | 0.0846 | 0.7000 |
| 130 | 0.0626 | 0.3900 |
| 131 | 0.0713 | 1.7498 |
| 132 | 0.1228 | 1.9311 |
| 133 | 0.1044 | 1.9999 |
| 134 | 0.0383 | 0.5999 |
| 135 | 0.0639 | 2.9999 |
| 136 | 0.0286 | 0.2533 |
| 137 | 0.0611 | 0.4250 |
| 138 | 0.0229 | 0.1206 |
| 139 | 0.0291 | 0.1205 |
| 140 | 0.0215 | 0.0843 |
| 141 | 0.0309 | 0.1383 |
| 142 | 0.0313 | 0.2250 |
| 143 | 0.0282 | 0.1065 |
| 144 | 0.0124 | 0.0230 |
| 145 | 0.0363 | 0.0681 |
| 146 | 0.0281 | 0.2675 |
| 147 | 0.0157 | 0.0600 |
| 148 | 0.0187 | 0.0340 |
| 149 | 0.0400 | 0.4300 |
| 150 | 0.0277 | 0.0733 |

TABLE 2-continued

Biological Assay Results

| ID No. | $^{125}$I-Glucagon Ki (μM) | cAMP Ki (μM) |
|---|---|---|
| 151 | 0.0165 | 0.1128 |
| 152 | 0.0316 | 0.1400 |
| 153 | 0.0329 | 0.0280 |
| 154 | 0.0301 | 0.0200 |
| 155 | 0.2348 | 2.1999 |
| 156 | 0.0378 | 0.1614 |
| 157 | 0.0335 | 0.1125 |
| 158 | 0.0200 | 0.1250 |
| 159 |  | 0.0458 |
| 160 |  | 0.6500 |
| 161 |  | 0.0387 |
| 162 |  | 0.0469 |
| 163 |  | 0.0144 |
| 164 |  | 0.0612 |
| 165 |  | 0.0064 |
| 166 |  | 0.0082 |
| 167 |  | 0.0108 |
| 168 | 0.0379 | 0.3700 |
| 169 | 0.0390 | 0.1423 |
| 170 | 0.0207 | 0.0668 |
| 171 | 0.0360 | 0.1175 |
| 172 | 0.0269 | 0.0692 |
| 173 | 0.0270 | 0.0675 |
| 174 | 0.0183 | 0.1100 |
| 175 | 0.0242 | 0.0458 |
| 176 | 0.0400 | 0.1600 |
| 177 |  | 0.0053 |
| 178 |  | 0.0063 |
| 179 |  | 0.0196 |

COMPARATIVE EXAMPLES

Comparative compounds wherein the —CH$_2$—NH-(optionally substituted biphenyl) portion of the compound of formula (I) is bound in a meta-configuration were prepared as described in Comparative Examples 1-5, below; and further tested according to the biological procedures described in Biological Examples 1-2, above, with results as listed in Table 3, below.

TABLE 3 meta-substituted Comparative Compounds

| ID No. | Q | $^{125}$I-Glucagon Ki (μM) | cAMP Ki (μM) |
|---|---|---|---|

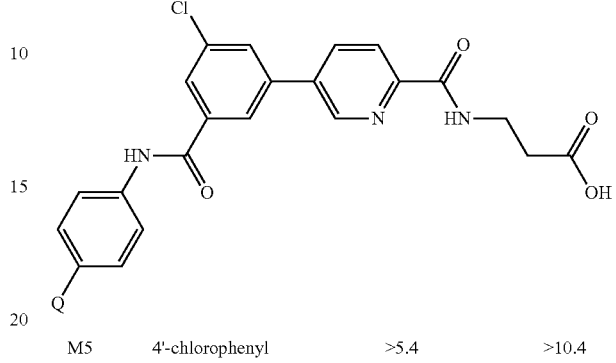

| M1 | 4'-fluorophenyl | >2.7 | >10.4 |
| M2 | 4'-methoxyphenyl | >2.7 | >10.4 |

TABLE 3-continued meta-substituted Comparative Compounds

| ID No. | Q | $^{125}$I-Glucagon Ki (μM) | cAMP Ki (μM) |
|---|---|---|---|
| M3 | 4'-chlorophenyl | >1.35 | >10.4 |
| M4 | 2',4'-dichlorophenyl | >1.35 | >10.4 |

| M5 | 4'-chlorophenyl | >5.4 | >10.4 |

Comparator Example 1

3-(5-(3-chloro-5-(((4'-fluoro-[1,1'-biphenyl]-4-yl)amino)methyl)phenyl)picolinamido)propanoic acid STEP A: Ethyl 3-(5-bromopicolinamido)propanoate Solid HATU (3.8 g, 9.9 mmol) was added to a THF solution (100 mL) of 5-bromopicolinic acid (2.0 g, 9.9 mmol), i-Pr$_2$NEt (5.2 mL, 29.7 mmol), and β-alanine ethyl ester hydrochloride (1.7 g, 10.9) and the resulting mixture was warmed to 45° C. After 16 h the mixture was diluted with EtOAc, washed with water and brine, dried (Na$_2$SO$_4$), concentrated and purified via column chromatography to yield the title compound.

STEP B: ethyl 3-(5-(4,4,5,5-tetramethyl-1,3,2-dioxaborolan-2-yl)picolinamido)propanoate Ethyl 3-(5-bromopicolinamido)propanoate, prepared as described in STEP A above (100 g, 0.32 mol), Bis(pinacolato)diboron (93.8 g, 0.36 mol), Pd(dppf)Cl$_2$ (13.8 g, 0.02 mol), and KOAc (97.8 g, 0.99 mol) were dissolved in 1,4-dioxane (1 L) and the resulting mixture was heated to 85° C. After 1 h the mixture was cooled to room temperature, diluted with EtOAc and water, filtered through CELITE and the layers were separated. The organic phase was washed with brine, dried (MgSO$_4$), and concentrated. The resulting oil was diluted with DCM and heptane and purified via silica gel column chromatography to yield the title compound.

STEP C: ethyl 3-(5-(3-chloro-5-formylphenyl)picolinamido)propanoate 3-bromo-5-chlorobenzaldehyde (502 mg, 2.3 mmol), ethyl 3-(5-(4,4,5,5-tetramethyl-1,3,2-dioxaborolan-2-yl)picolinamido)propanoate (794 mg, 2.3 mmol), Pd(dppf)Cl$_2$ (84 mg, 0.1 mmol), and K$_2$CO$_3$ (632 mg, 4.6 mmol) were dissolved in 1,4-dioxane (10 mL) and water (2 mL) and the resulting mixture was heated to 70° C. After 3 h the resulting mixture was cooled to room temperature, diluted with EtOAc, washed with water and brine, dried (Na$_2$SO$_4$), concentrated, and purified via column chromatography to yield the title compound.

STEP D: ethyl 3-(5-(3-chloro-5-(((4'-fluoro-[1,1'-biphenyl]-4-yl)amino)methyl)phenyl)picolinamido)propanoate Solid NaBH(OAc)$_3$ (106 mg, 0.50 mmol) was added to a DCE solution (10 mL) of ethyl 3-(5-(3-chloro-5-formylphenyl)picolinamido)propanoate (90 mg, 0.25 mmol), 4'-fluoro-[1,1'-biphenyl]-4-amine (47 g, 0.25 mmol), and AcOH (0.06 mL, 1.00 mmol) and the resulting mixture was heated to 50° C. After 16 h the mixture was concentrated and purified via column chromatography to yield the title compound.

STEP E: 3-(5-(3-chloro-5-(((4'-fluoro-[1,1'-biphenyl]-4-yl)amino)methyl)phenyl)picolinamido)propanoic acid A 1M aqueous solution of NaOH (0.47 mL, 0.47 mmol) was added to a THF solution (5 mL) of ethyl 3-(5-(3-chloro-5-(((4'-fluoro-[1,1'-biphenyl]-4-yl)amino)methyl)phenyl)picolinamido)propanoate (100 mg, 0.19 mmol) and the resulting mixture was heated to 40° C. After 4 h the resulting mixture was acidified with 1 M HCl and the aqueous phase was extracted with EtOAc. The combined organics were washed with water, dried (Na$_2$SO$_4$), and concentrated to yield the title compound.

$^1$H NMR (400 MHz, DMSO-d$_6$) δ 8.95 (d, J=2.20 Hz, 1H), 8.84 (t, J=5.99 Hz, 1H), 8.31 (dd, J=2.32, 8.19 Hz, 1H), 8.11 (d, J=8.07 Hz, 1H), 7.78 (s, 1H), 7.80 (s, 1H), 7.47-7.60 (m, 3H), 7.38 (d, J=8.56 Hz, 2H), 7.18 (t, J=8.93 Hz, 2H), 6.69 (d, J=8.56 Hz, 2H), 6.57 (t, J=6.11 Hz, 1H), 4.43 (d, J=6.11 Hz, 2H), 3.54 (q, J=6.85 Hz, 2H), 2.54-2.59 (m, 2H); MS m/z 504 (M+H).

Comparator Example 2

3-(5-(3-chloro-5-(((4'-methoxy-[1,1'-biphenyl]-4-yl)amino)methyl)phenyl)picolinamido)propanoic acid

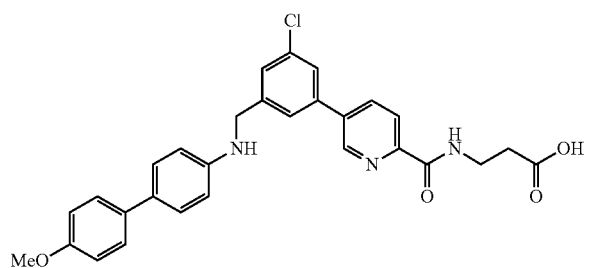 [SMILES: COc1ccc(-c2ccc(NCc3cc(Cl)cc(-c4ccc(C(=O)NCCC(=O)O)nc4)c3)cc2)cc1]

The title compound was prepared as described in Comparator Example 1 substituting 4'-methoxy-[1,1'-biphenyl]-4-amine for 4'-fluoro-[1,1'-biphenyl]-amine.

$^1$H NMR (400 MHz, DMSO-d$_6$) δ 8.95 (s, 1H), 8.84 (t, J=5.87 Hz, 1H), 8.26-8.35 (m, 1H), 8.11 (d, J=8.31 Hz, 1H), 7.78 (s, 1H), 7.80 (s, 1H), 7.51 (s, 1H), 7.44 (d, J=8.56 Hz, 2H), 7.29-7.38 (m, J=8.56 Hz, 2H), 6.87-6.99 (m, J=8.56 Hz, 2H), 6.67 (d, J=8.31 Hz, 2H), 6.48 (t, J=5.62 Hz, 1H), 4.41 (d, J=5.62 Hz, 2H), 3.75 (s, 3H), 3.54 (q, J=6.60 Hz, 2H), 2.54-2.60 (m, 2H); MS m/z 516 (M+H).

Comparator Example 3

3-(5-(3-chloro-5-(((4'-chloro-[1,1'-biphenyl]-4-yl)amino)methyl)phenyl)picolinamido)propanoic acid

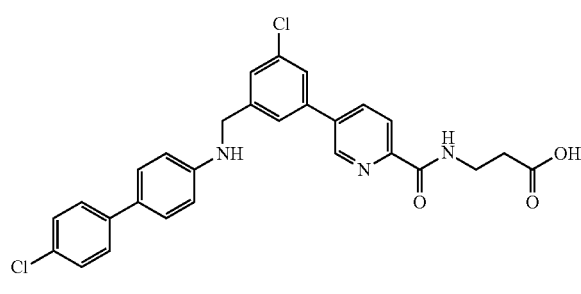 [SMILES: O=C(O)CCNC(=O)c1ccc(-c2cc(Cl)cc(CNc3ccc(-c4ccc(Cl)cc4)cc3)c2)cn1]

The title compound was prepared as described in Comparator Example 1, substituting 4'-chloro-[1,1'-biphenyl]-4-amine for 4'-fluoro-[1,1'-biphenyl]-4-amine.

$^1$H NMR (400 MHz, CHLOROFORM-d) δ 8.73 (d, J=1.71 Hz, 1H), 8.42-8.50 (m, 1H), 8.25 (d, J=8.31 Hz, 1H), 7.99 (dd, J=2.32, 8.19 Hz, 1H), 7.48-7.51 (m, 2H), 7.45 (d, J=3.91 Hz, 2H), 7.37-7.44 (m, 3H), 7.31-7.36 (m, 2H), 6.69 (d, J=8.80 Hz, 2H), 4.46 (s, 2H), 3.76-3.83 (m, 2H), 2.76 (t, J=6.11 Hz, 2H); MS m/z 520 (M+H).

Comparator Example 4

3-(5-(3-chloro-5-(((2',4'-dichloro-[1,1'-biphenyl]-4-yl)amino)methyl)phenyl)picolinamido)propanoic acid

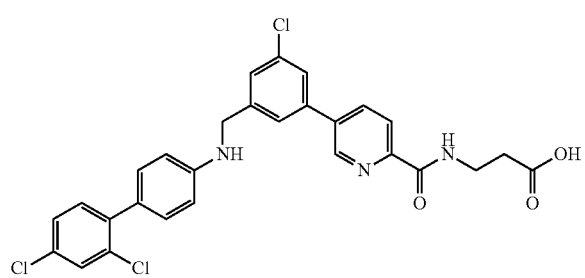 [SMILES: O=C(O)CCNC(=O)c1ccc(-c2cc(Cl)cc(CNc3ccc(-c4ccc(Cl)cc4Cl)cc3)c2)cn1]

The title compound was prepared as described in Comparator Example 1 substituting 2',4'-dichloro-[1,1'-biphenyl]-4-amine for 4'-fluoro-[1,1'-biphenyl]-4-amine.

$^1$H NMR (400 MHz, DMSO-d$_6$) δ 12.30 (br. s., 1H), 8.92-8.99 (m, 1H), 8.85 (t, J=5.99 Hz, 1H), 8.25-8.35 (m, 1H), 8.11 (d, J=8.07 Hz, 1H), 7.79 (s, 1H), 7.82 (s, 1H), 7.63 (d, J=1.71 Hz, 1H), 7.53 (s, 1H), 7.42 (dd, J=1.96, 8.31 Hz, 1H), 7.35 (d, J=8.31 Hz, 1H), 7.17 (d, J=8.31 Hz, 2H), 6.69 (d, J=8.56 Hz, 3H), 4.42 (d, J=5.62 Hz, 2H), 3.54 (q, J=6.60 Hz, 2H), 2.54-2.60 (m, 2H); MS m/z 554 (M+H).

Comparator Example 5

3-(5-(3-chloro-5-((4'-chloro-[1,1'-biphenyl]-4-yl)carbamoyl)phenyl)picolinamido)propanoic acid

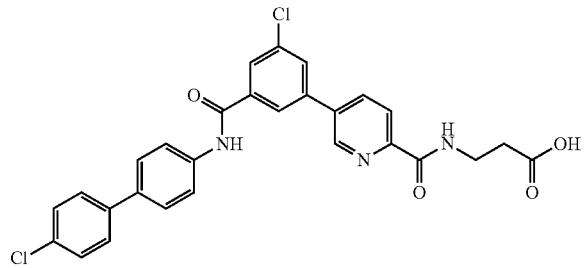 [SMILES: O=C(O)CCNC(=O)c1ccc(-c2cc(Cl)cc(C(=O)Nc3ccc(-c4ccc(Cl)cc4)cc3)c2)cn1]

STEP A: 3-bromo-5-chloro-N-(4'-chloro-[1,1'-biphenyl]-4-yl)benzamide

Neat i-Pr₂NEt (0.21 mL, 1.19 mmol) was added to a DCM mixture (5 mL) of 3-bromo-5-chlorobenzoic acid (140 mg, 0.60 mmol), 4'-chloro-[1,1'-biphenyl]-4-amine (145 mg, 0.71 mmol), HOBt (92 mg, 0.60 mmol) and EDCI (114 mg, 0.60 mmol) and the resulting mixture was stirred at room temperature. After 16 h the resulting precipitate was filtered off, washed with water and MeOH, and dried in vacuo to yield the title compound.

STEP B: ethyl 3-(5-(3-chloro-5-((4'-chloro-[1,1'-biphenyl]-4-yl)carbamoyl)phenyl)picolinamido)propanoate 3-bromo-5-chloro-N-(4'-chloro-[1,1'-biphenyl]-4-yl)benzamide (51 mg, 0.12 mmol), ethyl 3-(5-(4,4,5,5-tetramethyl-1,3,2-dioxaborolan-2-yl)picolinamido)propanoate (66 mg, 0.16 mmol), Pd(dppf)Cl₂ (9 mg, 0.01 mmol), and 2M aqueous K₂CO₃ (0.12 mL, 0.24 mmol) were dissolved in 1,4-dioxane (2 mL) and water (2 mL) and the resulting mixture was heated to 70° C. After 3 h the resulting mixture was cooled to room temperature, diluted with EtOAc, washed with water and brine, dried (Na₂SO₄), concentrated, and purified via column chromatography to yield the title compound.

STEP C: 3-(5-(3-chloro-5-((4'-chloro-[1,1'-biphenyl]-4-yl)carbamoyl)phenyl)picolinamido)propanoic acid A 1M aqueous solution of NaOH (2.0 mL, 2.0 mmol) was added to a THF (1 mL) and MeOH (5 mL) solution of ethyl 3-(5-(3-chloro-5-((4'-chloro-[1,1'-biphenyl]-4-yl)carbamoyl)phenyl)picolinamido)propanoate (40 mg, 0.07 mmol) and the resulting mixture was stirred at room temperature. After 16 h the mixture was acidified with 2 M HCl and the aqueous phase was extracted with EtOAc. The combined organics were washed with water, dried (Na₂SO₄), and concentrated to yield the title compound.

$^1$H NMR (400 MHz, DMSO-$d_6$) δ 10.58 (s, 1H), 9.09 (d, J=1.71 Hz, 1H), 8.84-8.93 (m, 1H), 8.45 (dd, J=2.32, 8.19 Hz, 1H), 8.33 (s, 1H), 8.13-8.20 (m, 2H), 8.08 (s, 1H), 7.86-7.94 (m, J=8.56 Hz, 2H), 7.73 (dd, J=1.34, 8.68 Hz, 4H), 7.48-7.55 (m, J=8.56 Hz, 2H), 3.55 (q, J=6.77 Hz, 2H), 2.56 (t, J=6.97 Hz, 2H); MS m/z 534 (M+H).

Formulation Example 1

Solid, Oral Dosage Form

Prophetic Example

As a specific embodiment of an oral composition, 100 mg of the compound prepared as in Example 43 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

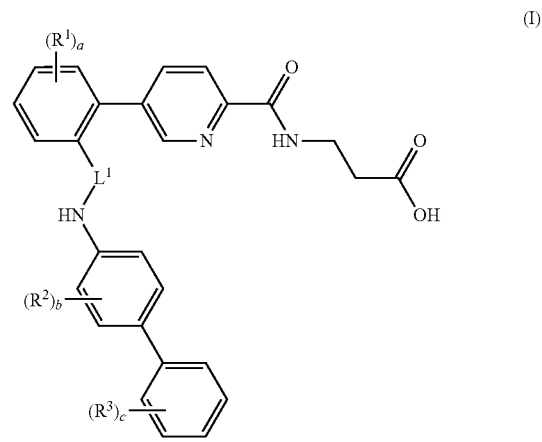

wherein
L¹ is selected from the group consisting of —CH₂—, —CH(CH₃)— and —C(O)—;
a is an integer from 0 to 3;
each R¹ is independently selected from the group consisting of halogen, hydroxy, cyano, $C_{1-4}$alkyl, fluorinated $C_{1-4}$alkyl, $C_{2-4}$alkenyl, $C_{1-4}$alkoxy, fluorinated $C_{1-4}$alkoxy, —SO₂—($C_{1-2}$alkyl), —C(O)—$C_{1-2}$alkyl, phenyl, $C_{3-6}$cycloalkyl and $C_{5-6}$cyaloalkenyl;
b is an integer from 0 to 3;
each R² is independently selected from the group consisting of halogen, cyano, $C_{1-4}$alkyl, fluorinated $C_{1-4}$alkyl, $C_{1-4}$alkoxy and fluorinated $C_{1-4}$alkoxy;
c is an integer from 0 to 4;
each R³ is independently selected from the group consisting of halogen, cyano, nitro, $C_{1-4}$alkyl, fluorinated $C_{1-4}$alkyl, $C_{1-4}$alkoxy, fluorinated $C_{1-4}$alkoxy and —C(O)—$C_{1-2}$alkyl;
or a pharmaceutically acceptable salt thereof.

2. A compound as in claim 1, wherein
L¹ is selected from the group consisting of —CH₂—, —CH(CH₃)— and —C(O)—;
a is an integer from 0 to 2;
each R¹ is independently selected from the group consisting of halogen, hydroxy, cyano, $C_{1-4}$alkyl, fluorinated $C_{1-4}$alkyl, $C_{1-4}$alkoxy, fluorinated $C_{1-2}$alkoxy, —SO₂—$C_{1-2}$alkyl, phenyl, $C_{3-6}$cycloalkyl and $C_{5-6}$cycloalkenyl;
b is an integer from 0 to 2;
each R² is independently selected from the group consisting of halogen, cyano, $C_{1-4}$alkyl, fluorinated $C_{1-2}$alkyl, $C_{1-2}$alkoxy and fluorinated $C_{1-2}$alkoxy;
c is an integer from 0 to 3;
each R³ is independently selected from the group consisting of halogen, $C_{1-4}$alkyl, fluorinated $C_{1-2}$alkyl, $C_{1-4}$alkoxy, fluorinated $C_{1-2}$alkoxy and —C(O)—$C_{1-2}$alkyl;
or a pharmaceutically acceptable salt thereof.

3. A compound as in claim 2, wherein
L¹ is selected from the group consisting of —CH₂—, —CH(CH₃)— and —C(O)—;

a is an integer from 0 to 2;
each R¹ is independently selected from the group consisting of halogen, hydroxy, cyano, $C_{1-4}$alkyl, fluorinated $C_{1-2}$alkyl, $C_{1-2}$alkoxy, —$SO_2$—$C_{1-2}$alkyl, phenyl, $C_{3-6}$cycloalkyl and cyclohexenyl;
b is an integer from 0 to 2;
each R² is independently selected from the group consisting of halogen, cyano, $C_{1-2}$alkyl, fluorinated $C_{1-2}$alkyl and $C_{1-2}$alkoxy;
c is an integer from 0 to 2;
each R³ is independently selected from the group consisting of halogen, $C_{1-2}$alkyl, fluorinated $C_{1-2}$alkyl, $C_{1-2}$alkoxy, fluorinated $C_{1-2}$alkoxy and —C(O)—$C_{1-2}$alkyl;
or a pharmaceutically acceptable salt thereof.

4. A compound as in claim 3, wherein
$L^1$ is selected from the group consisting of —$CH_2$—, —CH($CH_3$)— and —C(O)—;
a is an integer from 0 to 2;
each R¹ is independently selected from the group consisting of 3-chloro, 4-chloro, 5-chloro, 4-fluoro, 5-fluoro, 3-hydroxy, 6-cyano, 3-methyl, 5-methyl, 6-methyl, 3-isopropyl, 5-isopropyl, 5-(isopropen-1-yl), 3-trifluoromethyl, 4-trifluoromethyl, 5-trifluoromethyl, 6-trifluoromethyl, 3-methoxy, 4-methoxy, 5-methoxy, 5-(methylsulfonyl-), 3-phenyl, 5-phenyl, 3-cyclopropyl, 5-cyclohexyl and 5-(cyclohexen-1-yl);
b is an integer from 0 to 2;
each R² is independently selected from the group consisting of 2-chloro, 6-chloro, 2-fluoro, 3-fluoro, 2-cyano, 2-methyl, 2-trifluoromethyl and 5-methoxy;
c is an integer from 0 to 2;
each R³ is independently selected from the group consisting of 2'-chloro, 3'-chloro, 4'-chloro, 6'-chloro, 2'-fluoro, 3'-fluoro, 4'-fluoro, 5'-fluoro, 6'-fluoro, 2'-methyl, 3'-methyl, 4'-methyl, 4'-t-butyl, 2'-trifluoromethyl, 3'-trifluoromethyl, 4'-trifluoromethyl, 4'-methoxy, 2'-trifluoromethoxy, 3'-trifluoromethoxy, 4'-trifluoromethoxy and 4'-(methylcarbonyl-);
or a pharmaceutically acceptable salt thereof.

5. A compound as in claim 4, wherein
$L^1$ is selected from the group consisting of —$CH_2$— and —C(O)—;
a is an integer from 1 to 2;
each R¹ is independently selected from the group consisting of 3-chloro, 4-chloro, 5-chloro, 4-fluoro, 5-fluoro, 5-methyl, 5-isopropyl, 5-isopropenyl, 3-trifluoromethyl, 5-trifluoromethyl, 5-phenyl, 5-cyclohexyl and 5-cyclohexenyl;
b is an integer from 0 to 1;
R² is selected from the group consisting of 2-chloro, 2-fluoro, 3-fluoro, 2-cyano, 2-methyl and 5-methoxy;
c is an integer from 1 to 2;
each R³ is independently selected from the group consisting of 2'-chloro, 3'-chloro, 4'-chloro, 2'-fluoro, 3'-fluoro, 4'-fluoro, 6'-fluoro, 2'-methyl, 3'-methyl, 4'-methyl, 4'-t-butyl, 2'-trifluoromethyl, 3'-trifluoromethyl, 4'-trifluoromethyl, 4'-methoxy, 4'-trifluoromethoxy and 4'-(methylcarbonyl-);
or a pharmaceutically acceptable salt thereof.

6. A compound as in claim 5, wherein
$L^1$ is —$CH_2$—;
a is an integer from 1 to 2;
each R¹ is independently selected from the group consisting of 3-chloro, 4-chloro, 5-chloro, 4-fluoro, 5-fluoro, 5-isopropyl, 5-trifluoromethyl, 5-cyclohexyl and 5-cyclohexenyl;
b is an integer from 0 to 1;
R² is selected from the group consisting of 2-chloro, 2-fluoro and 2-methyl;

c is an integer from 1 to 2;
each R³ is independently selected from the group consisting of 2'-chloro, 3'-chloro, 4'-chloro, 2'-fluoro, 4'-fluoro, 2'-methyl, 3'-trifluoromethyl, 4'-trifluoromethyl and 4'-trifluoromethoxy;
or a pharmaceutically acceptable salt thereof.

7. A compound as in claim 6, wherein
$L^1$ is —$CH_2$—;
$(R^1)_a$ is selected from the group consisting of 5-chloro, 5-trifluoromethyl and 3-chloro-5-trifluoromethyl;
$(R^2)_b$ is 2-chloro;
$(R^3)_c$ is selected from the group consisting of 4'-chloro, 3'-chloro-4'-fluoro and 3'-trifluoromethyl-4'-fluoro;
or a pharmaceutically acceptable salt thereof.

8. A compound as in claim 4, wherein
$L^1$ is selected from the group consisting of —$CH_2$— and —C(O)—;
a is an integer from 1 to 2;
each R¹ is independently selected from the group consisting of 3-chloro, 4-chloro, 5-chloro, 4-fluoro, 5-fluoro, 3-hydroxy, 3-methyl, 5-methyl, 3-isopropyl, 3-trifluoromethyl, 5-trifluoromethyl, 3-methoxy, 3-hydroxy, 3-phenyl, 5-phenyl, 3-cyclopropyl and 5-cyclohexyl;
b is an integer from 0 to 1;
R² is selected from the group consisting of 2-chloro, 2-cyano, 2-methyl and 2-trifluoromethyl;
c is an integer from 1 to 2;
each R³ is independently selected from the group consisting of 2'-chloro, 3'-chloro, 4'-chloro, 6'-chloro, 2'-fluoro, 3'-fluoro, 4'-fluoro, 2'-methyl, 4'-methyl, 3'-trifluoromethyl, 4'-trifluoromethyl and 4'-trifluoromethoxy;
or a pharmaceutically acceptable salt thereof.

9. A compound as in claim 8, wherein
$L^1$ is selected from the group consisting of —$CH_2$— and —C(O)—;
a is an integer from 1 to 2;
each R¹ is independently selected from the group consisting of 3-chloro, 4-chloro, 5-chloro, 3-methyl, 3-isopropyl, 3-trifluoromethyl, 5-trifluoromethyl, 3-methoxy, 3-phenyl, 3-cyclopropyl, and 5-cyclohexyl;
b is an integer from 0 to 1;
R² is selected from the group consisting of 2-chloro, 2-methyl and 2-trifluoromethyl;
c is an integer from 1 to 2;
each R³ is independently selected from the group consisting of 2'-chloro, 3'-chloro, 4'-chloro, 2'-fluoro, 4'-fluoro, 2'-methyl, 3'-trifluoromethyl and 4'-trifluoromethyl;
or a pharmaceutically acceptable salt thereof.

10. A compound as in claim 9, wherein
$L^1$ is —$CH_2$—;
a is an integer from 1 to 2;
each R¹ is independently selected from the group consisting of 3-chloro, 3-methyl, 3-isopropyl, 3-trifluoromethyl, 5-trifluoromethyl, 3-phenyl and 3-cyclopropyl;
b is an integer from 0 to 1;
R² is selected from the group consisting of 2-chloro and 2-methyl;
c is an integer from 1 to 2;
each R³ is independently selected from the group consisting of 2'-chloro, 4'-chloro, 4'-fluoro, 2'-methyl, 3'-trifluoromethyl and 4'-trifluoromethyl;
or a pharmaceutically acceptable salt thereof.

11. A compound as in claim 4, wherein
$L^1$ is —$CH_2$—;
$(R^1)_a$ is selected from the group consisting of 3-chloro-5-trifluoromethyl, 3-methyl-5-trifluoromethyl and 3-cyclopropyl-5-trifluoromethyl;
$(R^2)_b$ is absent or selected from the group consisting of 2-chloro and 2-methyl;

$(R^3)_b$ is selected from the group consisting of 4'-chloro, 2'-methyl-4'-chloro and 2'-methyl-4'-trifluoromethyl;
or a pharmaceutically acceptable salt thereof.

12. A compound as in claim 4, wherein
$L^1$ is —CH$_2$—
$(R^1)_a$ is 5-trifluoromethyl;
$(R^2)_b$ is absent or is 2-chloro;
$(R^3)_b$ is selected from the group consisting of 2'-methyl-4'chloro, 2'-methyl-4'-trifluoromethyl and 4'-chloro;
or a pharmaceutically acceptable salt thereof.

13. A compound as in claim 4, selected from the group consisting of
3-(5-(2-(((2-chloro-2'-methyl-4'-(trifluoromethyl)-[1,1'-biphenyl]-4-yl)amino)methyl)-5-(trifluoromethyl)phenyl)picolinamido)propanoic acid;
and pharmaceutically acceptable salts thereof.

14. A pharmaceutical composition comprising a pharmaceutically acceptable carrier and a compound of claim 1.

15. A pharmaceutical composition made by mixing a compound of claim 1 and a pharmaceutically acceptable carrier.

16. A process for making a pharmaceutical composition comprising mixing a compound of claim 1 and a pharmaceutically acceptable carrier.

17. A method of treating a disorder ameliorated by antagonizing a glucagon receptor, wherein the disorder is selected from the group consisting of Type I diabetes, Type II diabetes mellitus, and obesity, comprising administering a therapeutically effective amount of the compound of claim 1.

18. A method of treating Type I diabetes, Type II diabetes mellitus, or obesity, comprising administering a therapeutically effective amount of the composition of claim 14.

19. A method of treating a condition selected from the group consisting of Type I diabetes, Type II diabetes mellitus, and obesity, comprising administering a therapeutically effective amount of the compound of claim 1.

20. A compound as in claim 1 for use as a medicament.

21. A compound as in claim 1, for use in the treatment of a disorder ameliorated by antagonizing a glucagon receptors, selected from the group consisting of Type I diabetes, Type II diabetes mellitus, and obesity.

22. A composition comprising a compound as in claim 1, for use in the treatment of a disorder ameliorated by antagonizing a glucagon receptor selected from the group consisting of Type I diabetes, Type II diabetes mellitus, and obesity.

* * * * *